US007704491B2

(12) United States Patent
Collins et al.

(10) Patent No.: US 7,704,491 B2
(45) Date of Patent: Apr. 27, 2010

(54) RECOMBINANT HUMAN METAPNEUMOVIRUS AND ITS USE

(75) Inventors: Peter L. Collins, Kensington, M

OTHER PUBLICATIONS

Connors et al., "A Cold-Passaged, Attenuated Strain of Human Respiratory Syncytial Virus Contains Mutations in the F and L Genes," *Virology* 208:478-484 (1995).

Connors et al., "Respiratory Syncytial Virus (RSV) F, G, M2 (22K), and N Proteins Each Induce Resistance to RSV Challenge, but Resistance Induced by M2 and N Proteins is Relatively Short-Lived," *J. Virol.* 65:1634-1637 (1991).

Dimock and Collins, "Rescue of Synthetic Analogs of Genomic RNA and Replicative-Intermediate RNA of Human Parainfluenza Virus Type 3," *J. Virol.* 67:2772-2778 (1993).

Durbin et al., "Human Parainfluenza Virus Type 3 (PIV3) Expressing the Hemagglutinin Protein of Measles Virus Provides a Potential Method for Immunization Against Measles Virus and PIV3 in Early Infancy," *J. Virol.* 74:6821-6831 (2000).

Durbin et al., "Mutations in the C, D, and V Open Reading Frames of Human Parainfluenza Virus Type 3 Attenuate Replication in Rodents and Primates," *Virology* 261:319-330 (1999).

Durbin et al., "Recovery of Infectious Human Parainfluenza Virus Type 3 from cDNA," *Virology* 235:323-332 (1997).

Feller et al., "Comparison of Identical Temperature-Sensitive Mutations in the L Polymerase Proteins of Sendai and Parainfluenza3 Viruses," *Virology* 276:190-201 (2000).

Firestone et al., "Nucleotide Sequence Analysis of the Respiratory Syncytial Virus Subgroup A Cold-Passaged (cp) Temperature Sensitive (ts) cpts-248-404 Live Attenuated Virus Vaccine Candidate," *Virology* 225:419-422 (1996).

Haller et al., "A Single Amino Acid Substitution in the Viral Polymerase Creates a Temperature-Sensitive and Attenuated Recombinant Bovine Parainfluenza Virus Type 3," *Virology* 288:342-350 (2001).

Hardy and Wertz, "The $Cys_3$-$His_1$ Motif of the Respiratory Syncytial Virus M2-1 Protein Is Essential for Protein Function," *J. Virol.* 74:5880-5885 (2000).

Hassett and Condit, "Targeted Construction of Temperature-Sensitive Mutations in Vaccinia Virus by Replacing Clustered Charged Residues with Alanine," *Proc. Natl. Acad. Sci. USA* 91:4554-4558 (1994).

He et al., "Recovery of Infectious SV5 From Cloned DNA and Expression of a Foreign Gene," *Virology* 237:249-260 (1997).

Hoffman and Banetjee, "An Infectious Clone of Human Parainfluenza Virus Type 3," *J. Virol.* 71:4272-4277 (1997).

Jin et al., "Respiratory Syncytial Virus That Lacks Open Reading Frame 2 of the M2 Gene (M2-2) Has Altered Growth Characteristics and Is Attenuated in Rodents," *J. Virol.* 74:74-82 (2000).

Jin et al., "Recombinant Human Respiratory Syncytial Virus (RSV) from a cDNA and Construction of Subgroup A and B Chimeric RSV," *Virology* 251:206-214 (1998).

Juhasz et al., "The Major Attenuating Mutations of the Respiratory Syncytial Virus Vaccine Candidate *cpts*530/1009 Specify Temperature-Sensitive Defects in Transcription and Replication and a Non-Temperature-Sensitive Alteration in mRNA Termination," *J. Virol.* 73:5176-5180 (1999).

Juhasz et al., "The Temperature-Sensitive (*ts*) Phenotype of a Cold-Passaged (*cp*) Live Attenuated Respiratory Syncytial Virus Vaccine Candidate, Designated *cpts*530, Results from a Single Amino Acid Substitution in the L Protein," *J. Virol.* 71:5814-5819 (1997).

Kato et al., "The Paramyxovirus, Sendai Virus, V Protein Encodes a Luxury Function Required for Viral Pathogenesis," *EMBO J.* 16:578-587 (1997).

Kretzsclunar et al., "Normal Replication of Vesicular Stomatitis Virus Without C Proteins," *Virology* 216:309-316 (1996).

Lambert et al., "Peptides from Conserved Regions of Paramyxovirus Fusion (F) Proteins are Potent Inhibitors of Viral Fusion," *Proc. Natl. Acad. Sci. USA* 93:2186-2191 (1996).

Lu et al., "Identification of Temperature-Sensitive Mutations in the Phosphoprotein of Respiratory Syncytial Virus That are Likely involved in Its Interaction with the Nucleoprotein," *J. Virol.* 76:2871-2880 (2002).

Newman et al., "Sequence Analysis of the Washington/1964 Strain of Human Parainfluenza Virus Type 1 (HPIV1) and Recovery and Characterization of Wild-Type Recombinant HPIV1 Produced by Reverse Genetics," *Virus Genes.* 24:77-92 (2002).

Peret et al., "Characterization of Human Metapneumoviruses Isolated from Patients in North America," *J. Infect. Dis.* 185:1660-1663 (2002).

Radecke and Billeter, "The Nonstructural C Protein is Not Essential for Multiplication of Edmonston B Strain Measles Virus in Cultured Cells," *Virology* 217:418-421 (1996).

Schmidt et al., "Bovine Parainfluenza Virus Type 3 (BPIV3) Fusion and Hemagglutinin-Neuraminidase Glycoproteins Make an Important Contribution to the Restricted Replication of BPIV3 in Primates," *J. Virol.* 74:8922-8929 (2000).

Skiadopoulos et al., "Determinants of the Host Range Restriction of Replication of Bovine Parainfluenza Virus Type 3 in Rhesus Monkeys are Polygenic," *J. Virol.* 77:1141-1148 (2003).

Skiadopoulos et al., "Generation of a Parainfluenza Virus Type 1 Vaccine Candidate by Replacing the HN and F Glycoproteins of the Live-Attenuated PIV3 cp45 Vaccine Virus With Their PIV1 Counterparts," *Vaccine* 18:503-510 (2000).

Skiadopoulos et al., "Attenuation of the Recombinant Human Parainfluenza Virus Type 3 cp45 Candidate Vaccine Virus is Augmented by Importation of the Respiratory Syncytial Virus cpts530 L Polymerase Mutation," *Virology* 260:125-135 (1999).

Skiadopoulos et al., "Identification of Mutations Contributing to the Temperature-Sensitive, Cold-Adapted, and Attenuation Phenotypes of the Live-Attenuated Cold-Passage 45 (*cp*45) Human Parainfluenza Virus 3 Candidate Vaccine," *J. Virol.* 73:1374-1381 (1999).

Skiadopoulos et al., "Three Amino Acid Substitutions in the L Protein of the Human Parainfluenza Virus Type 3 *cp*45 Live Attenuated Vaccine Candidate Contribute to Its Temperature-Sensitive and Attenuation Phenotypes," *J. Virol* 72:1762-1768 (1998).

Tang et al., "Clustered Charge-to-Alanine Mutagenesis of Human Respiratory Syncytial Virus L Polymerase Generates Temperature-Sensitive Viruses," *Virology* 302:207-216 (2002).

Tang et al., "Requirement of Cysteines and Length of the Human Respiratory Syncytial Virus M2-1 Protein for Protein Function and Virus Viability," *J. Virol.* 75:11328-11335 (2001).

Tao et al., "Construction of a Live-Attenuated Bivalent Vaccine Virus Against Human Parainfluenza Virus (PIV) Types 1 and 2 Using a Recombinant PIV3 Backbone," *Vaccine* 19:3620-3631(2001).

Tao et al., "A Live Attenuated Chimeric Recombinant Parainfluenza Virus (PIV) Encoding the Internal Proteins of PIV Type 3 and the Surface Glycoproteins of PIV Type 1 Induces Complete Resistance to PIV1 Challenge and Partial Resistance to PIV3 Challenge," *Vaccine* 17:1100-1108 (1999).

Tao et al., "Recovery of a Fully Viable Chimeric Human Parainfluenza Virus (PIV) Type 3 in Which the Hemagglutinin-Neuraminidase and Fusion Glycoproteins Have Been Replaced by Those of PIV Type 1," *J. Virol.* 72:2955-2961 (1998).

Teng et al., "Contribution of the Respiratory Syncytial Virus G Glycoprotein and its Secreted and Membrane-Bound Forms to Virus Replication In Vitro and In Vivo," *Virology* 289:283-296 (2001).

van den Hoogen et al., "Analysis of the Genomic Sequence of a Human Metapneumovirus," *Virology* 295:119-132 (2002).

van den Hoogen et al., "A Newly Discovered Human Pneumovirus Isolated from Young Children With Respiratory Tract Disease," *Nature Med.* 7:719-724 (2001).

van Wyke Coelingh and Tierney, "Antigenic and Functional Organization of Human Parainfluenza Virus Type 3 Fusion Glycoprotein," *J. Virol.* 63:375-382 (1989).

Wertman et al., "Systematic Mutational Analysis of the Yeast *ACT1* Gene," *Genetics* 132:337-350 (1992).

Whitehead et al., "Recombinant Respiratory Syncytial Virus Bearing a Deletion of Either the NS2 or SH Gene is Attenuated in Chimpanzees," *J. Virol.* 73:3438-3442 (1999).

Whitehead et al., "Addition of a Missense Mutation Present in the L Gene of Respiratory Syncytial Virus (RSV) *cpts*530/1030 to RSV Vaccine Candidate *cpts*248/404 Increases Its Attenuation and Temperature Sensitivity," *J. Virol.* 73:871-877 (1999).

Whitehead et al., "A Single Nucleotide Substitution in the Transcription Start Signal of the M2 Gene of Respiratory Syncytial Virus Vaccine Candidate cpts248/404 is the Major Determinant of the Temperature-Sensitive and Attenuation Phenotypes," *Virology* 247:232-239 (1998).

Whitehead et al., "Recombinant Respiratory Syncytial Virus (RSV) Bearing a Set of Mutations from Cold-Passaged RSV is Attenuated in Chimpanzees," *J. Virol.* 72:4467-4471 (1998).

Tang, R.S., et al., "Effects of Human Metapneumovirus and Respiratory Syncytial Virus Antigen Insertion in Two 3' Proximal Genome Postions of Bovine/Human Parainfluenza virus Type 3 on Virus Replication and Immunogenicity," J.Virol., vol. 77, No. 20, pp. 10819-10828 (2003).

Biacchesi, S., et al "Recovery of human metapneumovirus from cDNA: optimization of growth in vitro and expression of additional genes," J.Virol., vol. 321, No. 2, pp. 247-259 (2004).

Skiadopoulos, M.H., et al., "The Two Major Human Metapneumovirus Genetic Lineages Are Highly Related Antigenically, and the Fusion (F) Protein Is a Major Contributor to This Antigenic Relatedness," J.Virol., vol. 78, No. 13, pp. 6927-6937 (2004).

Herfst, S., "Recovery of Human Metapneumovirus Genetic Lineages A and B from Cloned cDNA," J.Virol., vol. 78, No. 15, pp. 8264-8270 (2004).

Biacchesi, S., et al., "Genetic diversity between human metapneumovirus subgroups," Virology, vol. 315, No. 1, pp. 1-9 (2003).

van den Hoogen, B.G., et al., "Analysis of the Genomic Sequence of a Human Metapneumovirus," Virology, vol. 295, No. 1, pp. 119-132 (2002).

Collins, P.L., et al., "Respiratory Syncytial Virus: Reverse Genetics and Vaccine Strategies," Virology, vol. 296, No. 2, pp. 204-211 (2002).

Crowe, James E., Jr., "Respiratory syncytial virus vaccine development," Vaccine, vol. 20, pp. S32-S37 (2001).

Biacchesi, S., et al., "Recombinant Human Metapneumovirus Lacking the Small Hydophobic SH and/or Attachment G Glycoprotein: Deletion of G Yields a Promising Vaccine Candidate," J.Virol., vol. 78, No. 23, pp. 12877-12887 (2004).

* cited by examiner

Fig. 2

Amino acid identity between HMPV83 and other Pneumoviruses for the indicated proteins

| | N | P | M | F | M 2-1 | M 2-2 | G | SH | L |
|---|---|---|---|---|---|---|---|---|---|
| HMPV 00-1 | 99 | 95 | 99 | 98 | 98 | 96 | 70 | 85 | 99 |
| HMPV 97-82 | 95 | 85 | 97 | 94 | ND | ND | ND | ND | ND |
| APV A | 70 | 58 | 77 | 68 | 73 | 25 | 12 | 20 | 64 |
| APV B | 69 | 53 | 76 | 67 | 71 | 27 | ND | 20 | ND |
| APV C | 88 | 68 | 87 | 81 | 83 | 56 | ND | ND | ND |
| HRSV A2 | 41 | 31 | 38 | 36 | 36 | 12 | 15 | 6 | 46 |
| HRSV B | 41 | 31 | 37 | 35 | 35 | 8 | 15 | 6 | 46 |
| BRSV | 41 | 31 | 37 | 37 | 35 | 14 | 19 | 10 | 46 |
| PVM | 45 | 28 | 38 | 40 | 36 | 12 | ND | 8 | ND |

ND: Comparison not done, usually because sequence was unavailable

Gene Start Signal

```
                    1            5         10        15
N       tacaaaaaacat GGGACAAGTGAAA ATGtctcttc
P       taattaaaaagt GGGACAAGTCAAA ATGtcattcc
M       aaaataaaaaat GGGACAAGTGAAA ATGgagtcct
F       atcaatcaagaac GGGACAAATAAAA ATGtcttgga
M2      taaaataaaattt GGGACAAATCATA ATGtctcgca
SH      aacacatcagagt GGGATAAGTGACA ATGataacat
G       aaaacaaaaatat GGGACAAGTAGTT ATGgaggtga
L       aaacagcatccaa GAGACAAATAGCA ATGgatcctc CONSENSUS    ...at GGGACAAGTGAAA ATGtc...
                   gc  A  T   A  AGTT      ga
                   ta                C C   at
```

Gene End Signal

```
                1         5       10
N       ttatg AGTAATTAAAAAA gt
P       tatgt AGTTTATAAAAAA taaaaaat
M       atttt AGTTATATAAAAA tcaagttagaat a
F       cagtt AGTTAATTAAAAA taaaataaaatt t
M2      actta AGTTAGTAAAAA cacatcagagt
SH      agttt AGTTATTTTAAAA tatttgagaata g
G       aaatt AGTTAACAAAAAA tacgagatagct c
L       atgat AGTTAATTAAAA ttaaaaattaaaa a CONSENSUS   ...tt AGTTAATTAAAAA ta...
                  ATTAAT        cc
                  ag      GC    gt

|  | C | X7 |  |  |  |  |  |  | C | X5 |  |  |  | C | X3 |  | H |  |
|---|---|---|---|---|---|---|---|---|---|---|---|---|---|---|---|---|---|---|---|
| HMPV-GFP M2 | M S R K A P | C | K | Y | E | V | R | G | K | C | N | R | G | S | E | C | K | F | N | H | N |
| HMPV-GFP M2 C7S | M S R K A P | S | K | Y | E | V | R | G | K | C | N | R | G | S | E | C | K | F | N | H | N |
| HMPV-GFP M2 Y9S | M S R K A P | C | K | S | E | V | R | G | K | C | N | R | G | S | E | C | K | F | N | H | N |
| HMPV-GFP M2 C15S | M S R K A P | C | K | Y | E | V | R | G | K | S | N | R | G | S | E | C | K | F | N | H | N |
| HMPV-GFP M2 N16S | M S R K A P | C | K | Y | E | V | R | G | K | C | S | R | G | S | E | C | K | F | N | H | N |
| HMPV-GFP M2 H25S | M S R K A P | C | K | Y | E | V | R | G | K | C | N | R | G | S | E | C | K | F | N | S | N |

Fig. 19

```
                    4711                                                                                                    4775
HMPV           GGGACAAATCATAAATG TCT CGC AAG GCT CCA TGC AAA TAT GAA GTG CGG GGC AAA TGC AAC AGA
rHMPV-GFP ΔN2-1              tag                       t  aa              t  aaa           t  aa
HMPV                      M   S   R   K   A   P   C   K   Y   E   V   R   G   K   C   N   R
rHMPV-GFP ΔN2-1                                        N           N              N       N
```

Fig. 21

Reduction of virus yield in presence of exogenous interferon (IFN) type I

| Virus | MOI | Fold reduction of virus yield | | |
|---|---|---|---|---|
| | | 10 U IFN | 100 U IFN | 1000 U IFN |
| rHMPV-GFP | 1.0 | 5 | 160 | 1680 |
| rHMPV-GFP$_\Delta$M2(1+2) | 1.0 | 19 | 1130 | no virus |
| rHMPV-GFP$_\Delta$M2-2 | 1.0 | 13 | 250 | no virus |
| RSV-GFP | 0.01 | 4 | 17 | 90 |

BPIV3 Mutation I1103V

I1103V

|  |  |  |  |  |  |  |
|---|---|---|---|---|---|---|
| bPIV3 | 1087 | R V G S R G - G E T Y N L R K K S N Y D D L Q Y E T L S | 1115 |
| hPIV3 | 1087 | R V G N R G - G E T Y S L R K K I N Y D D L Q Y E T L S | 1115 |
| hPIV1 | 1087 | R A S Y R R G - G E S Y S I L R R L I N Y D D I Q Y E T L T | 1115 |
| hRSV A2 | 1153 | K T S A I D L T D I D R A T E M M R K N I T L L I R I L P L | 1182 |
| hMPV 83 | 1078 | R T S A I N E D D I D R A V E M M R K N I T E L S R I L S V | 1107 |
| hMPV 001 | 1078 | R T S A I N G E D I D R A V E M M R K N L G E L S R I L S V | 1107 |

HPIV3 Mutation T1558I

T1558I

|  |  |  |  |  |  |  |
|---|---|---|---|---|---|---|
| hPIV3 | 1539 | F K R F W D C G V L N P I Y G P N T A S Q D Q I K L A S C | 1572 |
| hPIV1 | 1539 | F K R F W D A G V E P V Y S P N N I S N Q D K I L A S I C | 1572 |
| hRSV A2 | 1586 | K V I K Y L S Q D A S L H R F L S Q D K L H S N K I K R W | 1619 |
| hMPV 83 | 1507 | K V R K V T L Q D M L Y D K F L A G Y K G K E Q E Q R S | 1540 |
| hMPV 001 | 1507 | K V R K V T L Q D M L Y D V K F L V G Y K G K E Q E Q R S | 1540 |

RSV A2 Mutation C319Y

C319Y

|  |  |  |  |  |  |  |
|---|---|---|---|---|---|---|
| hPIV3 | 258 | K L Q S M Y Q K G N L A V E V I D K F P I M G E K T I D V | 288 |
| hPIV1 | 258 | R S K I T C K G E E L I D S L F P N L G E D N S | 288 |
| hRSV A2 | 302 | R C G F N V L T Q F E L Y G D C I L K L F H N E G T Y I W | 332 |
| hMPV 83 | 239 | R S N L Q G M L T N K Y M D V L A G C L A G S I S | 269 |
| hMPV 001 | 239 | R S N L Q G I T N K Y T E T N D G F L S G T V | 269 |

```
                                    C cpts 248/404
                           1    5    10   WT
RSV        M2              GGGGCAAATA
                                   ↑
                           1    5         15
HMPV       N            t  GGGACAAGTGAAA  ATG
           P            t  GGGACAAGTCAAA  ATG
           M

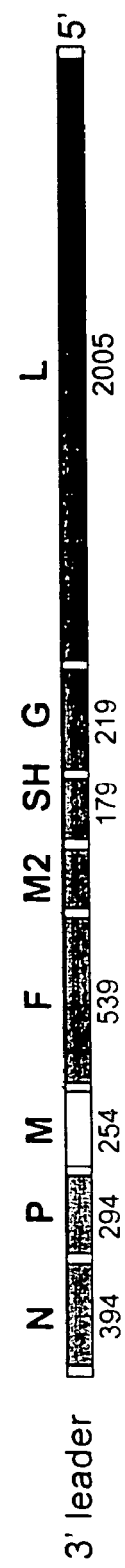
Fig. 30A

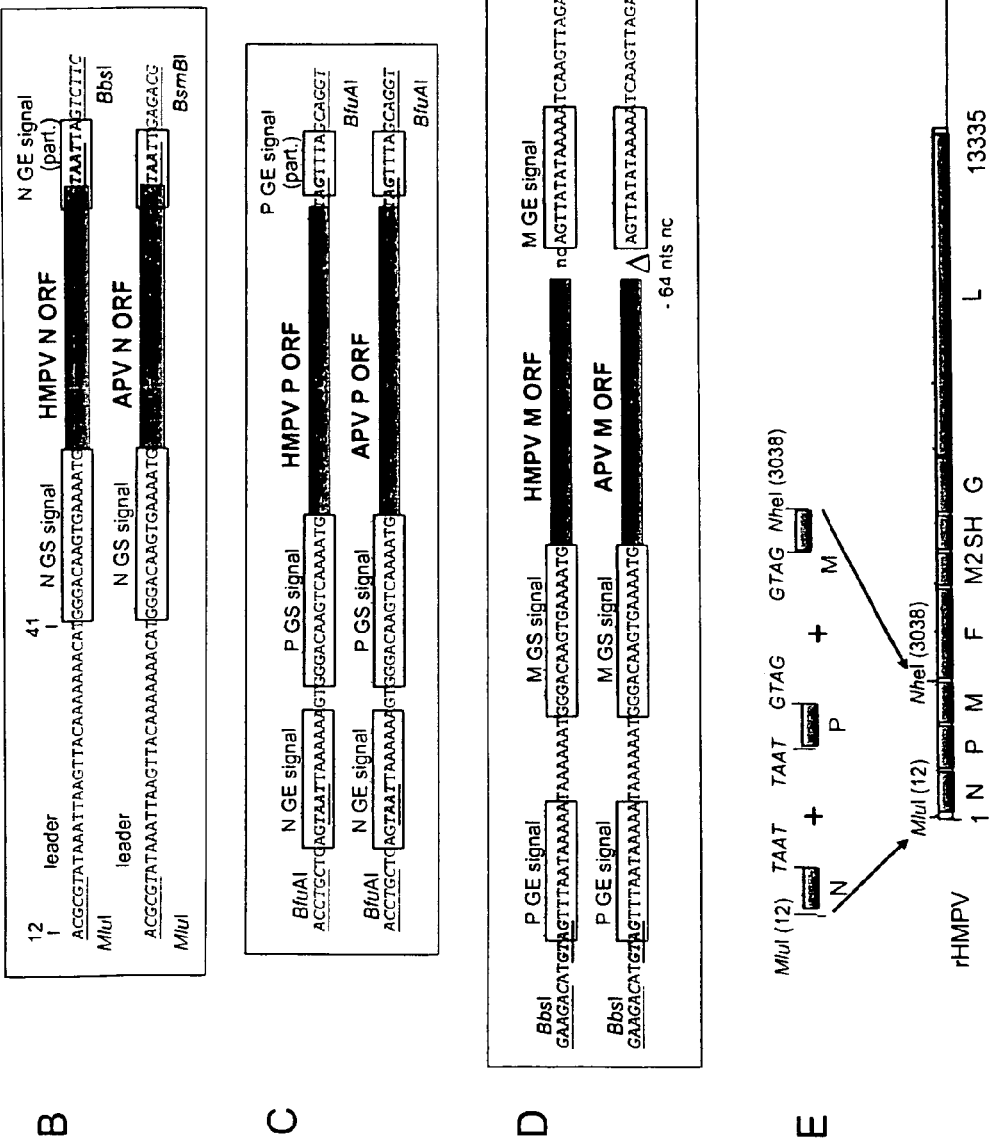
Fig. 30B-E

| | gene-end | intergenic | gene-start | |
|---|---|---|---|---|
| | 1                    13 | | 1                                16 | |
| le (83) | aattaAGTTAcaAAAAAcat | | GGGACAAgTgAaAAATGtctct | N (83) |
| (75) | aattaAaTTccaaAcAAAAc- | | GGGACAAaTaAaAAATGtctct | (75) |
| N (83) | ttatgAGTaAttaAAAAA-- | gt | GGGACAAgTcAaAAATGtcatt | P (83) |
| (75) | ttatgAGTaAttaAAAAA-- | ct | GGGACAAgTcAaAAATGtcatt | (75) |
| P (83) | tatgtAGTTtaatAAAAA-- | taaaaaat | GGGACAAgTgAaAATGgagtc | M (83) |
| (75) | catgtAGTTtaatAAAAA-- | taaacaat | GGGACAAgTcAagATGgagtc | (75) |
| M (83) | attttAGTTAtatAAAAA-- | tcaag- 24 nt -agaac | GGGACAAaTaAaAAATGtcttg | F (83) |
| (75) | attatAGTTAtatAAAAAA- | tttag- 20 nt -aaagc | GGGACAAgTaAaAAATGtcttg | (75) |
| F (83) | cagttAGTTAattAAAAA-- | taaaataaaattt | GGGACAAaTcAtAATGtctcg | M2(83) |
| (75) | tagtt AGTTAattAAAAAA- | t | GGGACAAaTcAtcATGtctcg | (75) |
| M2 (83) | acttaAGTTAgtAAAA--- | cacatcagagt | GGGAtAAgTgAcAATGataac | SH(83) |
| (75) | acttaAGTTAgtaAAAA--- | taaatagaat | GGGAtAAaTgAcAATGaaaac | (75) |
| SH (83) | agtttAGTTAtttAAAAA-- | tattt-114 nt -aatat | GGGACAAgTagtt ATGgaggt | G (83) |
| (75) | agtctAGTTAtttAAAAA-- | ctcta-107 nt -aaaat | GGGACAAgTggccATGgaagc | (75) |
| G (83) | aaattAGTTAcaAAAAA-- | tacga-180 nt -tccaa | GaGACAAaTagcAATGgatcc | L (83) |
| (75) | caagtAGTTAacaAAAAAA- | ctata-157 nt -ttcaa | GGGACAAaTaacAATGgatcc | (75) |
| L (83) | atgatAGTTAattAAAAA-- | ttaaa-91 nt | | tr (83) |
| (75) | ccattAGTTAattAAAAA-- | ttata-63 nt | | (75) |
| consensus | AGTTAnnnAAAAA | | GGGACAAnTnnnAATG | |

Fig. 31

Percent amino acid or nucleotide sequence identity between the indicated strains of HMPV or RSV for the indicated proteins and ORFs

| Viruses compared | percent amino acid sequence identity for indicated protein (percent nucleotide sequence identity for indicated ORF) | | | | | | | | |
|---|---|---|---|---|---|---|---|---|---|
| | N | P | M | F | M2-1 | M2-2 | SH | G | L |
| CAN97-83 vs CAN98-75 | 96 (84) | 85 (81) | 97 (85) | 95 (84) | 96 (85) | 89 (87) | 59 (69) | 37 (59) | 94 (84) |
| CAN97-83 vs 00-1 | 99 (94) | 95 (92) | 99 (94) | 98 (94) | 98 (94) | 96 (95) | 85 (88) | 70 (77) | 99 (95) |
| RSV A2 vs RSV B1 | 95 (85) | 90 (85) | 91 (85) | 89 (81) | 91 (84) | 61 (69) | 72 (77) | 55 (67) | 92 (85) |

Fig. 32

A. SH protein

```
CAN98-75    1  K           E  NQ      K    L   S PT      S  V   V  T   54
CAN97-83    1 MITLDVIKSDGSSKTCTHLKKIIKDHSGKVLIALKLILALLTFFTITITINYIK  54
00-1        1                                V         L V             54
              * *********** **..****** ****.**  * ***** *.***.** *
                             •

CAN98-75   55       A  L N    K TKL    T IRPIP LNAV  L     KH N  TKD 108
CAN97-83   55 VENNLQICQSKTESDKEDSPSNTTSVTTKTTLDHDITQYFKRLIQRYTDSVIN- 107
00-1       55               K  SS            N        SL    TN A   - 107
              ****** ** *.**** *.  **** *          ** * ***. * *
                      •

CAN98-75  109 R    R HT       KI       GSMN TNTD EEP V  DK    TMT KHRKA 162
CAN97-83  108 KDTCWKISRNQCTNITTYKFLCFKPEDSKINSCDRLTDLCRNKSKSAAEAYHTV 161
00-1      108 S      N               S  T T N  K         P P VGV  I   161
               ****.*  ******  ******     .  .*.  * **  * *       .
                 •       •         •           •     •

CAN98-75  163    RPH T  W HYL------- 177
CAN97-83  162 ECHCIYTIEWKCYHHSID---- 179
00-1      162        VK     YPT ETQS 183
              ***    *  * *
               •          •
```

Fig. 33A

B. G protein

```
CAN98-75     1   AR            F  KM    IRS    HR  T      S AP M    TL    DHA  54
CAN97-83     1 MEVKVENIRAIDMLKARVKNRVARSKCFKNASLILIGITTLSIALNIYLIINYT  54
00-1         1          T                           V                   K  54
               **  .*****.***  **..***.   ***  .**.*.*** *.  *.***   ***

CAN98-75    55 TS NMTKV  CVNM  V PS KTPMT AAD NTK  P QA  LT  DS SLA T 108
CAN97-83    55 IQKTSSESEHHTSSPPTESNKEASTISTDNPDINPNSQHPTQQSTENPTLNPAA 108
00-1        55 M  NT         S M  SR TP VP   S T SSP        GS  YF   108
                 *. .  **     * *   . .     .         *. ** .**  *    *.

CAN98-75   109 LEDHLH GTTP   A VSQQTT EH TLLRSTNRQ TQ TAEKKPTRATTKKET 162
CAN97-83   109 SVSPSETEPASTPDTTNRLSSVDRSTAQPSESRTKTKPTVHTRNNPSTASSTQS 162
00-1       109  A SP    T        PPF  TH TP  A     S A   K   R S R H  162
                     *  . ***.*      *  *.     .  .*  . .  .     ...     .

CAN98-75   163 TT T ST ATQTLNTTNQTSNG EA    AR RNNA   SSDQ TQ ADPS Q  216
CAN97-83   163 PPRATTKAIRRATTFRMSSTGKR-PTTTSVQSDSSTTTQNHEETGSANPQASVS 215
00-1       163       RTA  T  L T   R  - S A   P I A  HKN  ASP S  T A  215
                 *.*. .  .. .    .. *  .*.* .    .**.  ...  *    .* *

CAN98-75   217 QHTQKSTTTTHNTDTSSPSS- 236
CAN97-83   216 TMQN----------------- 219
00-1       216  TRIQRKSVEANTSTTYNQTS 236
```

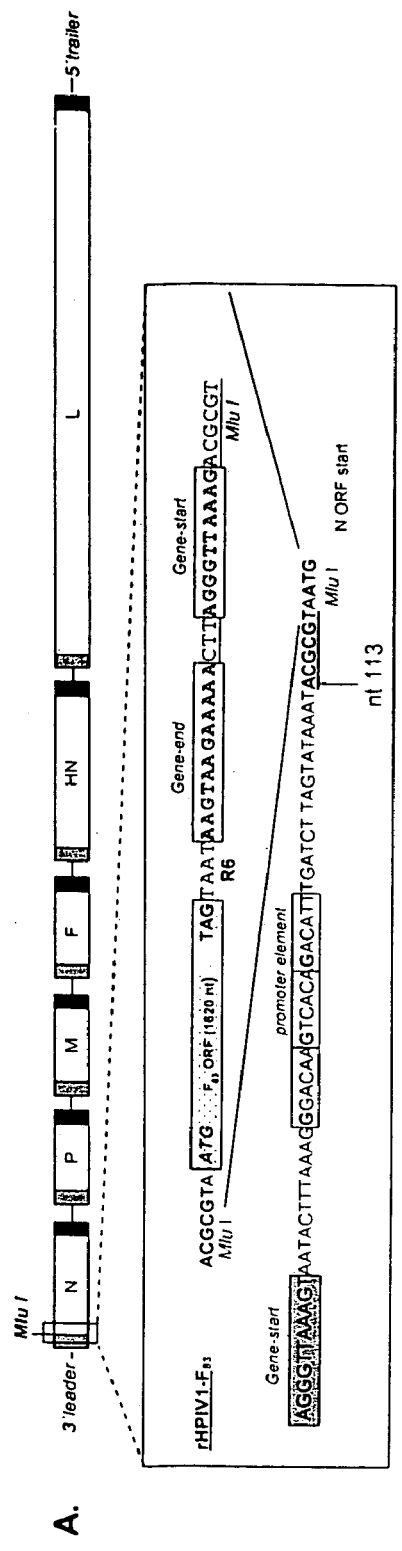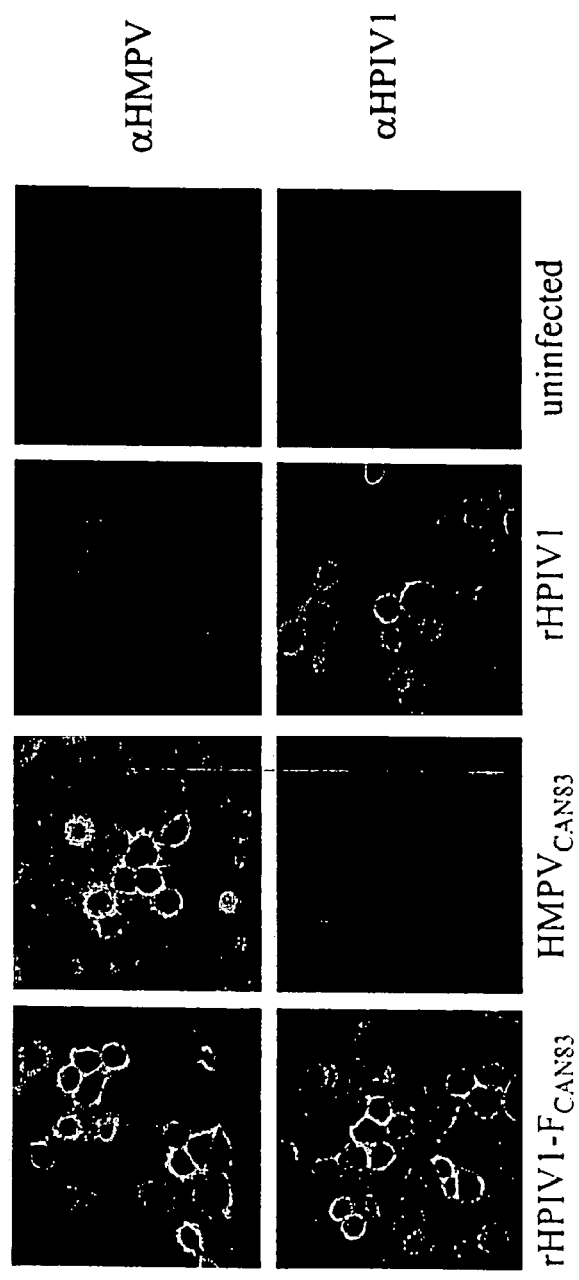
Fig. 36A & B

HMPV strain 83

```
         |  10      |  20      |  30      |  40      |  50        |  60      |  70      |  80      |  90      |  100
   1 ACGCGAAAAA AACGCGTATA AATTAAGTTA CAAAAAAACA TGGGACAAGT  GAAAATGTCT CTTCAAGGGA TTCACCTGAG TGATCTATCA TACAAGCATG 100
 101 CTATATTAAA AGAGTCTCAG TATACAATAA AGAGAGATGT AGGCACAACA  ACAGCAGTGA CACCCTCATC ATTGCAACAA GAAATAACAC TATTGTGTGG 200
 201 AGAAATTCTA TATGCTAAGC ATGCTGATTA CAAATATGCT GCAGAAATAG  GAATACAATA TATTAGCACA GCTCTAGGAT CAGAGAGAGT ACAGCAGATT 300
 301 CTAAGAAACT CAGGCAGTGA AGTCCAAGTG GTTTTAACCA GAACGTACTC  CTTGGGGAAA GTTAAAAACA ACAAAGGAGA AGATTTACAG ATGTTAGACA 400
 401 TACACGGAGT AGAGAAAAGC TGGGTGGAAG AGATAGACAA AGAAGCAAGA  AAAACAATGG CAACTTTGCT TAAAGAATCA TCAGGCAATA TTCCACAAAA 500
 501 TCAGAGGCCT TCAGCACCAG ACACACCTAT AATCTTATTA TGTGTAGGTG  CCTTAATATT TACCAAACTA GCATCAACTA TAGAAGTGGG ATTAGAGACC 600
 601 ACAGTCAGAA GAGCTAACCG TGTACTAAGT GATGCACTCA AAAGATACCC  TAGGATGGAC ATACCAAAAA TCGCTAGATC TTTCTATGAT TTATTTGAAC 700
 701 AAAAAGTGTA TTACAGAAGT TTGTTCATTG AGTATGGCAA AGCATTAGGC  TCATCCTCTA CAGGCAGCAA AGCAGAAAGT TTATTCGTTA ATATATTCAT 800
 801 GCAAGCTTAC GGTGCTGGTC AAACAATGCT GAGGTGGGGA GTCATTGCCA  GGTCATCTAA CAATATAATG TTAGGACATG TATCTGTCCA AGCTGAGTTA 900
 901 AAACAAGTCA CAGAAGTCTA TGACCTGGTG CGAGAAATGG GCCCTGAATC  TGGGCTCCTA CATTTAAGGC AAAGCCCAAA AGCTGGACTG TTATCACTAG 1000
1001 CCAATTGTCC CAACTTTGCA AGTGTTGTTC TCGGCAATGC CTCAGGCTTA  GGCATAATAG GTATGTATCG CGGGAGAGTG CCAAACACAG AACTATTTTC 1100
1101 AGCAGCAGAA AGCTATGCCA AGAGTTTGAA AGAAAGCAAT AAAATTAACT  TTTCTTCATT AGGACTCACA GATGAAGAAA AAGAGGCTGC AGAACACTTT 1200
1201 CTAAATGTGA GTGACGACAG TCAAAATGAT TATGAGTAAT TAAAAAAGTG  GGACAAGTCA AAATGTCATT CCCTGAAGGA AAAGATATTC TTTTCATGGG 1300
1301 TAATGAAGCG GCAAAATTGG CAGAAGCTTT CCAAAAATCA TTAAGAAAAC  CTAGTCATAA AAGATCTCAA TCTATTATAG GAGAAAAAGT GAACACTGTA 1400
1401 TCTGAAACAT TGGAATTACC TACTATCAGT AGACCTACCA AACCGACCAT  ATTGTCAGAG CCGAAGTTAG CATGGACAGA CAAAGGTGGG GCAATCAAAA 1500
1501 CTGAAGCAAA GCAAACAATC AAAGTTATGG ATCCTATTGA AGAAGAAGAG  TTTACTGAGA AAAGGGTGCT GCCCTCCAGT GATGGGAAAA CTCCTGCAGA 1600
1601 AAAGAAGTTG AAACCATCAA CCAATACTAA AAAGAAGGTC TCATTTACAC  CAAATGAACC AGGAAAATAC ACAAAGTTGG AGAAAGATGC TCTAGACTTG 1700
1701 CTTTCAGACA ATGAAGAAGA AGATGCAGAA TCCTCAATCT TAACCTTCGA  AGAAAGAGAT ACTTCATCAT TAAGCATTGA AGCCAGACTA GAATCGATTG 1800
1801 AGGAGAAATT AAGCATGATA TTAGGGCTAT TAAGAACACT CAACATTGCT  ACAGCAGGAC CCACAGCAGC AAGAGATGGG ATCAGAGATG CAATGATTGG 1900
1901 CATAAGGGAG GAACTAATAG CAGACATAAT AAAAGAAGCC AAGGGAAAAG  CAGCAGAAAT GATGGAAGAA GAAATGAACC AGCGGACAAA AATAGGAAAC 2000
2001 GGTAGTGTAA AATTAACTGA AAAGGCAAAG GAGCTCAACA AAATTGTTGA  AGACGAGAGC ACAAGTGGTG AATCCGAAGA AGAAGAAGAA CTAAAAGACA 2100
2101 CACAGGAAAA TAATCAAGAA GATGACATTT ACCAGTTAAT TATGTAGTTT  AATAAAAATA AAAAATGGGA CAAGTGAAAA TGGAGTCCTA TCTGGTAGAC 2200
2201 ACCTATCAAG GCATCCCTTA CACAGCAGCT GTTCAAGTTG ATCTAGTAGA  AAAGGACCTG TTACCTGCAA GCCTAACAAT ATGGTTCCCC CTGTTTCAGG 2300
2301 CCAATACACC ACCAGCAGTT CTGCTTGATC AGCTAAAGAC TCTGACTATA  ACTACTCTGT ATGCTGCATC ACAAAGTGGT CCAATACTAA AAGTGAATGC 2400
2401 ATCGGCCCAG GGTGCAGCAA TGTCTGTACT TCCCAAAAAG TTTGAAGTCA  ATGCGACTGT AGCACTTGAC GAATATAGCA AATTAGAATT TGACAAACTT 2500
2501 ACAGTCTGTG AAGTAAAAAC AGTTTACTTA ACAACCATGA AACCATATGG  GATGGTATCA AAGTTTGTGA GCTCGGCCAA ACCAGTTGGC AAAAAAACAC 2600
2601 ATGATCTAAT CGCATTATGC GATTTTATGG ATCTAGAAAA GAACACACCA  GTTACAATAC CAGCATTTAT CAAATCAGTT TCTATCAAGG AGAGTGAATC 2700
2701 AGCCACTGTT GAAGCTGCAA TAAGCAGTGA AGCAGACCAA GCTCTAACAC  AAGCCAAAAT TGCACCTTAT GCGGGACTGA TCATGATTAT GACCATGAAC 2800
2801 AATCCCAAAG GCATATTCAA GAAGCTTGGA GCTGGGACCC AAGTTATAGT  AGAACTAGGA GCATATGTCC AGGCTGAAAG CATAAGTAAA ATATGCAAGA 2900
2901 CTTGGAGCCA TCAAGGAACA AGATATGTGC TGAAGTCCAG ATAACAGCCA  AGCAACCTGA CCAAGAACTA CCAACTCTAT TCTATAGACT AAAAAGTCGC 3000
3001 CATTTTAGTT ATATAAAAAT CAAGTTAGAA TAAGAATTAA ATCAATCAAG  AACGGGACAA ATAAAAATGT CTTGGAAAGT GGTGATCATT TTTTCATTGC 3100
3101 TAATAACACC TCAACACGGT CTTAAAGAGA GCTACCTAGA AGAATCATGT  AGCACTATAA CTGAGGGATA TCTTAGTGTT CTGAGGACAG GTTGGTATAC 3200
3201 CAACGTTTTT ACATTAGAGG TGGGTGATGT AGAAAACCTT ACATGTTCTG  ATGGACCTAG CCTAATAAAA ACAGAATTAG ATCTGACCAA AAGTGCACTA 3300
3301 AGAGAGCTCA AAACAGTCTC TGCTGACCAA TTGGCAAGAG AGGAACAAAT  TGAGAATCCC AGACAATCTA GGTTTGTTCT AGGAGCAATA GCACTCGGTG 3400
3401 TTGCAACAGC AGCTGCAGTC ACAGCAGGTG TTGCAATTGC CAAAACCATC  CGGCTTGAGA GTGAAGTCAC AGCAATTAAG AATGCCCTCA AAACGACCAA 3500
3501 TGAAGCAGTA TCTACATTGG GGAATGGAGT TCGAGTGTTG GCAACTGCAG  TGAGAGAGCT GAAAGACTTT GTGAGCAAGA ATTTAACTCG TGCAATCAAC 3600
3601 AAAAACAAGT GCGACATTGA TGACCTAAAA ATGGCCGTTA GCTTCAGTCA  ATTCAACAGA AGGTTTCTAA ATGTTGTGCG GCAATTTTCA GACAATGCTG 3700
3701 GAATAACACC AGCAATATCT TTGGACTTAA TGACAGATGC TGAACTAGCC  AGGGCCGTTT CTAACATGCC GACATCTGCA GGACAAATAA AATTGATGTT 3800
```

Fig. 37A

HMPV strain 83 (continued)

3801 GGAGAACCGT GCGATGGTGC GAAGAAAGGG GTTCGGAATC CTGATAGGGG TCTACGGGAG CTCCGTAATT TACATGGTGC AGCTGCCAAT CTTTGGCGTT 3900
3901 ATAGACACGC CTTGCTGGAT AGTAAAAGCA GCCCCTTCTT GTTCCGGAAA AAAGGGAAAC TATGCTTGCC TCTTAAGAGA AGACCAAGGG TGGTATTGTC 4000
4001 AGAATGCAGG GTCAACTGTT TACTACCCAA ATGAGAAAGA CTGTGAAACA AGAGGAGACC ATGTCTTTTG CGACACAGCA GCGGGAATTA ATGTTGCTGA 4100
4101 GCAATCAAAG GAGTGCAACA TCAACATATC CACTACAAAT TACCCATGCA AAGTCAGCAC AGGAAGACAT CCTATCAGTA TGGTTGCACT GTCTCCTCTT 4200
4201 GGGGCTCTGG TTGCTTGCTA CAAAGGAGTA AGCTGTTCCA TTGGCAGCAA CAGAGTAGGG ATCATCAAGC AGCTGAACAA GGGTTGCTCC TATATAACCA 4300
4301 ACCAAGATGC AGACACAGTG ACAATAGACA ACACTGTATA TCAGCTAAGC AAAGTTGAGG GTGAACAGCA TGTTATAAAA GGCAGACCAG TGTCAAGCAG 4400
4401 CTTTGATCCA ATCAAGTTTC CTGAAGATCA ATTCAATGTT GCACTTGACC AAGTTTTTGA GAACATTGAA AACAGCCAGG CCTTGGTAGA TCAATCAAAC 4500
4501 AGAATCCTAA GCAGTGCAGA GAAAGGGAAT ACTGGCTTCA TCATTGTAAT AATTCTAATT GCTGTCCTTG GCTCTAGCAT GATCCTAGTG AGCATCTTCA 4600
4601 TTATAATCAA GAAAACAAAG AAACCAACGG GAGCACCTCC AGAGCTGAGT GGTGTCACAA ACAATGGCTT CATACCACAC AGTTAGTTAA TTAAAAAATAA 4700
4701 AATAAAATTT GGGACAAATC ATAATGTCTC GCAAGGCTCC ATGCAAATAT GAAGTGCGGG GCAAATGCAA CAGAGGAAGT GAGTGTAAGT TTAACCACAA 4800
4801 TTACTGGAGT TGGCCAGATA GATACTTATT AATAAGATCA AACTATCTAT TAAATCAGCT TTTAAGGAAC ACTGATAGAG CTGATGGCCT ATCAATAATA 4900
4901 TCAGGCGCAG GCAGAGAAGA CAGAACGCAA GATTTTGTTC TAGGTTCCAC CAATGTGGTT CAAGGTTATA TTGATGATAA CCAAAGCATA ACAAAAGCTG 5000
5001 CAGCCTGCTA CAGTCTACAC AACATAATCA AGCAACTACA AGAAGTTGAA GTTAGGCAGG CTAGAGATAG CAAACTATCT GACAGCAAGC ATGTGGCACT 5100
5101 CCATAACTTA ATCTTATCTT ACATGGAGAT GAGCAAAACT CCCGCATCTT TAATCAACAA TCTCAAAAGA CTGCCGAGAG AAAAACTGAA AAAATTAGCA 5200
5201 AAGCTGATAA TTGACTTATC AGCAGGCGCT GACAATGACT CTTCATATGC CCTGCAAGAC AGTGAAAGCA TTAATCAAGT GCAGTGAGCA TGGTCCTGTT 5300
5301 TTCATTACTA TAGAGGTTGA TGAAATGATA TGGACTCAAA AAGAATTAAA AGAAGCTTTG TCCGATGGGA TAGTGAAGTC TCACACCAAC ATTTACAATT 5400
5401 GTTATTTAGA AAACATAGAA ATTATATATG TCAAGGCTTA CTTAAGTTAG TAAAAACACA TCAGAGTGGG ATAAGTGACA ATGATAACAT TAGATGTCAT 5500
5501 TAAAAGTGAT GGGTCTTCAA AAACATGTAC TCACCTCAAA AAAATAATCA AAGACCATTC TGGTAAAGTG CTTATTGCAC TTAAGTTAAT ATTAGCTTTA 5600
5601 CTAACATTTT TCACAATAAC AATCACTATA AATTACATAA AAGTAGAAAA CAATCTACAA ATATGCCAGT CAAAAACTGA ATCAGACAAA GAAGACTCAC 5700
5701 CATCAAATAC CACATCCGTC ACAACCAAGA CCACTCTAGA CCATGATATA ACACAGTATT TTAAAAGATT AATTCAAAGG TATACAGATT CTGTAATAAA 5800
5801 CAAGGACACA TGCTGGAAAA TAAGCAGAAA TCAATGCACA AATATAACAA CATATAAATT TTTATGCTTT AAACCTGAGG ACTCAAAAAT CAACAGTTGT 5900
5901 GATAGACTGA CAGATCTATG CAGAAACAAA TCAAAATCAG CAGCTGAAGC ATATCATACA GTAGAATGCC ATTGCATATA CACAATTGAG TGGAAGTGCT 6000
6001 ATCACCACTC AATAGATTAA ACCCAATCTT GAATGTTAAA ACTAGACTAG GATCCGTCTA AGACTATCAG TTCAATAGTT TAGTTATTTT AAAATATTTG 6100
6101 AGAATAGGTA AGTTTCTATG GCACTTCATA GCAATAGGTA ATAATTAACA GCTTAATTAT AATTAAAACA TTATTTAAAA TCGTAACTAT TTAATTTACA 6200
6201 AAGTAAAAAC AAAAATATGG GACAAGTAGT TATGGAGGTG AAAGTAGAGA ACATTCGAGC AATAGACATG CTCAAAGCAA GAGTGAAAAA TCGTGTGGCA 6300
6301 CGTAGCAAAT GCTTTAAAAA TGCTTCTTTA ATCCTCATAG GAATAACTAC ACTGAGTATA GCTCTCAATA TCTATCTGAT CATAAACTAC ACAATACAAA 6400
6401 AAACCTCATC TGAATCAGAA CACCACACCA GCTCACCACC CACAGAATCC AACAAGGAAG CTTCAACAAT CTCCACAGAC AACCCAGACA TCAATCCAAA 6500
6501 CTCACAGCAT CCAACTCAAC AGTCCACAGA AAACCCCACA CTCAACCCCG CAGCATCAGT GAGCCCATCA GAAACAGAAC CAGCATCAAC ACCAGACACA 6600
6601 ACAAACCGCC TGTCCTCCGT AGACAGGTCC ACAGCACAAC CAAGTGAAAG CAGAACAAAG ACAAAACCGA CAGTCCACAC AAGAAACAAC CCAAGCACAG 6700
6701 CTTCCAGTAC ACAATCCCCA CCACGGGCAA CAACGAAGGC AATCCGCAGA GCCACCACTT TCCGCATGAG CAGCACAGGA AAAAGACCAA CCACAACATC 6800
6801 AGTCCAGTCC GACAGCAGCA CCACAACCCA AAATCATGAA GAAACAGGTT CAGCGAACCC ACAGGCATCT GTAAGCACAA TGCAAAACTA GCACACCAAC 6900
6901 AATATAAAAC CAAATTAGTT AACAAAAAAT ACGAGATAGC TCTAAAGTAA AACATGTAGG TACCAACAAT CAAGAAACCA AAAGACAACT CACAATCTCC 7000
7001 CTAAAACAGC AACGACACCA TGTCAGCTTT GCTCAAATCT CTCTGGGAGA AACTTTTGCC CACATACTAA CAACATCACA ACCATCTCAA GAAAAGAAAC 7100
7101 TGGGCAAAAC AGCATCCAAG AGACAAATAG CAATGGATCC TCTTAATGAA TCCACTGTTA ATGTCTATCT CCCTGATTCG TACCTTAAAG GAGTAATTTC 7200
7201 TTTTAGTGAA ACTAATGCAA TTGGTTCATG TCTCTTAAAA AGACCCTACT TAAAAAATGA CAACACTGCA AAAGTTGCCA TAGAGAATCC TGTTATTGAG 7300
7301 CATGTGAGAC TCAAAAATGC AGTCAATTCT AAAATGAAAA TATCAGATTA CAAGGTAGTA GAGCCAGTAA ACATGCAACA TGAAATAATG AAGAATGTAC 7400
7401 ACAGTTGTGA GCTCACACTA TTGAAACAGT TTTTAACAAG GAGTAAAAAC ATTAGCACTC TCAAATTGAA TATGATATGT GATTGGCTGC AATTAAAGTC 7500
7501 TACATCAGAT GATACCTCAA TCCTAAGTTT CATAGATGTA GAATTTATAC CTAGTTGGGT AAGCAACTGG TTTAGTAATT GGTACAATCT CAATAAGTTA 7600
7601 ATTTTGGAAT TCAGAAGAGA GGAAGTAATA AGAACCGGTT CAATCTTATG CAGGTCATTG GGTAAATTAG TTTTTATTGT ATCATCATAT GGATGTATCG 7700
7701 TCAAGAGCAA CAAAAGCAAA AGAGTGAGCT TCTTCACATA CAATCAACTG TTAACATGGA AAGATGTGAT GTTAAGTAGA TTTAATGCGA ATTTTTGTAT 7800

Fig. 37B

HMPV strain 83 (continued)

```
7801 ATGGGTAAGC AATAGTCTGA ATGAAAATCA GGAAGGGCTA GGGTTGAGAA GTAATCTGCA AGGTATGTTA ACTAATAAAC TATATGAAAC TGTAGATTAT 7900
7901 ATGCTAAGCT TATGTTGCAA TGAAGGTTTC TCACTTGTGA AAGAGTTCGA AGGTTTTATT ATGAGTGAGA TCCTTAGGAT TACTGAACAT GCTCAATTCA 8000
8001 GTACTAGATT TAGAAATACT TTATTGAATG GATTAACAGA TCAATTAACA AAATTAAAAA ATAAAAACAG ACTCAGAGTT CATAGTACCG TATTAGAAAA 8100
8101 TAATGATTAT CCAATGTATG AAGTTGTACT TAAATTATTA GGAGATACTT TGAGATGTAT CAAATTATTA ATCAATAAAA ACTTAGAGAA TGCTGCAGAA 8200
8201 TTATACTATA TATTCAGAAT TTTTGGTCAT CCAATGGTAG ATGAAAGAGA TGCAATGGAT GCTGTCAAAT TAAACAATGA AATCACAAAA ATCCTAAGGT 8300
8301 TGGAGAGCTT GACAGAACTA AGAGGGGCAT TCATATTAAG GATTATCAAA GGATTTGTGG ACAACAACAA AAGGTGGCCC AAAATTAAAA ACTTAAAAGT 8400
8401 GCTTAGCAAA AGATGGACTA TGTACTTCAA AGCTAAAAAT TACCCCAGTC AACTCGAATT AAGTGAACAA GACTTTCTAG AGCTTGCTGC AATACAATTT 8500
8501 GAACAAGAGT TTTCTGTTCC TGAAAAAACC AATCTTGAGA TGGTATTAAA TGACAAAGCC ATATCACCTC CTAAAAGATT AATATGGTCT GTGTATCCAA 8600
8601 AGAATTACTT ACCTGAGACG ATAAAAAATC GATATTTAGA AGAAACTTTC AATGCGAGTG ATAGTCTCAA AACAAGAAGA GTACTAGAGT ACTATTTAAA 8700
8701 AGATAATAAA TTTGATCAAA AGGAACTTAA AAGTTATGTA GTTAGACAAG AATATTTAAA CGATAAGGAG CACATTGTCT CATTAACTGG AAAAGAAAGA 8800
8801 GAATTAAGTG TAGGTAGAAT GTTTGCTATG CAACCAGGAA AACAGCGACA AATACAAATA TTGGCAGAAA AATTGTTAGC TGATAACATT GTACCTTTCT 8900
8901 TCCCGGAAAC CTTAACAAAG TATGGTGATC TAGATCTTCA GAGAATAATG GAAATCAAAT CAGAACTTTC TTCTATCAAA ACCAGAAGAA ATGATAGTTA 9000
9001 TAATAATTAC ATTGCAAGAG CATCCATAGT AACAGATTTG AGCAAGTTCA ACCAAGCCTT TAGATATGAA ACTACAGCGA TCTGTGCGGA TGTAGCAGAC 9100
9101 GAATTACATG GAACACAAAG CTTATTCTGT TGGTTACATC TTATCGTTCC TATGACTACA ATGATATGTG CCTATAGACA TGCACCACCA GAAACAAAAG 9200
9201 GTGAATATGA TATAGATAAG ATAGAAGAGC AAAGTGGTCT ATATAGATAT CACATGGGCG GTATTGAAGG ATGGTGTCAA AAACTCTGGA CAATGGAAGC 9300
9301 TATATCTTTA TTGGATGTTG TATCTGTAAA GACACGGTGT CAAATGACAT CTTTATTAAA CGGTGACAAC CAATCAATAG ATGTAAGTAA ACCAGTCAAG 9400
9401 TTATCTGAAG GTTTAGATGA AGTGAAGGCA GATTATCGCT TAGCAGTAAA AATGCTAAAA GAAATAAGAG ATGCATACAG AAATATAGGC CATAAACTTA 9500
9501 AAGAAGGGGA AACATATATA TCAAGGGATC TTCAGTTTAT AAGCAAGGTG ATTCAATCTG AAGGAGTGAT GCATCCTACC CCTATAAAAA AGGTCTTGAG 9600
9601 AGTAGGACCA TGGATAAACA CAATATTAGA TGACATTAAA ACTAGTGCTG AGTCAATAGG GAGTCTATGT CAAGAATTAG AATTTAGGGG AGAAAGCATA 9700
9701 ATAGTTAGTC TGATATTAAG AAACTTCTGG CTGTATAACT TATACATGCA TGAATCAAAG CAACATCCTT TGGCAGGGAA ACAGTTATTC AAACAACTAA 9800
9801 ATAAAACATT AACATCAGTG CAGAGATTTT TTGAAATTAA AAGGGAAAAT GAGGTAGTAG ATCTATGGAT GAACATACCA ATGCAATTTG GAGGAGGAGA 9900
9901 TCCAGTAGTC TTCTATAGAT CTTTCTATAG AAGGACCCCT GATTTTTTAA CTGAGGCAAT CAGCCATGTA GATATTCTGT TAAAAATATC AGCTAACATA 10000
10001 AAAAATGAAA CGAAAGTAAG TTTCTTCAAA GCCTTACTAT CAATAGAAAA AAATGAACGT GCTACACTGA CAACACTAAT GAGAGATCCT CAAGCTGTTG 10100
10101 GATCAGAACG ACAAGCAAAA GTAACAAGTG ACATCAATAG AACAGCAGTT ACCAGTATCT TAAGTCTTTC CCCAAATCAA CTTTTCAGTG ATAGTGCTAT 10200
10201 ACACTACAGC AGAAATGAAG AAGAAGTGGG AATCATTGCA GAAAACATAA CACCTGTTTA TCCTCATGGG CTGAGAGTAT TATATGAATC ATTGCCCTTT 10300
10301 CACAAAGCTG AAAAAGTTGT AAACATGATA TCAGGGACAA AATCTATAAC CAACTTATTA CAGAGAACAT CCGCTATTAA TGGTGAAGAT ATTGACAGGG 10400
10401 CTGTATCTAT GATGTTGGAG AATCTAGGAT TATTATCTAG AATATTGTCA GTAGTTGTTG ATAGTATAGA AATTCCAATC AAATCTAATG GTAGGCTGAT 10500
10501 ATGTTGTCAA ATCTCTAGGA CTTTAAGAGA GACATCATGG AATAATATGG AAATAGTTGG AGTAACATCT CCTAGCATCA CTACATGTAT GGATGTCATA 10600
10601 TATGCAACTA GTTCTCATTT GAAAGGGATA ATTATAGAAA AGTTCAGCAC TGACAGAACT ACAAGGGGTC AAAGAGGTCC AAAAAGCCCT TGGGTAGGGT 10700
10701 CGAGTACTCA AGAGAAAAAA TTAGTACCTG TTTATAACAG ACAAATTCTC TCAAAACAAC AAAGAGAACA GCTAGAAGCA ATTGGAAAAA TGAGATGGGT 10800
10801 GTATAAAGGG ACACCAGGCT TGCGACGATT ACTCAACAAG ATCTGTCTTG GGAGTTTAGG CATTAGCTAC AAATGTGTAA AACCTTTATT ACCTAGGTTT 10900
10901 ATGAGTGTAA ATTTCTTACA TAGATTATCT GTCAGTAGTA GACCTATGGA ATTCCCAGCA TCAGTTCCAG CTTATAGAAC AACAAATTAC CATTTCGACA 11000
11001 CTAGTCCTAT TAATCAAGCA CTAAGTGAGA GATTTGGGAA TGAAGATATT AACTTGGTCT TCCAAAATGC AATCAGCTGT GGAATTAGCA TAATGAGTGT 11100
11101 AGTAGAACAA TTAACAGGTA GAAGCCCAAA ACAGTTAGTT TTAATACCCC AATTAGAAGA AATAGACATT ATGCCACCAC CAGTGTTTCA AGGGAAATTC 11200
11201 AATTATAAAT TAGTAGATAA GATAACTTCT GATCAACATA TCTTTAGTCC GGACAAAAATA GATATGTTAA CACTAGGGAA AATGCTCATG CCCACTATAA 11300
11301 AAGGTCAGAA AACAGATCAG TTCTTAAATA AGAGAGAAAA TTATTTCCAT GGAAACAATC TTATTGAGTC TTTATCAGCA GCATTAGCAT GTCATTGGTG 11400
11401 TGGGATATTA ACAGAACAAT GCATAGAAAA TAATATTTTC AAGAAAGACT GGGGTGACGG GTTTATATCA GATCATGCTT TTATGGACTT CAAAATATTC 11500
11501 CTATGTGTCT TTAAAACTAA ACTTTTATGT AGTTGGGGAT CTCAAGGGAA AAACATTAAA GATGAAGATA TAGTAGATGA ATCAATAGAT AAATTGTTAA 11600
11601 GGATTGACAA TACTTTTTGG AGAATGTTCA GCAAAGTTAT GTTTGAACCA AAGGTTAAGA AAAGGATAAT GTTATATGAT GTAAAATTCC TATCACTAGT 11700
11701 AGGCTACATA GGGTTTAAGA ACTGGTTTAT AGAGCAGTTG AGATCAGCTG AATTGCATGA AATACCTTGG ATTGTCAATG CCGAAGGTGA TTTGGTTGAG 11800
```

Fig. 37C

HMPV strain 83 (continued)

```
11801 ATCAAGTCAA TTAAAATCTA TTTGCAACTG ATAGAACAAA GCTTATTTTT AAGAATAACT GTTTGAACT ATACAGATAT GGCACATGCT CTCACAC

Fig. 38A

Fig. 38B rHMPV-GFP (continued)

```
7801  CTTTTGCCCA CATACTAACA ACATCACAAC CATCTCAAGA AAAGAAACTG  GGCAAAACAG CATCCAAGAG ACAAATAGCA ATGGATCCTC TTAATGAATC 7900
7901  CACTGTTAAT GTCTATCTCC CTGATTCGTA CCTTAAAGGA GTAATTTCTT  TTAGTGAAAC TAATGCAATT GGTTCATGTC TCTTAAAAAG ACCCTACTTA 8000
8001  AAAAATGACA ACACTGCAAA AGTTGCCATA GAGAATCCTG TTATTGAGCA  TGTGAGACTC AAAAATGCAG TCAATTCTAA AATGAAAATA TCAGATTACA 8100
8101  AGGTAGTAGA GCCAGTAAAC ATGCAACATG AAATAATGAA GAATGTACAC  AGTTGTGAGC TCACACTATT GAAACAGTTT TTAACAAGGA GTAAAAACAT 8200
8201  TAGCACTCTC AAATTGAATA TGATATGTGA TTGGCTGCAA TTAAAGTCTA  CATCAGATGA TACCTCAATC CTAAGTTTCA TAGATGTAGA ATTTATACCT 8300
8301  AGTTGGGTAA GCAACTGGTT TAGTAATTGG TACAATCTCA ATAAGTTAAT  TTTGGAATTC AGAAGAGAGG AAGTAATAAG AACCGGTTCA ATCTTATGCA 8400
8401  GGTCATTGGG TAAATTAGTT TTTATTGTAT CATCATATGG ATGTATCGTC  AAGAGCAACA AAAGCAAAAG AGTGAGCTTC TTCACATACA ATCAACTGTT 8500
8501  AACATGGAAA GATGTGATGT TAAGTAGATT TAATGCGAAT TTTTGTATAT  GGGTAAGCAA TAGTCTGAAT GAAAATCAGG AAGGGCTAGG GTTGAGAAGT 8600
8601  AATCTGCAAG GTATGTTAAC TAATAAACTA TATGAAACTG TAGATTATAT  GCTAAGCTTA TGTTGCAATG AAGGTTTCTC ACTTGTGAAA GAGTTCGAAG 8700
8701  GTTTTATTAT GAGTGAGATC CTTAGGATTA CTGAACATGC TCAATTCAGT  ACTAGATTTA GAAATACTTT ATTGAATGGA TTAACAGATC AATTAACAAA 8800
8801  ATTAAAAAAT AAAAACAGAC TCAGAGTTCA TAGTACCGTA TTAGAAAATA  ATGATTATCC AATGTATGAA GTTGTACTTA AATTATTAGG AGATACTTTG 8900
8901  AGATGTATCA AATTATTAAT CAATAAAAAC TTAGAGAATG CTGCAGAATT  ATACTATATA TTCAGAATTT TTGGTCATCC AATGGTAGAT GAAAGAGATG 9000
9001  CAATGGATGC TGTCAAATTA AACAATGAAA TCACAAAAAT CCTAAGGTTG  GAGAGCTTGA CAGAACTAAG AGGGGCATTC ATATTAAGGA TTATCAAAGG 9100
9101  ATTTGTGGAC AACAACAAAA GGTGGCCCAA AATTAAAAAC TTAAAAGTGC  TTAGCAAAAG ATGGACTATG TACTTCAAAG CTAAAAATTA CCCCAGTCAA 9200
9201  CTCGAATTAA GTGAACAAGA CTTTCTAGAG CTTGCTGCAA TACAATTTGA  ACAAGAGTTT TCTGTTCCTG AAAAAACCAA TCTTGAGATG GTATTAAATG 9300
9301  ACAAAGCCAT ATCACCTCCT AAAAGATTAA TATGGTCTGT GTATCCAAAG  AATTACTTAC CTGAGACGAT AAAAAATCGA TATTTAGAAG AAACTTTCAA 9400
9401  TGCGAGTGAT AGTCTCAAAA CAAGAAGAGT ACTAGAGTAC TATTTAAAAG  ATAATAAATT TGATCAAAAG GAACTTAAAA GTTATGTAGT TAGACAAGAA 9500
9501  TATTTAAACG ATAAGGAGCA CATTGTCTCA TTAACTGGAA AAGAAAGAGA  ATTAAGTGTA GGTAGAATGT TTGCTATGCA ACCAGGAAAA CAGCGACAAA 9600
9601  TACAAATATT GGCAGAAAAA TTGTTAGCTG ATAACATTGT ACCTTTCTTC  CCGGAAACCT TAACAAAGTA TGGTGATCTA GATCTTCAGA GAATAATGGA 9700
9701  AATCAAATCA GAACTTTCTT CTATCAAAAC CAGAAGAAAT GATAGTTATA  ATAATTACAT TGCAAGAGCA TCCATAGTAA CAGATTTGAG CAAGTTCAAC 9800
9801  CAAGCCTTTA GATATGAAAC TACAGCGATC TGTGCGGATG TAGCAGACGA  ATTACATGGA ACACAAAGCT TATTCTGTTG GTTACATCTT ATCGTTCCTA 9900
9901  TGACTACAAT GATATGTGCC TATAGACATG CACCACCAGA AACAAAAGGT  GAATATGATA TAGATAAGAT AGAAGAGCAA AGTGGTCTAT ATAGATATCA 10000
10001 CATGGGCGGT ATTGAAGGAT GGTGTCAAAA ACTCTGGACA ATGGAAGCTA  TATCTTTATT GGATGTTGTA TCTGTAAAGA CACGGTGTCA AATGACATCT 10100
10101 TTATTAAACG GTGACAACCA ATCAATAGAT GTAAGTAAAC CAGTCAAGTT  ATCTGAAGGT TTAGATGAAG TGAAGGCAGA TTATCGCTTA GCAGTAAAAA 10200
10201 TGCTAAAAGA AATAAGAGAT GCATACAGAA ATATAGGCCA TAAACTTAAA  GAAGGGGAAA CATATATATC AAGGGATCTT CAGTTTATAA GCAAGGTGAT 10300
10301 TCAATCTGAA GGAGTGATGC ATCCTACCCC TATAAAAAAG GTCTTGAGAG  TAGGACCATG GATAAACACA ATATTAGATG ACATTAAAAC TAGTGCTGAG 10400
10401 TCAATAGGGA GTCTATGTCA AGAATTAGAA TTTAGGGGAG AAAGCATAAT  AGTTAGTCTG ATATTAAGAA ACTTCTGGCT GTATAACTTA TACATGCATG 10500
10501 AATCAAAGCA ACATCCTTTG GCAGGGAAAC AGTTATTCAA ACAACTAAAT  AAAACATTAA CATCAGTGCA GAGATTTTTT GAAATTAAAA GGGAAAATGA 10600
10601 GGTAGTAGAT CTATGGATGA ACATACCAAT GCAATTTGGA GGAGGAGATC  CAGTAGTCTT CTATAGATCT TTCTATAGAA GGACCCCTGA TTTTTTAACT 10700
10701 GAGGCAATCA GCCATGTAGA TATTCTGTTA AAAATATCAG CTAACATAAA  AAATGAAACG AAAGTAAGTT TCTTCAAAGC CTTACTATCA ATAGAAAAAA 10800
10801 ATGAACGTGC TACACTGACA ACACTAATGA GAGATCCTCA AGCTGTTGGA  TCAGAACGAC AAGCAAAAGT AACAAGTGAC ATCAATAGAA CAGCAGTTAC 10900
10901 CAGTATCTTA AGTCTTTCCC CAAATCAACT TTTCAGTGAT AGTGCTATAC  ACTACAGCAG AAATGAAGAA GAAGTGGGAA TCATTGCAGA AAACATAACA 11000
11001 CCTGTTTATC CTCATGGGCT GAGAGTATTA TATGAATCAT TGCCCTTTCA  CAAAGCTGAA AAAGTTGTAA ACATGATATC AGGGACAAAA TCTATAACCA 11100
11101 ACTTATTACA GAGAACATCC GCTATTAATG GTGAAGATAT TGACAGGGCT  GTATCTATGA TGTTGGAGAA TCTAGGATTA TTATCTAGAA TATTGTCAGT 11200
11201 AGTTGTTGAT AGTATAGAAA TTCCAATCAA ATCTAATGGT AGGCTGATAT  GTTGTCAAAT CTCTAGGACT TTAAGAGAGA CATCATGGAA TAATATGGAA 11300
11301 ATAGTTGGAG TAACATCTCC TAGCATCACT ACATGTATGG ATGTCATATA  TGCAACTAGT TCTCATTTGA AAGGGATAAT TATAGAAAAG TTCAGCACTG 11400
11401 ACAGAACTAC AAGGGGTCAA AGAGGTCCAA AAAGCCCTTG GGTAGGGTCG  AGTACTCAAG AGAAAAAATT AGTACCTGTT TATAACAGAC AAATTCTCTC 11500
11501 AAAACAACAA AGAGAACAGC TAGAAGCAAT TGGAAAAATG AGATGGGTGT  ATAAAGGGAC ACCAGGCTTG CGACGATTAC TCAACAAGAT CTGTCTTGGG 11600
11601 AGTTTAGGCA TTAGCTACAA ATGTGTAAAA CCTTTATTAC CTAGGTTTAT  GAGTGTAAAT TTCTTACATA GATTATCTGT CAGTAGTAGA CCTATGGAAT 11700
11701 TCCCAGCATC AGTTCCAGCT TATAGAACAA CAAATTACCA TTTCGACACT  AGTCCTATTA ATCAAGCACT AAGTGAGAGA TTTGGGAATG AAGATATTAA 11800
```

Fig. 38C rHMPV-GFP (continued)

```
11801 CTTGGTCTTC CAAAATGCAA TCAGCTGTGG AATTAGCATA ATGAGTGTAG TAGAACAATT AACAGGTAGA AGCCCAAAAC AGTTAGTTTT AATACCCCAA 11900
11901 TTAGAAGAAA TAGACATTAT GCCACCACCA GTGTTTCAAG GGAAATTCAA TTATAAATTA GTAGATAAGA TAACTTCTGA TCAACATATC TTTAGTCCGG 12000
12001 ACAAAATAGA TATGTTAACA CTAGGGAAAA TGCTCATGCC CACTATAAAA GGTCAGAAAA CAGATCAGTT CTTAAATAAG AGAGAAAATT ATTTCCATGG 12100
12101 AAACAATCTT ATTGAGTCTT TATCAGCAGC ATTAGCATGT CATTGGTGTG GGATATTAAC AGAACAATGC ATAGAAAATA ATATTTTCAA GAAAGACTGG 12200
12201 GGTGACGGGT TTATATCAGA TCATGCTTTT ATGGACTTCA AAATATTCCT ATGTGTCTTT AAAACTAAAC TTTTATGTAG TTGGGGATCT CAAGGGAAAA 12300
12301 ACATTAAAGA TGAAGATATA GTAGATGAAT CAATAGATAA ATTGTTAAGG ATTGACAATA CTTTTTGGAG AATGTTCAGC AAAGTTATGT TTGAACCAAA 12400
12401 GGTTAAGAAA AGGATAATGT TATATGATGT AAAATTCCTA TCACTAGTAG GCTACATAGG GTTTAAGAAC TGGTTTATAG AGCAGTTGAG ATCAGCTGAA 12500
12501 TTGCATGAAA TACCTTGGAT TGTCAATGCC GAAGGTGATT TGGTTGAGAT CAAGTCAATT AAAATCTATT TGCAACTGAT AGAACAAAGC TTATTTTTAA 12600
12601 GAATAACTGT TTTGAACTAT ACAGATATGG CACATGCTCT CACACGATTA ATCAGAAAGA AGTTAATGTG TGATAATGCA CTGTTAACCC CAATTTCATC 12700
12701 CCCAATGGTT AACTTAACTC AAGTTATTGA TCCCACAACA CAATTAGATT ACTTCCCCAA GATAACATTC GAAAGGCTAA AAAATTATGA CACAAGTTCA 12800
12801 AATTATGCTA AAGGGAAGCT AACAAGAAAT TACATGATAC TATTGCCATG GCAGCATGTT AATAGATATA ACTTTGTCTT TAGTTCTACT GGATGTAAAG 12900
12901 TTAGTCTGAA AACATGTATT GGAAAACTTA TGAAAGACCT AAATCCTAAA GTTTTGTACT TTATTGGAGA AGGAGCAGGA AATTGGATGG CCAGAACAGC 13000
13001 ATGTGAATAT CCTGATATTA AATTTGTATA TAGAAGTCTG AAAGATGACC TTGATCATCA TTATCCTCTG GAATACCAGA GAGTGATAGG TGAATTAAGC 13100
13101 AGAATCATAG ATAGTGGTGA AGGACTTTCA ATGGAAACAA CAGACGCAAC TCAAAAAACT CATTGGGATT TGATACACAG GGTAAGCAAA GATGCTTTAT 13200
13201 TAATAACTTT ATGTGATGCA GAATTTAAGG ACAGAGATGA TTTTTTTAAG ATGGTAATTC TATGGAGAAA ACATGTATTA TCATGCAGAA TTTGCACTAC 13300
13301 TTATGGGACG GACCTCTATT TATTCGCAAA GTATCATGCT AAAGACTGCA ATGTAAAATT ACCTTTTTTT GTGAGATCAG TTGCTACTTT CATTATGCAG 13400
13401 GGTAGTAAGC TGTCAGGTTC AGAATGCTAC ATACTCTTAA CACTAGGCCA CCACAACAGT TTACCTTGCC ATGGAGAAAT ACAAAATTCT AAGATGAAAA 13500
13501 TAGCAGTGTG TAATGATTTT TATGCTGCAA AAAAACTCGA CAATAAATCA ATTGAAGCTA ATTGTAAATC ACTTTTGTCA GGGCTAAGAA TACCTATAAA 13600
13601 TAAGAAGGAA CTAGATAGAC AGAGAAGATT ATTAACACTA CAAAGCAATC ATTCTTCTGT AGCAACAGTT GGCGGTAGCA AGATCATAGA GTCTAAGTGG 13700
13701 TTAACAAACA AAGCAAGTAC AATAATTGAT TGGTTAGAAC ATATTTTAAA TTCTCCAAAG GGCGAATTAA ATTATGATTT TTTTGAAGCA TTGGAGAACA 13800
13801 CTTACCCTAA TATGATTAAA CTAATAGATA ACTTAGGGAA TGCAGAGATT AAAAAACTGA TCAAAGTAAC AGGATACATG CTTGTAAGTA AAAAATGAAA 13900
13901 AATGATGAAG ATGACAAAAT AGATGACAAC TTCATACTAT TCTAAATTAA TTATTTGATT ATGCAATTAT ATGATAGTTA ATTAAAATTA AAAATTAAAA 14000
14001 ATCAAAAGTT AAAATTTAAA ACCTATCATT AAGTTTATTA AAAATAAGAA ATTATAATTG AATGTATACG GTTTTTTTGC CGT 14083
         |    10    |    20    |    30    |    40    |    50     |    60    |    70    |    80    |    90    |    100
```

Fig. 38D

HMPV strain 75

```
           |  10       |  20       |  30       |  40       |  50        |  60       |  70       |  80       |  90       |  100
   1 ACGCGAAAAA AACGCGTATA AATTAAATTC CAAACAAAAC GGGACAAATA  AAAATGTCTC TTCAAGGGAT TCACCTAAGT GATCTGTCAT ATAAACATGC 100
 101 TATATTAAAA GAGTCTCAAT ACACAATAAA AAGAGATGTA GGCACCACAA  CTGCAGTGAC ACCTTCATCA TTGCAGCAAG AGATAACACT TTTGTGTGGA 200
 201 GAGATTCTTT ACACTAAACA TACTGATTAC AAATATGCTG CAGAGATAGG  GATACAATAT ATTTGCACGG CTCTAGGATC AGAAAGAGTA CAACAGATTT 300
 301 TAAGAAATTC AGGCAGTGAA GTTCAGGTGG TTCTAACCAA GACATACTCT  TTAGGGAAAG GTAAAAATAG TAAAGGGGAA GAGTTGCAAA TGTTAGATAT 400
 401 ACATGGAGTG GAAAAGAGTT GGGTAGAAGA AATAGACAAA GAGGCAAGAA  AAACAATGGT GACTTTGCTA AAGGAATCAT CAGGTAACAT CCCACAAAAC 500
 501 CAGAGGCCTT CAGCACCAGA CACACCAATA ATTTTATTAT GTGTAGGTGC  TTTAATATTC ACTAAACTAG CATCAACAAT AGAAGTTGGA CTAGAGACTA 600
 601 CAGTTAGAAG AGCTAACAGA GTGCTAAGTG ATGCGCTCAA AAGATACCCT  AGGGTAGATA TACCGAAGAT TGCTAGATCT TTCTATGAAC TATTTGAGCA 700
 701 GAAAGTGTAT TACAGGAGTC TATTCATTGA GTATGGGAAA GCTTTAGGCT  CATCTTCAAC AGGAAGCAAA GCAGAAAGTT TGTTTGTAAA TATATTTATG 800
 801 CAAGCTTATG GAGCCGGTCA AACAATGCTA AGGTGGGGTG TCATTGCCAG  ATCATCTAAC AACATAATGC TAGGACATGT GTCTGTGCAA GCTGAATTGA 900
 901 AGCAAGTTAC AGAGGTTTAT GATTTGGTGA GAGAAATGGG TCCTGAATCT  GGGCTTTTAC ATCTAAGACA AAGTCCAAAG GCAGGACTGT TATCGTTGGC 1000
1001 CAATTGCCCC GATTTTGCTA GTGTTGTTCT TGGTAATGCT TCAGGTCTAG  GTATAATCGG AATGTACAGA GGAAGAGTGC CAAACACAGA GCTATTTTCT 1100
1101 GCAGCAGAAA GTTATGCCAG AAGCTTAAAA GAAAGCAACA AAATCAACTT  CTCCTCATTA GGGCTCACAG ACGAAGAAAA AGAAGCTGCA GAACACTTCT 1200
1201 TAAACATGAG TGATGACAAT CAAGATGATT ATGAGTAATT AAAAAACTGG  GACAAGTCAA AATGTCATTC CCTGAAGGAA AAGATATCCT GTTCATGGGT 1300
1301 AATGAAGCAG CAAAAATAGC AGAAGCTTTC CAGAAATCAC TAAAAAGATC  AGGTCACAAA AGAACCCAGT CTATTGTAGG GGAAAAAGTA AACACTATAT 1400
1401 CAGAAACTCT AGAGCTACCT ACCATCAGCA AACCTGCACG ATCATCTACA  CTGCTAGAGC CAAAATTGGC ATGGGCAGAC AGCAGCAGAG CCACCAAAAC 1500
1501 CACAGAAAAA CAAACAACCA AAACAACAGA TCCTGTTGAA GAAGAGGAAC  TCAATGAAAA GAAGATATCA CCTTCCAGTG ATGGGAAGAC TCCCGCAGAG 1600
1601 AAAAAATCAA AATCTCCAAC CAATGTAAAA AAGAAAGTTT CCTTCACATC  AAATGAACCA GGGAAATATA CCAAACTAGA AAAAGATGCC CTAGATTTGC 1700
1701 TCTCAGACAA TGAGGAAGAA GACGCAGAGT CCTCAATCTT AACCTTTGAA  GAGAGAGACA CATCATCACT AAGCATTGAG GCTAGACTAG AATCAATAGA 1800
1801 AGAGAAGCTA AGCATGATAT TAGGACTGCT TCGTACACTT AACATTGCAA  CAGCAGGACC AACGGCTGCA AGAGATGGAA TCAGAGATGC AATGATTGGT 1900
1901 ATAAGAGAAG AACTAATAGC AGAAATAATA AAAGAAGCAA AGGGAAAAGC  AGCTGAAATG ATGGAAGAGG AAATGAATCA AAGGTCAAAA ATAGGTAATG 2000
2001 GCAGTGTAAA ACTAACCGAG AAGGCAAAAG AACTTAATAA AATTGTTGAA  GACGAGAGCA CAAGCGGTGA ATCAGAAGAA GAAGAAGAAC CAAAAGAAAC 2100
2101 TCAGGATAAC AATCAAGGAG AAGATATTTA CCAGTTAATC ATGTAGTTTA  ATAAAAATAA ACAATGGGAC AAGTCAAGAT GGAGTCCTAT CTAGTGGACA 2200
2201 CTTATCAAGG CATTCCCTAC ACAGCTGCTG TTCAAGTTGA TCTGGTAGAA  AAAGACTTAC TACCAGCAAG TTTGACAATA TGGTTTCCTC TATTCCAAGC 2300
2301 CAACACACCA CCAGCGGTTT TGCTCGATCA GCTAAAGACC TTGACAATAA  CAACTCTGTA TGCTGCATCA CAGAATGGTC CAATACTCAA GGTAAATGCA 2400
2401 TCAGCTCAGG GTGCTGCTAT GTCTGTACTT CCCAAAAAAT TCGAAGTAAA  TGCAACTGTG GCACTTGATG AATACAGCAA ACTTGACTTT GACAAGTTAA 2500
2501 CGGTTTGCGA TGTTAAAACA GTTTATTTGA CAACCATGAA ACCATATGGG  ATGGTGTCAA AATTTGTGAG TTCAGCCAAA TCAGTTGGCA ACAAGACACA 2600
2601 TGATCTAATT GCACTGTGTG ACTTCATGGA CCTAGAGAAA AATATACCTG  TGACAATACC AGCATTCATA AAGTCAGTTT CAATCAAAGA GAGTGAGTCA 2700
2701 GCCACTGTTG AAGCTGCAAT AAGCAGTGAG GCCGACCAAG CATTAACACA  AGCCAAAATT GCACCCTATG CAGGACTAAT CATGATCATG ACCATGAACA 2800
2801 ATCCAAAAGG TATATTCAAG AAACTAGGAG CTGGAACACA AGTGATAGTA  GAGCTAGGGG CATATGTTCA AGCCGAGAGC ATCAGCAGGA TCTGCAAGAG 2900
2901 CTGGAGTCAC CAAGGAACAA GATATGTACT AAAATCCAGA TAAAAATAAC  TGTCCTAATC AATAATTGCT TATATAATCT TAAAGATCAA TGAGCTTATT 3000
3001 ATTATAGTTA TATAAAAAAA TTTAGAACTA GGAAGGTATT AATAGAAAGC  GGGACAAGTA AAAATGTCTT GGAAAGTGAT GATTATCATT TCGTTACTCA 3100
3101 TAACACCTCA GCACGGACTA AAGGAAAGTT ATTTAGAAGA ATCATGTAGT  ACTATAACTG AAGGATATCT CAGTGTTTTA AGAACAGGTT GGTACACCAA 3200
3201 TGTCTTTACA TTAGAAGTTG GTGATGTTGA AAATCTTACA TGTACTGATG  GACCTAGCTT AATCAAAACA GAACTTGACC TAACCAAAAG TGCTCTAAGA 3300
3301 GAACTCAAAA CAGTTTCTGC TGATCAGTTA GCGAGAGAAG AACAAATTGA  AAATCCCAGA CAATCAAGGT TTGTCCTAGG TGCAATAGCT CTTGGTGTTG 3400
3401 CCACAGCAGC AGCAGTCACA GCAGGCATTG CGATAGCCAA AACCATAAGG  CTTGAGAGTG AAGTGAATGC AATCAAAGGT GCTCTCAAAA CAACCAATGA 3500
3501 GGCAGTATCC ACACTAGGAA ATGGAGTGCG AGTCCTAGCC ACCGCAGTAA  GAGAGCTGAA AGAATTTGTG AGCAAAAACC TGACTAGTGC AATTAACAAG 3600
3601 AACAAATGTG ACATTGCTGA TCTGAAGATG GCTGTCAGCT TCAGTCAATT  CAACAGAAGA TTCCTAAATG TTGTGCGGCA GTTTTCAGAC AATGCAGGGA 3700
3701 TAACACCAGC AATATCATTG GACCTAATGA CTGATGCTGA GCTGGCCAGA  GCTGTATCAT ACATGCCAAC ATCTGCAGGA CAGATAAAAC TAATGTTAGA 3800
```

Fig. 39A

HMPV strain 75 (continued)

```
3801 GAACCGTGCA ATGGTGAGGA GAAAAGGATT TGGAATCTTG ATAGGGGTCT  ACGGAAGCTC CGTGATTTAC ATGGTCCAGC TGCCGATCTT TGGTGTCATA 3900
3901 GATACACCTT GTTGGATAAT CAAGGCAGCT CCCTCTTGTT CAGAAAAAGA  TGGAAACTAT GCTTGCCTCC TAAGAGAGGA TCAAGGGTGG TATTGTAAAA 4000
4001 ATGCAGGATC CACTGTTTAC TACCCAAATA AAAAAGACTG CGAAACAAGA  GGTGATCATG TTTTTTGTGA CACAGCTGCA GGGATCAATG TTGCTGAGCA 4100
4101 ATCAAGAGAA TGCAACATCA ACATATCTAC AACCAACTAC CCATGCAAAG  TCAGCACAGG AAGACACCCT ATCAGCATGG TTGCACTATC ACCTCTCGGT 4200
4201 GCTTTGGTGG CTTGCTACAA AGGGGTTAGC TGTTCAATTG GCAGTAATCG  GGTTGGAATA ATCAAACAAC TACCTAAAGG CTGCTCATAC ATAACTAACC 4300
4301 AGGACGCAGA CACTGTAACA ATTGACAACA CTGTGTATCA ACTAAGCAAA  GTTGAGGGTG AACAGCATGT AATAAAAGGG AGACCAGTTT CAAGCAGTTT 4400
4401 CGATCCAATC AAGTTTCCTG AGGATCAGTT CAATGTTGCG CTTGATCAAG  TCTTTGAAAG CATTGAAAAC AGTCAAGCAC TAGTGGACCA GTCAAACAAA 4500
4501 ATTCTGAACA GTGCAGAAAA AGGAAACACT GGCTTCATTA TTGTAATAAT  TTTGATTGCT GTTCTTGGGT TAACCATGAT TTCAGTGAGC ATCATCATCA 4600
4601 TAATCAAAAA AACAAGGAAA CCCACAGGGG CACCTCCAGA GCTGAATGGT  GTTACCAACG GCGGTTTTAT ACCGCATAGT TAGTTAATTA AAAAATGGGA 4700
4701 CAAATCATCA TGTCTCGTAA AGCTCCATGC AAATATGAAG TACGGGGCAA  GTGCAACAGG GGAAGTGAGT GCAAATTCAA CCACAATTAC TGGAGTTGGC 4800
4801 CTGATAGGTA TTTATTGTTA AGATCAAATT ATCTCTTGAA TCAGCTTTTA  AGAAACACTG ATAAGGCTGA TGGTTTGTCA ATAATATCAG GAGCAGGTAG 4900
4901 AGAAGACAGG ACTCAAGACT TTGTTCTTGG TTCTACTAAT GTGGTTCAAG  GGTACATTGA TGACAATCAA GGAATAACAA AGGCTGCAGC TTGCTATAGT 5000
5001 CTACATAACA TAATAAAACA GCTACAAGAA ATAGAAGTAA GACAGGCCAG  AGATAATAAG CTTTCTGACA GCAAACATGT GGCACTTCAC AACTTGATAT 5100
5101 TATCCTATAT GGAGATGAGC AAAACTCCTG CATCCCTGAT TAATAACCTA  AAGAAACTAC CAAGAGAAAA ACTGAAAAAA TTAGCGAAAT TAATAATTGA 5200
5201 TTTATCAGCA GGAACTGATA ATGACTCTTC ATATGCCTTG CAAGACAGTG  AAAGCACTAA TCAAGTGCAG TAAGCATGGT CCCAAATTCA TCACCATAGA 5300
5301 GGCAGATGAT ATGATATGGA CACACAAAGA ATTAAAAGAG ACACTGTCTG  ATGGGATAGC AAAATCACAC ACCAATATTT ACAGTTGTTA TTTAGAAAAT 5400
5401 ATAGAAATAA TATATGTTAA AGCTTACTTA AGTTAGTAAA AAATAAATAG  AATGGGATAA ATGACAATGA AAACATTAGA TGTCATAAAA AGTGACGGAT 5500
5501 CCTCAGAAAC ATGTAATCAA CTCAAAAAAA TAATAAAAAA ACACTCAGGT  AAATTGCTTA TTGCATCAAA ACCGACATTG GCCTTATTGA CGTCCTTCAC 5600
5601 AGTAACAATT ACTGTCAACT ATACAAAAGT AGAAAATAAT TTGCAGGCAT  GTCAATTAAA AAATGAATCA GACAAAAAGG ACACAAAGCT AAATACCACA 5700
5701 TCAACAACAA TCAGACCCAT TCCTGATCTA AATGCAGTAC AGTACCTGAA  AAGGCTGATT CAGAAACACA CCAACTCTGT CACAAAAGAC AGAGATACCT 5800
5801 GTTGGAGAAT ACACACGAAT CAATGCACAA ATATAAAAAT ATATAAGTTC  TTATGTTTTG GGTCTATGAA TTCAACAAAT ACAGACTGTG AAGAACCAAC 5900
5901 AGTTCTATGC GACAAAAAGT CAAAAACCAT GACAGAAAAA CATAGGAAAG  CAGAGTGTCA CCGTCCACAT ACAACCGAGT GGTGGTGCCA TTATCTTTAA 6000
6001 GAGAAAACTC AGTTTTCAAC ATTAAAATCA GAACAAATCA TATCTAGATC  TATTAATATA ATAGTCTAGT TATTTAAAAA CTCTAAATAT TGTCTAGACT 6100
6101 TCACAACACC CTGCGGTCAT ATGCAATAAT CAATGGTCAA ACCACTGTTG  CAAACCCACC TATAATACAA TCACTGAGTA ATACAAAACA AGAAAATGGG 6200
6201 ACAAGTGGCC ATGGAAGCAA GAGTGGAGAA CATTCGGGCA ATAGACATGT  TCAAAGCAAA GATGAAAAAC CGTATAAGAA GTAGCAAGTG CCATAGAAAT 6300
6301 GCTACACTGA TCCTTATTGG ATCAACAGCA CCAAGTATGG CACTCAACAC  CCTTTTAATC ATTGATCATG CAACATCAAA AAACATGACC AAAGTGGAAC 6400
6401 ACTGTGTCAA CATGCCGCCG GTAGAACCAA GCAAGAAGAC CCCAATGACC  TCTGCAGCAG ACCCAAACAC CAAACCCAAT CCACAGCAGG CAACACAGCT 6500
6501 GACCACAGAG GATTCAACAT CTCTAGCAGC AACCCTAGAG GACCATCTAC  ACACAGGGAC AACTCCAACA CCAGATGCAA CAGTCTCCCA GCAAACCACA 6600
6601 GACGAGCACA CAACACTGCT GAGATCAACC AACAGACAGA CCACCCAAAC  AACCGCAGAG AAAAAGCCAA CCAGAGCAAC AACCAAAAAA GAAACCACAA 6700
6701 CTCGAACCAC AAGCACAGCT GCAACCCAAA CACTCAACAC CACCAACCAA  ACTAGCAATG GAAGAGAGGC AACCACAACA TCTGCCAGAT CCAGAAACAA 6800
6801 TGCCACAACT CAAAGCAGCG ATCAAACAAC CCAGGCAGCA GACCCAAGCT  CCCAATCACA ACATACACAG AAAAGCACAA CAACAACACA CAACACAGAC 6900
6901 ACATCTTCTC CAAGTAGTTA ACAAAAAAAC TATAAAATAA CCATGAAAAC  CAAAAAACTA GAAAAGTTAA TTTGAACTCA GAAAAGAACA CAAACACTAT 7000
7001 ATGAATTGTT TGAGCGTATA TACTAATGAA ATAGCATCTG TTTGTGCATC  AATAATACCA TCATTATTTA AGAAATAAGA AGAAGCTAAA ATTCAAGGGA 7100
7101 CAAATAACAA TGGATCCGTT TTGTGAATCC ACTGTCAATG TCTATCTTCC  TGATTCATAT CTCAAAGGAG TAATATCTTT CAGTGAAACC AATGCAATTG 7200
7201 GCTCATGCCT TTTGAAAAGA CCCTATCTTA AAAAAGATAA CACTGCTAAA  GTTGCTGTAG AAAACCCTGT TGTTGAACAT GTCAGACTTA GAAATGCAGT 7300
7301 CATGACCAAA ATGAAGATAT CAGATTATAA AGTGGTTGAA CCAATTAATA  TGCAGCATGA AATAATGAAA AATATACACA GTTGTGAGCT CACATTATTA 7400
7401 AAACAATTCT TAACAAGAAG TAAAAACATT AGCTCCCTAA AATTAAGTAT  GATATGTGAT TGGTTACAGT TAAAATCCAC CTCAGATAAC ACATCAATTC 7500
7501 TTAATTTTAT AGATGTGGAG TTTATACCCG TTTGGGTGAG CAATTGGTTT  AGTAACTGGT ATAATCTCAA TAAATTAATC TTAGAGTTTA GAAGAGAGGA 7600
7601 AGTAATAAGA ACTGGTTCAA TTTTATGCAG ATCACTAGGC AAGTTAGTTT  TCATTGTATC ATCTTATGGG TGTGTAGTAA AAAGCAACAA AAGTAAAAGA 7700
7701 GTAAGTTTTT TCACATATAA CCAACTGTTA ACATGGAAAG ATGTGATGTT  AAGTAGGTTC AATGCAAACT TTTGTATATG GGTAAGTAAC AACCTGAACA 7800
```

Fig. 39B

HMPV strain 75 (continued)

```
 7801 AAAATCAAGA AGGACTAGGA TTTAGAAGTA ATCTACAAGG TATGTTAACT AATAAATTAT ATGAAACTGT TGATTATATG TTAAGTCTAT GTAGCAATGA 7900
 7901 AGGGTTCTCA CTAGTGAAAG AGTTCGAAGG CTTTATTATG AGTGAAATTC TTAAAATTAC TGAGCATGCT CAATTCAGTA CTAGGTTTAG GAATACTTTA 8000
 8001 TTAAATGGGT TGACTGAACA ATTATCAATG TTGAAAGCTA AAAACAGATC TAGAGTTCTT GGCACTATAT TAGAAAACAA TGATTACCCC ATGTATGAAG 8100
 8101 TAGTACTTAA ATTATTAGGG GACACTTTGA AAAGTATAAA ATTATTAATT AACAAGAATT TAGAAAATGC TGCAGAATTA TATTATATAT TCAGAATTTT 8200
 8201 TGGACACCCT ATGGTAGATG AGAGGGAAGC AATGGATGCT GTTAAATTAA ATAATGAGAT TACAAAAATT CTTAAACTGG AGAGCTTAAC AGAACTAAGA 8300
 8301 GGAGCATTTA TACTAAGAAT TATAAAAGGG TTTGTAGATA ATAATAAAAG ATGGCCTAAA ATTAAGAATT TAAAAGTGCT CAGTAAAAGA TGGGTTATGT 8400
 8401 ATTTCAAAGC TAAAAGTTAC CCTAGCCAAC TTGAGCTAAG TGTACAAGAT TTTTTAGAAC TTGCTGCAGT ACAATTCGAA CAGGAATTTT CTGTCCCTGA 8500
 8501 AAAAACCAAT CTTGAGATGG TATTAAATGA TAAAGCAATA TCTCCACCAA AAAAGTTAAT ATGGTCGGTA TATCCAAAAA ATTATCTACC TGAAATTATA 8600
 8601 AAAAATCAAT ATTTAGAAGA GGTCTTCAAT GCAAGTGACA GTCAAAGAAC GAGGAGAGTC TTAGAATTTT ACTTAAAAGA TTGCAAATTT GATCAAAAAG 8700
 8701 ACCTCAAACG TTATGTAACT AAACAAGAGT ATCTAAATGA CAAAGACCAC ATTGTCTCAT TAACTGGGAA AGAAAGAGAA TTAAGTGTAG GCAGGATGTT 8800
 8801 TGCAATGCAA CCTGGCAAAC AAAGACAAAT ACAGATACTA GCCGAGAAAC TTTTAGCTGA TAATATTGTA CCCTTTTTCC CAGAAACTTT AACAAAGTAT 8900
 8901 GGTGACTTGG ATCTCCAAAG AATTATGGAA ATGAAATCAG AACTTTCTTC CATTAAAACT AGGAAGAATG ATAGTTACAA CAATTATATT GCAAGAGCCT 9000
 9001 CCATAGTAAC AGACCTAAGT AAATTCAATC AAGCCTTTAG ATATGAAACC ACAGCTATCT GCGCAGACGT AGCAGATGAG TTACATGGCA CGCAAAGCTT 9100
 9101 ATTTTGTTGG TTACATCTTA TTGTTCCCAT GACCACAATG ATATGTGCAT ACAGACATGC ACCACCAGAA ACAAAGGGGG AGTATGATAT AGACAAAATA 9200
 9201 GAAGAGCAAA GTGGGCTATA CAGATACCAT ATGGGAGGGA TTGAAGGGTG GTGTCAGAAG TTATGGACAA TGGAGGCGAT ATCCTTGTTA GATGTAGTAT 9300
 9301 CTGTTAAGAC TCGTTGTCAG ATGACCTCTC TATTAAACGG AGACAATCAA TCAATAGATG TCAGTAAACC AGTAAAATTG TCTGAAGGTA TAGATGAAGT 9400
 9401 AAAAGCAGAT TATAGCTTAG CAATTAAAAT GCTTAAAGAG ATAAGAGATG CCTATAAAAA CATTGGCCAT AAACTCAAAG AAGGTGAAAC ATATATATCA 9500
 9501 AGAGATCTTC AATTTATAAG TAAGGTGATT CAATCTGAGG GGGTCATGCA TCCTACCCCC ATAAAAAAGA TATTAAGGGT AGGTCCCTGG ATAAATACAA 9600
 9601 TACTAGATGA CATTAAAACT AGTGCAGAAT CAATAGGGAG TCTGTGTCAA GAACTAGAGT TCAGAGGAGA AAGTATACTA GTTAGCTTGA TATTAAGGAA 9700
 9701 TTTCTGGCTG TATAACTTAT ACATGCATGA GTCAAAACAG CATCCGTTAG CTGGAAAACA ACTGTTTAAA CAATTGAACA AAACACTAAC ATCTGTGCAA 9800
 9801 AGATTTTTTG AGCTGAAGAA AGAAAATGAT GTGGTTGACC TATGGATGAA TATACCAATG CAGTTTGGAG GGGGAGACCC AGTAGTTTTT TACAGATCTT 9900
 9901 TTTACAGAAG GACTCCTGAT TTCTTGACTG AAGCAATCAG CCATGTGGAT TTACTGTTAA AAGTTTCAAA CAATATTAAA AATGAGACTA AGATACGATT 10000
10001 CTTTAAAGCC TTATTATCTA TAGAAAAGAA TGAACGTGCT ACATTAACAA CACTAATGAG AGACCCCCAG GCGGTAGGAT CGGAAAGACA AGCTAAGGTA 10100
10101 ACAAGTGATA TAAATAGAAC AGCAGTTACT AGCATACTGA GTCTATCTCC GAATCAGCTA TTTTGTGATA GTGCTATACA CTATAGCAGA AATGAAGAAG 10200
10201 AAGTAGGGAT CATTGCAGAC AACATAACAC CTGTTTATCC TCACGGATTG AGAGTGCTCT ATGAATCACT ACCTTTTCAT AAGGCTGAAA AGGTTGTCAA 10300
10301 TATGATATCA GGTACAAAGT CTATAACTAA CCTATTGCAG AGAACATCTG CTATCAATGG TGAAGATATT GATAGAGCAG TGTCTATGAT GTTAGAGAAC 10400
10401 TTAGGGTTGT TATCTAGGAT ATTGTCAGTA ATAATTAATA GTATAGAAAT ACCAATTAAG TCCAATGGCA GATTGATATG CTGTCAAATT TCTAAGACTT 10500
10501 TGAGAGAAAA ATCATGGAAC AATATGGAAA TAGTAGGAGT GACATCTCCA AGTATTGTAA CATGTATGGA TGTTGTGTAT GCGACTAGTT CTCATTTAAA 10600
10601 AGGAATAATT ATTGAAAAAT TCAGTACTGA CAAGACCACA AGAGGTCAGA GGGGACCAAA AAGCCCTTGG GTAGGATCAA GCACTCAAGA GAAAAAATTA 10700
10701 GTTCCTGTTT ATAACAGACA AATTCTTTCA AAACAACAAA AAGAGCAACT GGAAGCAATA GGAAAAATGA GGTGGGTGTA TAAAGGAACT CCAGGGCTAA 10800
10801 GAAGATTGCT CAATAAGATT TGCATAGGAA GTTTAGGTAT TAGCTATAAA TGTGTAAAAC CTCTATTACC AAGATTTATG AGTGTAAACT TCTTACATAG 10900
10901 GTTATCTGTT AGTAGCAGAC CCATGGAATT CCCAGCTTCT GTTCCAGCTT ATAGGACAAC AAATTACCAC TTTGACACTA GTCCAATCAA CCAAGCATTA 11000
11001 AGTGAGAGGT TCGGGAACGA AGACATTAAT CTAGTGTTCC AAAATGCAAT CAGCTGCGGA ATTAGTATAA TGAGTGTTGT AGAACAGTTA ACTGGTAGAA 11100
11101 GCCCAAAACA ATTAGTCTTA ATCCCCCAAT TAGAAGAGAT AGATATTATG CCCCCTCCTG TATTTCAAGG AAAATTCAAT TATAAACTAG TTGATAAAAT 11200
11201 AACCTCCGAT CAACACATCT TCAGTCCTGA CAAAATAGAC ATATTAACAC TAGGGAAGAT GCTTATGCCT ACTATAAAAG GTCAAAAAAC TGATCAGTTC 11300
11301 TTAAATAAGA GAGAAAACTA TTTCCATGGA AATAATTTAA TTGAATCTTT ATCTGCAGCA CTTGCATGCC ATTGGTGTGG AATATTAACA GAACAGTGTG 11400
11401 TAGAAAACAA TATCTTTAGG AAAGACTGGG GTGATGGGTT CATATCAGAT CATGCCTTCA TGGATTTCAA GATATTTCTA TGTGTATTTA AAACCAAACT 11500
11501 TTTATGTAGT TGGGGATCCC AAGGGAAAAA TGTAAAAGAT GAAGATATAA TAGATGAATC CATTGACAAA TTATTAAGAA TTGACAACAC TTTTTGGAGA 11600
11601 ATGTTCAGCA AAGTCATGTT TGAATCAAAG GTCAAAAAAA GAATAATGTT ATATGATGTA AAATTCCTAT CATTAGTAGG TTATATAGGA TTTAAAAACT 11700
11701 GGTTTATAGA GCAGTTAAGA GTAGTAGAAT TGCATGAAGT ACCCTGGATT GTCAATGCTG AAGGGGAGCT AGTTGAAATT AAACCAATCA AAATTTATTT 11800
```

Fig. 39C

HMPV strain 75 (continued)

```
11801 GCAGTTAATA GAACAAAGTC TATCTTTAAG AATAACTGTT TTGAATTATA CAGACATGGC ACATGCTCTT ACACGATTAA TTAGGAAGAA ATTGATGTGT 11900
11901 GATAATGCAC TCTTTAATCC AAGTTCATCA CCAATGTTTA GTCTAACTCA AGTTATTGAT CCTACAACAC AGCTAGACTA TTTTCCTAAG GTAATATTTG 12000
12001 AAAGGTTAAA A

US 7,704,491 B2

RECOMBINANT HUMAN METAPNEUMOVIRUS AND ITS USE

PRIORITY CLAIM

This application claims the benefit of U.S. Provisional Patent Application No. 60/451,119, filed Feb. 28, 2003, and U.S. Provisional Patent Application No. 60/478,667, filed Jun. 13, 2003. Both of the provisional applications are incorporated by reference herein in their entirety.

FIELD OF THE DISCLOSURE

This invention relates to the field of virology and, more specifically, to methods for producing recombinant human metapneumovirus (rHMPV), for producing replication competent derivatives with desirable properties such as attenuation and protective efficacy, and to uses of rHMPV in immunoprophylaxis and therapy.

BACKGROUND

Human metapneumovirus (HMPV) is a virus that was first recovered in the Netherlands from infants and children experiencing acute respiratory tract disease (van den Hoogen et al. Nat. Med. 7:719-724, 2001; De Jong et al. WO 02/057/302 A2).

HMPV is worldwide in prevalence and resembles human respiratory syncytial virus (RSV or HRSV) with regard to disease signs and the ability to infect and cause disease in the young infant as well as individuals of all ages (for a review, see Heikkinen and Jarvinen, Lancet 361:51-59, 2003).

HMPV is characterized as an enveloped virus with a genome that is a single negative strand of RNA of approximately 13 kb. The virus has been classified presumptively in the Metapneumovirus genus, Pneumovirus subfamily, Paramyxovirus family of the Order Mononegavirales, comprising the nonsegmented negative strand RNA viruses or mononegaviruses. Mononegaviruses also are called nonsegmented negative strand RNA viruses. The Paramyxovirus family has two subfamilies, Paramyxovirinae and Pneumovirinae (also referred to as paramyxoviruses and pneumoviruses, respectively).

Several other mononegaviruses are important agents of respiratory tract disease in pediatric and other populations, for example, RSV and human parainfluenza virus types 1, 2 and 3 (HPIV1, HPIV2 and HPIV3). Although these viruses have some similarities with HMPV, their sequences are different from the HMPV viruses disclosed herein.

Since HMPV was described only recently, there is little documented experience with its propagation, manipulation and stability, and there are no well established or widely available reference strains, mutant strains, reported vaccine candidates, or reference virus-specific antibodies or comparable reagents or systems or experimental animals models to facilitate characterization. Because HMPV is associated with severe respiratory tract disease, there is a need to develop methods to engineer safe and effective vaccines to alleviate the serious health problems attributable to this pathogen, particularly among young infants.

BRIEF SUMMARY OF SPECIFIC EMBODIMENTS

HMPV is a significant agent of human respiratory tract disease. Methods and compositions are provided herein for recovering infectious, recombinant HMPV. Recombinant HMPV is disclosed herein, including the complete nucleic acid sequence encoding all of the protein products of HMPV. Compositions and methods for introducing defined, predetermined structural and phenotypic changes into an infectious HMPV are disclosed, as are attenuated forms of HMPV as well as forms of HMPV that have been modified to have improved qualities relevant to immunogenicity, safety, protective efficacy, and breadth of vaccine coverage. Thus, methods are disclosed for generating an immune response against HMPV in a subject. The methods include administering to the subject an attenuated HMPV, thereby producing the immune response. Also described is the identification of a set of viral ORFs whose expression is sufficient to direct viral transcription and RNA replication, and to produce infectious HMPV entirely from cDNA.

The foregoing and other features and advantages will become more apparent from the following detailed description of several embodiments, which proceeds with reference to the accompanying figures.

BRIEF DESCRIPTION OF THE FIGURES

FIG. 2 is a diagram showing sequence alignments between the 3' leader (top) and 5' trailer (bottom) regions and flanking areas of the genome of HMPV strain 83 (SEQ ID NO: 18 and SEQ ID NO: 22, respectively), avian pneumovirus (APV or AMPV, SEQ ID NO: 19 and SEQ ID NO: 23, respectively), and HRSV strain A2 (SEQ ID NO: 20 and SEQ ID NO: 24, respectively). The sequences are in genome (negative) sense. Nucleotide assignments that are the same in two or more sequences between HMPV 83, APV and RSV are shaded; sequence gaps introduced to make optimal alignments are indicated by dashes. The bars over the left hand end of each sequence indicates regions whose spacing and sequence had not been previously determined for any HMPV. The partial sequences available for HMPV strain 00-1 3' leader and 5' trailer regions (SEQ ID NO: 17 and SEQ ID NO: 21, respectively) are indicated at the top: nucleotide assignments in strain 00-1 that are identical to those of HMPV 83 are indicated by asterisks while nucleotide differences are indicated. Sequences: APV (Randhawa et al., J. Virol. 71:9849-54, 1997), RSV (Mink et al., Virology 185:615-24, 1991), HMPV 00-1 (van den Hoogen et al., Nat. Med. 7:719-24, 2001).

FIG. 5 is a chart showing the percent amino acid sequence identity for the predicted, putative proteins of HMPV 83 compared to those of two oilier strains of HMPV (00-(1), and 97-82), three different antigenic types of APV (A, B and C), the two subgroups of human RSV (A and B), bovine RSV (BRSV), and pneumonia virus of mice (PVM, a murine counterpart of HRSV). Note that HMPV is most closely related to APV C. ND indicates that a comparison was not done for the indicated subject.

FIG. 8 is a diagram showing putative transcription signals for HMPV strain 83 based on the identification of semi-conserved sequence motifs located between the major ORFs in the complete sequence. Sequences are in positive (mRNA) sense. The semi-conserved sequence motif that precedes most of the ORFs in the complete sequence is shown is the putative gene start (GS) signal, with some of the most highly conserved sequences shown in upper case letters and with flanking sequence on either side in lower case. The individual GS motifs are named according to the putative ORF, that each precedes (SEQ ID NO: 1, bases 29-64 for N; bases 1237-1272 for P; bases 2154-2189 for M; bases 3041-3076 for F; bases 4698-4733 for M2; bases 5455-5490 for SH; bases 6206-6241 for G; and bases 7107-7142 for L). A consensus sequence is shown underneath (SEQ ID NO: 25). For positions where alternative assignments can occur, these are listed below the consensus (SEQ ID NOs: 26 and 27). By this analysis, the major element of the GS signal is contained within sixteen nucleotides, of which positions 1, 3, 4, 6, 7, 9, and 14-16 were exactly conserved, with 14-16 also serving as potential translation start sites. Similarly, the semi-conserved sequence motif that follows most of the ORFs in the complete sequence is shown as the putative gene end (GE) signal, with some of the most highly conserved sequences shown in upper case and flanking sequence in lower case. The individual GE motifs are named according to the ORF that each follows (SEQ ID NO: 1, bases 1230-1249 for N; bases 2141-2166 for P; bases 3002-3032 for M; bases 4680-4710 for F; bases 5440-5467 for M2; bases 6077-6107 for SH; bases 6912-6942 for G; and bases 13223-13253 for L). A consensus sequence is shown underneath (SEQ ID NO: 28). For positions where alternative assignments can occur, these are listed below the consensus (SEQ ID NOs: 29 and 30). By this analysis, the major element of the GE signal is contained within 12-13 nucleotides, of which positions 1-3 and 10-12 are exactly conserved.

FIG. 17A is a graph illustrating multi-step growth of rHMPV-GFP-ΔSH, rHMPV-GFP-ΔG, and rHMPV-GFP-ΔSH/G compared to rHMPV and rHMPV-GFP, performed in LLC-MK2 cells as described above for FIG. 13. Since the deletions had been introduced into rHMPV-GFP, rHMPV-GFP is the "wild type" equivalent for comparison.

FIG. 19 is a diagram illustrating the introduction of single amino acid substitutions into the Cys3-His1 motif of the M2-1 protein of rHMPV-GFP (strain 83). This motif consists of three cysteine residues (C7, C15 and C21) and one histidine residue (H25); it is also found in RSV and other pneumoviruses, and thus represents a conserved pneumovirus motif. The amino acid sequence shown is from methionine (M) 1 to asparagine (N) 26 of the deduced complete M2-1 amino acid sequence (SEQ ID NO: 4). Each of these mutants was successfully recovered as infectious recombinant virus.

FIG. 21 is a diagram illustrating silencing of the M2-1 ORF in rHMPV-GFP (strain 83) by replacing the ATG translational start site (shaded) with a TAG translational termination codon, and by replacing additional ATG triplets (underlined) in each reading frame with slop colons. The top line shows the nucleotide sequence of the upstream end of the M2-1 mRNA (corresponding to nucleotides 4711 to 4775 in the complete HMPV antigenome sequence. SEQ ID NO: 1). The second line shows nucleotide substitutions (lower case letters) introduced into the M2-1 sequence of rHMPV-GFP to yield rHMPV-GFP-ΔM2-1. The third line shows the first 17 amino acids of the HMPV M2-1 protein (SEQ ID NO: 4), and the fourth line shows coding changes introduced by the point mutations in rHMPV-GFP-ΔM2-1, with termination codons in the M2-1 ORF indicated by asterisks. Note that the next in-frame ATG in the M2-1 ORF is at codon 134 out of the total of 187 codons in the ORF (SEQ ID NO: 4). This mutant was successfully recovered as infectious recombinant virus.

FIG. 22C is a chart demonstrating increased sensitivity of HMPV ΔM2(1+2) and ΔM2-2 mutants to type I interferon. Replicate cultures of Vero cells were treated overnight with the indicated amount of interferon per $1.5 \times 10^6$ cells. The cells were infected with the indicated amount of wild type rHMPV-GFP, rHMPV-GFPΔM2(1+2), rHMPV-GFPΔM2-2, or rgRSV, the last being a recombinant RSV that expresses the GFP gene. The GFP marker was used to visually monitor virus growth during the experiment to judge the appropriate time of harvest, and is otherwise irrelevant to this experiment. The cells were harvested on day 4 and the yield of each virus was determined and compared with additional replicate cultures that had been mock-interferon treated, infected and harvested in parallel. The results are expressed as the fold reduction of each interferon-treated culture compared to its untreated counterpart.

FIGS. 26A-26F are diagrams illustrating amino acid locations in the strain 83 HMPV L protein (SEQ ID NO: 7) that are targets for mutagenesis based on mapping of attenuating mutations in a heterologous virus (HRSV A2, SEQ ID NO: 13; HPIV3, SEQ ID NO: 14; HPIV1, SEQ ID NO: 15; or BPIV3, SEQ ID NO: 16, as indicated). HMPV strain 001, SEQ ID NO: 12, is included in the alignments for comparison. Numbers at the left indicate the positional reference of the first residue in the partial amino acid sequence shown, and numbers to the right indicate the positional reference number of the terminal residue in the partial sequence. The more highly conserved or similar residues are denoted by shading. Dashes indicate a gap in the particular sequence introduce to maximize the alignment.

FIG. 28 is a diagram illustrating the GS signal of the M2 gene of wild type (WT) RSV (SEQ ID NO: 31), and a highly-attenuating T to C nucleotide substitution at position nine in the GS signal of the M2 gene of the attenuated cpts248/404 RSV mutant (Whitehead et al., J. Virol. 72:4467-4471, 1998). There is a corresponding T residue that is highly conserved among all of the putative GS signals of HMPV. The individual GS motifs are named according to the putative ORF that each precedes (SEQ ID NO: 1, bases 41-57 for N; bases 1249-1265 for P; bases 2166-2182 for M; bases 3053-3069 for F; bases 4710-4726 for M2; bases 5467-5483 for SH; bases 6218-6234 for G; and bases 7119-7135 for L). The sequence at the bottom (SEQ ID NO: 32) indicates in upper case letters those positions in the putative HMPV GS signal that are exactly conserved among all of the signal in strain 83, which includes the T at position nine.

FIG. 30 is a diagram illustrating the construction of chimeric viruses constructed with genes of HMPV and APV, which represent potential vaccine candidates. Part A illustrates the genome of HMPV83 and derivatives in which the N, P or M ORF is replaced individually by its APV counterpart (unshaded boxes). Parts B, C and D illustrate the structures of cDNAs containing the N, P and M genes, respectively of HMPV (upper line in each box) compared to a version containing the indicated substituted APV ORF (lower line in each box). Each ORF is shown as a shaded box and is flanked by HMPV GS (SEQ ID NO: 1, bases 12-57 for the leader/N GS signal; bases 1235-1265 for the N GE/P GS signal; and bases 2146-2182 for the P GE/M GS signal) and GE (SEQ ID NO: 1, bases 1235-1242 for the partial N GE signal; bases 2146-2151 for the partial P GE signal; and bases 3007-3037 for the M GE signal) transcription signals (boxed). In the case of the APV M gene, 64 nt of noncoding sequence that separates the ORF from the GE signal have been deleted (−64 nts nc). The GE and GS signals in turn are flanked by restriction sites selected from the following list, as indicated: BbsI, BsmBI, BfuAI, BbsI. Each of these sites consists of a recognition sequence (underlined) and has the property of cutting in a sequence-independent fashion at a second site outside of the recognition site (underlined tetranucleotide, bold) to leave a 4-nt 5'-protruding overhang. Here, the overhangs were TAAT or GTAG, as indicated, which matches the natural HMPV assignments at these positions. Part E illustrates a novel assembly strategy that utilizes the 4-nt overhangs, plus the flanking MluI and NheI sites, for ligation of the N, P and M cDNAs simultaneously into the HMPV backbone. By this strategy, this can be used to mix HMPV and APV N, P and M genes in whatever combinations desired to make replacements of single HMPV genes (as in part A) or to replace two or three genes simultaneously.

FIG. 31 is a diagram showing the comparison of the predicted gene boundaries, cis-acting GS and GE signals, and intergenic regions of HMPV strains 83 (SEQ ID NO: 1) and 75 (SEQ ID NO: 2), shown as positive-sense sequence. The top alignment shows the leader/N gene boundary, specifically the last 16-18 nucleotides of the leader region followed by the first 15 nucleotides of the N gene. The second alignment shows the N/P gene boundary, specifically the last 15 nucleotides of the N gene, followed by the adjoining intergenic region, followed by the first 15 nucleotides of the P gene. Subsequent alignments show the P/M, M/F, F/M2, M2/SH, SH/G, G/L, and L/trailer boundaries. Conserved sequence motifs at the end (gene end) and beginning (gene start) of each gene are indicated in bold upper case, and a consensus is given below (SEQ ID NOs: 34 and 35). Positions within these conserved motifs are numbered. Translational stop and start codons are underlined. Intergenic sequences are shown: in the case of the longer intergenic regions, only the first 5 nucleotides on the upstream and downstream ends are shown and the number of nucleotides not shown is indicated. For each assignment in the consensus sequence, no more than two of the sequence pairs (HMPV 83 versus 75) could have a heterologous assignment in both subgroup sequences.

FIG. 32 is a chart illustrating the percent amino acid and nucleotide sequence identity (the latter given in parentheses) between the predicted proteins and ORFs of: HMPV 83 versus HMPV 75, representing a comparison across subgroups; HMPV83 versus HMPV 00-1, representing a comparison within a subgroup; and RSV A2 versus RSV B1, representing a comparison across the two well-characterized RSV antigenic subgroups A and B, which serve here as a benchmark for assessing the magnitude and anticipated significance of the differences in the HMPV subgroups. Amino acid sequence identities were calculated based on the complete predicted proteins; in the case of G and SH, overhangs on the carboxy-terminal side of alignments due to length differences were not included in the calculations. Nucleotide sequence identities for the corresponding ORFs are shown in parentheses and are based on the protein-coding sequence exclusive of flanking noncoding sequence. For comparison, the HMPV intergenic regions were 48% identical between subgroups and noncoding gene sequences exclusive of conserved transcription signals were 54% identical, compared to values of 42% and approximately 50% for RSV (Johnson et al., J. Gen. Virol. 69:2901-2906, 1988).

FIGS. 33A-33B are diagrams showing the alignment of the amino acid sequences of the SH (FIG. 33A) and G (FIG. 33B) proteins of HMPV strains 75 (SEQ ID NOs: 8 and 9, respectively), 83 (SEQ ID NOs: 5 and 6, respectively) and 00-1 (SEQ-ID NOs: 10 and 11, respectively). This includes comparison between (75 versus 83) and within (83 versus 00-1) the proposed HMPV genetic subgroups. For strains 75 and 00-1, assignments that differ from that of 83 are shown; dashes indicate gaps introduced to maximize the alignment or to denote the absence of corresponding amino acids. Stars underneath each alignment denote amino acid identity among all three sequences; small dots indicate amino acid similarity among all three. Proposed signal/transmembrane domains are boxed. Motifs for N-linked carbohydrate are underlined (N-X-T/S, where X is not proline). In panel A, cysteine residues conserved among all three SH proteins are indicated with large dots, and potential sites for O-linked glycosylation (Hansen et al., Glycoconj. J. 15:115-130, 1998) of the SH proteins are as follows: HMPV 83, 75, 77, 78, 81; HMPV 75, 78, 79, 81; 00-1, 77, 78, 81. The ectodomain of the G protein of each virus contained more than 40 potential acceptor sites for O-linked carbohydrate.

FIGS. 36A-36B are a diagram and digitized images showing the construction and expression of a recombinant HPIV1 vector expressing the F protein of HMPV CAN83 (rHPIV1-$F_{83}$). The HPIV1 genome was modified by the creation of an MluI restriction site (HPIV1 nt 113-118) one nucleotide prior to the translational start codon of the N ORF (HPIV1 nt 119-121). The F ORF of HMPV strain CAN83 (1620 nt in length and encoding a 539 aa polypeptide; bases 30544697 of SEQ ID NO: 1) was engineered by PCR to be followed by the tetranucleotide TAAT and an HPIV1 gene junction consisting of a GE signal, CTT intergenic region, and a GS signal. The length of the entire cassette was 1656 nt and was designed, upon insertion into the MluI site, to conform to the rule of six and to maintain the HPIV1 GS signal sequence phasing. GS and GE signals are indicated (FIG. 36A). A portion of the predicted viral promoter that lies within the N gene is shown (FIG. 36A). LLC-MK2 cells were infected with rHPIV-F83, HMPV CAN83, rHPIV1 or mock-infected, as indicated, incubated for 72 hr, and analyzed by indirect immunofluorescence using anti-HMPV polyclonal hamster serum or a mixture of two mouse monoclonal antibodies to the HPIV1 HN protein, as indicated (FIG. 36B).

FIGS. 37A-37D are the complete sequence of the genome of biologically-derived strain 83, shown as positive sense DNA (SEQ ID NO: 1). See also, GenBank Accession No. AY297749.

Figure 38A:
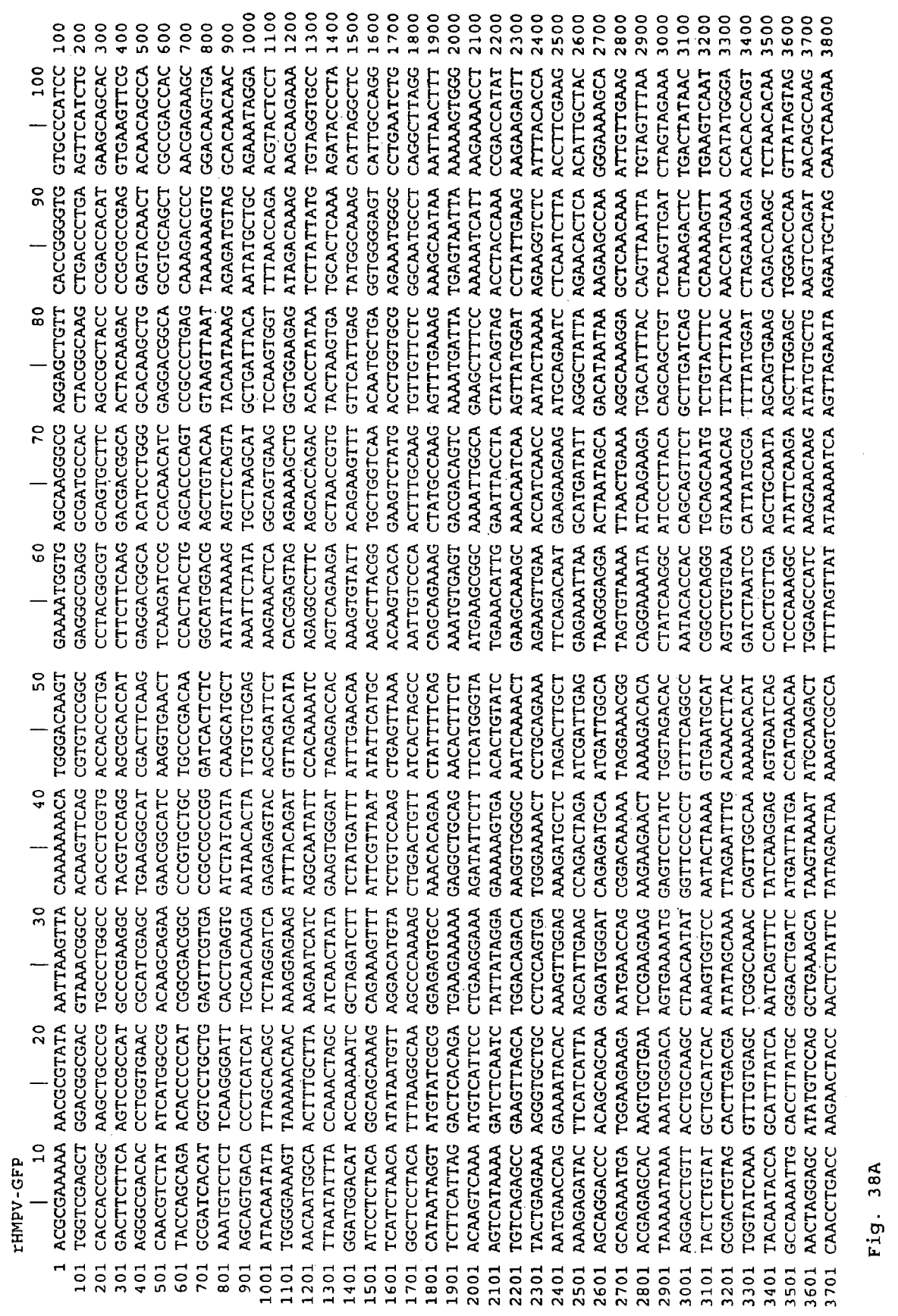
Figure 38B:
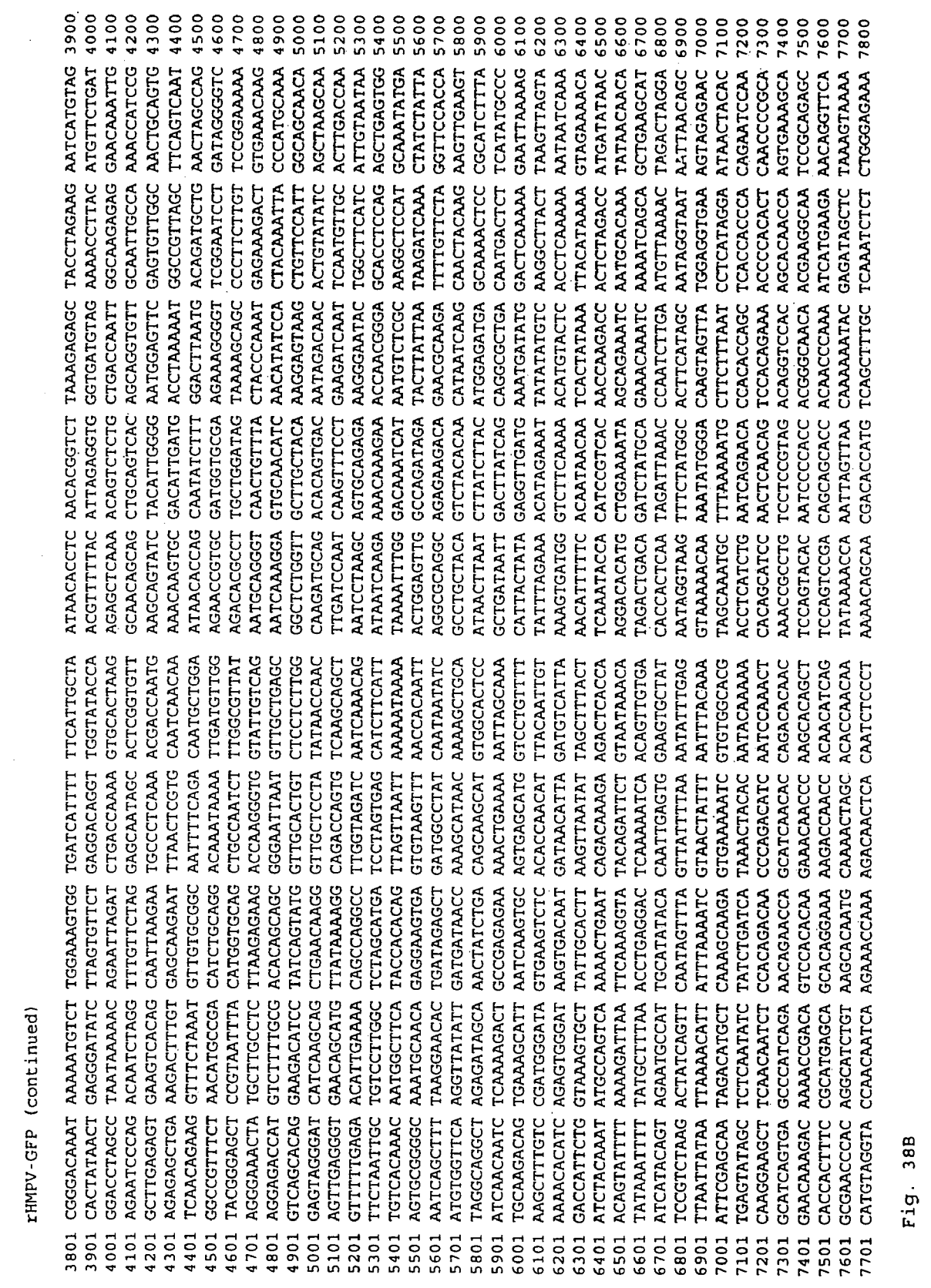

FIGS. 38A-38D are the complete sequence of the genome of recombinant strain 83 bearing a transcription cassette expressing GFP, which recombinant strain exemplifies rHMPV-GFP of the current disclosure (SEQ ID NO: 3).

FIGS. 39A-39D are the complete sequence of the genome of biologically-derived, biologically-cloned HMPV CAN75 (SEQ ID NO: 2). See also, GenBank Accession No. AY297748.

SEQUENCE LISTING

Figure 1:
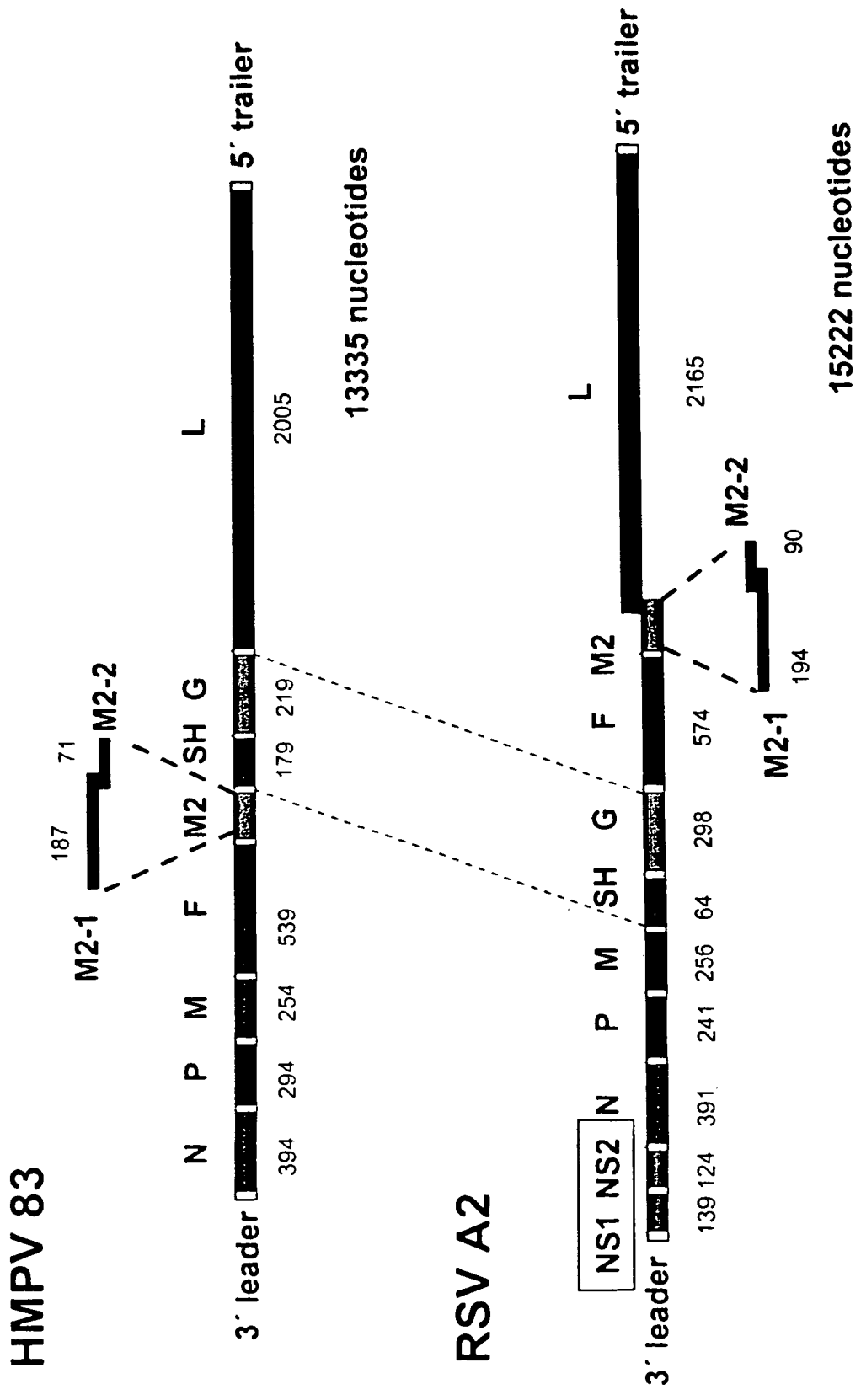
FIG. 1 is a diagrammatic representation of the negative sense genomes of HMPV strain CAN97-83 (hereafter referred to as 83 or CAN-83) and RSV strain A2, showing a comparison of the two genomes. Individual proposed genes are shown as shaded boxes separated by proposed intergenic regions represented by open bars. The 3' extragenic leader and 5' extragenic trailer regions also are shown as open boxes. Tentative HMPV gene assignments are based on ORFs whose potential protein exhibits partial amino acid sequence identity or structural similarity with a known protein from RSV. Note that HMPV lacks apparent counterparts to the NS1 and NS2 genes present in RSV (boxed), and that the putative F and M2 gene pair precedes the SH-G gene pair in HMPV but follows it in RSV (the difference in the position of SH-G is indicated with dotted lines). The M2 and L genes overlap in RSV but may not do so in HMPV. In both viruses, the M2 gene contains two ORFs M2-1 and M2-2, depicted as filled bars. Amino acid lengths are shown for the deduced unmodified viral proteins. Each of the RSV proteins has been directly identified; none of the proposed HMPV proteins had been directly identified prior to the current disclosure. Abbreviations (with HMPV assignments by analogy to RSV): N, major nucleocapsid protein; P, nucleocapsid phosphoprotein; M, inner virion matrix protein; M2-1 and M2-2, products of the first and second ORFs, respectively, in the M2 mRNA; SH, small hydrophobic protein; G, heavily glycosylated protein involved in attachment, F, fusion protein involved in penetration; L, large polymerase protein: NS1 and NS2, nonstructural protein 1 and 2, respectively. This and all subsequent diagrams are not to scale.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 shows the nucleic acid sequence of the genome of biologically-derived HMPV (strain 83) as positive sense DNA.

SEQ ID NO: 2 shows the nucleic acid sequence of the genome of biologically-derived HMPV (strain 75) as positive sense DNA.

SEQ ID NO: 3 shows the nucleic acid sequence of the genome of recombinant HMPV (strain 83) with a transcription cassette expressing GFP as positive sense DNA.

SEQ ID NO: 4 shows the amino acid sequence of the HMPV (strain 83) M2-1 protein.

SEQ ID NO: 5 shows the amino acid sequence of the HMPV (strain 83) SH protein.

SEQ ID NO: 6 shows the amino acid sequence of the HMPV (strain 83) G protein.

SEQ ID NO: 7 shows the amino acid sequence of the HMPV (strain 83) L protein.

SEQ ID NO: 8 shows the amino acid sequence of the HMPV (strain 75) SH protein.

SEQ ID NO: 9 shows the amino acid sequence of the HMPV (strain 75) G protein.

SEQ ID NO: 10 shows the amino acid sequence of the HMPV (strain 00-1) SH protein.

SEQ ID NO: 11 shows the amino acid sequence of the HMPV (strain 00-1) G protein.

SEQ ID NO: 12 shows the amino acid sequence of the HMPV (strain 00-1) L protein.

SEQ ID NO: 13 shows the amino acid sequence of the HRSVA2 L protein.

SEQ ID NO: 14 shows the amino acid sequence of the HPIV3 L protein.

SEQ ID NO: 15 shows the amino acid sequence of the HPIV1 L protein.

SEQ ID NO: 16 shows the amino acid sequence of the BPIV1 L protein.

SEQ ID NO: 17 shows the nucleic acid sequence of the HMPV (strain 00-1) 3' leader.

SEQ ID NO: 18 shows the nucleic acid sequence of the HMPV (strain 83) 3' leader.

SEQ ID NO: 19 shows the nucleic acid sequence of the APV 3' leader.

SEQ ID NO: 20 shows the nucleic acid sequence of the RSV 3' leader.

SEQ ID NO: 21 shows the nucleic acid sequence of the HMPV (strain 00-1) 5' trailer.

SEQ ID NO: 22 shows the nucleic acid sequence of the HMPV (strain 83) 5' trailer.

SEQ ID NO: 23 shows the nucleic acid sequence of the APV 5' trailer.

SEQ ID NO: 24 shows the nucleic acid sequence of the RSV 5' trailer.

SEQ ID NO: 25 shows the nucleic acid sequence of the HMPV (strain 83) GS consensus sequence.

SEQ ID NO: 26 shows the nucleic acid sequence of the HMPV (strain 83) GS consensus sequence, with alternative nucleic acid assignments.

SEQ ID NO: 27 shows the nucleic acid sequence of the HMPV (strain 83) GS consensus sequence, with alternative nucleic acid assignments.

SEQ ID NO: 28 shows the nucleic acid sequence of the HMPV (strain 83) GE consensus sequence.

SEQ ID NO: 29 shows the nucleic acid sequence of the HMPV (strain 83) GE consensus sequence, with alternative nucleic acid assignments.

SEQ ID NO: 30 shows the nucleic acid sequence of the HMPV (strain 83) GE consensus sequence, with alternative nucleic acid assignments.

SEQ ID NO: 31 shows the nucleic acid sequence of the RSV M2 GS sequence.

SEQ ID NO: 32 shows the nucleic acid sequence of the HMPV (strain 83) GS consensus sequence, with uniformly conserved bases.

SEQ ID NO: 33 shows the nucleic acid sequence of a polylinker used in the cloning and expression of rHMPV.

SEQ ID NO: 34 shows the nucleic acid sequence of the HMPV (strain 83/75) GE consensus sequence.

SEQ ID NO: 35 shows the nucleic acid sequence of the HMPV (strain 83/75) GS consensus sequence.

SEQ ID NO: 36 shows the nucleic acid sequence of the genome of HMPV (strain 00-1) as positive sense DNA.

DETAILED DESCRIPTION OF SEVERAL EMBODIMENTS

In one embodiment, methods and compositions are provided for producing an infectious, self-replicating, recombinant HMPV from one or more isolated polynucleotide molecules encoding viral sequences. The methods and compositions generally involve coexpressing in a cell or cell-free system one or more expression vectors comprising a polynucleotide molecule that encodes a partial or complete, recombinant HMPV genome or antigenome and one or more polynucleotide molecules encoding HMPV N, P, and L proteins, so as to produce an infectious HMPV particle. In certain embodiments, the methods and compositions for producing the recombinant HMPV further include expression of the M2-1 gene.

Typically, the polynucleotide molecule that encodes the recombinant HMPV genome or antigenome is a cDNA. Thus, disclosed herein are polynucleotides such as cDNAs and their equivalents that encode a recombinant HMPV. Expression vectors and constructs that incorporate a polynucleotide molecule encoding a recombinant HMPV genome or antigenome are also disclosed herein.

The HMPV genome or antigenome, and the N, P, M2-1 and L proteins can all be produced from a single expression vector. However, the genome or antigenome can be produced by a separate expression vector, and the N, P, M2-1 and L proteins can be produced by one, two, or more additional expression vectors. One or more of the N, P, M2-1 and L proteins can be supplied by expression of a recombinant HMPV genome or antigenome. These proteins can also be supplied by coinfection with the same or different HMPV. Thus, in several embodiments, one or more of the N, P, M2-1 and L proteins are from a heterologous HMPV.

Infectious, recombinant, self-replicating viral particles are disclosed that are produced according to the foregoing methods. These particles include complete viruses as well as viruses that lack one or more non-essential proteins or non-essential portions (for example, a cytoplasmic, transmembrane or extracellular domain) of a viral protein. Viruses of the current disclosure that lack one or more such non-essential components (for example, a gene or genome segment from the HMPV SH, G, M2-2 open reading frame (ORF) or comparable accessory ORFs, or a segment of one or more other ORFs, or an intergenic or other non-coding or non-essential genome component) are referred to herein as incomplete viruses or "subviral particles." Exemplary subviral particles can lack any selected structural element, including a gene, gene segment, protein, protein functional domain, etc. that is present in a complete virus (that is, an assembled virion including a complete genome or antigenome, nucleocapsid and envelope). For example, a subviral particle of the current disclosure can include an infectious nucleocapsid containing a genome or antigenome, and the products of the N, P, and L genes. Other subviral particles are produced by partial or complete deletions or substitutions of non-essential genes and/or their products among other non-essential structural elements.

Complete viruses and subviral particles produced by the methods disclosed herein are typically infectious and self-replicative through multiple rounds of replication in a mammalian host amenable to infection by HMPV. These hosts include various in vitro mammalian cell populations, in vivo animal models widely known and accepted in the art as reasonably predictive of HMPV activity in humans (including, mice, hamsters, cotton rats, non-human primates including African green monkeys and chimpanzees), and humans, including seronegative and seropositive infants, children, juveniles, and adults. However, viruses and subviral particles also can be produced that are highly defective for replication in vivo.

In one embodiment, the polynucleotide molecule encodes a sequence of a wild type HMPV (either the genome or the antigenome). The term "wild type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In another embodiment, the genome or antigenome can include one or more mutations from a biologically derived mutant HMPV, or any combination of recombinantly-introduced mutations; including one or more polynucleotide insertions, deletions, substitutions, or rearrangements that is/are selected to yield desired phenotypic effects in the recombinant virus.

Thus, the recombinant HMPV genome or antigenome can be engineered using the methods disclosed herein to incorporate a recombinantly-introduced restriction site marker, or a translationally silent point mutation for handling or marking purposes. In other embodiments, the polynucleotide molecule encoding the recombinant HMPV genome or antigenome can incorporate one or more recombinantly-introduced attenuating mutations. In specific examples, the recombinant HMPV genome or antigenome incorporates one or more recombinantly-introduced, temperature sensitive (ts) or host range (hr) attenuating (att) mutations.

The recombinant HMPV genome or antigenome can incorporate one or more attenuating mutations identified in a biologically derived mutant HMPV strain, or in another mutant nonsegmented negative stranded RNA virus. For example, a mutation in a L, M, N, P, M2-1, M2-2, SH, F, or G protein, or in an extragenic sequence selected from a 3' leader or in a control signal such as the M2 GS sequence. Where the mutation is of one or more particular amino acid residues, the recombinant HMPV genome or antigenome can incorporate multiple nucleotide changes in the codons specifying the mutation to stabilize the modification against reversion.

The recombinant HMPV genome or antigenome can include an additional nucleotide modification specifying a phenotypic change, such as an alteration in growth characteristics, attenuation, temperature-sensitivity, cold-adaptation, plaque size, host-range restriction, or a change in immunogenicity. These additional modifications can alter one or more of the HMPV N, P, M, SH, G, F, M2-1, M2-2 and/or L genes and/or a 3' leader, 5' trailer, a cis-acting sequence such as a GS or GE sequence, and/or intergenic region within the HMPV genome or antigenome. For example, one or more HMPV genes can be deleted in whole or in part, or expression of the genes can be reduced or ablated by a frameshift mutation, by a mutation that alters a translation start site, by introduction of one or more stop codons in an ORF of the gene, or by a mutation in a transcription signal. In several embodiments, the recombinant HMPV genome or antigenome is modified by a partial or complete deletion of the HMPV SH, G, or M2-2 gene or ORFs, or one or more nucleotide changes that reduces or ablates expression of one or more HMPV genes yet yields a viable, replication competent, infectious viral construct. In other embodiments, the recombinant HMPV genome or antigenome is modified to encode a non-HMPV molecule such as a cytokine, a T-helper epitope, a restriction site marker, or a protein of a microbial pathogen capable of eliciting a protective immune response in a mammalian host.

A recombinant HMPV genome or antigenome can include a partial or complete HMPV "vector" genome or antigenome combined with one or more heterologous genes or genome segments (nucleic acid sequences) encoding one or more antigenic determinants of one or more heterologous pathogens to form a chimeric HMPV genome or antigenome. The heterologous genes or genome segments encoding the antigenic determinants can be added as supernumerary genes or genome segments adjacent to or within a noncoding region of the partial or complete HMPV vector genome or antigenome, or can be substituted for one or more counterpart genes or genome segments in a partial HMPV vector genome or antigenome. The heterologous genes or genome segments can include one or more heterologous coding sequences and/or one or more heterologous regulatory elements comprising all extragenic 3' leader or 5' trailer region, a GS signal, GE signal, editing region, translational start site, intergenic region, or a 3' or 5' non-coding region.

In additional embodiments, the heterologous pathogen is one or more heterologous pneumoviruses (for example, a heterologous HMPV or RSV) and the heterologous genes or genome segments encodes one or more HMPV or RSV N, P, M, SH, G, 1, M2-1, M2-2 and/or L proteins or fragments thereof. Thus, the antigenic determinants can be from a heterologous HMPV or RSV G, SH and F glycoproteins, and antigenic domains, fragments and epitopes thereof, that is/are added to or substituted within the partial or complete HMPV genome or antigenome. In several examples, genes encoding G, SH and F glycoproteins of a heterologous HMPV or RSV are substituted for counterpart HMPV G, SH and F genes in a partial HMPV vector genome or antigenome. In additional examples, genes encoding the G, SH, and F glycoproteins of a heterologous HMPV or RSV are expressed in addition to the HMPV sequences. In this manner, a plurality of heterologous genes or genome segments encoding antigenic determinants of multiple heterologous pneumoviruses can be added to or incorporated within the partial or complete HMPV vector genome or antigenome. In other embodiments, one or more genes from APV or a related pneumovirus exhibiting a host range restriction in humans is used to replace the corresponding genes in humans to achieve an attenuated derivative and other improved properties.

The disclosed recombinant human metapneumoviruses (HMPVs) can be used to generate a desired immune response against one or more HMPVs, or against HMPV and one or more non-HMPV pathogens, in a subject susceptible to infection. Recombinant HMPV as disclosed herein are capable of eliciting a mono- or poly-specific immune response in an infected mammalian host, yet are sufficiently attenuated so as to not cause unacceptable symptoms of disease in the immunized host. The attenuated viruses, including complete viruses and subviral particles, can be present in a cell culture supernatant, isolated from the culture, or partially or completely purified. The virus can also be lyophilized, and can be combined with a variety of other components for storage or delivery to a host, as desired.

Immunogenic compositions are also disclosed herein that include a physiologically acceptable carrier and/or adjuvant and an isolated attenuated recombinant HMPV virus. In one embodiment, the immunogenic composition includes a recombinant HMPV having at least one, at least two, or more attenuating mutations or other nucleotide modifications that specify a suitable balance of attenuation and immunogenicity. In specific examples, the immunogenic composition can be formulated in a dose of $10^3$ to $10^7$ PFU of attenuated virus. The immunogenic composition can include an attenuated recombinant HMPV that elicits an immune response against a single HMPV strain or against multiple HMPV strains or serotypes or other pathogens such as RSV and/or HPIV. In this regard, recombinant HMPV can be combined in formulations with other HMPV strains, or with other candidate viruses such as a live attenuated RSV. Methods are also disclosed herein for stimulating the immune system of a mammalian subject to elicit an immune response against one or more HMPVs, or against HMPV and a non-HMPV pathogen. Thus, a method is provided herein for inducing an immune response against a single HMPV, against multiple HMPVs, or against one or more HMPVs and a non-HMPV pathogen such as RSV.

The disclosed recombinant HMPVs can be used to elicit a monospecific immune response or a polyspecific immune response against multiple HMPVs, or against one or more HMPVs and a non-HMPV pathogen. Alternatively, recombinant HMPV having different immunogenic characteristics can be combined in a mixture or administered separately in a coordinated treatment protocol to elicit an immune response against one HMPV, against multiple HMPVs, or against one or more HMPVs and a non-HMPV pathogen such as RSV. In one example, the immunogenic compositions are administered to the upper respiratory tract, for example, by spray, droplet or aerosol.

An operable set of viral open reading frames (ORFs) sufficient to direct viral transcription and RNA replication are disclosed herein. Diagnostic assays using this set of ORFs are provided that determine viral activities based either on infectious virus or on the expression of isolated polynucleotide molecules encoding viral sequences. In one example, an infectious HMPV recombinant virus is disclosed herein that expresses a detectable marker or label, such as a recombinant HMPV expressing the jellyfish green fluorescent protein (GFP). These and related tools are effective, for example, to determine and characterize HMPV infection in vitro and in vivo. In one exemplary embodiment, recombinant HMPV expressing a detectable label can be utilized in assays and related compositions for the detection of HMPV-neutralizing antibodies in biological specimens (for example, serum of patients at risk of HMPV infection or presenting with respiratory symptoms). In additional embodiments the recombinant HMPV expressing a detectable label can be used to screen compounds for antiviral activity.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptide are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

As described above, methods and compositions for the production and use of novel, recombinant HMPVs are provided herein. The recombinant HMPVs are infectious and immunogenic in humans and other mammals and are useful as immunogenic compositions to produce immune responses against one or more HMPVs or other pneumoviruses. Thus, the recombinant HMPVs can be used to produce an immune response to, for example, RSV and/or one or more HMPV or other pneumoviral strains, serotypes, or subgroups. Chimeric HMPVs are provided herein that can be used to elicit an immune response against a selected HMPV and one or more additional pathogens, for example against multiple HMPVs or against a HMPV and a non-HMPV virus such as RSV, or parainfluenza virus (PIV). The immune response elicited can involve either or both humoral and/or cell mediated responses. The HMPVs can be attenuated to yield a desired balance of attenuation and immunogenicity.

Methods are provided herein for designing and producing attenuated, HMPVs that are useful as agents for eliciting a desired immune response against HMPV and other pathogens. Thus, using the methods disclosed herein, recombinant HMPVs can be produced that have a defined genome sequence and predictable characteristics.

An exemplary recombinant HMPV (rHMPV) includes a recombinant HMPV genome or antigenome and encodes (or the antisense of which encodes) HMPV major nucleocapsid (N) protein, nucleocapsid phosphoprotein (P), and large polymerase protein (L) (see FIG. 1 and exemplary sequence information provided in FIG. 37). In additional embodiments, the rHMPV can incorporate a recombinant HMPV genome or antigenome, N, P, and L proteins, and a HMPV M2-1 protein. In further embodiments, one or more of the N, P, L, and/or M2-1 proteins can be a mutant protein or partial protein, or include a corresponding homologous protein or protein fragment of a heterologous HMPV or non-HMPV virus such as APV. One or more additional HMPV proteins can be coexpressed with the recombinant HMPV genome or antigenome, in various combinations, to provide a range of infectious viruses. As used herein the term "recombinant HMPV" or "rHMPV" includes recombinantly produced subviral particles lacking one or more non-essential viral components, complete viruses having all native viral components, and viruses containing supernumerary proteins, antigenic determinants or other additional components. A recombinant virus is produced entirely from cloned cDNA.

As set forth in the Examples below, a complete consensus sequence was determined for the genomic RNA of an exemplary wild type strain of HMPV. The sequence thus identified was used to generate a full-length antigenomic cDNA and to recover a wild type rHMPV. The biological properties of rHMPV in vitro and in vivo demonstrates that the exemplary rHMPV sequence corresponds to a wild type virus. This critical finding demonstrates that the recombinant HMPV sequence disclosed herein is that of an authentic wild type virus. This rHMPV serves as a novel substrate for recombinant introduction of attenuating mutilations for the generation of live-attenuated HMPV and HMPV-based chimeric and vectors that can be used for immunogenic compositions.

As disclosed herein, infectious recombinant HMPVs can be produced by a recombinant coexpression system that permits introduction of defined changes into the recombinant HMPV and provides for the generation, with high frequency and fidelity, of HMPV having a defined genome sequence. These modifications are useful in a wide-variety of applications, including the development of live attenuated viral strains bearing predetermined, defined attenuating mutations. Infectious HMPV can be produced by intracellular or cell-free coexpression of one or more isolated polynucleotide molecules that encode the HMPV genome or antigenome RNA, together with one or more polynucleotides encoding viral proteins to generate a transcribing, replicating nucleocapsid. An "infectious virus" is a viral particle that has the ability to deliver its genome to the cytoplasm of a host cell.

The cDNAs encoding a HMPV genome or antigenome are constructed for intracellular or in vitro coexpression with the selected viral proteins to form infectious HMPV. A "HMPV antigenome" is an isolated positive-sense polynucleotide molecule which serves as a template for synthesis of progeny HMPV genome. In one embodiment a cDNA is constructed which is a positive-sense version of the HMPV genome that corresponds to the replicative intermediate RNA, or antigenome. This minimizes the possibility of hybridizing with positive-sense transcripts of complementing sequences encoding proteins necessary to generate a transcribing, replicating nucleocapsid. A "replication competent virus" is a viral particle capable of initiating an infection that produces viral progeny.

In some embodiments the genome or antigenome of a recombinant HMPV contains only those genes or portions thereof necessary to render the viral or subviral particles encoded thereby infectious. Further, the genes or portions thereof may be provided by more than one polynucleotide molecule, that is, a gene may be provided by complementation or the like from a separate nucleotide molecule. In other embodiments, the HMPV genome or antigenome encodes all functions necessary for viral growth, replication, and infection without the participation of a helper virus or viral function provided by a plasmid or helper cell line.

A "recombinant HMPV particle" is a HMPV or HMPV-like viral or subviral particle derived directly or indirectly from a recombinant expression system or propagated from virus or subviral particles produced there from. The recombinant expression system can employ a recombinant expression vector which includes an operably linked transcriptional unit comprising an assembly of at least a genetic element or elements having a regulatory role in HMPV gene expression, for example, a promoter, a structural or coding sequence which is transcribed into HMPV RNA, and appropriate transcription initiation and termination sequences. A first nucleic acid sequence is "operably linked" with a second nucleic acid sequence when the first nucleic acid sequence is placed in a functional relationship with the second nucleic acid sequence.

To produce infectious HMPV from a cDNA-expressed HMPV genome or antigenome, the genomic or antigenome is coexpressed with those HMPV or heterologous viral proteins necessary to produce a nucleocapsid capable of RNA replication, and render progeny nucleocapsids competent for both RNA replication and transcription. Transcription by the genome nucleocapsid provides the other HMPV proteins and initiates a productive infection. Alternatively, additional HMPV proteins useful for a productive infection can be supplied by coexpression.

In certain embodiments, complementing sequences encoding proteins necessary to generate a transcribing, replicating HMPV nucleocapsid are provided by one or more helper viruses. Such helper viruses can be wild type or mutant. In one embodiment, the helper virus can be distinguished phenotypically from the virus encoded by the HMPV cDNA. For example, it may be desirable to provide monoclonal antibodies that react immunologically with the helper virus but not the virus encoded by the HMPV cDNA. Such antibodies can be neutralizing antibodies. In some embodiments, the antibodies can be used in affinity chromatography to separate the helper virus from the recombinant virus. To aid the procurement of such antibodies, mutations can be introduced into the HMPV cDNA to provide antigenic diversity from the helper virus, such as in the HMPV glycoprotein genes.

Expression of the HMPV genome or antigenome and proteins from transfected plasmids can be achieved, for example, by each cDNA being under the control of a selected promoter (for example, for T7 RNA polymerase), which in turn is supplied by infection, transfection or transduction with a suitable expression system (for example, for the T7 RNA polymerase, such as a vaccinia virus MVA strain recombinant which expresses the T7 RNA polymerase, as described by Wyatt et al., Virology 210:202-205, 1995). The viral proteins, and/or T7 RNA polymerase, can also be provided by transformed mammalian cells (see Buchholz et al., J. Virol. 73:251-259, 1999) or by transfection of preformed mRNA or protein.

A HMPV genome or antigenome can be constructed for use by, for example, assembling cloned cDNA segments, representing in aggregate the complete genome or antigenome, by PCR or the like (described in, for example, U.S. Pat. Nos. 4,683,195 and 4,683,202, and PCR Protocols: A Guide to Methods and Applications, Innis et al., eds., Academic Press, San Diego, 1990) of reverse-transcribed copies HMPV mRNA or genome RNA. For example, a first construct can be generated which includes cDNAs containing the left hand end of the antigenomic, spanning from an appropriate promoter (for example, T7 RNA polymerase promoter) and assembled in an appropriate expression vector, such as a plasmid, cosmid, phage, or DNA virus vector. The vector can be modified by mutagenesis and/or insertion of a synthetic polylinker containing unique restriction sites designed to facilitate assembly. For case of preparation the N, P, L and other desired HMPV proteins can be assembled in one or more separate vectors. The right hand end of the antigenome plasmid may contain additional sequences as desired, such as a flanking ribozyme and single or tandem T7 transcriptional terminators. The ribozyme can be hammerhead type, which would yield a 3' end containing a single nonviral nucleotide, or can be any of the other suitable ribozymes such as that of hepatitis delta virus (Perrotta et al., Nature 350:434-436, 1991) that would yield a 3' end free of non-PIV nucleotides.

Alternative means to construct cDNA encoding the HMPV genome or antigenome include RT-PCR using different PCR conditions (for example, as described in Cheng et al., Proc. Natl. Acad. Sci. USA 91:5695-5699, 1994) to reduce the number of subunit cDNA components to as few as one or two pieces. In other embodiments different promoters can be used (for example, T3, SPQ or different ribozymes, such as that of a hammerhead variety. Different DNA vectors (for example, cosmids) can be used for propagation to better accommodate the larger size genome or antigenome.

By "infectious clone" or "infectious cDNA" of HMPV is meant cDNA or its product, synthetic or otherwise, as well as RNA capable of being directly incorporated into infectious virions which can be transcribed into genomic or antigenomic HMPV RNA that can serve as a template to produce the genome of infectious HMPV viral or subviral particles. As noted above, defined mutations can be introduced into an infectious HMPV clone by a variety of conventional techniques (for example, site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA constructs provide for better ease of manipulation than large cDNA constructs, and then readily assembled into a complete cDNA.

Isolated polynucleotides (for example, cDNA) encoding the HMPV genome or antigenome can be introduced into cells that can support a productive HMPV infection by transfection, electroporation, mechanical insertion, transduction or the like. Exemplary cells of use are HEp-2, FRhL-DBS2, LLC-MK2, MRC-5, baby hamster kidney (BHK), and Vero cells. Isolated polynucleotide sequences can be introduced into cultured cells by, for example, calcium phosphate-mediated transfection (Wigler et al., Cell 14:725, 1978; Corsaro et al., Somatic Cell Genetics 7:603, 1981; Graham et al., Virology 52:456, 1973, electroporation (Neumann et al., EMBO J. 1:841-845, 1982), DEAE-dextran mediated transfection (Ausubel et al., (ed.) Current Protocols in Molecular Biology, John Wiley and Sons, Inc., NY, 1987), cationic lipid-mediated transfection (Hawley-Nelson et al., Focus 15:73-79, 1993) or a commercially available transfection regent, for example, Lipofectamine-2000 (Invitrogen, Carlsbad, Calif.) or the like.

By providing infectious clones of HMPV, a wide range of alterations can be recombinantly produced within the HMPV genome (or antigenome), yielding defined mutations that specify desired phenotypic changes. The compositions and methods disclosed herein for producing recombinant HMPV permit ready detailed analysis and manipulation of HMPV molecular biology and pathogenic mechanisms using, for example, defined mutations to alter the function or expression of selected HMPV proteins. Using these methods and compositions, one can readily distinguish mutations responsible for desired phenotypic changes from silent incidental mutations, and select phenotype-specific mutations for incorporation into a recombinant HMPV genome or antigenome. In this context, a variety of nucleotide insertions, deletions, substitutions, and rearrangements can be made in the HMPV genome or antigenome during or after construction of the cDNA. For example, specific desired nucleotide sequences can be synthesized and inserted at appropriate regions in the cDNA using convenient restriction enzyme-sites. Alternatively, such techniques as site-specific mutagenesis, alanine scanning mutagenesis, PCR mutagenesis, or other such techniques well known in the art can be used to introduce mutations into the cDNA.

Recombinant modifications of HMPV can be directed toward the production of improved candidate viruses, for example, to enhance viral attenuation and immunogenicity, to ablate epitopes associated with undesirable immunopathology, to accommodate antigenic drift, etc. To achieve these and other objectives, the compositions and methods disclosed herein allow for a wide variety of modifications to be introduced into a HMPV genome or antigenome for incorporation into infectious, recombinant HMPV. For example, foreign genes or gene segments encoding antigenic determinants (for example, protective antigens or immunogenic epitopes) can be added within a HMPV clone to generate recombinant HMPVs capable of inducing immunity to both HMPV and another virus or pathogenic agent from which the antigenic determinants was/were derived. Alternatively, foreign genes can be inserted, in whole or in part, encoding modulators of the immune system, such as cytokines, to enhance immunogenicity of a candidate virus. Other mutations that can be included within HMPV clones are, for example, substitution of heterologous genes or gene segments (for example, a gene segment encoding a cytoplasmic tail of a glycoprotein gene) with a counterpart gene or gene segment in a HMPV clone. Alternatively, the relative order of genes within a HMPV clone can be changed, a HMPV genome promoter or other regulatory element can be replaced with its antigenome counterpart, or selected HMPV genes rendered non-functional (for example, by functional ablation involving introduction of a stop codon to prevent expression of the gene). In addition, the codon selection of genes such as those encoding the major protective antigens can be modified to improve the efficiency of translation. Other modifications in a HMPV clone can be made to facilitate manipulations, such as the insertion of unique restriction sites in various non-coding or coding regions of the HMPV genome or antigenome. In addition, nontranslated gene sequences or intergenic regions can be shortened or removed to increase capacity for inserting foreign sequences.

As noted above, it is often desirable to adjust the phenotype of recombinant HMPVs for use by introducing additional mutations that attenuate the virus, affect the virulence of the virus, or otherwise alter the phenotype of the recombinant virus. One of skill in the art can readily identify methods and procedures for mutagenizing, isolating and characterizing HMPV to obtain attenuated mutant strains (for example, temperature sensitive (ts), cold passaged (cp), cold-adapted (ca), small plaque (sp) and host-range restricted (hr) mutant strains) and for identifying the genetic changes that specify the attenuated phenotype (see, for example, Durbin et al., Virology 235:323-332, 1997; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), and U.S. Provisional Application No. 60/059,385, filed Sep. 19, 1997). Thus, methods are provided herein for determining replication, immunogenicity, genetic stability and immunogenic efficacy of biologically derived and recombinantly produced attenuated HMPVs in accepted model systems reasonably correlative of human activity, including hamster or rodent and non-human primate model systems.

In additional embodiments, rHMPV candidates are constructed by introduction of nucleotide or amino acid point mutations that confer attenuation or other desired phenotypes. Such mutations can involve substitution of one or more nucleotides or amino acids at a given locus, or can involve small deletions in which one or more nucleotides or amino acids at a given locus are deleted. These mutations are termed "point mutations" here to denote that each particular mutation is circumscribed. For example, a typical mutation can involve changing a single amino acid by substituting 1, 2 or 3 nucleotides in the corresponding codon. As another example, the three nucleotides might be deleted altogether, resulting in the deletion of a single amino acid in the encoded protein. Point mutations can be identified empirically, such as by systematically replacing charged amino acids in one or more of the HMPV proteins with ones that are uncharged, for example, replacing aspartate, glutamate, lysine or arginine with alanine.

Alternatively, attenuating amino acid substitutions and other mutations can be devised using existing mononegavirus mutations as a guide, for example mutations in a different "biologically derived" HMPV, non-human pneumovirus, such as an APV, or non-HMPV virus, such as a RSV or PIV. By "biologically derived" is meant any virus not produced by recombinant DNA methods. Thus, biologically derived HMPV include all naturally occurring HMPVs, including, for example, naturally occurring HMPV having a wild type genomic sequence and HMPV having allelic or mutant genomic variations from a reference wild type HMPV sequence, for example, HMPV having a mutation specifying an attenuated phenotype. Likewise, biologically derived HMPV include HMPV mutants derived from a parental HMPV by, inter alia, artificial mutagenesis and selection procedures not involving direct recombinant DNA manipulation. Attenuating mutations in biologically derived HMPV and other nonsegmented negative stranded RNA viruses for incorporation within recombinant HMPV can occur naturally or can be introduced into wild type HMPV strains and thereafter identified and characterized by well known mutagenesis and analytic procedures. For example, incompletely attenuated parental HMPV or other heterologous viral mutant strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture. In addition, known mutations in existing mononegaviruses that have been produced by recombinant methods also can serve as a guide for devising desired mutations in HMPV. Such known mutations in heterologous viruses can be ones that had been deliberately introduced by directed mutagenesis, or can be ones that arose spontaneously during the process of DNA manipulation and virus recovery and propagation, or can ones that arose in recombinantly derived viruses that were exposed subsequently to mutagenic agents or passaged in a manner designed to favor phenotypic changes, such as described above for generating mutations in biologically derived viruses.

In certain embodiments, the HMPV genome or antigenome is recombinantly modified to incorporate an attenuating mutation at an amino acid position corresponding to an amino acid position of an attenuating mutation identified in a heterologous, mutant nonsegmented negative stranded RNA virus. The virus can be either biologically derived or of recombinant origin. Based on routine sequence alignments and other analyses, mutations previously identified in a heterologous HMPV or non-HMPV virus are mapped to a corresponding position in HMPV for "transfer" (that is, introduction of an identical, conservative or non-conservative mutation, potentially including a substitution, deletion or insertion, at a homologous or corresponding position identified by the alignment) into recombinant HMPV. In many cases, an alignment of the two sequences of interest is sufficient to identify the corresponding residue in HMPV, particularly if the percent amino acid identity is substantial (for example, approximately 35-40% identity or greater) or high (for example, 70% identity or greater, such as at least about 80%, 90%, 95%, or 99% identity). In other cases, particularly when the amino acid relatedness is not substantial (for example, less than approximately 35% identity), additional heterologous related viruses can be included in the alignment in order to obtain reliably identify conserved residues that serve as markers to identify corresponding positions. In one embodiment, the percentage of sequence identity associated with the terms "substantial" or "high" or "not high" are used herein in the context of comparison of heterologous viruses from different serotypes or taxonomic groups.

A large assemblage of such candidate mutations are available for transfer into rHMPV of the current disclosure (see, for example, (Durbin et al., Virology 235:323-332, 1997; Skiadopoulos et al., J. Virol. 72:1762-1768, 1998; Skiadopoulos et al., J. Virol. 73:1374-1381, 1999; Skiadopoulos et al., Virology 260:125-35, 1999; Durbin et al., Virology 261:319-30, 1999; Newman et al., Virus Genes 24:77-92, 2002; Feller et al., Virology 276:190-201, 2000; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078); U.S. Provisional Application No. 60/059,385, filed Sep. 19, 1997; U.S. patent application Ser. No. 10/302,547, filed Nov. 21, 2002 and priority U.S. Provisional Application No. 60/331,961, filed Nov. 21, 2001; and U.S. Provisional Application No. 60/412,053, filed Sep. 18, 2002).

Within these embodiments, it is often desired to modify the recipient recombinant HMPV genome or antigenome to encode an alteration at the subject site of mutation that corresponds conservatively to the alteration identified in the heterologous mutant virus. For example, if an amino acid substitution marks a site of mutation in the mutant virus compared to the corresponding wild type sequence, then a similar substitution can be engineered at the corresponding residues in the recombinant HMPV. In one example, the substitution will specify an identical or conservative amino acid to the substitute residue present in the mutant viral protein (see below for a description of conservative substations). However, it is also possible to alter the native amino acid residue at the site of mutation non-conservatively with respect to the substitute residue in the mutant protein (for example, by using any other amino acid to disrupt or impair the function of the wild type residue). Negative stranded RNA viruses from which exemplary mutations are identified and transferred into a recombinant HMPV of the current disclosure include heterologous strains of HMPV, other non-HMPV pneumoviruses (for example, human RSV, bovine RSV, APV, pneumonia virus of mice (PVM)), PIVs (for example, HPIV1, HPIV2, HPIV3, BPIV3, and MPIV1), Newcastle disease virus (NDV), simian virus 5 (SV5), measles virus (MeV), rinderpest virus, canine distemper virus (CDV), rabies virus (RaV), and vesicular stomatitis virus (VSV), among others.

As depicted in FIGS. 26A-26F, one or more corresponding sites of mutation that specify a desired phenotypic change in a heterologous virus (for example, when indicated wild type residues at the designated positions is/are altered, for example, by substitution) is identified by conventional sequence alignment. The corresponding target sites for mutation (see, for example, boxed sites in FIGS. 26A-26F) in HMPV is thereby mapped for transfer of the mutation into a recombinant HMPV to yield attenuation or other desired phenotypic changes. More specifically, corresponding amino acids between the compared heterologous mutant and HMPV sequences represent target sites for identical or conservative transfer (for example, by recombinant engineering involving site-directed mutagenesis of a HMPV antigenomic cDNA) of the subject mutation into a recombinant HMPV. In some embodiments, attenuating and other desired mutations identified in one negative stranded RNA virus are thereby targeted for transfer (for example, to be copied identically or conservatively by substitution mutagenesis) into a corresponding position within the genome or antigenome of a recombinant HMPV of the current disclosure. Related methods for rational design of other recombinant mutant RNA viruses are described, for example, in International Application No. PCT/US00/09695, filed Apr. 12, 2000, published as WO 00/61737 on Oct. 19, 2000 corresponding to U.S. National Phase application Ser. No. 09/958,292, filed on Jan. 8, 2002, and claiming priority to U.S. Provisional Patent Application Ser. No. 60/129,006, filed on Apr. 13, 1999. Additional description pertaining to this aspect of the current disclosure is provided in Newman et al., Virus Genes 24:77-92, 2002; Feller et al., Virology 10; 276:190-201, 2000; Skiadopoulos et al., Virology 260:125-35, 1999; and Durbin et al., Virology 261:319-30, 1999.

In one exemplary embodiment, amino acid sequence alignments are made between the L gene of HMPV and the L genes of other mononegaviruses for which one or more attenuating substitutions in the L protein have been identified. This embodiment of the current disclosure is illustrated in FIGS. 26A-26F, which depict sequence alignments of various segments of the putative L protein of HMPV with corresponding segments of L proteins of a number of other mononegaviruses in which attenuating mutations have been mapped. As exemplified in FIGS. 26A-26F, various mutations identified in the L gene of a heterologous negative stranded RNA virus can be incorporated into recombinant HMPV to yield attenuation or other desired phenotypic changes. These figures provide exemplary, partial L gene sequence alignments between an HMPV wild type virus and the indicated viruses (including as examples, a different HMPV, RSV, HPIV1 HPIV3, and BPIV3). The examples of attenuating mutations include ones identified in viruses of biological or recombinant origin. The alignments are employed to identify regions containing known attenuating mutations in the heterologous virus.

Figure 26A:
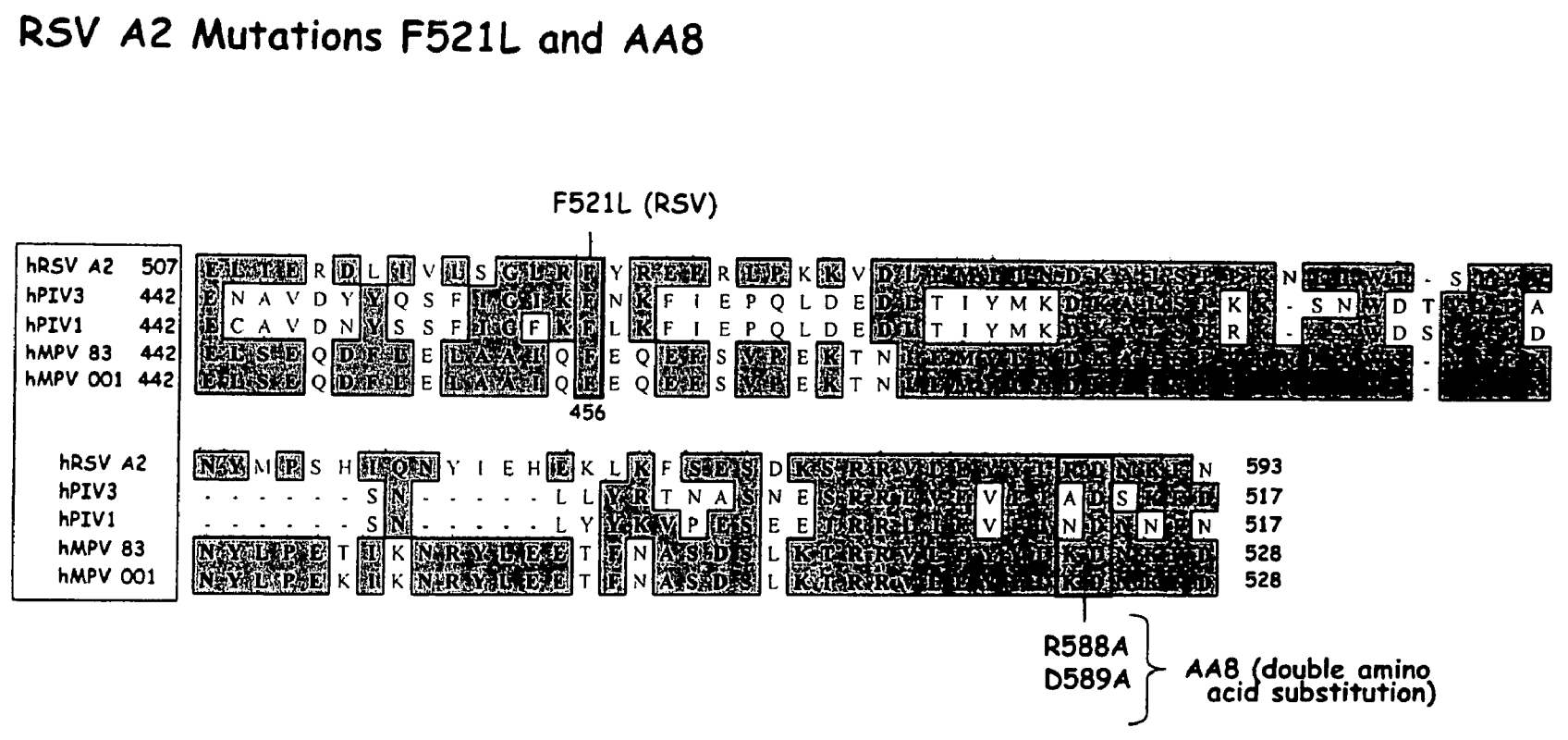
Figure 26B:
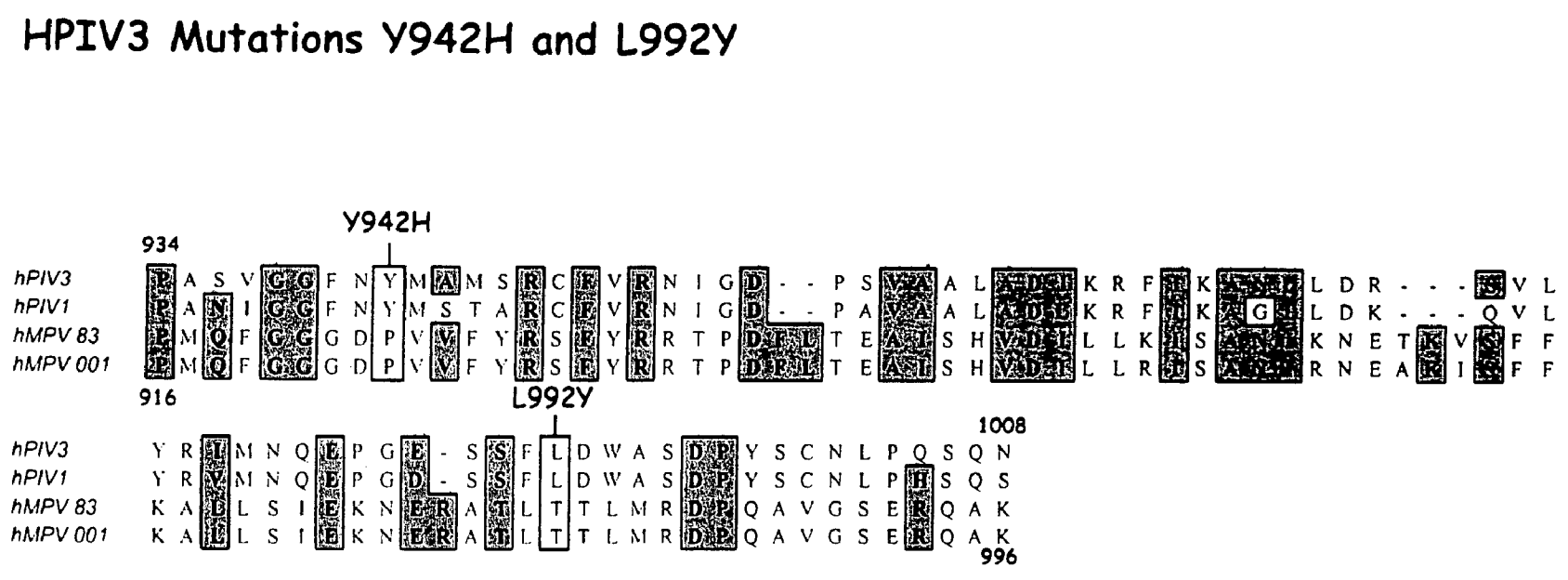
Figure 26D:
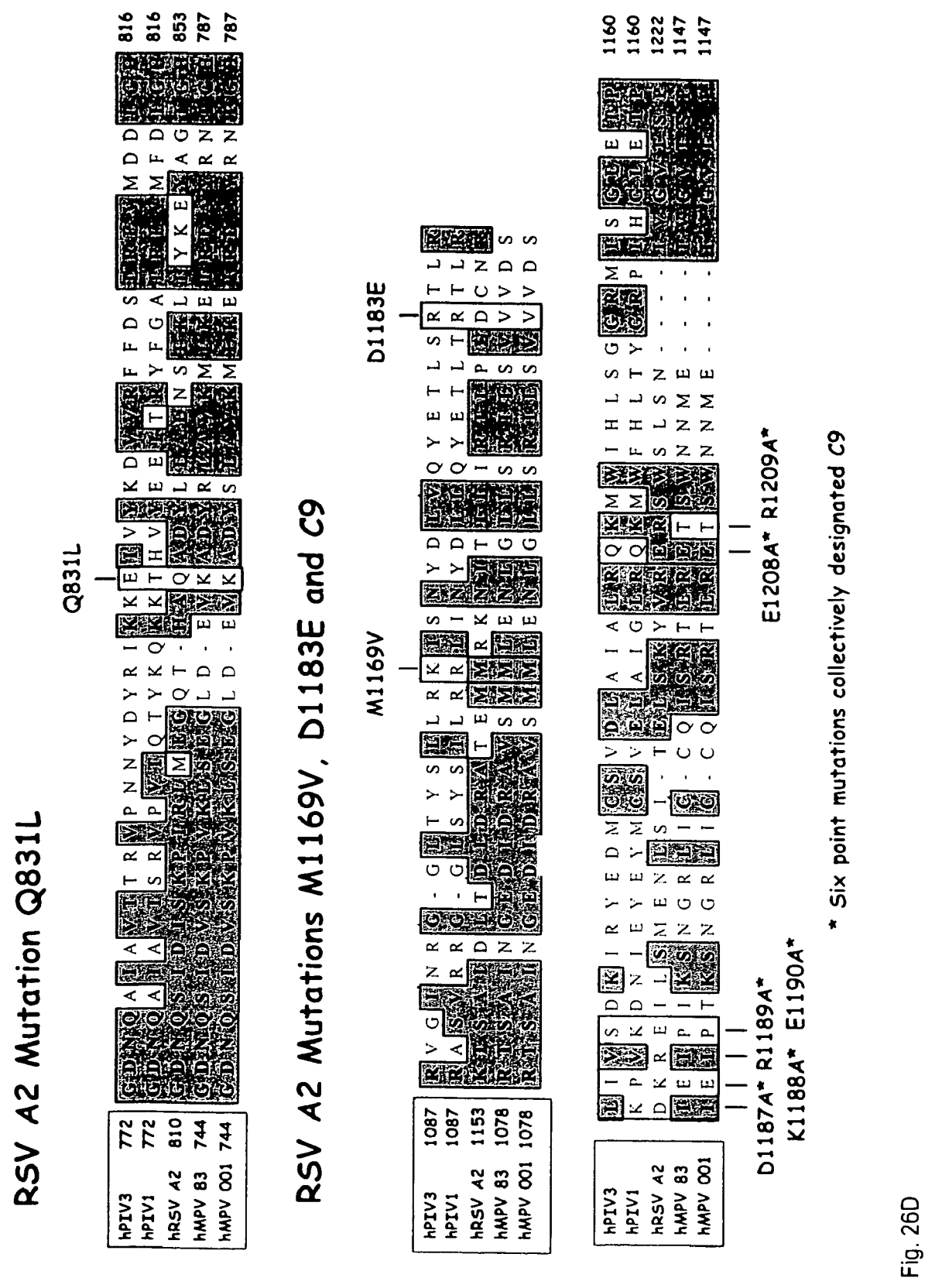
Figure 26E:
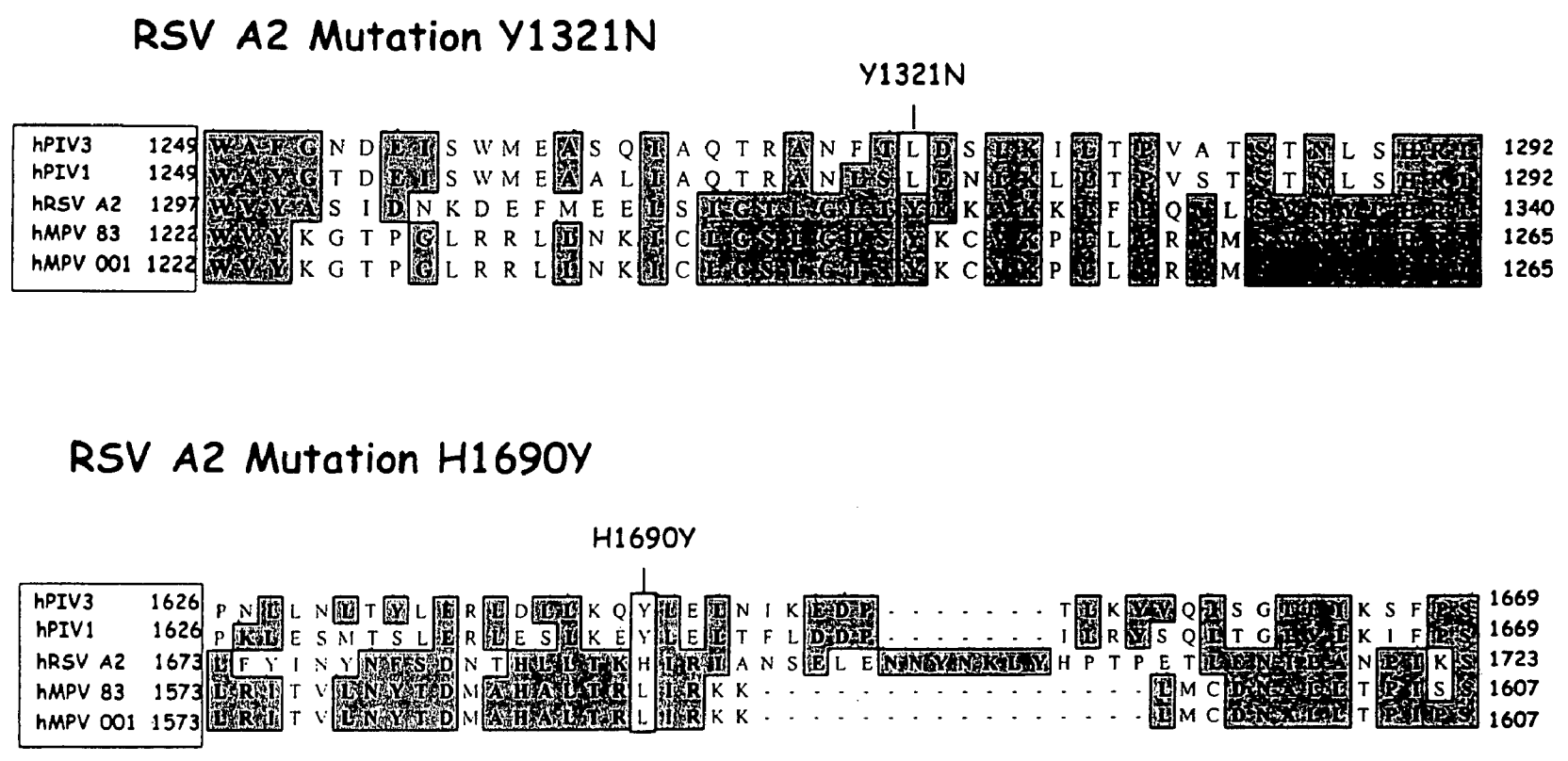
Figure 26F:
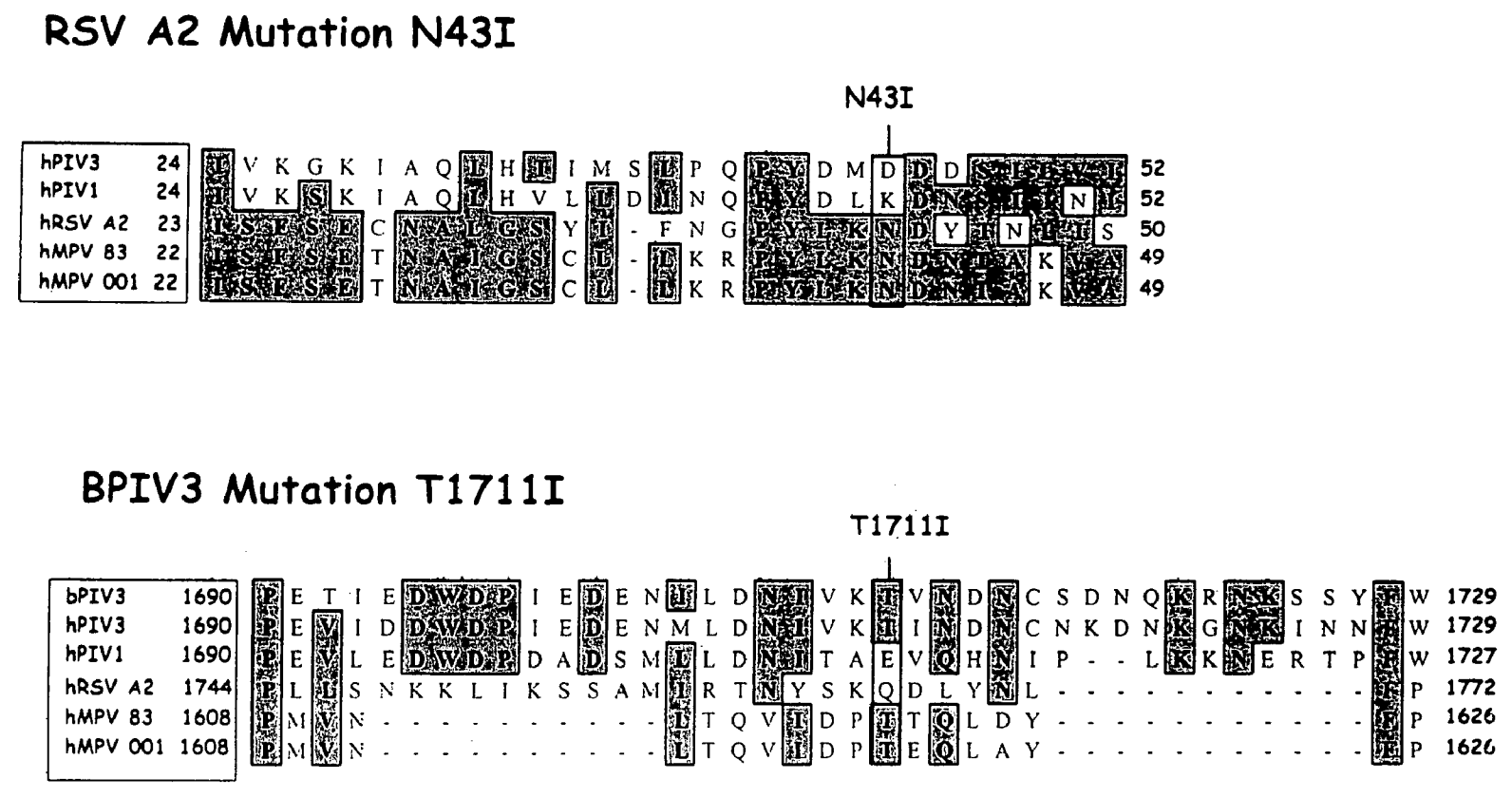

FIGS. 26A-26F illustrate the identification and mapping of various exemplary attenuating mutations in the L gene for transfer into rHMPV (note that the numbers at the left indicate the positional reference number of the first residue in the partial sequence shown, and the numbers at the right indicate the positional reference number of the terminal residue in the partial sequence). FIG. 26A shows a Phenylalanine-521 to Leucine (F521L) substitution in the L protein specified by a mutation in the L gene of an RSV cold-passage temperature-sensitive (cpts) mutant cpts530 (Juhasz et al., J. Virol. 71:5814-9, 1999). Also shown is an attenuating double mutation of Arginine-588-Alanine (R588A) and Aspartate-589-Alanine (D589A) that was originally developed in RSV (Tang et al., Virology 302:207-16, 2002). FIG. 26B shows the positions of attenuating Tyrosine-942-Histidine (Y942H) and Leucine-992-Tyrosine (L992Y) mutations identified in the PIV3 cp45 vaccine candidate (Skiadopoulos et al. J. Virol. 72:31762-8, 1998; U.S. patent application Ser. No. 10/302,547, filed Nov. 21, 2002 and priority U.S. Provisional Application No. 60/331,961, filed Nov. 21, 2001; and U.S. Provisional Application No. 60/412,053, filed Sep. 18, 2002). FIG. 26C shows the positions of the attenuating Isoleucine-1103-Valine (I1103V) mutation originally identified in BPIV3 (Haller et al., Virology 288:342-50, 2001), the attenuating Threonine-1558-Isoleucine (T1558I) mutation identified in PIV3 cp45 (Skiadopoulos et al., J. Virol. 72:31762-8, 1998), and the Cysteine-319-Tyrosine (C)319Y) mutation identified the attenuated cpRSV vaccine candidate (Connors et al., Virology 208:478-84, 1995). FIG. 26D shows the positions of the attenuating Glutamine-831-Leucine (Q831L) mutation identified in cpts248 RSV (Firestone et al., Virology 225:419-22, 1996), the attenuating Methinone-1169-Valine (M1169V) mutation identified in the RSV mutant cpts530/109 (Juhasz et al., J. Virol. 73:5176-80), the Aspartate-1183-Glutamate (D1183) mutation identified in the RSV mutant cpts248/404 (Firestone et al., Virology 225:419-22, 1996), and the combination of six point mutations that constitute the attenuating C9 cluster characterized in recombinant RSV (Tang et al., Virology 302:207-16, 2002): Aspartate-1187-Alanine (D1187A), Lysine-1188-Alanine (K1188A), Arginine-1189-Alanine (R1189A), Glutamate-1190-Alanine (E1190A), Glutamate-1208-Alanine (E1208A), and Arginine-1209-Alanine (R1209A). FIG. 26E shows the position of the attenuating Tyrosine-1321-Asparagine (Y1321N) mutation of RSV cpts530/1030 (Whitehead et al., J. Virol. 73:871-7, 1999), and the Histidine-1690-Tyrosine (H1690Y) mutation of the attenuated cpRSV derivative (Connors et al., Virology 208, 478-84, 1995). FIG. 26F shows the positions of an attenuating Asparagine-43-Isoleucine (N43I) mutation identified in the cpts RSV mutant 248/955, and the attenuating Threonine-1711-Isoleucine (T1711I) mutation characterized in the chimeric virus rHPIV3-L$_B$, consisting of HPIV3 in which the L gene was replaced by that of BPIV3 (Skiadopoulos et al., J. Virol. 77:1141-8, 2003).

The foregoing alignments show, for example, that the F521 residue in the RSV sequence is exactly conserved among most of the other mononegaviruses examined (23 out of 24 paramyxoviruses and 1 out of 3 rhabdoviruses) and, in particular, is present in HMPV. It should be noted that the amino acid position of the corresponding residue is not the same in each L protein, reflecting differences in length as well as small deletions and insertions elsewhere in the various individual molecules. Thus, the corresponding residue is F456 in HMPV. From this comparative mapping analysis, the F456 residue in HMPV is identified as a target for either an identical, conservative, or even non-conservative amino acid substitution (for example, substitution of the F456 residue by a leucine, or by a conservative or non-conservative amino acid as compared to leucine). The same alignment (FIG. 26A) shows that the D589 assignment is also exactly conserved in each of sequences. The R588 assignment is not conserved in each, but it is represented by the homologous assignment of Lysine in HMPV. With respect to the attenuating Tyrosine-942-Histidine (Y942H) and Leucine-992-Tyrosine (L992Y) mutations of PIV3 cp45, in both of these instances the exact amino acid assignment was not conserved, but the presence of various highly-conserved residues throughout the alignment show that these positions correspond (FIG. 26B). Positional correspondence in this context indicates that the aligned, corresponding target site for mutation (whether it is occupied by an amino acid that is identical, conservative or divergent in structural character compared the corresponding residue in the wild type (for example, a non-attenuated parent) sequence of the heterologous virus) will often yield an attenuation or other desired phenotype in a rHMPV upon mutation from the HMPV wild type sequence to a different residue (that is, to a residue identity that is the same, conservative, or even distinct structurally in comparison to the corresponding residue in the heterologous mutant).

In addition to the foregoing L gene mutations, two temperature sensitive (ts) mutations that were reported in the P protein of recombinant RSV, namely Glycine-172-Serine and Glutamate-176-Glycine (Lu et al., J. Virol. 76:2871-80, 2002), can be transferred to yield a predicted attenuation phenotype in a rHMPV P), by altering the corresponding one or both of the HMPV residues Glycine-213 and Glutamate-217, respectively. Likewise, a mutation in the N protein of the attenuated derivative cpRSV, specifying a Valine-267-Isoleucine substitution (Connors et al. Virology 208:478-84, 1996), maps to Serine-268 in HMPV, whereby an Ile or other, conservative or non-conservative, substitution of this residue in a rHMPV can yield useful candidates for identification of additional attenuated derivatives. In the same manner, two mutations in the F protein of cpRSV, namely Glutamate-218-Alanine and Threonine-523-Isoleucine (Connors et al. Virology 208:478-84, 1996), correspond to Lysine-188 and Threonine-489, respectively, in the HMPV F protein, which therefore represent target sites for introduction of an attenuating amino acid substitution in rHMPV.

In other embodiments, mutations in a cis-acting regulatory sequence or other non-coding sequence are identified in a heterologous virus (including biologically or otherwise derived mutant HMPV of the same or different strain, subtype, species, RSV, PIV, APV, etc.) and incorporated in a rHMPV of the current disclosure. For example, the identification of the GS and GE motifs identifies these as targets for mutagenesis. The short, circumscribed nature of these signals is amenable to a systematic evaluation of the effects of mutations at each position. Mutations in RNA signals such as these can be readily assayed in a mini-replicon system as well as in complete virus.

FIG. 28 shows an example of transferring a mutation that involves a cis-acting RNA signal. A potent attenuating point mutation identified for the cpts 248/404 derivative of RSV involves a point mutation in the GS signal of the M2 gene: specifically, the T residue (positive sense) at position nine was changed to C (see, for example, Whitehead et al., Virology 247:232-9, 1998). In the proposed GS signal of HMPV, a T residue at position nine is conserved in each of the proposed HMPV genes (FIG. 28). This substitution can be made in any of the HMPV genes.

In accordance with the foregoing description, a large panel of desired mutations identified in heterologous viruses can be "transferred" into a rHMPV, even in cases of low sequence relatedness. In these embodiments, there is not a strict requirement that the corresponding wild type or final mutant amino acid assignment be identical to that of the heterologous virus. Also, rather than an amino acid substitution, it is possible to delete one or several amino acids or, alternatively, insert one or several amino acids. In designing substitution mutations for HMPV, a useful strategy is to evaluate all possible alternative amino acid assignments at this position. This is a useful method for evaluating the full range of possible attenuation phenotypes involving this position, and can produce mutants exhibiting a range of temperature sensitivity and attenuation (see, for example, U.S. patent application Ser. No. 10/302,547, filed Nov. 21, 2002 and priority U.S. Provisional Application No. 60/331,961, filed Nov. 21, 2001; and U.S. Provisional Application No. 60/412,053, filed Sep. 18, 2002). In addition, the choice of codon for substitution can be made to involve the greatest number of nucleotide differences relative to both the wild type and to any possible alternative amino acid assignments that are found to not yield attenuated phenotypes. This has the effect of reducing the probability of reversion or mutation to lose the attenuated phenotype. Specifically, it is estimated that the frequency of reversion at any single nucleotide position is $10^{-4}$ to $10^{-5}$, and hence the frequency of reversion/mutation at two nucleotide positions is $10^{-8}$ to $10^{-10}$, and the frequency of reversion/mutation involving three nucleotides is $10^{-12}$ to $10^{-15}$. Thus, point mutations involving multiple nucleotide substitutions can greatly increase genetic and phenotypic stability. Also, the mutation can be designed to involve deletion of a single amino acid or more than one amino acid, which can reduce the possibility of reversion.

It should be noted that the mutations illustrated in FIGS. 26A-26F are only exemplary by virtue that the depicted mapping exercise was limited to examples involving amino acid changes in the L protein, whereas the same strategy can be applied in accordance with the tools and description provided herein to transfer attenuating mutations involving any viral protein. For example, two ts mutations that were developed in the P protein of recombinant RSV, namely Glycine-172-Serine and Glutamate-176-Glycine (Lu et al., J. Virol. 76:2871-80, 2002), correspond to HMPV P residues Glycine-213 and Glutamate-217, respectively. A mutation in the N protein of the attenuated derivative cpRSV, namely Valine-267-Isoleucine (Connors et al. Virology 208:478-84, 1996), corresponds to Serine-268 in HMPV. Also, two mutations in the F protein of cpRSV, namely Glutamate-218-Alanine and Threonine-523-Isoleucine (Connors et al. Virology 208:478-84, 1996), correspond to Lysine-188 and Threonine-489, respectively, in the HMPV F protein. Thus, any known mutation having a desirable phenotypic property present in any nucleotide or amino acid sequence is a useful candidate for incorporation in rHMPV by mutation of corresponding residues in a rHMPV RNA or protein employing the novel tools and methods of the current disclosure.

Another method for devising attenuating or otherwise desirable amino acid substitution mutations involve "charge-to-alanine" or "alanine scanning" mutagenesis where, for example, one or more charged amino acid residues are each changed to alanine residues (Wertman et al., Genetics 132: 337-50, 1992; Hassett and Condit, Proc. Natl. Acad. Sci. USA 91:4554-58, 1994; Tang et al., Virology 302:207-16, 2002. A typical target is a pair of residues, but residues can be changed singly or in larger combinations. It is often useful to systematically change ("scan") residues across an encoded protein. Any protein can be a target, although the L protein is the most common locus of mutations in attenuated mononegaviruses. Alternatively, one advantage of this strategy is that one can target proteins that are not represented in available mutants. This strategy can be readily addressed with the methods disclosed herein. In particular, the minireplicon system offers a method for screening mutations in the N, P, L and M2-1 proteins. In that strategy, mutations are introduced into the appropriate support plasmid, such as the one encoding the L protein, and evaluated for the ability to direct the replication and transcription of a minigenome containing a reporter gene. For example, the assay can be done in replica at 32° C. and 37° C. (or any temperature in the range of 35° C.-41° C.) to identify ts mutations that operate at the lower, permissive temperature and are inhibited at the higher temperature. This offers a more rapid and technically simple method for performing an initial screening, after which appropriate mutations can be introduced into complete recombinant virus.

Thus, the methods disclosed herein can be used to develop mutations that confer improved properties to HMPV for the purposes of developing an immunogenic composition or for other purposes, such as purifying viral proteins. Mutations can be optimized, such as by evaluating all possible amino acid or nucleotide assignments at a given position, or by making amino acid changes involve codon choices that will be less likely to revert to wild type or to an alternative assignment that yields a wild type phenotype. Other changes can be made that fundamentally alter the viral backbone, such as changes in gene order or movement of major protective antigen genes to a promoter-proximal position. Importantly, these various modifications can be introduced into rHMPV in combination to develop viruses for use in immunogenic compositions or for other purposes. The methods described herein allows for the systematic modification of viruses as necessary, such as the introduction of additional attenuating mutations into a recombinant virus in response to clinical studies.

As noted above, production of a sufficiently attenuated biologically derived HMPV or other viral mutant can be accomplished by several known methods. One such procedure involves subjecting a partially attenuated virus to passage in cell culture at progressively lower, attenuating temperatures. For example, partially attenuated mutants are produced by passage in cell cultures at suboptimal temperatures. Thus, a cold-adapted (ca) mutant or other partially attenuated HMPV strain is adapted to efficient growth at a lower temperature by passage in culture. This selection of mutant HMPV during cold-passage substantially reduces any residual virulence in the derivative strains as compared to the partially attenuated parent. Alternatively, specific mutations can be introduced into biologically derived HMPV by subjecting a partially attenuated parent virus to chemical mutagenesis, for example, to introduce ts mutations or, in the case of viruses which are already ts, additional ts mutations sufficient to confer increased attenuation and/or stability of the ts phenotype of the attenuated derivative. Means for the introduction of ts mutations into HMPV include replication of the virus in the presence of a mutagen such as 5-fluorouridine according to generally known procedures. Other chemical mutagens can also be used. Attenuation can result from a ts mutation in almost any HMPV gene, although a particularly amenable target for this purpose has been found to be the polymerase (L) gene. The level of temperature sensitivity of replication in exemplary attenuated HMPV can be determined by comparing its replication at a permissive temperature with that at several restrictive temperatures. The lowest temperature at which the replication of the virus is reduced 100-fold or more in comparison with its replication at the permissive temperature is termed the "shutoff temperature." In experimental animals and humans, both the replication and virulence of HMPV correlate with the mutant's shutoff temperature.

From biologically and recombinantly derived HMPV and other nonsegmented negative stranded RNA viruses, a large "menu" of attenuating mutations is identifiable by the teachings herein, each of which can be combined with any other mutations for adjusting the level of attenuation, immunogenicity and genetic stability in recombinant HMPV. In this context, many recombinant HMPV candidates will include one or more, and preferably two or more, mutations from a biologically derived HMPV or other heterologous viral mutant, for example, any one or combination of mutations identified in APV, HPIV, BPIV3, and/or RSV. Preferred recombinant HMPVs can incorporate a plurality of mutations thus identified. Often, these mutations are stabilized against reversion in recombinant HMPV by multiple nucleotide substitutions in a codon specifying each mutation.

Mutations compiled into a "menu" as described above are introduced as desired, singly or in combination, to adjust recombinant HMPV to an appropriate level of attenuation, immunogenicity, genetic resistance to reversion from an attenuated phenotype, etc. In accordance with the foregoing description, the ability to produce infectious recombinant HMPV from cDNA permits introduction of specific engineered changes within the recombinant HMPV. In particular, infectious, recombinant HMPVs can be employed for further identification of specific mutations in biologically derived, attenuated HMPV strains, for example mutations that specify ts, ca, att and other phenotypes. Desired mutations identified by this and other methods are introduced into recombinant HMPV candidate strains. The capability of producing virus from cDNA allows for routine incorporation of these mutations, individually or in various selected combinations, into a full-length cDNA clone, where after the phenotypes of rescued recombinant viruses containing the introduced mutations can be readily determined.

By identifying and incorporating specific mutations associated with desired phenotypes, for example, a ca or ts phenotype, into infectious recombinant HMPV, additional site-specific modifications at, or within close proximity to, the identified mutation are identified. Whereas most attenuating mutations produced in biologically derived HMPVs are single nucleotide changes, other "site specific" mutations can also be incorporated by recombinant techniques into a recombinant HMPV. As used herein, site-specific mutations include insertions, substitutions, deletions or rearrangements of from about 1 to about 3, up to about 5-15 or more altered nucleotides (for example, altered from a wild type HMPV sequence, from a sequence of a selected mutant HMPV strain, or from a parent recombinant HMPV clone subjected to mutagenesis). Such site-specific mutations can be incorporated at, or within the region of, a selected, biologically derived point mutation. Alternatively, the mutations can be introduced in various other contexts within a recombinant HMPV clone, for example at or near a cis-acting regulatory sequence or nucleotide sequence encoding a protein active site, binding site, immunogenic epitope, etc.

Site-specific recombinant HMPV mutants typically retain a desired attenuating phenotype, but can additionally exhibit altered phenotypic characteristics unrelated to attenuation, for example, enhanced or broadened immunogenicity, and/or improved growth. Further examples of desired, site-specific mutants include recombinant HMPV mutants engineered to incorporate additional, stabilizing nucleotide mutations in a codon specifying an attenuating point mutation. Where possible, two or more nucleotide substitutions are introduced at codons that specify attenuating amino acid changes in a parent mutant or recombinant HMPV clone, yielding a recombinant HMPV with greater genetic resistance to reversion from an attenuated phenotype. In other embodiments, site-specific nucleotide substitutions, additions, deletions or rearrangements are introduced upstream or downstream, e.g., from about 1 to about 3, about 5-10 and tip to 15 nucleotides or more 5' or 3', relative to a targeted nucleotide position, for example, to construct or ablate an existing cis-acting regulatory element.

In addition to single and multiple point mutations and site-specific mutations, changes to the recombinant HMPV include deletions, insertions, substitutions or rearrangements of one or more genes or genome segments to increase, decrease, ablate or otherwise alter gene expression. Expression of one or more non-essential genes can be reduced or ablated by modifying the recombinant HMPV genome or antigenome, for example, to incorporate a mutation that alters the coding assignment of an initiation codon or mutations that introduce one or one or more stop codons. Alternatively, one or more non-essential genes or genome segments can be deleted in whole or in part to render the corresponding proteins partially or entirely non-functional or to disrupt protein expression altogether. Exemplary recombinant HMPV within these aspects of the current disclosure are provided herein that exhibit partial or complete deletions of the G, SH and/or M2-2 ORFs, including an exemplary mutant that has both the G and SH genes deleted. These and other recombinants can be engineered, and selected to possess highly desirable phenotypic characteristics for development of immunogenic compositions. For example, these modifications can specify one or more desired phenotypic changes including (i) altered growth properties in cell culture, (ii) attenuation in the upper and/or lower respiratory tract of mammals, (iii) a change in viral plaque size, (iv) a change in cytopathic effect, (v) a change in immunogenicity, and (vi) a change in RNA replication and gene expression.

Thus a recombinant HMPV can incorporate one or more partial or complete gene deletions, knock out mutations, or mutations that simply reduce or increase expression of an HMPV gene. This can be achieved, for example, by introducing a frame shift mutation or termination codon within a selected coding sequence, altering translational start sites, changing the position of a gene or introducing an upstream start codon to alter its rate of expression, changing GS and/or GE transcription signals to alter phenotype, or modifying an RNA editing site (for example, growth, temperature restrictions on transcription, etc.). In several examples, recombinant HMPVs are provided in which expression of one or more genes, for example, a SH, G, or M2-2 ORF, is ablated at the translational or transcriptional level without deletion of the gene or of a segment thereof, by, for example, introducing multiple translational termination codons into a translational ORF, altering an initiation codon, or modifying an editing site. In one embodiment, expression of the M2-2 ORF is ablated by removal of both potential translational start codons, in combination with partial deletion of the M2-2 ORF. These and other forms of knock-out virus will often exhibit reduced growth rates and small plaque sizes in tissue culture. This, additional novel types of attenuating mutations are provided herein which ablate or alter expression of a viral gene. In this context, knockout virus phenotypes produced without (deletion of a gene or genome segment can be alternatively produced by deletion mutagenesis, as described, to effectively preclude correcting mutations that may restore synthesis of a target protein. Other gene knock-outs can be made using alternate designs and methods that are well known in the art (as described, for example, in (Kretschmer et al., Virology 216:309-316, 1996; Radecke et al., Virology 217:418-421, 1996; Kato et al., EMBO J. 16:578-587, 1987; and Schneider et al., Virology 277:314-322, 1996).

Nucleotide modifications that may be introduced into recombinant HMPV constructs can alter small numbers of bases (for example, from 15-30 bases, up to 35-50 bases or more), large blocks of nucleotides (for example, about 50-100, about 100-300, about 300-500, about 500-1,000 bases), or nearly complete or complete genes (for example, about 1,000-1,500 nucleotides, about 1,500-2,500 nucleotides, about 2,500-5,000, nucleotides, about 5,000-6,0000 nucleotides or more) in the vector genome or antigenome or heterologous, donor gene or genome segment, depending upon the nature of the change (that is, a small number of bases may be changed to insert or ablate an immunogenic epitope or change a small genome segment, whereas large blocks of bases are involved when genes or large genome segments are added, substituted, deleted or rearranged).

In related aspects, the current disclosure provides for supplementation of mutations adopted into a recombinant HMPV clone from biologically derived HMPV, for example, ca and ts mutations, with additional types of mutations involving the same or different genes in a further modified recombinant HMPV. Each of the HMPV genes can be selectively altered in terms of expression levels, or can be added, deleted, substituted or rearranged, in whole or in part, alone or in combination with other desired modifications, to yield a recombinant HMPV exhibiting novel characteristics. Thus, in addition to or in combination with attenuating mutations adopted from biologically derived HMPV and/or non-HMPV mutants, the current disclosure also provides a range of additional methods for attenuating or otherwise modifying the phenotype of a recombinant HMPV based on recombinant engineering of infectious HMPV clones. A variety of alterations can be produced in an isolated polynucleotide sequence encoding a targeted gene or genome segment, including a donor or recipient gene or genome segment in a recombinant HMPV genome or antigenome for incorporation into partially attenuated, infectious clones. More specifically, to achieve desired structural and phenotypic changes in recombinant HMPV, the current disclosure allows for introduction of modifications which delete, substitute, introduce, or rearrange a selected nucleotide or nucleotide sequence from a parent genome or antigenome, as well as mutations which delete, substitute, introduce or rearrange whole genes or genome segments, within a recombinant HMPV.

Thus provided are modifications in recombinant HMPV which simply alter or ablate expression of a selected gene, for example, by introducing a termination codon within a selected HMPV coding sequence or altering its translational start site or RNA editing site, changing the position of a HMPV gene relative to an operably linked promoter, introducing an upstream start codon to alter rates of expression, modifying (for example, by changing position, altering an existing sequence, or substituting an existing sequence with a heterologous sequence) GS and/or GE transcription signals to alter phenotype (for example, growth, temperature restrictions on transcription, etc.), and various other deletions, substitutions, additions and rearrangements that specify quantitative or qualitative changes in viral replication, transcription of selected genes, or translation of selected proteins. In this context, any HMPV gene or genome segment which is not essential for growth can be ablated or otherwise-modified in a recombinant HMPV to yield desired effects on virulence, pathogenesis, immunogenicity and other phenotypic characters. In addition to coding sequences, noncoding, leader, trailer and intergenic regions can be similarly deleted, substituted or modified and their phenotypic effects readily analyzed, for example, by the use of minireplicons, and the recombinant HMPV described herein.

In addition to these changes, the order of genes in a recombinant HMPV construct can be changed, a HMPV genome promoter replaced with its antigenome counterpart or vice versa, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Other mutations for incorporation into recombinant HMPV constructs of the current disclosure include mutations directed toward cis-acting signals, which can be readily identified, for example, by mutational analysis of HMPV minigenomes. For example, insertional and deletional analysis of the leader, trailer and/or flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also can be employed to identify many mutations that affect RNA replication or transcription. Any of these mutations can be inserted into a chimeric HMPV antigenome or genome as described herein. Evaluation and manipulation of transacting proteins and cis-acting RNA sequences using the complete antigenome cDNA is assisted by the use of HMPV minigenomes as described in the above-incorporated references.

Additional mutations within recombinant HMPVs can also include replacement of the 3' end of genome with its counterpart from antigenome or vice versa, which is associated with changes in RNA replication and transcription. In one exemplary embodiment, the level of expression of specific HMPV proteins, such as the protective HN and/or F antigens, can be increased by substituting the natural sequences with ones which have been made synthetically and designed to be consistent with efficient translation. In this context, it has been shown that codon usage can be a major factor in the level of translation of mammalian viral proteins (Haas et al., Current Biol. 6:315-324, 1996). Optimization by recombinant methods of the codon usage of the mRNAs encoding one or more immunogenic glycoproteins of recombinant HMPV will provide improved expression for these genes.

In another exemplary embodiment, a sequence surrounding a translational start site (preferably including a nucleotide in the −3 position relative to the AUG start site) of a selected HMPV gene or donor gene incorporated in an HMPV vector is modified, alone or in combination with introduction of an upstream start codon, to modulate gene expression by specifying up- or down-regulation of translation. Alternatively, or in combination with other recombinant modifications disclosed herein, gene expression of a recombinant HMPV can be modulated by altering a transcriptional GS or GE signal of any selected genes of the virus. In alternative embodiments, levels of gene expression in a recombinant HMPV candidate are modified at the level of transcription. In one aspect, the position of a selected gene in the HMPV gene map can be changed to a more promoter-proximal or promoter-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild type levels often attended by a commensurate decrease in expression levels for reciprocally, positionally substituted genes. These and other transpositioning changes yield novel recombinant HMPVs having attenuated phenotypes, for example due to decreased expression of selected viral proteins involved in RNA replication, or having other desirable properties such as increased antigen expression.

In the latter context, any one or combination of antigenic glycoproteins, prospectively including F, G, and SH, or antigenic determinants thereof can be produced at elevated or decreased levels (or with otherwise enhanced immunogenic activity) by, for example, changing the promoter-relative position of the subject gene or genome segment. For example, the wild type gene order of the SH, G and F ORFs of HMPV are located at gene positions 6, 7 and 4, respectively. Recombinantly altering the promoter proximity of one or more of these genes will modulated its expression, and/or expression of normally "upstream" and "downstream" genes. The change in gene expression due to the relocation of genes or to the addition of a second copy can have other desirable effects, such as increased or decreased growth in vitro or in vivo. In exemplary embodiments, placement of putative protective antigen genes such as SH, G, and F more proximal to the promoter, either singly, as a pair, or as a triplet, will result in more efficient expression. As described herein, exemplary embodiments of "promoter-shifted" HMPV are provided wherein the position of the SH-G gene pair was altered, for example by moving the pair from its wild type gene order position following the M2 gene to a position preceding the F gene. This resulted in a gene order in that region of the genome that mimics that of RSV. In another exemplary embodiment, the SH-G pair was moved to be upstream of the F gene, and a second copy of the pair was inserted, resulting in multiple copies of the SH and G prospective antigens. In yet additional embodiments, the prospective antigens comprising one or more of the G and F proteins are modified in their expression by promoter-relative shifting of these genes (having wild type gene order positions at the 7th and 4th gene positions, respectively, in the HMPV genome map) to more promoter-proximal positions.

In other embodiments, recombinant HMPVs useful in immunogenic compositions can be conveniently modified to accommodate antigenic drift in circulating virus. In this context, the Examples below provide the complete sequence for an HMPV genome, and also provide a detailed comparison of complete genome sequences for HMPV isolates representing two distinct antigenic subgroups of HMPV, that are generally comparable in sequence divergence to the antigenic subgroups of HRSV. Identification and characterization of these distinct antigenic subgroups, including detailed mapping of their prospective antigenic glycoprotein gene structure, provides for construction of novel recombinant HMPVs for use in immunogenic compositions to elicit an immune response against one or more HMPV strains, including in bivalent immunogenic composition to immunize against multiple HMPV strains and/or accommodate antigenic drift. Typically the recombinant HMPV will have a modification in one or more of the Sit, G, and/or F glycoproteins. For example, an entire SH, G, and/or F gene, or a genome segment encoding a particular antigenic determinant (for example, immunogenic region or epitopes) thereof), from one HMPV strain or group can be incorporated into a recombinant HMPV genome or antigenome cDNA by replacement of a corresponding region in a recipient clone of a different HMPV strain or group, or by adding one or more copies of the gene, such that multiple antigenic forms are represented in the recombinant virus. Progeny virus produced from the modified recombinant HMPV can then be used in immunization protocols against multiple, and emerging, HMPV strains.

In certain aspects of the current disclosure, replacement of a HMPV coding sequence or non-coding sequence (for example, a promoter, GE, GS, intergenic or other cis-acting element) with a heterologous (for example, non-HMPV) counterpart yields chimeric HMPV having a variety of possible attenuating and other phenotypic effects. For example, host range and other desired effects can be engineered by importing an APV or other non-HMPV virus (for example, RSV, SV5, SV41, NDV, PIV) protein, protein domain, gene or genome segment into a recombinant HMPV "background" genome or antigenome, wherein the heterologous or "donor" gene or genome segment does not function efficiently in a human cell, for example, from incompatibility of the heterologous sequence or protein with a biologically interactive HMPV sequence or protein (that is, a sequence or protein that ordinarily cooperates with the substituted sequence or protein for viral transcription, translation, assembly, etc.) or, more typically in a host range restriction, with a cellular protein or some other aspect other cellular milieu which is different between the permissive and less permissive host. In exemplary embodiments, APV, pneumovirus of mice, or RSV sequences are selected for introduction into HMPV based on aspects of HMPV structure and function described herein.

Methods are provided herein for attenuating recombinant HMPV candidates based on the construction of chimeras between HMPV and a non-human pneumovirus or other negative stranded RNA virus, for example APV, RSV, HPIV, MPIV1 (Sendai virus), BPIV3, SV5, SV4I, and/or NDV (for example, as disclosed in U.S. patent application Ser. No. 09/586,479, filed Jun. 1, 2000 by Schmidt et al. (corresponding to PCT Publication WO 01/04320); Schmidt et al., J. Virol. 74:8922-9, 2000). In exemplary embodiments, the recombinant HMPV genome or antigenome is combined with a heterologous gene or genome segment, such as an N, P, M, or L, ORF derived from a non-HMPV paramyxovirus.

Paramyxoviruses are enveloped RNA viruses that include two subfamilies (Paramyxovirinae and Pneumovirinae). Subfamily Paramyxovirinae has five different genera, including Respirovirus (containing parainfluenza viruses 1 and 3), Rubulavirus (containing parainfluenza viruses 2 and 4 and mumps), and Morbillivirus (containing measles and canine distemper viruses). Subfamily Pneumovirinae has two genera, namely Pneumovirus (containing RSV) and Metapneumovirus (containing HMPV). Paramyxoviruses encoded 6-11 proteins. Proteins common to all paramyxoviruses include the nucleocapsid N protein that associates tightly with the RNA genome to form the nucleocapsid, the phosphoprotein P and large L polymerase protein that also associate with the nucleocapsid, the matrix M protein that associates with the inner face of the viral envelope, the transmembrane fusion F glycoprotein that mediates penetration, and the attachment protein that, depending on the virus, is called glycoprotein G, or the hemagglutinin HA or the hemagglutinin-neuraminidase HN. Other proteins are found in some viruses but not others, such as the nonstructural NS1 and NS2 proteins of RSV, the M2-1 and M2-2 proteins found in RSV and, as disclosed here, in HMPV, the SH protein that is found in mumps, simian virus 5, RSV and HMPV, and the C, D and V proteins found in certain parainfluenza viruses. The sequences of non-HMPV HN, M, N, P, L, F, G, and SH proteins, and nucleic acids encoding these proteins are known in the art (see, Lamb, R A and Kolakofsky, D. pp 1305-1340 in Fields Virology, 4$^{th}$ addition, Knipe and Howley (eds) Lippincott Williams and Wilkins, Philadelphia, 2001, Chanock, Murphy and Collins, pp 1341-1379, ibid, Collins, Chanock and Murphy, pp 1443-1485, ibid.).

Chimeric HMPV are therefore provided herein that include a partial or complete "background" HMPV genome or antigenome derived from or patterned after HMPV combined with one or more heterologous genes or genome segments of a non-HMPV virus to form the chimeric HMPV genome or antigenome. In one embodiment, chimeric HMPV of this type incorporate a partial or complete HMPV background genome or antigenome combined with one or more heterologous genes or genome segments. The partial or complete background genome or antigenome typically acts as a recipient backbone into which the heterologous genes or genome segments of the counterpart, non-HMPV virus are incorporated. Heterologous genes or genome segments from the counterpart virus represent "donor" genes or polynucleotides that are combined with, or substituted within, the background genome or antigenome to yield a chimeric HMPV that exhibits novel phenotypic characteristics compared to one or both of the contributing viruses. For example, addition or substitution of heterologous genes or genome segments within a selected recipient HMPV strain may result in an increase or decrease in attenuation, growth changes, altered immunogenicity, or other desired phenotypic changes as compared with a corresponding phenotypes of the unmodified recipient and/ or donor (see, for example, U.S. patent application Ser. No. 09/586,479, filed Jun. 1, 2000 by Schmidt et al.; Schmidt et al., J. Virol. 74:8922-9, 2000).

Genes and genome segments that can be selected for use as heterologous substitutions or additions within chimeric HMPV include genes or genome segments encoding a HMPV N, P, M, F, M2, SH, G and/or L proteins or portions thereof. In addition, genes and genome segments encoding proteins found in other viruses, (for example, an SH protein as found in mumps, RSV, and SV5 viruses), may be incorporated within additional chimeric HMPV recombinants of the current disclosure. Regulatory regions from heterologous viruses, for example the extragenic 3' leader or 5' trailer regions, and GS, GE, intergenic regions, or 3' or 5' non-coding regions, are also useful as substitutions or additions within recombinant HMPV. In exemplary aspects, chimeric HMPV bearing one or more non-HMPV genes or genome segments exhibit a high degree of host range restriction, for example, in the respiratory tract of mammalian models of human HMPV infection such as hamsters and non-human primates. In more detailed embodiments HMPV is attenuated by the addition or substitution of one or more APV or RSV genes or genome segments selected from N, P, M, F, M2, SH, G and/or L genes and genome segments to a partial or complete HMPV background genome or antigenome.

In one embodiment, the degree of host range restriction exhibited by chimeric HMPV for use within immunogenic compositions of the current disclosure is comparable to the degree of host range restriction exhibited by the respective non-HMPV "donor" strain. For example, the restriction should have a true host range phenotype, that is, it should be specific to the host in question and should not restrict replication in vitro in a suitable cell line. In addition, chimeric HMPV bearing one or more heterologous genes or genome segments elicit a desired immunogenic response in hosts susceptible to HMPV infection. Thus, the current disclosure provides a new basis for attenuating a live HMPV virus vector for developing immunogenic compositions against HMPV and other pathogens based on host range effects.

In combination with the host range phenotypic effects provided in the chimeric HMPV, it is often desirable to adjust the attenuation phenotype by introducing additional mutations that increase or decrease attenuation of the chimeric virus. Thus, in additional embodiments, attenuated, chimeric HMPV are produced in which the chimeric genome or antigenome is further modified by introducing one or more attenuating mutations specifying an attenuating phenotype in the resultant virus or subviral particle. These can include mutations generated de novo and tested for attenuating effects according to a rational design mutagenesis strategy. Alternatively, the attenuating mutations may be identified in existing biologically derived mutant HMPV or non-HMPVs and thereafter incorporated into a chimeric HMPV of the current disclosure. Exemplary mutations specify lesions in RNA regulatory sequences or in encoded proteins.

In certain chimeric HMPV, attenuation marked by replication in the lower and/or upper respiratory tract in an accepted animal model that is reasonably correlated with HMPV replication and immunogenic activity in humans (for example, hamsters, rhesus monkeys or chimpanzees), is reduced by at least about two-fold, more often about 5-fold, 10-fold, or 20-fold, and preferably 50-100-fold and up to 1,000-fold or greater overall (for example, as measured between 3-8 days following injection) compared to growth of the corresponding wild type or mutant parental strains.

Within the methods disclosed herein, additional genes or genome segments can be inserted into or proximate to a recombinant or chimeric HMPV genome or antigenome: For example, various supernumerary heterologous genes or genome segments can be inserted at any of a variety of sites within the recombinant genome or antigenome, for example at a position 3' to N, between the N/P, P/M, M/F, F/M2, M2/SH, SH/G, and/or G/L genes, or at another non-coding region of the HMPV vector genome or antigenome (see FIG. 1). The inserted genes can be under common control with recipient genes, or can be under the control of an independent set of transcription signals. Genes of interest in this context include genes encoding cytokines, for example, an interleukin (IL-2 through IL-18, for example, interleukin 2 (IL-2), interleukin 4 (IL-4), interleukin 5 (IL-5), interleukin 6 (IL-6), interleukin 18 (IL-18), tumor necrosis factor alpha (TNFα), interferon gamma (IFNγ), or granulocyte-macrophage colony stimulating factor (GM-CSF) (see, for example, U.S. application Ser. No. 09/614,285, filed Jul. 12, 2000 and priority U.S. Provisional Application Ser. No. 60/143,425 filed Jul. 13, 1999). Coexpression of these additional proteins provides the ability to modify and improve immune responses against recombinant HMPV quantitatively and/or qualitatively.

In additional embodiments, insertion of heterologous nucleotide sequences into recombinant HMPV candidates are employed separately to modulate the level of attenuation of candidate recombinants, for example, for the upper respiratory tract. Thus, it is possible to insert nucleotide sequences into a recombinant HMPV that both direct the expression of a foreign protein and that attenuate the virus in an animal host, or to use nucleotide insertions separately to attenuate candidate viruses. To define some of the rules that govern the effect of gene insertion on attenuation, gene units of varying lengths are inserted into a wild type HMPV backbone and the effects of gene unit length on attenuation examined. Novel gene unit insertions are contemplated in this regard that do not contain a significant ORF, permitting identification of the effect of gene unit length independently of an effect of the expressed protein of that gene. These heterologous sequences may be inserted as an extra gene unit of various sizes, for example, from about 150 or more nts in length up to 3,000 nts or more in length. Gene unit (GU) insertions of about 1,000 or 2,000 nts in length will often substantially attenuate rHMPV candidates for the upper respiratory tract of mammalian subjects. In addition, gene unit insertions can have the dual effect of both attenuating a candidate virus and inducing an immunogenic response against a second virus. Alternately, gene extensions in the 3'-noncoding region (NCR) of a HMPV gene which cannot express additional proteins, can also be attenuating in and of themselves. Within these methods of the current disclosure, gene insertion length is a determinant of attenuation (see, for example, U.S. patent application Ser. No. 10/302,547, filed Nov. 21, 2002 and priority U.S. Provisional Application No. 60/331,961, filed Nov. 21, 2001; and U.S. Provisional Application No. 60/412,053, filed Sep. 18, 2002).

Deletions, insertions, substitutions and other mutations involving changes of whole viral genes or genome segments within rHMPV yield highly stable candidates, which are particularly important in the case of immunosuppressed individuals. Many of these changes will result in attenuation of resultant strains, whereas others will specify different types of desired phenotypic changes. For example, accessory (that is, not essential for in vitro growth) genes are excellent candidates to encode proteins that specifically interfere with host immunity (see, for example, Kato et al., EMBO. J. 16:578-87, 1997). Ablation of such genes in candidate viruses can reduce virulence and pathogenesis and/or improve immunogenicity.

In more detailed embodiments, chimeric HMPVs are constructed using a HMPV "vector" genome or antigenome that is recombinantly modified to incorporate one or more antigenic determinants of a heterologous pathogen. The vector genome or antigenome includes a partial or complete HMPV genome or antigenome, which may itself incorporate nucleotide modifications such as attenuating mutations. The vector genome or antigenome is modified to form a chimeric structure though incorporation of a heterologous gene or genome segment. More specifically, chimeric HMPVs of the current disclosure are constructed through a cDNA-based virus recovery system that yields recombinant viruses that incorporate a partial or complete vector or "background" HMPV genome or antigenome combined with one or more "donor" nucleotide sequences encoding the heterologous antigenic determinants. In exemplary embodiments a HMPV vector genome or antigenome is modified to incorporate one or more genes or genome segments that encode antigenic determinants of one or more heterologous negative stranded RNA viruses (for example, another HMPV, RSV, PIV, or measles virus). Thus constructed, chimeric HMPVs can elicit, for example, an immune response against a specific HMPV or against a non-HMPV pathogen. Alternatively, compositions and methods are provided employing a HMPV-based chimeric virus to elicit a polyspecific immune response against multiple HPIVs, against one or more HMPVs and a non-PIV pathogen such as RSV, PIV, or measles virus.

A chimeric HMPV in this context can incorporate a partial or complete human HMPV incorporating one or more heterologous polynucleotides encoding one or more antigenic determinants of the heterologous pathogen. These heterologous polynucleotides can be added to or substituted within the HMPV vector genome or antigenome to yield the chimeric HMPV recombinant. The chimeric HMPV virus thus acquires the ability to elicit all immune response in a selected host against the heterologous pathogen. In addition, the chimeric virus can exhibit other novel phenotypic characteristics compared to one or both of the vector HMPV and heterologous pathogens. In addition to providing novel immunogenic characteristics, the addition or substitution of heterologous genes or genome segments within the vector HMPV strain may confer an increase or decrease in attenuation, growth changes, or other desired phenotypic changes as compared with the corresponding phenotypes of the unmodified vector and donor viruses.

Heterologous genes or genome segments of a different HMPV or non-HMPV virus can be added as a supernumerary genomic element to a partial or complete genome or antigenome of a rHMPV. Alternatively, one or more heterologous genes or genome segments may be substituted into the rHMPV at a position corresponding to a wild type gene order position of a counterpart genes or genome segments that is deleted within the HMPV vector genome or antigenome. In yet additional embodiments, the heterologous gene or genome segment is added or substituted at a position that is more promoter-proximal or promoter-distal compared to a wild type gene order position of the counterpart gene or genome segment within the vector genome or antigenome to enhance or reduce, respectively, expression of the heterologous gene or genome segment. Additional methods and compositions that are useful for engineering chimeric HMPV employ certain known techniques, for example, as disclosed for PIV viruses (Durbin et al., Virology 235:323-332, 1997; Skiadopoulos et al., J. Virol. 72:1762-1768, 1998; Tao et al., J Virol 72:2955-2961, 1998; Skiadopoulos et al., J. Virol. 73:1374-1381, 1999; Skiadopoulos et al., Vaccine 18:503-510, 1999; Tao et al., Vaccine 17:1100-1108, 1999; Tao et al., Vaccine 18:1359-1366, 2000; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), and U.S. Provisional Application No. 60/059,385, filed Sep. 19, 1997).

Chimeric HMPV can also be constructed that express a chimeric protein, for example an immunogenic glycoprotein having a cytoplasmic tail and/or transmembrane domain specific to a HMPV vector fused to a heterologous ectodomain (the ectodomain being that part of a transmembrane surface protein that extends into the luminal or extracellular space) of a different HMPV or non-HMPV pathogen to provide a fusion protein that elicits an immune response against the heterologous pathogen. For example, a heterologous genome segment encoding a glycoprotein ectodomain from a RSV F, SH, M2, or G glycoprotein can be joined with a genome segment encoding the corresponding HMPV glycoprotein cytoplasmic and transmembrane domains to form a chimeric glycoprotein that elicits an immune response against RSV.

Briefly, HMPV expressing a chimeric glycoprotein includes a major nucleocapsid protein, a nucleocapsid phosphoprotein, a large polymerase protein, and a HMPV vector genome or antigenome that is modified to encode a chimeric glycoprotein. The chimeric glycoprotein incorporates one or more heterologous antigenic domains, fragments, or epitopes of a second, antigenically distinct HMPV or non-HMPV pathogen. In one embodiment, this is achieved by substitution within the HMPV vector genome or antigenome of one or more heterologous genome segments of the second virus that encodes one or more antigenic domains, fragments, or epitopes, whereby the recombinant genome or antigenome encodes the chimeric glycoprotein that is antigenically distinct from the parent, vector virus. In several examples, the heterologous genome segment or segments can encode a glycoprotein ectodomain or immunogenic portion or epitope thereof. The heterologous genome segment can also include other portions of the heterologous or "donor" glycoprotein, for example both an ectodomain and transmembrane region that are substituted for counterpart glycoprotein ecto- and transmembrane domains in the vector genome or antigenome.

As used herein, the term "gene" generally refers to a portion of a subject genome, for example, a HMPV genome, encoding an mRNA and typically begins at the upstream end with a GS signal and ends at the downstream end with the GE signal. The term gene is also interchangeable with the term "translational open reading frame," or "ORF," particularly in the case where a protein, such as the HPIV1 or HPIV3 C protein, is expressed from an additional ORF rather than from a unique mRNA. The viral genome of all mononegaviruses also contains extragenic leader and trailer regions, possessing part of the promoters required for viral replication and transcription, as well as non-coding and intergenic regions. Transcription initiates at the 3' end and proceeds by a sequential stop-start mechanism that is guided by short conserved motifs found at the gene boundaries. The upstream end of each gene contains a GS signal, that directs initiation of its respective mRNA. The downstream terminus of each gene contains a GE motif that directs polyadenylation and termination. The current disclosure provides operative identification of transcription signals and insertion sites, and provides the identification of the GS, GE and potential insertion sites within the genome.

To construct-chimeric HMPVs, one or more HMPV genes or genome segments can be deleted, inserted or substituted in whole or in part. This means that partial or complete deletions, insertions and substitutions may include ORFs and/or cis-acting regulatory sequences of any one or more of the HMPV genes or genome segments. By "genome segment" is meant any length of continuous nucleotides from the HMPV genome, which might be part of an ORF, a gene, or an extragenic region, or a combination thereof. In several examples, at least about 10, at least about 20, at least about 30, at least about 50, or at least about 100 continuous nucleotides are deleted, inserted or substituted. When a subject genome segment encodes an antigenic determinant, the genome segment encodes at least one immunogenic epitope capable of eliciting a humoral or cell mediated immune response in a mammalian host. The genome segment can also encode an immunogenic fragment or protein domain. For example, the donor genome segment can encode multiple immunogenic domains or epitopes, including recombinantly synthesized sequences that comprise multiple, repeating or different, immunogenic domains or epitopes.

Chimeric HMPV can be engineered to express one or more major antigenic determinants of a wide range of non-HMPV pathogens. The methods disclosed herein are generally adaptable for incorporation of antigenic determinants from, for example, subgroup A and subgroup B RSVs, HMPV, measles virus, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses, among other pathogens. Pathogens that can be targeted for development of immunogenic compositions include viral and bacterial pathogens, as well as protozoans and multicellular pathogens. Useful antigenic determinants from many important human pathogens in this context are known or readily identified for incorporation within chimeric HMPV. Thus, major antigens have been identified for the foregoing exemplary pathogens, including the measles virus HA and F proteins; the F, G, SH and M2 proteins of RSV, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, flavivirus E and NS1 proteins, and alphavirus E protein. These major antigens, as well as other antigens known in the art for the enumerated pathogens and others, are well characterized to the extent that many of their antigenic determinants, including the full length proteins and their constituent antigenic domains, fragments and epitopes, are identified, mapped and characterized for their respective immunogenic activities.

Among the numerous, exemplary mapping studies that identify and characterize major antigens of diverse pathogens for use in the methods a chimeric HMPV disclosed herein are epitope mapping studies directed, for example, to immunogenic glycoproteins of PIV. Exemplifying the subject methods and tools, van Wyke Coelingh et al. (J. Virol. 63:375-382, 1989) described twenty-six monoclonal antibodies (MAbs) (14 neutralizing and 12 nonneutralizing) that were used to examine the antigenic structure, biological properties, and natural variation of the fusion (F) glycoprotein of HPIV3. Analysis of laboratory-selected antigenic variants and of PIV3 clinical isolates indicated that the panel of MAbs recognizes at least 20 epitopes, 14 of which participate in neutralization. Competitive binding assays confirmed that the 14 neutralization epitopes are organized into three nonoverlapping principal antigenic regions (A, B, and C) and one bridge site (AB), and that the 6 nonneutralization epitopes form four sites (D, E, F, and G). Most of the neutralizing MAbs were involved in nonreciprocal competitive binding reactions, suggesting that they induce conformational changes in other neutralization epitopes. These and related methods will serve to readily determine candidate antigenic determinants among heterologous viruses for expression by HMPV vectors of the current disclosure.

Other antigenic determinants for use within the current disclosure have been identified and characterized for RSV. For example, Beeler et al., J. Virol. 63:2941-2950, 1989, employed eighteen neutralizing monoclonal antibodies (MAbs) specific for the fusion glycoprotein of the A2 strain of RSV to construct a detailed topological and operational map of epitopes involved in RSV neutralization and fusion. Competitive binding assays identified three nonoverlapping antigenic regions (A, B, and C) and one bridge site (AB). Thirteen MAb-resistant mutants (MARMs) were selected, and the neutralization patterns of the MAbs with either MARMs or RSV clinical strains identified a minimum of 16 epitopes. MARMs selected with antibodies to six of the site A and AB epitopes displayed a small-plaque phenotype, which is consistent with an alteration in a biologically active region of the F molecule. Analysis of MARMs also indicated that these neutralization epitopes occupy topographically distinct but conformationally interdependent regions with unique biological and immunological properties. Antigenic variation in F epitopes was then examined by using 23 clinical isolates (18 subgroup A and 5 subgroup B) in cross-neutralization assays with the 18 anti-F MAbs. This analysis identified constant, variable, and hypervariable regions on the molecule and indicated that antigenic variation in the neutralization epitopes of the RSV F glycoprotein is the result of a noncumulative genetic heterogeneity. Of the 16 epitopes, 8 were conserved on all or all but 1 of 23 subgroup A or subgroup B clinical isolates. These antigenic determinants, including the full length proteins and their constituent antigenic domains, fragments and epitopes, all represent useful candidates for integration within chimeric HMPV of the current disclosure to elicit novel immune responses as described above. (See also, Anderson et al., J. Infect. Dis. 151:626-633, 1985; Coelingh et al., J. Virol. 63:375-382, 1989; Fenner et al., Scand. J. Immunol. 24:335-340, 1986; Fernie et al., Proc. Soc. Exp. Biol. Med. 171:266-271, 1982; Sato et al., J. Gen. Virol. 66:1397-1409, 1985; Walsh et al., J. Gen. Virol. 67:505-513, 1986, and Olmsted et al.; J. Virol. 63:411-420, 1989).

To express antigenic determinants of heterologous HMPVs and non-HMPV pathogens, numerous methods and constructs are provided herein. In certain detailed embodiments, a transcription unit comprising an ORF of a gene encoding an antigenic protein (for example, an RSV F or G gene) is added to a HMPV vector genome or antigenome at various positions, yielding exemplary chimeric "vector" candidates. In exemplary embodiments, chimeric HMPVs are engineered that incorporate heterologous nucleotide sequences encoding protective antigens from RSV to produce infectious, attenuated candidates (see U.S. patent application Ser. No. 08/720,132, filed Sep. 27, 1996, corresponding to International Publication WO 97/12032 published Apr. 3, 1997, and U.S. Provisional Patent Application No. 60/007,083, filed Sep. 27, 1995; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. patent application Ser. No. 08/892,403, filed Jul. 15, 1997 corresponding to International Publication No. WO 98/02530 published on Jan. 22, 1998; U.S. patent application Ser. No. 09/291,894, filed on Apr. 13, 1999 corresponding to International Publication No. WO 00/61611 published Oct. 19, 2000, and priority U.S. Provisional Patent Application Ser. No. 60/129,006, filed on Apr. 13, 1999; U.S. patent application Ser. No. 09/602,212, filed Jun. 23, 2000 and corresponding International Publication No. WO 01/04335 published on Jan. 18, 2001, and priority U.S. Provisional Patent Application Nos. 60/129,006, filed Apr. 13, 1999, 60/143,097, filed Jul. 9, 1999, and 60/143,132, filed Jul. 9, 1999; International Publication No. WO (0/61737 published on Oct. 19, 2000; Collins et al., Proc Nat. Acad. Sci. U.S.A. 92:11563-11567, 1995; Bukreyev et al., J. Virol. 70:6634-41, 1996, Juhasz et al., J. Virol. 71:5814-5819, 1997; Durbin et al., Virology 235:323-332, 1997; He et al. Virology 237:249-260, 1997; Baron et al. J. Virol. 71:1265-1271, 1997; Whitehead et al., Virology 247:232-9, 1998a; Whitehead et al., J. Virol. 72:4467-4471, 1998b; Jin et al. Virology 251:206-214, 1998; and Whitehead et al., J. Virol. 73:3438-3442, 1999, and Bukreyev et al., Proc. Nat. Acad. Sci. U.S.A. 96:2367-72, 1999). Other reports and discussion incorporated or set forth herein identify and characterize RSV antigenome determinants that are useful within the current disclosure.

HMPV chimeras incorporating one or more RSV antigenic determinants, can include a HMPV vector genome or antigenome combined with a heterologous gene or genome segment encoding an antigenic RSV glycoprotein, protein domain (for example, a glycoprotein ectodomain) or one or more immunogenic epitopes. In one embodiment, one or more genes or genome segments from RSV SH, M2, F, and/or G genes is/are combined with the HMPV vector genome or antigenome to form the chimeric HMPV candidate. Certain of these constructs will express chimeric proteins, for example fusion proteins having a cytoplasmic tail and/or transmembrane domain of HMPV fused to an ectodomain of a corresponding RSV glycoprotein to yield a novel attenuated virus that optionally elicits a multivalent immune response against both HMPV and RSV.

In certain embodiments, it is useful to administer immunogenic compositions comprising a rHMPV in a predetermined schedule with one or more additional immunogenic components, for example a second immunogenic composition against RSV or PIV administered before or after the anti-HMPV composition. RSV and HPIV3 cause significant illness within the first four months of life whereas most of the illness caused by HPIV1 and HPIV2 occur after six months of age (Chanock et al., in Parainfluenza Viruses, Knipe et al. (Eds.), pp. 1341-1379, Lippincott Williams & Wilkins, Philadelphia, 2001; Collins et al., In Fields Virology, Vol. 1, pp. 1205-1243, Lippincott-Raven Publishers, Philadelphia, 1996; Reed et al., J. Infect. Dis. 175:807-13, 1997). Accordingly, certain sequential immunization protocols involve administration of a immunogenic composition as described herein that elicits an immune response against HMPV before, simultaneous with (for example, as a combined immunogenic composition), or subsequent to, administration of a second immunogenic composition directed toward another virus. In one embodiment, an immunogenic composition that elicits an immune response against HMPV, or against HMPV and RSV is administered one, two or more times early in life, with the first dose administered at or before one month of age, followed by an immunogenic composition against HPIV1 and/or HPIV2 at about four and six months of age. Alternatively, it might be advantageous to administer immunogenic components against HMPV, RSV, and one or more PIVs at the same time, perhaps as a multi-component immunogenic composition.

Thus, combinatorial immunogenic compositions and coordinate immunization protocols are provided herein for multiple pathogenic agents, including HMPV, RSV, and one or more PIVs. In exemplary embodiments, these methods and formulations are temporally selected to target early immunization against HMPV, RSV and/or PIV3. One exemplary immunization sequence employs one or more live attenuated immunogenic compositions against HMPV, RSV and/or PIV3 as early as one month of age (for example, at one and two months of age) followed by mono- or bivalent PIV1 and/or PIV2 immunogenic composition at four and six months of age. The methods disclosed herein can be used to administer multiple immunogenic compositions, including one or more chimeric HMPV candidates, coordinately, for example, simultaneously in a mixture or separately in a defined temporal sequence (for example, in a daily or weekly sequence), wherein each virus preferably expresses, for example, a different heterologous protective antigen. Such a coordinate/sequential immunization strategy, which is able to induce secondary antibody responses to multiple viral respiratory pathogens, provides a highly powerful and extremely flexible immunization regimen that is driven by the need to immunize against multiple pathogens in early infancy.

As noted above, the current disclosure permits a wide range of alterations to be recombinantly produced within the HMPV genome or antigenome, yielding defined mutations that specify desired phenotypic changes. Defined mutations can be introduced by a variety of conventional techniques (for example, site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA constructs provide for better ease of manipulation than large cDNA constructs, and then readily assembled into a complete cDNA. Thus, the complete antigenome or genome cDNA, or a selected subfragment thereof, can be used as a template for oligonucleotide-directed mutagenesis. This can be through the intermediate of a single-stranded phagemid form, such as using the MUTA-Gen® kit of Bio-Rad Laboratories (Richmond, Calif.), or a method using the double-stranded plasmid directly as a template such as the Chameleon® mutagenesis kit of Strategene (La Jolla, Calif.), or by the PCR employing either an oligonucleotide primer or a template which contains the mutations of interest. A mutated subfragment can then be assembled into the complete antigenome or genome cDNA. A variety of other mutagenesis techniques are known and can be routinely adapted for use in producing the mutations of interest in a HMPV antigenome or genome cDNA of the current disclosure.

Thus, in one illustrative embodiment mutations are introduced by using the MUTA-Gene® phagemid in vitro mutagenesis kit available from Bio-Rad Laboratories. In brief, cDNA encoding a HMPV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

Mutations can vary from single nucleotide changes to the introduction, deletion or replacement of large cDNA segments containing one or more genes or genome segments. Genome segments can correspond to structural and/or functional domains, for example, cytoplasmic, transmembrane or ectodomains of proteins, active sites such as sites that mediate binding or other biochemical interactions with different proteins, epitopic sites, for example, sites that stimulate antibody binding and/or humoral or cell mediated immune responses, etc. Useful genome segments in this regard range from about 15-35 nucleotides in the case of genome segments encoding small functional domains of proteins, for example, epitopic sites, to about 50, about 75, about 100, about 200-500, and about 500-1,500 or more nucleotides.

The ability to introduce defined mutations into infectious recombinant HMPV has many applications, including the manipulation of HMPV pathogenic and immunogenic mechanisms. For example, the functions of HMPV proteins, including the N, P, M, F, M2, SH, G and/or L proteins can be manipulated by introducing mutations which ablate or reduce the level of protein expression, or which yield mutant protein. Various genome RNA structural features, such as promoters, intergenic regions, and transcription signals, can also be routinely manipulated within the methods and compositions of the current disclosure. The effects of trans-acting proteins and cis-acting RNA sequences can be readily determined, for example, using a complete antigenome cDNA in parallel assays employing HMPV minigenomes (Dimock et al., J. Virol. 67:2772-8, 1993 in its entirety), whose rescue-dependent status is useful in characterizing those mutants that may be too inhibitory to be recovered in replication-independent infectious virus.

Certain substitutions, insertions, deletions or rearrangements of genes or genome segments within recombinant HMPV (for example, substitutions of a genome segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or genome segment from the same or different HMPV or other source. Such modifications yield novel recombinants having desired phenotypic changes compared to wild type or parental HMPV or other viral strains. For example, recombinants of this type may express a chimeric protein having a cytoplasmic tail and/or transmembrane domain of one HMPV, or of a non-HMPV virus such as PIV or RSV, fused to an ectodomain of a rHMPV of the current disclosure. Other exemplary recombinants of this type express duplicate protein regions, such as duplicate immunogenic regions.

As used herein, "counterpart" genes, genome segments, proteins or protein regions, are typically from heterologous sources (for example, from different HMPV genes, or representing the same (that is, homologous or allelic) gene or genome segment in different HMPV types or strains). Typical counterparts selected in this context share gross structural features, for example, each counterpart can encode a comparable protein or protein structural domain, such as a cytoplasmic domain, transmembrane domain, ectodomain, binding site or region, epitopic site or region, etc. Counterpart domains and their encoding genome segments embrace an assemblage of species having a range of size and sequence variations defined by a common biological activity among the domain or genome segment variants.

Counterpart genes and genome segments, as well as other polynucleotides disclosed herein for producing recombinant HMPV, often share substantial sequence identity with a selected polynucleotide "reference sequence," for example, with another selected counterpart sequence. As used herein, a "reference sequence" is a defined sequence used as a basis for sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) include a sequence (that is, a portion of the complete polynucleotide sequence) that is similar between the two polynucleotides, and (2) can further include a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (that is, gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, (Adv. Appl. Math. 2:4821-1981), by the homology alignment algorithm of Needleman & Wunsch, (J. Mol. Biol. 48:443, 1970), by the search for similarity method of Pearson & Lipman, (Proc. Natl. Acad. Sci. U.S.A. 85:2444, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (that is, resulting in the highest percentage of sequence similarity over the comparison window) generated by the various methods is selected. The term "sequence identity" means that two polynucleotide sequences are identical (that is, on a nucleotide-by-nucleotide basis) over the window of comparison. The term "percentage of sequence identity" is calculated by comparing two optimally aligned sequences over the window of comparison, determining the number of positions at which the identical nucleic acid base (for example, A, T, C, G, U, or I) occurs in both sequences to yield the number of matched positions, dividing the number of matched positions by the total number of positions in the window of comparison (that is, the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant HMPV are also typically selected to have conservative relationships, that is, to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (that is, conservative substitutions) at corresponding positions. The term "substantial sequence identity" means that two peptide sequences, when optimally aligned, such as by the programs GAP or BESTFIT using default gap weights, share at least 80 percent sequence identity, such as at least 90 percent sequence identity, at least 95 percent sequence identity or more (for example, 97, 98, or 99 percent sequence identity). The term "substantial similarity" means that two peptide sequences share corresponding percentages of sequence similarity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (Immunology—A Synthesis, 2nd ed., E. S. Golub & D. R. Gren, eds., Sinauer Associates, Sunderland, Mass., 1991). Stereoisomers (for example, D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the current disclosure. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and iminio acids (for example, 4-hydroxyproline). Moreover, amino acids may be modified by glycosylation, phosphorylation and the like.

To select candidate viruses, the criteria of viability, attenuation and immunogenicity are determined according to well-known methods. Viruses that will be most desired in immunogenic compositions must maintain viability, have a stable attenuation phenotype, exhibit replication in an immunized host (albeit at lower levels), and effectively elicit production of an immune response in a recipient sufficient to elicit a desired immune response. The recombinant HMPVs are not only viable and appropriately attenuated, they are more stable genetically in vivo—retaining the ability to stimulate an immune response and in some instances to expand the immune response elicited by multiple modifications, for example, induce an immune response against different viral strains or subgroups, or to stimulate a response mediated by a different immunologic basis, for example, secretory versus serum immunoglobulins, cellular immunity, and the like.

Recombinant HMPVs can be tested in various well-known and generally accepted in vitro and in vivo models to confirm adequate attenuation, resistance to phenotypic reversion, and immunogenicity. In in vitro assays, the modified virus (for example, a multiply attenuated, biologically derived or recombinant HMPV) is tested, for example, for temperature sensitivity of virus replication, that is, ts phenotype, and for the small plaque or other desired phenotype. Modified viruses are further tested in animal models of HMPV infection. A variety of animal models have been described and are summarized in various references incorporated herein. HMPV model systems, including rodents and non-human primates, for evaluating attenuation and immunogenic activity of HMPV candidates are widely accepted in the art, and the data obtained there from correlate well with HMPV infection, attenuation and immunogenicity in humans.

In accordance with the foregoing description, the present disclosure also provides isolated, infectious recombinant HMPV for use in immunogenic compositions. The attenuated virus which is a component of an immunogenic composition is in an isolated and typically purified form. By "isolated" is meant to refer to HMPV which is in other than a native environment of a wild type virus, such as the nasopharynx of an infected individual. More generally, isolated is meant to include the attenuated virus as a component of a cell culture or other artificial medium where it can be propagated and characterized in a controlled setting. For example, attenuated HMPV can be produced by an infected cell culture, separated from the cell culture and added to a stabilizer.

For use in immunogenic compositions, recombinant HMPV produced according to the current disclosure can be used directly in formulations, or lyophilized, as desired, using lyophilization protocols well known to the artisan. Lyophilized virus will typically be maintained at about 4° C. When ready for use the lyophilized virus is reconstituted in a stabilizing solution, for example, saline or comprising SPG, $Mg^{++}$ and HEPES, with or without adjuvant, as further described herein.

HMPV-based immunogenic compositions contain as an active ingredient an immunogenically effective amount of a recombinant HMPV produced as described herein. The modified virus can be introduced into a host with a physiologically acceptable carrier and/or adjuvant. Useful carriers are well known in the art, and include, for example, water, buffered water, 0.4%, saline, 0.3%, glycine, hyaluronic acid and the like. The resulting aqueous solutions may be packaged for use as is or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPL™ (3-O-deacylated monophosphoryl lipid A; Corixa, Hamilton Ind.) and IL-12 (Genetics Institute, Cambridge Mass.), among many other suitable adjuvants well known in the art.

Upon immunization with a recombinant HMPV composition, via aerosol, droplet, oral, topical or other route, the immune system of the host responds to the immunogenic composition by producing antibodies specific for HMPV proteins, for example, F and G glycoproteins. As a result of the immunization with an immunogenically effective amount of a recombinant HMPV produced as described herein, the host becomes at least partially or completely immune to infection by the targeted HMPV or non-HMPV pathogen, or resistant to developing moderate or severe infection there from, particularly of the lower respiratory tract.

The host to which the immunogenic compositions are administered can be any mammal which is susceptible to infection by HMPV or a selected non-HMPV pathogen and which host is capable of generating an immune response to the antigens of the immunizing strain. Accordingly, methods are provided for creating immunogenic compositions for a variety of human and veterinary uses.

The compositions containing the recombinant HMPV are administered to a host susceptible to or otherwise at risk for HMPV infection to enhance the host's own immune response capabilities. Such an amount is defined to be a "immunogenically effective dose." In this use, the precise amount of recombinant HMPV to be administered within an effective dose will depend on the host's state of health and weight, the mode of administration, the nature of the formulation, etc., but will generally range from about $10^3$ to about $10^7$ plaque forming units (PFU) or more of virus per host, more commonly from about $10^4$ to $10^6$ PFU virus per host. In any event, the formulations should provide a quantity of modified HMPV of the current disclosure sufficient to elicit a detectable immune response in the host patient against the subject pathogens.

The recombinant HMPV can be combined with viruses of other HMPV serotypes or strains to elicit a desired immune response against multiple HMPV serotypes or strains. Alternatively, an immune response against multiple HMPV serotypes or strains can be achieved by combining protective epitopes of multiple serotypes or strains engineered into one virus, as described herein. Typically when different viruses are administered they will be in admixture and administered simultaneously, but they can also be administered separately. Immunization with one strain may immunize against different strains of the same or different serotype.

In some instances it may be desirable to combine the recombinant HMPV immunogenic compositions with immunogenic compositions that induce immune responses to other agents, particularly other childhood viruses. In another aspect of the current disclosure the recombinant HMPV can be employed as a vector for protective antigens of other pathogens, such as RSV, by incorporating the sequences encoding those protective antigens into the recombinant HMPV genome or antigenome that is used to produce infectious virus, as described herein.

In all subjects, the precise amount of recombinant HMPV administered, and the timing and repetition of administration, will be determined using conventional methods based on the patient's state of health and weight, the mode of administration, the nature of the formulation, etc. Dosages will generally range from about $10^3$ to about $10^7$ plaque forming units (PFU) or more of virus per patient, more commonly from about $10^4$ to $10^6$ PFU virus per patient. In any event, the formulations should provide a quantity of attenuated recombinant HMPV sufficient to effectively stimulate or induce an anti-HMPV or other anti-pathogenic immune response, for example, as can be determined by hemagglutination inhibition, complement fixation, plaque neutralization, and/or enzyme-linked immunosorbent assay, among other methods. In this regard, individuals are also monitored for signs and symptoms of upper respiratory illness. As with administration to chimpanzees, the attenuated virus of grows in the nasopharynx of recipients at levels approximately 10-fold or more lower than wild type virus, or approximately 10-fold or more lower when compared to levels of incompletely attenuated virus.

In neonates and infants, multiple administrations can be required to elicit sufficient levels of immunity. Administration should begin within the first month of life, and at intervals throughout childhood, such as at two months, six months, one year and two years, as necessary to maintain an immune response against native (wild type) HMPV infection. Similarly, adults who are particularly susceptible to repeated or serious HMPV infection, such as, for example, health care workers, day care workers, family members of young children, the elderly, individuals with compromised cardiopulmonary function, can require multiple immunizations to establish and/or maintain immune responses. Levels of induced immunity can be monitored by measuring amounts of neutralizing secretory and serum antibodies, and dosages adjusted or vaccinations repeated as necessary to maintain desired levels of immune response. Further, different candidate viruses may be indicated for administration to different recipient groups. For example, an engineered HMPV expressing a cytokine or an additional protein rich in T cell epitopes may be particularly advantageous for adults rather than for infants.

HMPV-based immunogenic compositions can be combined with viruses expressing antigens of another subgroup or strain of HMPV to elicit an immune response against multiple HMPV subgroups or strains. Alternatively, the candidate virus can incorporate protective epitopes of multiple HMPV strains or subgroups engineered into one HMPV clone, as described herein.

The recombinant HMPV immunogenic compositions elicit production of an immune response that reduces or alleviates serious lower respiratory tract disease, such as pneumonia and bronchiolitis when the individual is subsequently infected with wild type HMPV. While the naturally circulating virus is still capable of causing infection, particularly in the upper respiratory tract, there is a very greatly reduced possibility of rhinitis as a result of the vaccination. Boosting of resistance by subsequent infection by wild type virus can occur. Following immunization, there are delectable levels of host engendered serum and secretory antibodies which are capable of neutralizing homologous (of the same subgroup) wild type virus in vitro and in vivo.

In one embodiment, recombinant HMPV candidates exhibit a very substantial diminution of virulence when compared to wild type virus that naturally infects humans. The virus is sufficiently attenuated so that symptoms of infection will not occur in most immunized individuals. In some instances the attenuated virus can still be capable of dissemination to nonimmunized individuals. However, its virulence is sufficiently abrogated such that severe lower respiratory tract infections in the immunized host do not occur.

The level of attenuation of recombinant HMPV candidates can be determined by, for example, quantifying the amount of virus present in the respiratory tract of an immunized host and comparing the amount to that produced by wild type HMPV or other attenuated HMPV which have been evaluated as candidate strains. For example, the attenuated virus will have a greater degree of restriction of replication in the upper respiratory tract of a highly susceptible host, such as a chimpanzee, compared to the levels of replication of wild type virus, for example, 10- to 1000-fold less. In order to further reduce the development of rhinorrhea, which is associated with the replication of virus in the upper respiratory tract, a useful candidate virus should exhibit a restricted level of replication in both the upper and lower respiratory tract. However, the attenuated viruses must be sufficiently infectious and immunogenic in humans to elicit a desired immune response in immunized individuals. Methods for determining levels of HMPV in the nasopharynx of an infected host are well known in the literature and facilitated by the methods and compositions disclosed herein.

Levels of induced immunity provided by the immunogenic compositions of the current disclosure can also be monitored by measuring amounts of neutralizing secretory and serum antibodies. Based on these measurements, dosages can be adjusted or immunizations repeated as necessary to maintain desired levels of immune response. Further, different candidate viruses can be advantageous for different recipient groups. For example, an engineered recombinant HMPV strain expressing an additional protein rich in T cell epitopes may be particularly advantageous for adults rather than for infants.

In another embodiment, the recombinant HMPV is employed as a vector for transient gene therapy of the respiratory tract. According to this embodiment the recombinant HMPV genome or antigenome incorporates a sequence that is capable of encoding a gene product of interest. The gene product of interest is under control of the same or a different promoter from that which controls HMPV expression. The infections recombinant HMPV produced by coexpressing the recombinant HMPV genome or antigenome with the N, P, L and other desired HMPV proteins, and containing a sequence encoding the gene product of interest, is administered to a patient. Administration is typically by aerosol, nebulizer, or other topical application to the respiratory tract of the patient being treated. Recombinant HMPV is administered in an amount sufficient to result in the expression of therapeutic or prophylactic levels of the desired gene product. Representative gene products that may be administered within this method are preferably suitable for transient expression, including, for example, interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl-transferase, cytotoxins, tumor suppressor genes, antisense RNAs, and other candidate antigens.

The following examples are provided by way of illustration, not limitation. These examples describe the development of a novel reverse genetics system for the recovery of HMPV from cDNA, and the use of this system for construction of novel recombinant HMPV candidates. Thus, the subject matter of the current disclosure is illustrated by the following non-limiting Examples.

EXAMPLES

The mononegaviruses generally have a genome that comprises a single negative-sense strand of RNA tightly encapsidated in a nucleocapsid. There is a virally encoded polymerase that associates with the nucleocapsid and directs transcription of the genome by a process that initiates at the 3' end and copies the linear array of genes by a sequential stop-start mechanism that yields subgenomic mRNAs. Replication involves the synthesis of a complete positive sense copy called the antigenome, which in turn serves as the template for producing progeny genomes. Newly synthesized viral glycoproteins are transported to and accumulate at the plasma membrane. Progeny virus is formed when the nucleocapsid associates with these areas of modified plasma membrane and acquires a lipid envelope by budding.

RSV is the leading cause of hospitalization for viral lower respiratory tract disease in infants and young children, followed by HPIV3 (Collins et al., 4th ed. In "Fields Virology," D. M. Knipe, P. M. Howley, Eds., Vol. 1, pp. 1443-1485, Lippincott-Williams and Wilkins Publishers, Philadelphia, 2001; Crowe et al., Vaccine 13:415421, 1995; Marx et al., J. Infect. Dis. 176:1423-1427, 1997). HPIV1 and HPIV2 are the principal etiologic agents of laryngotracheobronchitis (croup), and can also cause pneumonia and bronchiolitis (Chanock et al., 4th ed. In "Fields Virology," D. M. Knipe, P. M. Howley. Eds., Vol. 1 pp. 1341-1:379, Lippincott-Williams and Wilkins Publishers, Philadelphia, 2001). RSV and the PIVs also are important causes of respiratory tract disease in adults. The available evidence indicates that HMPV is also a significant agent of human respiratory tract disease, particularly in young infants and children but occurring in all age groups (Boivin et al. J. Infect. Dis. 186:1330-6, 2002).

HMPV replicates slowly and inefficiently in cell culture, rendering it relatively challenging to maintain and study in laboratory. In addition, trypsin reportedly must be present in the medium in order to activate infectivity of the virus, which complicates the lengthy incubations that are necessary to successfully propagate the virus. Indeed, the difficulty in propagating HMPV provides an explanation for why it previously escaped detection as an important respiratory pathogen despite several decades of widespread cultivation of respiratory tract specimens in cell culture in many hospitals and research facilities across the world.

Methods for the production of RSV and PIV are known in the art, and compositions to induce an immune response against these viruses have been described (see Durbin et al., Virology 235:323-332, 1997; Skiadopoulos et al., J. Virol. 72:1762-1768, 1998; Skiadopoulos et al., J. Virol. 73:1374-1381, 1999; Tao et a., Vaccine 19:3620-3631, 2001; Durbin et al., J. Virol. 74:6821-6831, 2000; U.S. patent application Ser. No. 09/083,793, filed May 22, 1998; U.S. patent application Ser. No. 09/458,813, filed Dec. 10, 1999; U.S. patent application Ser. No. 09/459,062, filed Dec. 10, 1999; U.S. Provisional Application No. 60/047,575, filed May 23, 1997 (corresponding to International Publication No. WO 98/53078), U.S. Provisional Application No. 60/059,385, filed Sep. 19, 1997; U.S. Provisional Application No. 60/170,195 filed Dec. 10, 1999; and U.S. patent application Ser. No. 09/733,692, filed Dec. 8, 2000 (corresponding to International Publication No. WO 01/42445A2), each incorporated herein by reference). However, HMPV provides a contrasting situation in which there are no available reference reagents such as monoclonal antibodies or available reference viral strains, and no established methods for the detection and analysis of HMPV. Knowledge concerning the molecular biology of HMPV has remained rudimentary and was previously based largely on extrapolation from other viruses. Because HMPV has only recently been identified and its characterization had been very incomplete, there were many challenges to generating suitably attenuated, immunogenic and genetically stable for use in immunogenic and diagnostic compositions. To facilitate these goals, it is necessary to produce recombinant infectious HMPV from cDNA to serve as a starting point for manipulations that include the development and staged introduction of predetermined attenuating mutations; the deletion, modification or rearrangement of existing genes, the introduction of foreign genes, the swapping of protective antigens between strains, and the swapping of attenuating or other desired mutations between HMPV strains and between HMPV and other related viruses, and to provide additional tools to generate immunogenic compositions, vectors and immunization methods. The present disclosure describes the production of recombinant infectious HMPV from cDNA, and attenuating mutations with this cDNA, as well as the specific deletions and substitutions within existing genes, the introduction heterologous nucleic acid sequences, and additional methods and compositions that are of use in methods designed to generate an immune response against HMPV.

Example 1

Determination of a Complete Consensus Sequence for the Genome of HMPV

The present Example provides the complete genomic sequence of a HMPV. The subject viral strain for this analysis is strain CAN97-83 (Peret et al., J. Infect. Dis. 185:1660-3, 2002), hereafter referred to as strain 83 or CAN83. The sequence was determined by direct analysis of uncloned RT-PCR products of viral RNA and thus represents a consensus or majority sequence of a viable virus. The virulence, and hence wild type status, of this virus was confirmed by the ability to induce respiratory tract disease signs in chimpanzees following intranasal inoculation, as described in a following Example. The determination of a complete authentic wild type HMPV sequence is a necessary step in developing a system to produce HMPV of defined sequence and characteristics for use in immunogenic compositions and methods.

Cell Lines and Viruses

HEp-2 (ATCC CCL 23), Vero (ATCC CCL-81) and LLC-MK2 (ATCC CCL 7.1) cells were maintained in OptiMEM I (Invitrogen GIBCO) supplemented with 5% fetal bovine serum and, in some instances, gentamicin sulfate (50 µg/mL). BSR T7/5 cells are baby hamster kidney 21 (BHK-21) cells that have been transformed and constitutively express T7 RNA polymerase (Buchholz et al., J. Virol. 73:251-9). They were maintained in Glasgow MEM supplemented with glutamine and amino acids (Invitrogen) and 5% fetal bovine serum. The BSR T7/5 cells were subjected to geneticine (1 mg/ml) selection every second passage. Biological and recombinant HMPV were propagated in Vero, LLC-MK2, or BSR T7/5 cells in the absence of serum and the presence of 5 µg/ml of trypsin.

Virion RNA Isolation

Confluent monolayers of LLC-MK2 cells were infected with HMPV and incubated at 32° C. in the presence of 5 µg/ml trypsin. 10-14 days post-infection, clarified supernatants were harvested. Virion RNA (vRNA) was isolated directly from the clarified supernatants using the QIAamp viral RNA purification kit (Qiagen) according to the manufacturer's instructions. Alternatively, virus was purified by sucrose gradient centrifugation. Supernatant and infected cells were harvested by scraping with a rubber policeman, mixed with HEPES buffer and $MgSO_4$ at a final concentration of 50 mM and 0.1 M, respectively, and then submitted to three cycles of freezing and thawing. The mixture was clarified by low-speed centrifugation and the virus was pelleted by centrifugation at 7000 rpm overnight at 4° C. The virus pellet was resuspended in OptiMEM (Invitrogen) containing 50 mM of HEPES buffer and 0.1 M of $MgSO_4$. The viral suspension was layered on a 30 to 60% sucrose gradient and was centrifuged for 90 min at 26,000 rpm in an SW28 rotor. The upper virus-containing fraction was collected, diluted in TEN (10 mM Tris-HCl [pH 7.4], 0.1 M NaCl, 1 mM EDTA) and virus particles were pelleted by centrifugation at 25,000 rpm in an SW28 rotor for 90 min. The virus pellet was resuspended in TEN and vRNA was isolated directly from an aliquot using the RNeasy kit (Qiagen) according to the manufacturer's instructions.

Reverse Transcription, Polymerase Chain Reaction and Nucleotide Sequencing vRNA was reverse transcribed using specific primers generated from the published partial sequence of HMPV strain 00-1. In most cases these failed to yield RT-PCR products, presumably reflecting nucleotide sequence differences between these two strains. Therefore additional primers were designed based on the regions between ORFs in the 00-1 sequence that, by analogy to other mononegaviruses, would likely contain cis-acting signals that would be more highly conserved between HMPV strains. This strategy provided RT-PCR products for strain 83 that, upon sequence analysis, provided information for designing strain 83-specific primers. Purified RNA was mixed with 50 pmol of different primers in a final volume of 14 µl in water and incubated for 5 min at 70° C. and 25 min at 60° C. for denaturing and annealing steps. Then, 5 µl of 5× first-strand buffer 11, 1 µl of 10 mM deoxynucleoside triphosphates (dNTPs), 2 µl of 0.1 M dithiothreitol, 1 µl of RNaseOUT (40 U/µl; Invitrogen) and 2 µl of Superscript II reverse transcriptase (Invitrogen) were added to the reaction. Synthesis of cDNA by RT was conducted at 44° C. for 1 h and 30 min at 51° C. to minimize the formation of RNA secondary structures. PCR was carried out on the reverse transcribed cDNA product using 50 pmol each of specific forward and reverse primers, 5 µl of 10× Pfx amplification buffer, 1 µl of dNTP mixture, 3 µl of $MgSO_4$ and 1 µl of Platinum Pfx DNA polymerase in a total volume of 50 µl. The PCRs were conducted on a Peltier Thermal Cycler (PTC-200; MJ Research) as follows: 3 min at 94° C. and then 40 s at 94° C., 40 s at 55° C. and 1 min/Kb at 68° C. for 30 cycles and a final extension reaction for 7 min at 68° C. RT and PCR primers designed from the 00-1 strain sequence to prime within ORFs usually were not successful generating RT-PCR products from the 83 strain, presumably reflecting sequence differences relative to the 00-1 strain. Therefore, primers were designed from the semi-conserved sequence motifs flanking the viral ORFs (see FIG. 8), which resulted in the successful generation of cDNA. The nucleotide sequences of cDNA products were determined by direct sequence analysis of the RT-PCR products using a ABI 3100 sequencer with the Big-Dye terminator ready reaction kit v1.1 (Applied Biosystems). Finally, the sequence was assembled from overlapping RT-PCR products.

To map and sequence the 3' end of the HMPV genome, vRNA was converted into cDNA and amplified using the 3' RACE System for Rapid Amplification of cDNA Ends (Invitrogen, Inc.) as specified by the manufacturer. Briefly, vRNA was polyadenylated at its 3'-end using poly A polymerase (Invitrogen. Inc.) followed by first-strand cDNA synthesis primed with oligo (dT) and PCR using an HMPV specific reverse primer and a forward UAP primer supplied with the kit. Then, RACE products were used as template for a nested-PCR using an internal HMPV specific reverse primer and the AUAP primer supplied with the kit to improve the specificity of the reaction. Finally, the amplified cDNA nested-PCR products were sequenced directly.

To map and sequence the 5' end of the HMPV genome, vRNA was processed by first-strand cDNA synthesis, terminal transferase tailing, and PCR amplification as specified by the 5' RACE System for Rapid Amplification of cDNA 5' end Version 2.0 (Invitrogen, Inc.) using the AAP primer supplied with the kit. Then, the amplified cDNA RACE products were used as template for a nested-PCR using an internal HMPV specific primer and the AUAP primer supplied with the kit to improve the specificity of the reaction. Finally, the amplified cDNA nested-PCR products were sequenced directly.

The 5' and 3' ends of the HMPV genome also were confirmed by genomic RNA ligation and RT-PCR followed by sequencing. Briefly, vRNA, isolated from sucrose gradient purified virus using the RNeasy kit (Qiagen), was ligated in presence of 10 U of T4 RNA ligase (Epicentre) for 3 h at 25°

C. and 3 h at 37° C. A cDNA corresponding to the junction of the ligated ends was amplified by RT-PCR using HMPV specific primers. The RT-PCR products were used as template for a nested-PCR using HMPV internal specific primers to improve the specificity of the reaction. Finally, the nested-PCR products were cloned into a blunt vector (pSTBlue-1; Novagen) and 20 clones were sequenced, thereby confirming the length, content and sequence of the two previously-uncharacterized ends of the HMPV genome.

The complete sequence of HMPV strain 83 was determined to be 13335 nucleotides in length, and is set forth in FIGS. 37A-37D. This sequence was determined directly from uncloned RT-PCR products and thus represents the authentic majority, consensus sequence of a virulent, wild type virus. This discovery provides a necessary step in the development of a reverse genetics system for recovering complete infectious virus and recombinantly engineered derivatives from cloned cDNAs. A partial sequence had been published representing a portion of the genome of HMPV strain 00-1 (van den Hoogen et al., Virology 295:119-132, 2002).

A genomic map for HMPV 83 is shown in FIG. 1. Compared to RSV, the prototype pneumovirus, HMPV lacks the NS1 and NS2 genes and contains a significant difference in gene order. Specifically, the SH-G gene pair precedes the F-M2 gene pair in RSV, whereas SH-G follows F-M2 in HMPV. Identification of HMPV genes was made based on the presence of ORFs whose predicted protein products exhibit significant amino acid sequence relatedness with counterpart ORFs in RSV (N, P, M, F, M2-1 and L) or, in cases where sequence relatedness was unclear, gene identifications were made by genome position and by the characteristics of the predicted protein (M2-2, G, SH). In these analyses, RSV was chosen for comparison because all of its proteins have been directly identified and in most cases functions have been assigned. In a number of cases, the size of the predicted HMPV protein was substantially different from that of its RSV counterpart. For example, the putative HMPV SH protein was 180% larger than that of RSV (179 amino acids compared to 64) and the HMPV G protein was 27% shorter (219 amino acids compared to 298) and lacked certain characteristic structural features such as the conserved cysteine noose (Johnson et al., Proc. Natl Acad. Sci. USA 84:5625-9, 1987) and CX3C chemokine domain (Tripp et al., Nat. Med. 2:732-8, 2001). Even the putative HMPV P and L proteins exhibited significant differences in length, being 22% larger and 7% shorter, respectively, than the proposed RSV counterparts.

The ends of the HMPV genome were mapped and sequenced. The deduced sequences of the 3' leader and 5' trailer regions are shown in FIG. 2. This analysis ruled out the possibility that one or more additional genes might follow the L gene or precede the N gene, comparable to the NS1 and NS genes of RSV. Comparison of the leader and trailer regions of HMPV 83 with that of APV (Randhawa et al., J. Virol. 71:9849-9854, 1997) and RSV (Mink et al., Virology 185: 615-624, 1991) showed a high degree of sequence identity between the first 22-23 nucleotides at each end, consistent with the idea that these conserved sequences represent important functional domains. In the case of RSV, it was directly demonstrated that the first 11 nucleotides of the RSV genome represent the core promoter essential for both transcription and RNA replication (Fearns et al., J. Virol. 76:1663-1672, 2002).

Thus, the published partial sequence for strain 00-1 appears to lack the core element of both the genomic and antigenomic promoters, and probably lacks any HMPV promoter whatsoever. It is noteworthy that, within the first 12 nucleotides at either end of the HMPV genome, there were at least one (3' leader) or two (5' trailer) sequence differences compared to the other pneumoviruses. Thus, the expedient of using the termini of APV or RSV to supplement the incomplete HMPV 00-1 sequence by constructing a chimeric molecule would not have yielded an authentic HMPV sequence at either end. While the functional significance of these particular differences have yet to be fully elucidated, studies with RSV showed that any point mutations within the genomic promoter affected transcription or RNA replication or both, and in most cases these effects were severe (Fearns et al., J. Virol. 76:1663-1672, 2002). In any event, for the development of a genetic system to engineer recombinant HMPV for use in immunogenic compositions, it is critical to begin with a verified authentic wild type sequence, as provided herein. This sequence was used as a starting point; confirmation that the sequence indeed is authentic and encodes a functional virus is provided by the recovery of infectious, wild type-like recombinant virus. This demonstration is provided in examples below.

Figure 3:
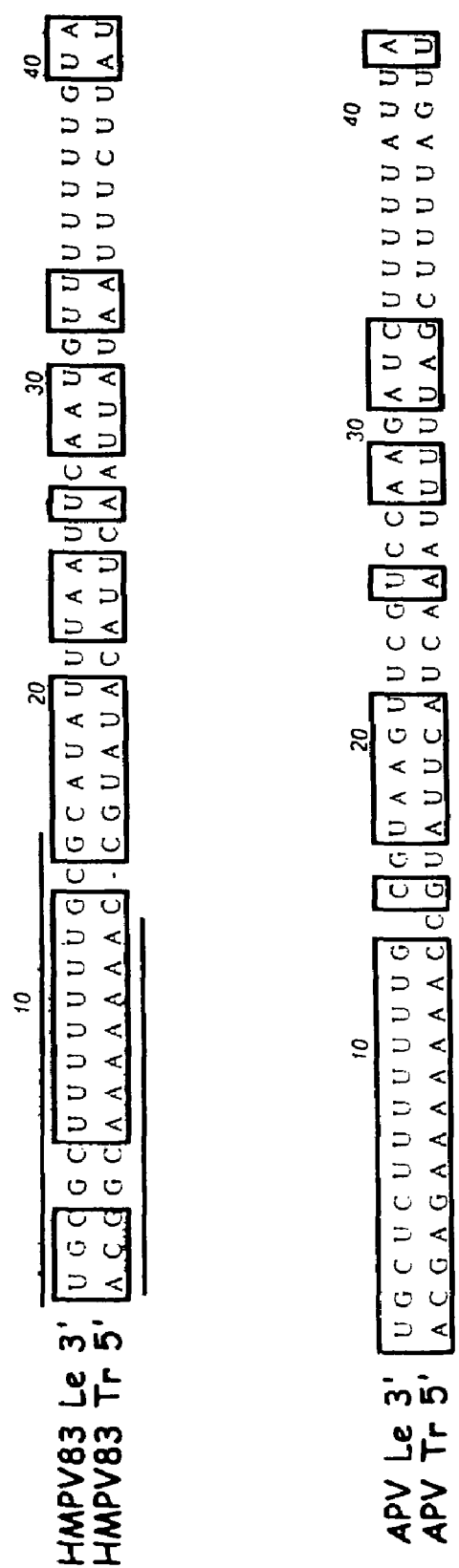
FIG. 3 is a diagram showing sequence alignments between the 3' and 5' ends of the genome of HMPV strain 83 (top; bases 1-41 of SEQ ID NO: 18 and bases 1-40 of SEQ ID NO: 22, respectively) and APV (bottom; bases 1-41 of SEQ ID NO: 19 and bases 1-42 of SEQ ID NO: 23, respectively), with complementary nucleotides boxed. This shows that the last 13 nucleotides of the two ends of APV are perfect complements, whereas HMPV unexpectedly has two noncomplementary nucleotides. Sequences for HMPV that were not previously available are indicated with solid lines above (leader, Le strand) or below (trailer, Tr strand) the sequence.

Another important feature of mononegavirus genomic RNA is that the 3' and 5' ends typically exhibit terminal complementarity, meaning that the two ends are complementary when aligned in an antiparallel fashion. This reflects the presence of a conserved sequence at each end that probably reflects a conserved promoter core. This terminal complementarity is shown for HMPV 83 and APV in FIG. 3. For typical mononegaviruses, the two ends exhibit a high degree of complementarity for at least the first 12 nucleotides and often more, and typically within this region the complementarity is exact or has at most one mismatch. As shown in FIG. 3, the APV genome indeed has an exact match for the first 13 nucleotides whereas, surprisingly, the HMPV 83 genome has two adjacent mismatches. This further illustrates that extrapolation from other pneumoviruses to develop a HMPV genetic system based on an incomplete sequence could not have yielded an authentic HMPV sequence.

Figure 4:
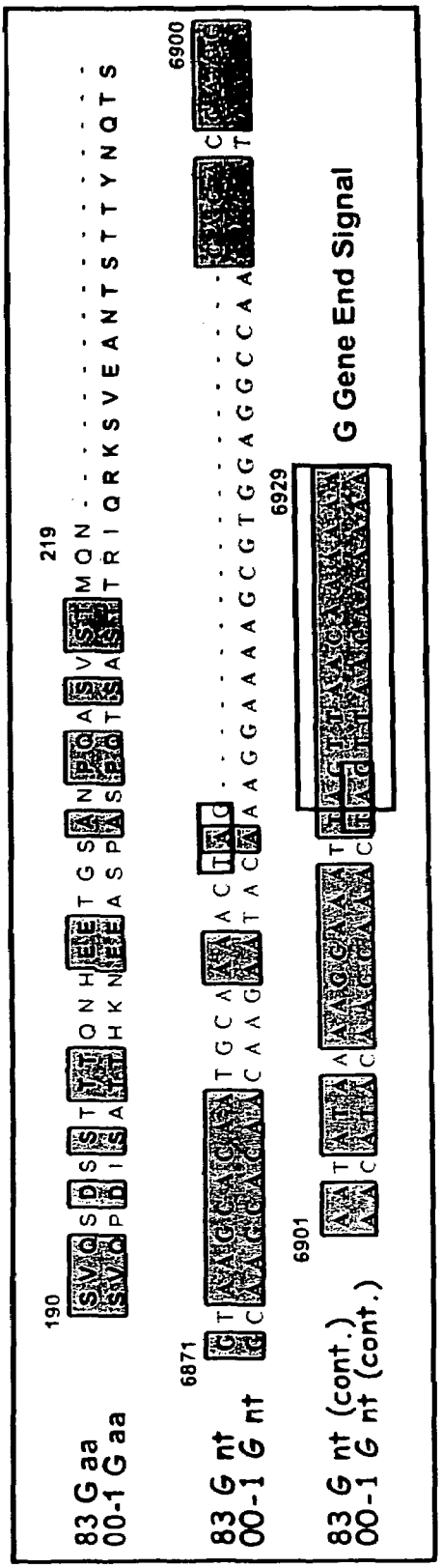
FIG. 4 is a diagram showing several examples of differences in nucleotide and amino acid lengths between HMPV strains 83 and 00-1. The differences in G are illustrated by partial amino acid sequences (upper alignment; amino acids 190-219 of SEQ ID NO: 6 and amino acids 190-236 of SEQ ID NO: 11, respectively) and partial nucleotide sequences (second alignment; bases 6871-6929 of SEQ ID NO: 1 and bases 6886-6964 of SEQ ID NO: 36, respectively). The sequences are numbered according to the amino acid sequence of HMPV 83 G (top alignment) or the complete nucleotide sequence of the antigenome of HMPV 83 (second alignment). Examples of differences include, (1) the SH protein for 83 is shorter by 4 aa due to an earlier stop codon; (2) the G protein for 83 is shorter by 17 aa due to an earlier stop codon, which is followed by a deletion in the downstream noncoding region; and (3) the intergenic region between the F and M2 genes of 83 is 13 nucleotides (nt) compared to 41 nt for 00-1. Taken together, these show that the G ORF and encoded G protein of strain 83 are shorter by the equivalent of 17 amino acids from that of strain 00-1.

The sequence of HMPV 83 contained a number of differences compared to that published for strain 00-1. As examples, FIG. 4 shows that the SH ORF terminated four codons earlier in the 83 sequence than in that for strain 00-1, yielding a shorter SH protein. Also, the G ORF in the HMPV 83 sequence contained a deletion that shortened the G protein by 17 amino acids, and the intergenic region between the F and M2 genes was 13 nucleotides for 83 instead of 41 nucleotides. The significance of differences such as shown in FIG. 4 can be directly evaluated with the reverse genetics system of this current disclosure.

The percent amino acid sequence identity between the predicted proteins of HMPV strain 83 and those of other pneumoviruses is shown in FIG. 5. It should be noted that a subsequent Example provides a more extensive comparison between strain 83 and another HMPV strain, 75, that forms part of the current disclosure, demonstrating the extent of sequence diversity between and within the proposed HMPV subgroups. It is noteworthy that, among all of the pneumoviruses shown in FIG. 5, reverse genetics systems for the recovery of complete infectious virus have been reported only in the case of bovine RSV (BRSV) and human RSV subgroup A. This is despite that fact that PVM has been known for almost 65 years and has been the subject of extensive molecular analysis beginning in the late 1980's, and despite the fact that APV has been known for almost 25 years and also is the subject of molecular analysis. The fact that reverse genetics systems are not yet available despite considerable interest in their development illustrates the difficulty of producing such systems. As has already been noted, HRSV and BRSV differ from HMPV with regard to the lack of two genes (NS1 and NS2) and the rearrangement of other genes (SH and G). HRSV and BRSV also differ extensively from HMPV with regard to amino acid sequence identity of the predicted HMPV proteins. Three of the potential HMPV proteins (SH, G, and M2-2), share only 6-15% sequence identity with their putative HRSV counterparts, whereas low sequence identity values (for example, less than 25% identity) are generally considered at best to correspond to remote homologs or, alternatively, to proteins that are unrelated. Conversely, the highest value for percent identity is only 46%, in the case of the L protein. Thus, HMPV is quite distinct from any virus for which a reverse genetics system for the recovery of virus has been developed. It should be further noted in this context that the function of a protein in HMPV cannot be reliably predicted by extrapolation from results obtained for a related protein of a related virus, not even for a closely related virus. Briefly, there is initial uncertainty in deducing proteins from nucleotide sequence. For example, despite the reported existence of an M2-2 ORF in APV, the available evidence suggests that this ORF is not expressed (Ahmadian et al., J. Gen. Virol. 80:2011-2016, 1999), whereas it clearly is expressed in RSV and has been shown to have a role in regulating RNA synthesis (Bermingham and Collins, Proc. Natl. Acad. Sci. USA 96:11259-11264, 1999; Jin et al., J. Virol. 74:74-82, 2000). Thus, the presence of an ORF is not proof alone of significance. As another example, in the Filovirus family, both Ebola and Marburg viruses express a protein called VP30 that is highly related between the two viruses. However, these two proteins have different functions (Weik et al. J. Virol. 76:8532-9, 2002; Muhlberger et al., J. Virol. 73:2333-42, 1999). These are but two examples of the uncertainty in predicting the existence and function of a protein based on nucleotide sequence alone. This highlights the importance of direct, relevant assays as provided hereon for the demonstration of protein function. These are presented in the current disclosure in two forms: (i) the development of a mini-replicon that is capable of transcription and replication when supplied with appropriate viral proteins, and importantly (ii) the development of a system for the recovery of complete infectious virus completely from cDNA, which provides the basis for analysis of the function of all elements of the genome and its encoded RNA and protein products and infectious virus.

Figure 6:
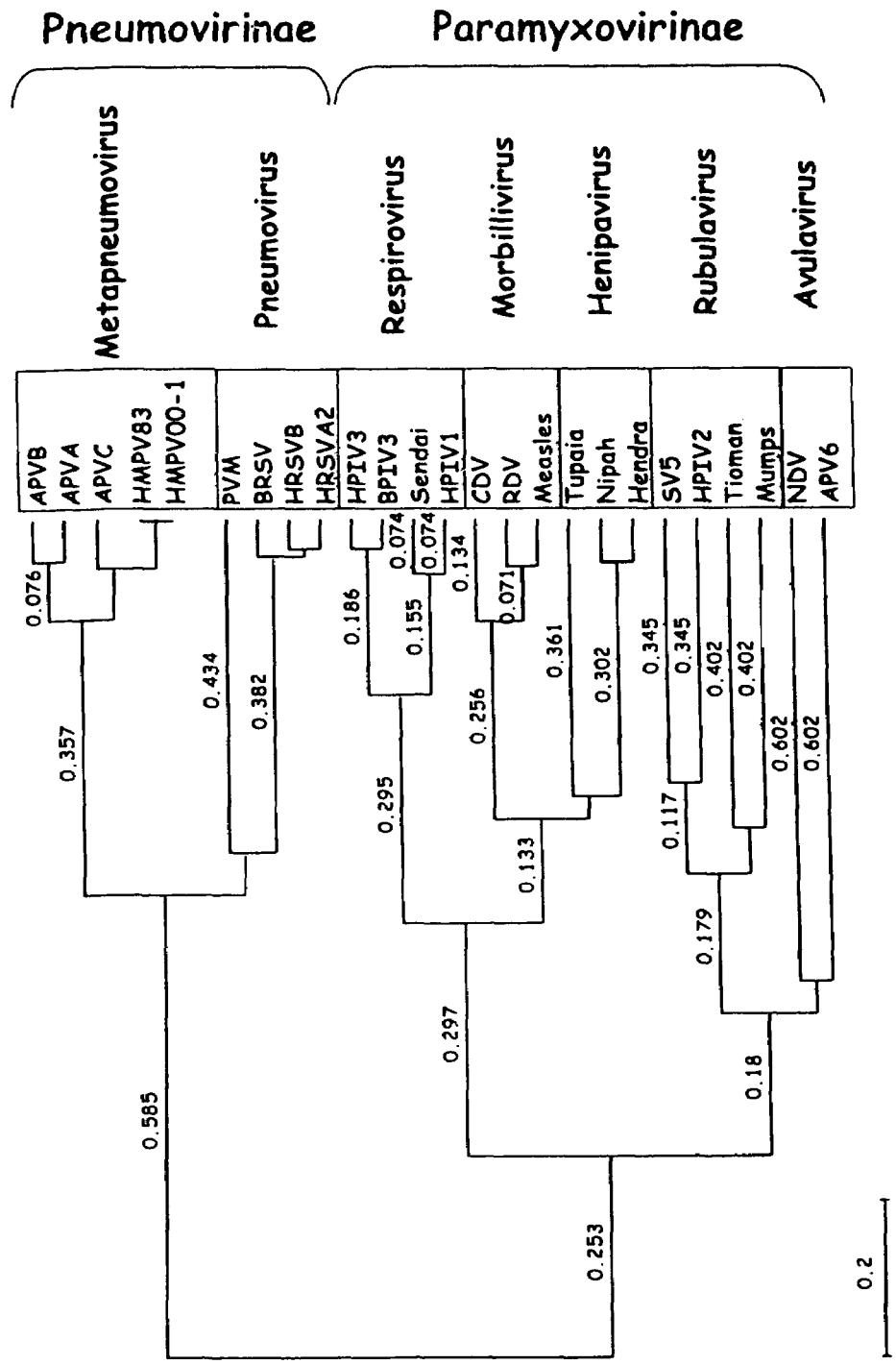
FIG. 6 is a taxonomy tree, illustrating putative phylogenetic relationships between HMPV and other paramyxoviruses based oil comparisons of the amino acid sequences of proposed matrix M proteins. Pneumovirinae and Paramyxovirinae are the two subfamilies of the Paramyxovirus family. The other taxonomic names refer to genera. The numbers refer to the extent of amino acid sequence divergence (percentage non-identity) divided by 100; hence, 0.2 refers to 20% amino acid differences. Note that a system for recovering and modifying infectious recombinant virus has not been reported for any member of genus Metapneumovirus even though the avian members of this genus have been known for almost 25 years.

The amino acid sequence of the predicted M protein of HMPV 83 was used to estimate the phylogenetic relationships between HMPV and other members of the Paramyxovirus family, as illustrated in FIG. 6. As shown in this figure, the Paramyxovirus family consists of two subfamilies Pneumovirinae and Paramyxovirinae, herein referred to as pneumoviruses and paramyxoviruses, respectively. These subfamilies are further divided into genera, the genus of HMPV being the Metapneumoviruses. A system for producing infectious recombinant virus did not exist previously for any member of this genus. This analysis provided further evidence of evolutionary distance and distinction from pneumoviruses such as RSV and, in particular, from paramyxovirus such as Sendai, measles, mumps, human parainfluenza, and New-castle disease viruses that constitute the more well-known and more extensively-characterized members of the Paramyxovirus family.

Example 2

Figure 7:
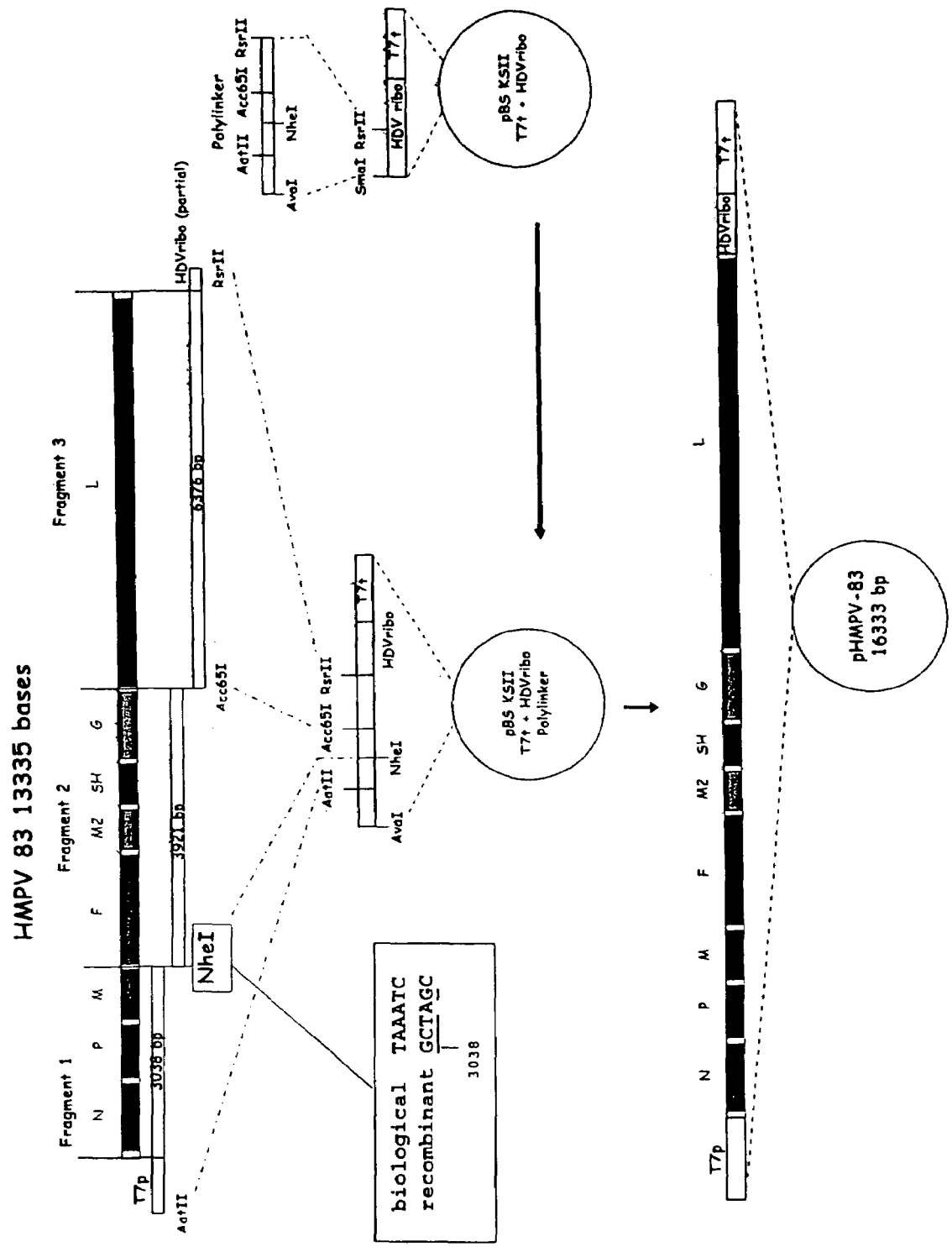
FIG. 7 is a diagram illustrating the construction of a cDNA encoding the complete antigenome of HMPV strain 83, designed from the complete consensus genomic sequence. Three separate subgenomic cloned fragments were created: fragment 1 contains the putative N, P and M genes and is bordered on the upstream (left) side by an added promoter for bacteriophage T7 RNA polymerase (T7p) and on the right hand side by an NheI site that was added to the putative M-F intergenic region as a marker. The sequence changes involved in introducing the NheI site are shown. The T7 promoter was designed to add three nonviral G residues to the 5' end of the antigenome, a configuration chosen to improve the efficiency of the T7 promoter. Fragment 2 included the putative F, M2, SH and G genes and is bordered on the upstream side by the added NheI site and on the downstream side by a naturally occurring Acc65I site. Fragment 3 consists of the L gene followed by part of the hepatitis delta virus ribozyme (HD-Vribo) (Perrotta and Been, Nature 350:434-6, 1991) bordered by an RsrII site that occurs naturally within that ribozyme. The vector for cloning and expressing the HMPV 83 antigenome cDNA was pBSKSII, which is a derivative of a modified Bluescript II KS+ (Stratagene) vector described previously (Durbin et al., Virology 71:4272-7, 1997) and contains the hepatitis delta virus ribozyme followed by a terminator for T7 RNA polymerase (T7t). This vector was modified by the insertion of a polylinker containing AvaI, AatII, NheI, and Acc65I sites, which in turn served to accept the cloned fragments 1, 2 and 3. The final cDNA encodes the complete 13335-nucleotide HMPV 83 antigenome containing three added nonviral G residues at the 5' end. The complete pHMPV-83 recombinant plasmid ("antigenome plasmid") contains 16333 bp.

Assembly of a Full-Length HMPV Antigenomic cDNA Clone Containing a GFP Transcription Cassette and Recovery of Infectious Recombinant HMPV The complete, authentic, consensus sequence (FIGS. 37A-37D) determined for HMPV strain 83 provided the basis for designing a system for producing infectious recombinant virus. FIG. 7 illustrates the construction of a cDNA clone encoding the complete antigenome of HMPV strain 83 designed from the complete consensus sequence. Three separate cloned subgenomic fragments were created: fragment 1 contains the putative N, P and M genes and is bordered on the upstream (left) side by an added promoter for bacteriophage T7 RNA polymerase (T7pr) and on the right hand side by an NheI site that was added to the putative N-F intergenic region as a marker. The T7 promoter was designed to add three nonviral G residues to the 5' end of the antigenome, a configuration chosen to improve the efficiency of the T7 promoter. Fragment 2 included the putative 1, M2, SH and G genes and is bordered on the upstream side by the added NheI site and on the downstream side by a naturally-occurring Acc65I site. The NheI site serves as a marker to distinguish between cDNA-derived and biologically-derived HMPV. Fragment 3 consists of the putative L gene followed by half of the hepatitis delta virus ribozyme (HDVribo) bordered by an RsrII site that occurs naturally within the ribozyme. The sequence of each cloned cDNA fragment was confirmed. The vector for cloning and expressing the HMPV 83 antigenome cDNA is pBSKSII, which contains the hepatitis delta virus ribozyme followed by a terminator for T7 RNA polymerase (T7t) and was derived from vector p3/7 that was used previously for the recovery of recombinant HPIV1, HPIV2 and HPIV3 (Durbin et al., Virology 235:323-332, 1997; Schmidt et al., J. Virol. 74:8922-9, 2000; Skiadopoulos et al., J. Virol. 77:270-9, 2003; Newman et al., Virus Genes 24:77-92, 2002). This vector was modified by the insertion of a polylinker containing AvaI, AatII, NheI, and Acc65I sites, which in turn served to accept the fragment 1, 2 and 3 restriction sites. Specifically, the polylinker consists of the following sequence, CCCGGGGACGTCCTAGCTAGCTAGGG-TACCCCGCTCGAGCGGTCCG (SEQ ID NO: 33; SmaI and RsrII sites italicized), and was inserted between the SmaI and RsrII sites of the vector p3/7 of Durbin et al. (Durbin et al., Virology 235:323-332, 1997). The final cDNA encodes the complete 13335-nucleotide HMPV 83 antigenome containing three added nonviral G residues at the 5' end. The complete pHMPV-83 recombinant plasmid ("antigenome plasmid") contains 16333 bp.

It was anticipated that the poor growth and lack of established reference reagents and assays for HMPV could complicate the recovery and identification of recombinant HMPV recovered from cDNA. Therefore, the strategy was adopted to modify the antigenomic cDNA to insert a foreign marker gene encoding a detectable label, whereby expression of the marker gene could be readily monitored. The gene that was chosen encodes the well-known marker or label GFP, a cnidarian protein whose presence can be visualized by green fluorescent emission when observed under a fluorescent microscope. The GFP cDNA was the Enhanced GFP cDNA of Clonetech, Inc. Expression of a detectable marker in this manner, directly linked with HMPV production, makes it possible to monitor expression of GFP by recombinant HMPV in living cells without loss of viability or sterility, and to thereby detect and quantify the recovery of rHMPV at all stages of transfection and passage.

Among the obstacles to this strategy were the lack of direct information on HMPV transcription and the lack of direct mapping of gene boundaries. It therefore was necessary to identify sequence that, when attached to the foreign ORF, would render it capable of being expressed during the HMPV transcriptional program. It also was necessary to identify a site within the HMPV genome that could accommodate the insertion of a foreign gene without disrupting HMPV growth. The transcription of a typical mononegavirus genome initiates at or near the 3' end and proceeds by a sequential start-stop mechanism by which the individual genes are transcribed into individual, separate mRNAs. Typically, monon- egavirus transcription is guided by short sequence motifs that flank the viral genes. For example, the genes of RSV, which is the most thoroughly characterized pneumovirus, contain a highly-conserved 10-nucleotide GS signal on the upstream end of each gene and a semi-conserved 12- to 13-nucleotide GE signal at the downstream end of each gene. These motifs were first noticed when RSV mRNAs were isolated from infected cells and their termini were directly mapped and sequenced. It is thought that the GS signal directs initiation of transcription of the individual gene, and the GE signal directs polyadenylation and termination. The polymerase remains bound to the template and crosses the intergenic region to resume transcription at the next gene. In the case of RSV, the analysis of the mRNA ends showed that the arrangement of genes was unexpectedly complex. Specifically, the GS signal of the L gene was found to differ from that of the others, and furthermore was found to be located within its upstream neighbor rather than downstream of it. As another example, the M2-1 and M2-2 ORFs were found to be contained in a single mRNA rather than two. Also, there was no consistency of spacing of the RSV GS and GE signals with respect to the ORFs, such that there were instances where the GS signals overlapped the ORFs or, alternatively, were separated from the ORFs by as many as 85 nucleotides. Similarly, certain RSV GE signals overlapped the respective ORF or were separated by as many as 173 nucleotides. Furthermore, the spacing between the RSV genes was irregular, ranging from the overlapped genes mentioned above to ones separated by as many as 56 nucleotides. This indicates the uncertainty of predicting gene boundaries based on the locations of putative ORFs and potential sequence motifs. However, the methods of this current disclosure provide for the direct identification of appropriate transcription signals and insertion sites.

The complete sequence of HMPV strain 83 was examined for potential GS and GE motifs, as shown in FIG. 8. These motifs were identified on the basis of being located between ORFs and by exhibiting partial sequence conservation among themselves. For example, the putative HMPV GS motif has the sequence GgGAcAAgTgaaaATG, where the nucleotide assignments in upper case are conserved in each of the putative genes. In sharp contrast to RSV, the putative GS signals were found in close proximity to the start of their respective putative ORFs, with the putative initiation ATG codon located at positions 14-16 relative to each putative GS signal. It should be noted that the L ORF was preceded by two potential GS sequences, either of which was a reasonable fit for the proposed consensus sequence. One of these is shown in FIG. 8, while the second is located 18 nt upstream (7102- GGGCAAAACAGCATCC). Typically mononegavirus genes each have a single GS site, and it is not known which one of these is functional for the HMPV L gene. However, this can now be readily determined by the methods of this current disclosure, by mapping the 5' end of the putative L mRNA by RT-PCR, or by testing each potential GS signal for functionality in a mini-replicon system, or by destroying each potential signal in the complete antigenome and evaluating each mutant for virus recovery and efficiency of growths.

The putative GE motif has the sequence AGTtaattaAAAA, where the upper case assignments are conserved in each of the putative genes. The limited number of highly-conserved nucleotide assignments in these motifs made their identification speculative, particularly since not a single HMPV signal had been directly identified to use as a benchmark. While these conserved motifs appear to contain the core of the GS and GE signals, it would not be surprising to find that either sequence as described here might be shortened at one or both ends by one or several nucleotides without complete loss of activity, or that one or more additional nucleotides added to either side might affect the activity of either signal. As an indication of the uncertainty of deducing transcription signals from sequence data alone, van den Hoogen et al. noted two different types of consensus sequences between genes, one of which corresponds to that noted above (van den Hoogen et al., Virology 295:119-132, 2002). In this regard, these authors concluded that they could clearly identify this particular consensus sequence for two genes, F and L (although, as noted above, there would appear to be two candidates to be the GS signal for the L gene), found "variants" in several other genes, failed to detect a counterpart for the G gene, and noted that "another [different] repeated sequence . . . was found downstream of each of the hMPV ORFs except G", raising further uncertainty as to which, if any, of these sequence motifs might function as a transcription signal. Thus, it was important to directly identify transcription signals that could render a foreign sequence competent for expression by HMPV.

Figure 9:
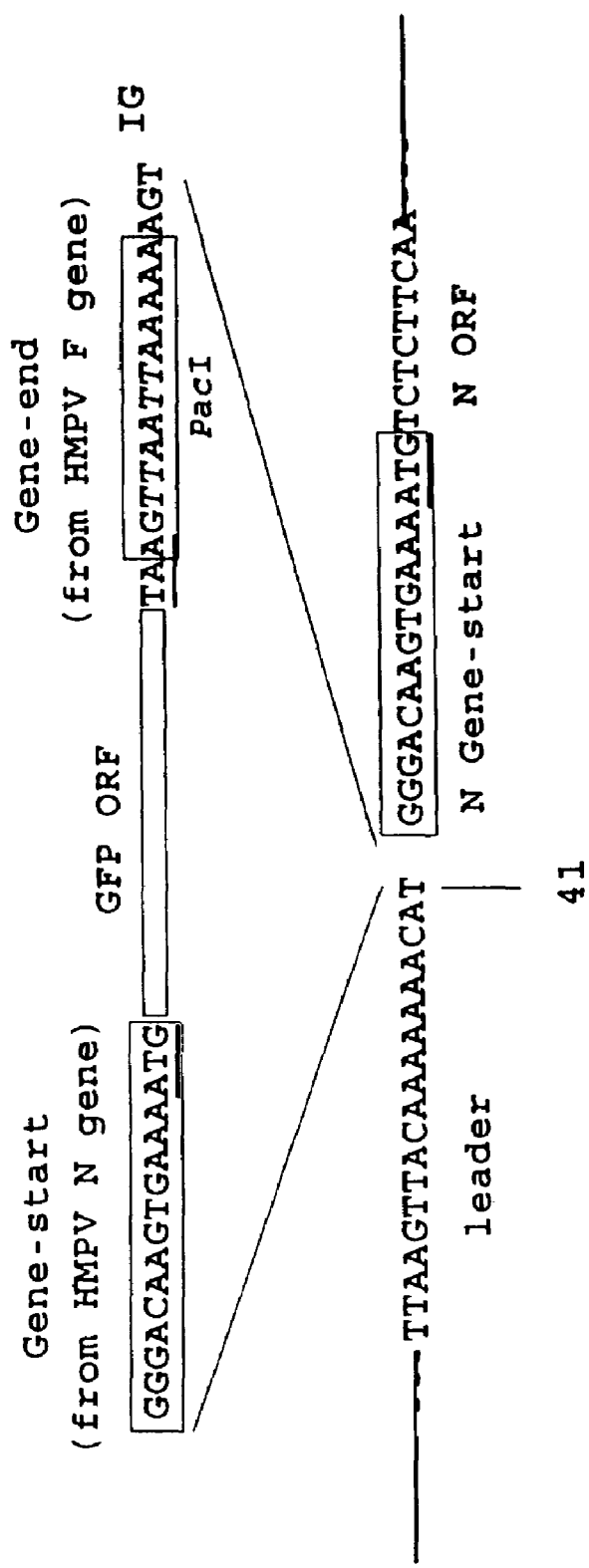
FIG. 9 is a diagram illustrating the construction of a transcription cassette containing the ORF for jellyfish GFP under the control of HMPV transcription GS and GE signals, and insertion of this cassette into the HMPV strain 83 antigenomic cDNA clone following antigenomic position 41. Sequence representing part of the 3' leader region (bases 23-41 of SEQ ID NO: 1) and the putative N GS signal and beginning of the putative N ORF (bases 42-66 of SEQ ID NO: 1) is shown at the bottom. The GFP transcription cassette consists of a 714-nucleotide cDNA containing the GFP ORF flanked on the upstream side by 16 nucleotides (which include the initiating ATG of the GFP ORF) representing the conserved putative N GS signal (bases 42-57 of SEQ ID NO: 1) and flanked on the downstream side by 13 nucleotides representing the putative F GE signal (bases 46854697 of SEQ ID NO: 1; which include the termination codon of the GFP ORF) followed by the trinucleotide AGT designed to function as an intergenic (IG) region. The total length of the transcription cassette including the trinucleotide intergenic region is 748 nucleotides. The F GE signal contains a naturally occurring PacI site (italicized).

In order to directly identify sequence signals that can confer gene expression, the 16-nucleotide putative GS sequence and 13-nucleotide putative GE sequence of the N gene were attached to a cDNA containing the GFP ORF. In this configuration, the ATG present in the GS signal replaced that of the GFP ORF. As shown in FIG. 9, this transcription-cassette was inserted into the HMPV antigenomic cDNA following nucleotide 41, resulting in an antigenome in which the GFP gene was placed first in the 5' to 3' order. In the corresponding HMPV-GFP genome, the GFP gene would be the most promoter-proximal of the genes. The complete sequence of the antigenomic rHMPV-GFP cDNA (FIGS. 38A-38D) and flanking plasmid regions was confirmed by sequence analysis.

Initially four of the ORFs of HMPV, namely the putative N, P, L and M2-1 ORFs, were selected to be expressed in separate plasmids to complement recovery. This initial recovery protocol focused on proteins predicted to be "internal" proteins (as opposed to components of the envelope). Examination of the HMPV genome identified ORFs whose potential products share 41%, 31%, 36%, and 46% identity with the RSV N, P, M2-1 and L proteins, respectively (FIG. 5), and these ORFs were selected as candidates for inclusion. The putative M2-1 HMPV ORF also was included in the recovery because it is a possible internal protein, and studies with RSV, Ebola virus and Marburg virus indicate that possible M2-1 counterparts can be involved in RNA synthesis. In this regard it is noted that the presumed M2-1 counterparts appear to play different roles in Ebola and Marburg viruses despite their high degree of relatedness (Weik et al. J. Virol. 76:8532-9, 2002: Muhlberger et al., J. Virol. 73:2333-42, 1999). Also, the putative HMPV M2-1 protein contains a Cys-7/Cys-15/Cys- 21/His-25 motif (numbered according to the complete deduced HMPV M2-1 amino acid sequence, designated herein the Cys3-1-His1 motif) that is a potential zinc binding domain that might indicate a role in interacting with nucleotides or nucleic acid. On the other hand, the putative M2-2 ORF was not included in the initial recovery system, and there is evidence from APV that a seemingly-corresponding M2-2 ORF is not expressed (Ahmadian et al., J. Gen. Virol. 80:2011-2016, 1999).

The ORFs for the G, F and SH proteins of HMPV were not included in the initial recovery system, because these ORFs were predicted to encode transmembrane surface proteins—based on the presence of putative hydrophobic signals and anchors in the deduced amino acid sequences. Notably, the predicted HMPV F protein shares 36% amino acid sequence relatedness to that of RSV. The percent amino acid identity for the putative G and SH proteins between HMPV and RSV are 15% and 6%, respectively. Despite this substantial departure in primary structure, other features of the amino acid sequences, such as the presence of potential glycosylation sites support the identification of these proteins herein. It is generally acknowledged in the field that the envelope proteins do not have a known role in genome transcription and RNA replication. This does not preclude the possibility that the expression of these additional ORFs might facilitate recovery, perhaps by increasing the efficiency of virion assembly. However, an important aspect of the current disclosure involves identification of a minimal complement of support plasmids necessary for HMPV recovery. Once minimal recovery elements were shown to be successful, additional embodiments can now be constructed and evaluated to optimize the efficiency of recovery. For example, although the expression of the M2-1 ORF from a separate plasmid is shown herein to be non-essential for recovery, it may nonetheless be a desired complement that could function to influence transcription or RNA replication or some other aspect of HMPV replication. Accordingly, expression plasmids were constructed in which the N, P, L and M2-1 ORFs were placed under the control of a T7 transcription promoter and terminator.

Support plasmids encoding putative HMPV nucleocapsid and polymerase proteins were prepared as follows (FIG. 10): to prepare a support plasmid expressing the putative N protein, vRNA was subjected to RT-PCR using a positive sense primer designed to hybridize at beginning of the putative N ORF (nucleotides 55 to 76 in the HMPV genome) and a reverse primer designed to hybridize at the end of the putative N ORF (nucleotides 1239 to 1220 in the HMPV genome). The PCR product was digested with XhoI and subjected to a partial digestion with AflIII, which was done because the putative N ORF contains a naturally-occurring AflIII and a partial digest would yield some product that had been cleaved at the terminal site and not at the internal site. The products were into pTM1 (Durbin et al., Virology 235:323-332, 1997; Durbin et al, Virology 234:74-83, 1997; Elroy-Stein et al., Proc. Natl. Acad. Sci. USA. 86:6126-30, 1998) that was digested with NcoI (which leaves overhangs compatible with AflIII) and XhoI, and clones containing the complete putative N ORF were selected and the sequence confirmed.

To construct a support plasmid containing the putative P ORF: of HMPV (pT7-P) (FIG. 10), vRNA was subjected to RT-PCR using a positive sense primer designed to hybridize at beginning of the putative P ORF (nucleotides 1263 to 1279 in the HMPV genome) and a reverse primer designed to hybridize at the end of the putative P ORF (nucleotides 2147 to 2132 in the HMPV genome). The PCR product was digested with AflIII and XhoI and cloned into pTM1 that was digested with NcoI and XhoI. In the final cloned recombinant plasmid, the sequence of the HMPV insert and flanking plasmid regions was confirmed by sequence analysis.

A comparable putative M2-1 support plasmid for HMPV (pT17-M2-1) was generated (FIG. 10). vRNA was subjected to RT-PCR using a positive sense primer designed to hybridize at beginning of the putative M2-1 ORF (nucleotides 4724 to 4740 in the HMPV genome) and a reverse primer designed to hybridize at the end of the putative M2-1 ORF (nucleotides 5287 to 5272 in the HMPV genome). The PCR product was digested with AflIII and BamHI and cloned into pTM1 that was digested with NcoI and BamHI. In the final cloned recombinant plasmid, the sequence of the HMPV insert and flanking plasmid regions was confirmed by sequence analysis.

Figure 10:
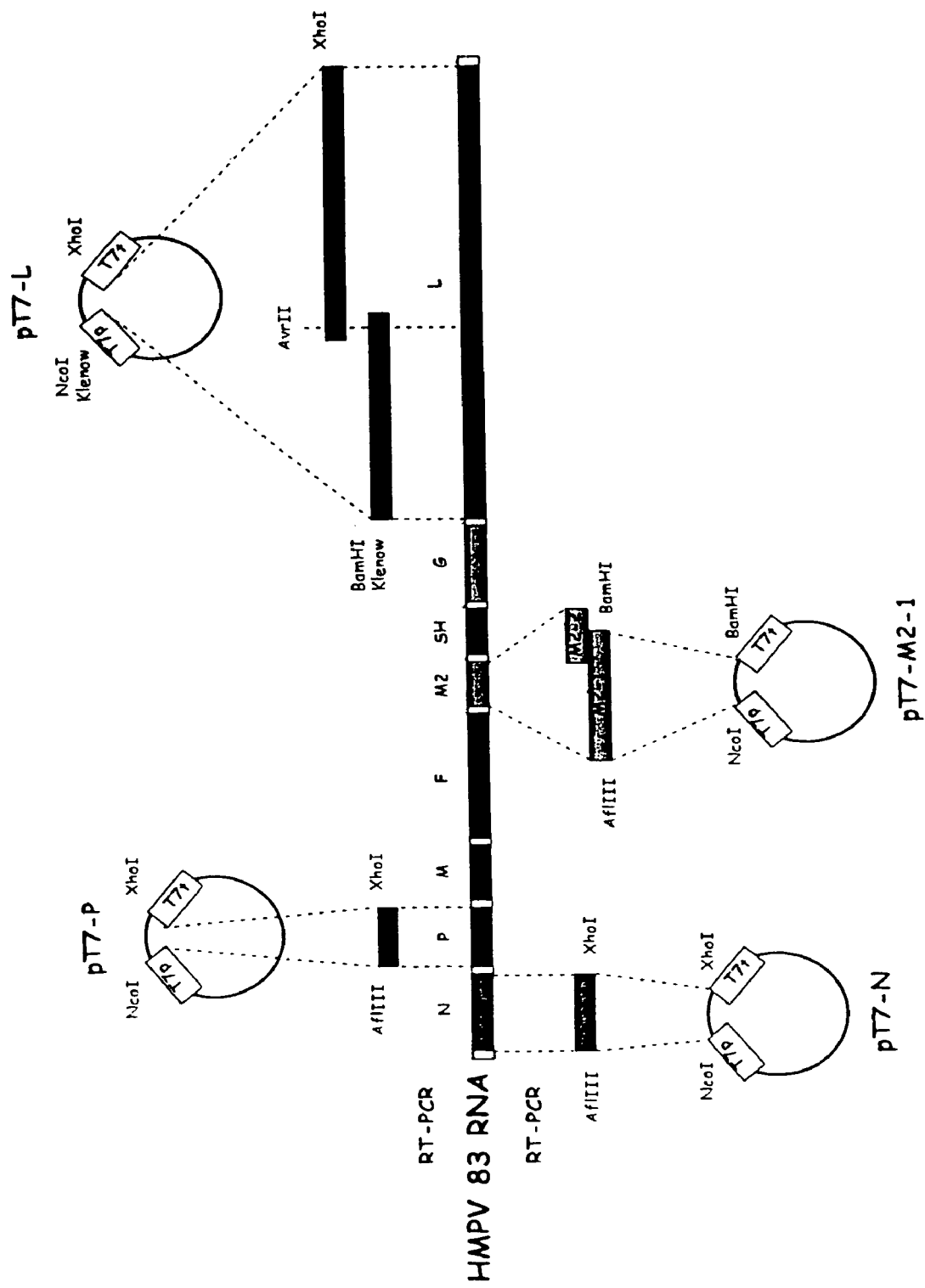
FIG. 10 is a diagram illustrating the construction of expression vectors comprising support plasmid that contain ORFs corresponding to the proposed nucleocapsid and polymerase proteins of HMPV strain 83: N, P, M2-1 and L. These ORFs were clarified in part based on sequence relatedness to the respective RSV ORF (see, for example, FIG. 5). Each ORF was placed under the control and 8, molecular weight markers; lane 3, a negative control in which RNA from recovered recombinant HMPV was subjected to the RT-PCR procedure with the omission of RT enzyme; lanes 2 and 4-7, RT-PCR products representing the indicated viruses.

A support plasmid containing the putative L ORF of HMPV (pT7-L; FIG. 10) was made by RT-PCR amplification of two overlapping fragments and cloned separately into pTM1 vector. The first fragment was amplified by RT-PCR using a positive sense primer designed to hybridize at the beginning of the putative L ORF (nucleotides 7133 to 7157 in the HMPV genome) and a reverse primer designed to hybridize downstream to a unique AvrII (nucleotides 10892 to 10897 in the HMPV genome) restriction site (nucleotides 11037 to 11018 in the HMPV genome), and the second using a positive sense primer designed to hybridize upstream to the unique AvrII site (nucleotides 10845 to 10866 in the HMPV genome) and a reverse primer designed to hybridize at the end of the putative L ORF (nucleotides 13150 to 13124 in the HMPV genome). Then, the first fragment was treated by BamHI and the Klenow fragment of the *E. coli* polymerase I to generate a blunt end, digested by AvrII and cloned into pTM1 that was treated by NcoI and Klenow enzyme and digested by AvrII. Finally, the second fragment of the putative L ORF was digested by AvrII and XhoI and cloned in the intermediate construct digested by the same enzymes, leading to the final construct pT7-L. In the final cloned recombinant plasmid, the sequence of the HMPV insert and flanking plasmid regions was confirmed by sequence analysis.

To provide an initial functional evaluation of these support plasmids, a mini-replicon system was developed. A cloned cDNA was constructed so that its expression from a T7 promoter yielded a negative-sense mini-replicon RNA, or minigenome, that contained, in 3'- to 5' order: the leader end of the HMPV genome and adjoining putative N GS signal followed by a negative sense copy of the ORF encoding bacterial chloramphenicol acetyl transferase (CAT), followed by the putative L GE signal and the trailer end of the HMPV genome. The correct 3' end was generated by a HDV ribozyme as described above. In this minigenome, the CAT gene would be under the control of putative HMPV GS and GE signals, and would be expressed as a subgenomic mRNA. The minigenome plasmid was transfected into HEp-2 cells together with the N, P, M2-1 and L support plasmids with simultaneous coinfection by vTF-7, a vaccinia virus recombinant that expresses T7 RNA polymerase. 48 h post transfection, intracellular RNA was isolated and analyzed by Northern blot hybridization using a double stranded probe specific to the CAT cDNA. This analysis demonstrated that coexpression of the N, P, and L genes with the minigenome plasmid yielded RNA species of the appropriate size to represent progeny minigenomes, antigenomes, and subgenomic CAT mRNA. In this assay, the further addition of the M2-1 gene did not alter the profile of RNA products. This indicated that in this assay N, P and L coexpression was sufficient to reconstitute RNA replication and transcription. These findings are in sharp contrast to RSV, where the expression of M2-1 is necessary to achieve efficient synthesis of mRNA (Collins et al., Proc. Natl. Acad. Sci. USA 93:81-85, 1996; Fearns and Collins, J. Virol. 73:5852-64, 1999). These preliminary results do not rule out any role for M2-1 in HMPV RNA synthesis, since it is possible that M2-1 might have one or more functions that are not required for minigenome replication and transcription but might be essential to launch infection by complete recombinant virus. The current disclosure provides the methods to expeditiously evaluate the role of M2-1 (and M2-2) in viral recovery, gene expression, and replication.

To test the ability to generate infectious recombinant HMPV from cDNA, the full-length HMPV-GFP antigenome plasmid was cotransfected with the N, P, M2-1 and L plasmids into BSR T7/5 cells, which are baby hamster kidney-21 (BHK-21) cells that constitutively express T7 RNA polymerase (Buchholz et al. J. Virol. 73:251-59, 1999). Transfections were done in 6-well dishes with 5 µg of antigenome plasmid, 2 µg each of N and P support plasmid, and 1 µg each of M2-1 and L support plasmid per well. Transfections were done with SuperFect (Qiagen) or Lipofectamine 2000 (Invitrogen) in medium without trypsin or serum. One day post transfection trypsin was added to 5 µg/ml. Also, to maintain the cells in an active state, they typically were split and reseeded at a 1:3 ratio one or two days post transfection. In another, alternative permutation, fresh trypsin was added one day post transfection, the cells were incubated for one or more hours, the cells were scraped into the medium, and the total suspension was passaged to fresh LLC-MK2 or Vero cells. Approximately 12-24 h later the medium was replaced with fresh medium containing 5 µg/ml trypsin (unless otherwise noted, 5 µg/ml trypsin was the concentration that was routinely used).

When examined by fluorescent microscopy on successive days post-transfection, green cells were visualized that initially consisted of scattered isolated cells and subsequently formed small foci that consisted of two or more cells and exhibited cytopathic effect consistent with HMPV. When the transfection monolayer was split into new cultures, single green cells were visualized within one day and developed over successive days into multicellular syncytia. The expression of GFP was monitored by fluorescent microscopy and photographed 8 days post-transfection. The nature of the cytopathology was indistinguishable from that produced by biologically-derived HMPV. The recovered virus replicated in LLC-MK2 cells with kinetics and cytopathogenicity consistent with HMPV.

The ability to monitor the infection in live cells without compromising sterility can be used to expeditiously examine conditions to improve growth. For example, it was found that the replenishment of trypsin by the addition of further amounts during incubation resulted in a greater number of infected cells. In a preliminary experiment, the addition of fresh trypsin to a concentration of 2.5 or 5 µg/ml at two-day intervals resulted in the highest level of GFP expression and virus spread. However, the higher level also was associated with increased syncytium formation, which has the potential to cause more rapid cell death and decreased yield. Further experimentation, combined with assay of released infectious virus (an assay that also is facilitated by the expression of the GFP marker), will serve to identify the condition of incubation and level of trypsin that is optimal for the production of infectious virus. The most optimal schedule found to date has been to add 5 µg/ml fresh trypsin at intervals of 2 or 3 days.

The expression of GFP by cells infected with the recovered virus provided evidence that the virus was cDNA-derived and was not contaminating biologically-derived HMPV. Further identification of the virus as recombinant HMPV was made in two ways, by immunofluorescence and by detection of the NheI restriction site marker. In the immunofluorescence assay, antibodies from hamsters that had been infected with biologically-derived HMPV reacted specifically with cells infected with the putative recovered rHMPV-GFP. For this assay, BSR T7/5 cells were transfected for the recovery of recombinant HMPV-GFP as described above. Four days later the cells were split again at a ratio of 1:3 and incubated on a coverslip for nine more days. Incubations were in the presence of 5 µg/ml trypsin. The cells were fixed with 80% acetone for 15 min at 4° C., followed by incubation with serum from hamsters that had been infected with HMPV, followed by incubation with goat antibodies that were specific to hamster IgG and had been labeled with the fluorescent tag Alexa-488. The same field of cells was visualized by confocal microscopy with visible light and under conditions for fluorescence. This demonstrated strong fluorescence that was specific to foci in HMPV-infected cultures.

Figure 12A:
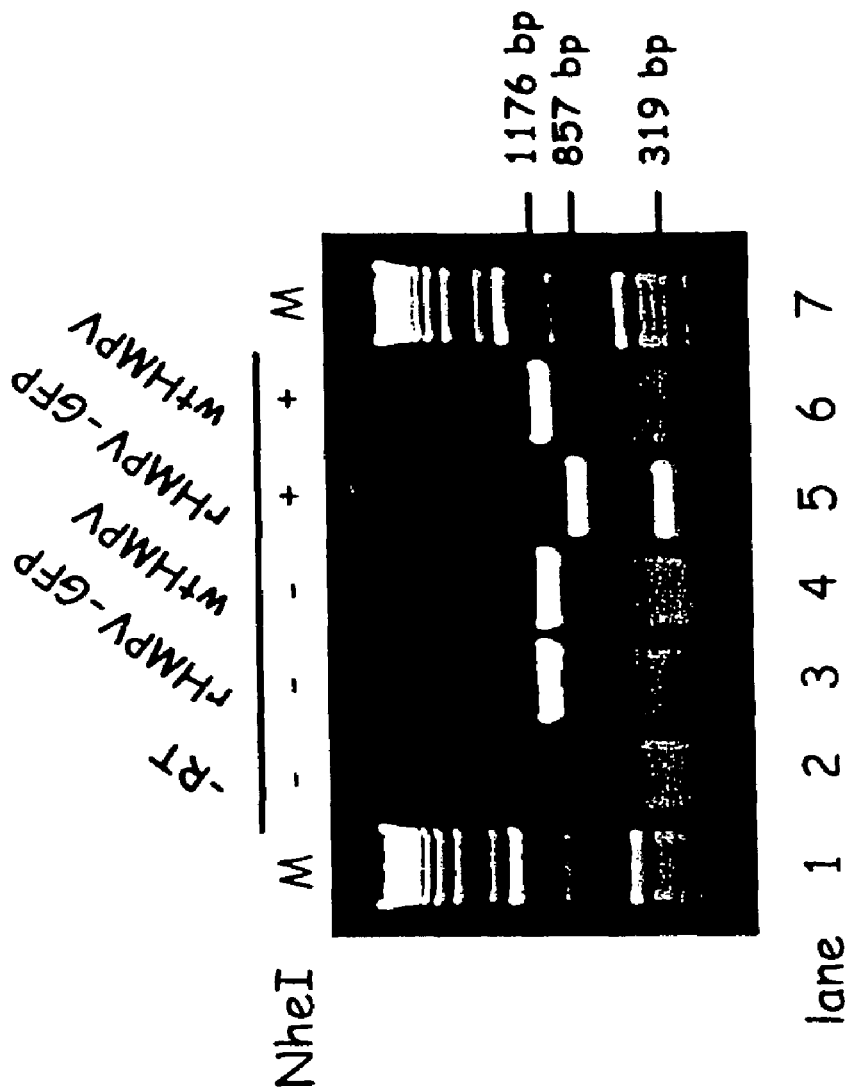

In a related assay series, RT-PCR was performed to amplify nucleotides 2719 to 3894 (numbered according to their position in the wild type HMPV sequence exclusive of GFP) in the rHMPV-GFP genomic RNA (FIG. 12A). This RT-PCR procedure yielded a product of the expected size when the template was RNA from cells infected with biologically-derived HMPV or recombinant HMPV-GFP, but only in the latter case was the cDNA cleaved by NheI, confirming the presence of the added NheI site specific to the recombinant antigenomic cDNA from which the recombinant virus was derived. Amplification of RT-PCR products was dependent on the addition of RT, indicating that the template was indeed viral RNA and not contaminating DNA. Infectious recombinant HMPV-GFP also was recovered when the M2-1 support plasmid was omitted from the panel of support plasmids. Although these results suggest that M2-1 is not required for recovery, it is possible that M2-1 is expressed from the antigenome plasmid, as was found in the case of RSV (Collins et al. Virology 295: 251-255, 1999). Also, it may be that co-expression of M2-1 will have some qualitative or quantitative effect on recovery. This is suggested by the observation that, in a typical experiment, three times more infectious virus was recovered in the presence of M2-1. It is believed that the minimal complement of proteins required for recovery of HMPV is N, P and L.

Figure 12B:
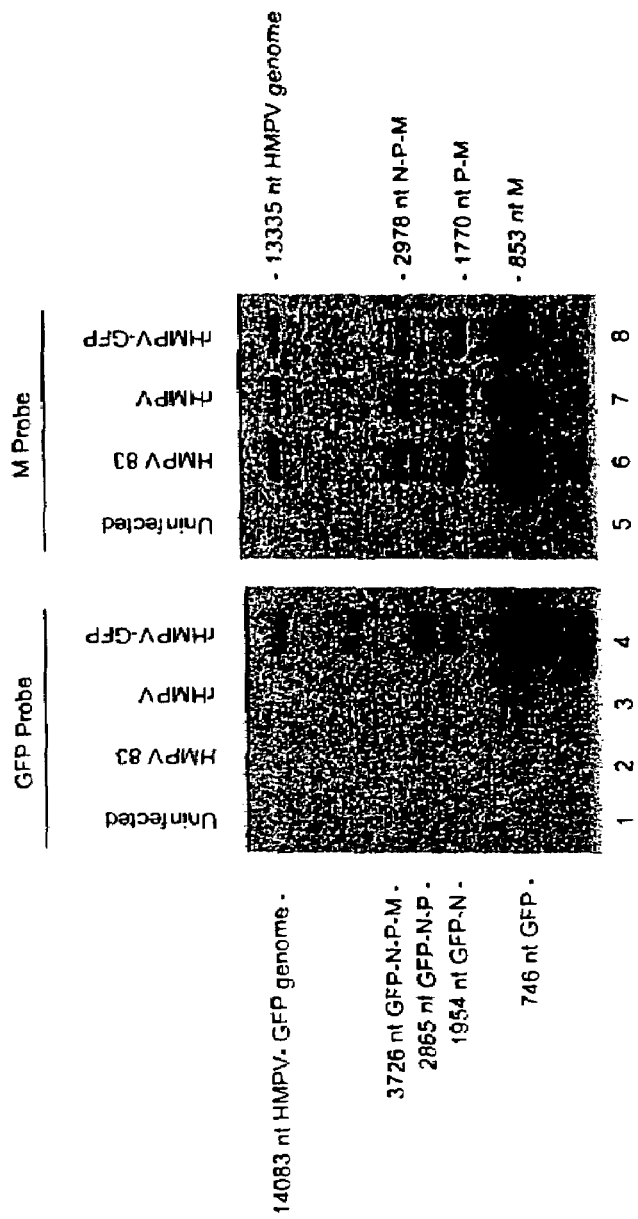

The expression of the inserted GFP coding sequence also was characterized by Northern blot hybridization. Cells were infected with biologically-derived HMPV83, rHMPV, rHMPV-GFP, or were mock infected, and total intracellular RNA was isolated three days later and analyzed by Northern blot hybridization with double-stranded DNA probes specific to the GFP or M genes. As shown in FIG. 12B, the GFP-specific probe hybridized only with RNA from rHMPV-GFP-infected cells (lane 4), and detected an abundant RNA band of the appropriate size to be the predicted 746-nt (exclusive of polyA) GFP mRNA transcribed from the inserted transcription cassette. This showed that the putative HMPV GS and GE transcription signals indeed functioned in the context of the foreign ORF to direct the efficient synthesis of a monocistronic GFP RNA. The GFP probe also hybridized to several larger RNAs that were of low abundance and appeared to represent GFP-N, GFP-N-P and GFP-N-P-M read-through mRNAs, as well as to a large, faint band that was of the appropriate size to contain rHMPV-GFP genome and antigenome RNA. The very low levels of read-though mRNAs indicated that termination at the end of the GFP transcription cassette was very efficient, and hence an HMPV GE signal indeed had been correctly identified. Analysis with the M-specific probe identified in each of the viruses bands of the appropriate sizes to be the predicted 853-nt monocistronic M mRNA as well as bands representing the P-M and N-P-M read-through mRNAs. The M probe also detected the genome and antigenome RNA band for each virus, which in the case of rHMPV-GFP would be 748 nt larger than HMPV83 or rHMPV due to the presence of the GFP transcription cassette (FIG. 12B, lanes 6, 7 and 8).

Figure 11:
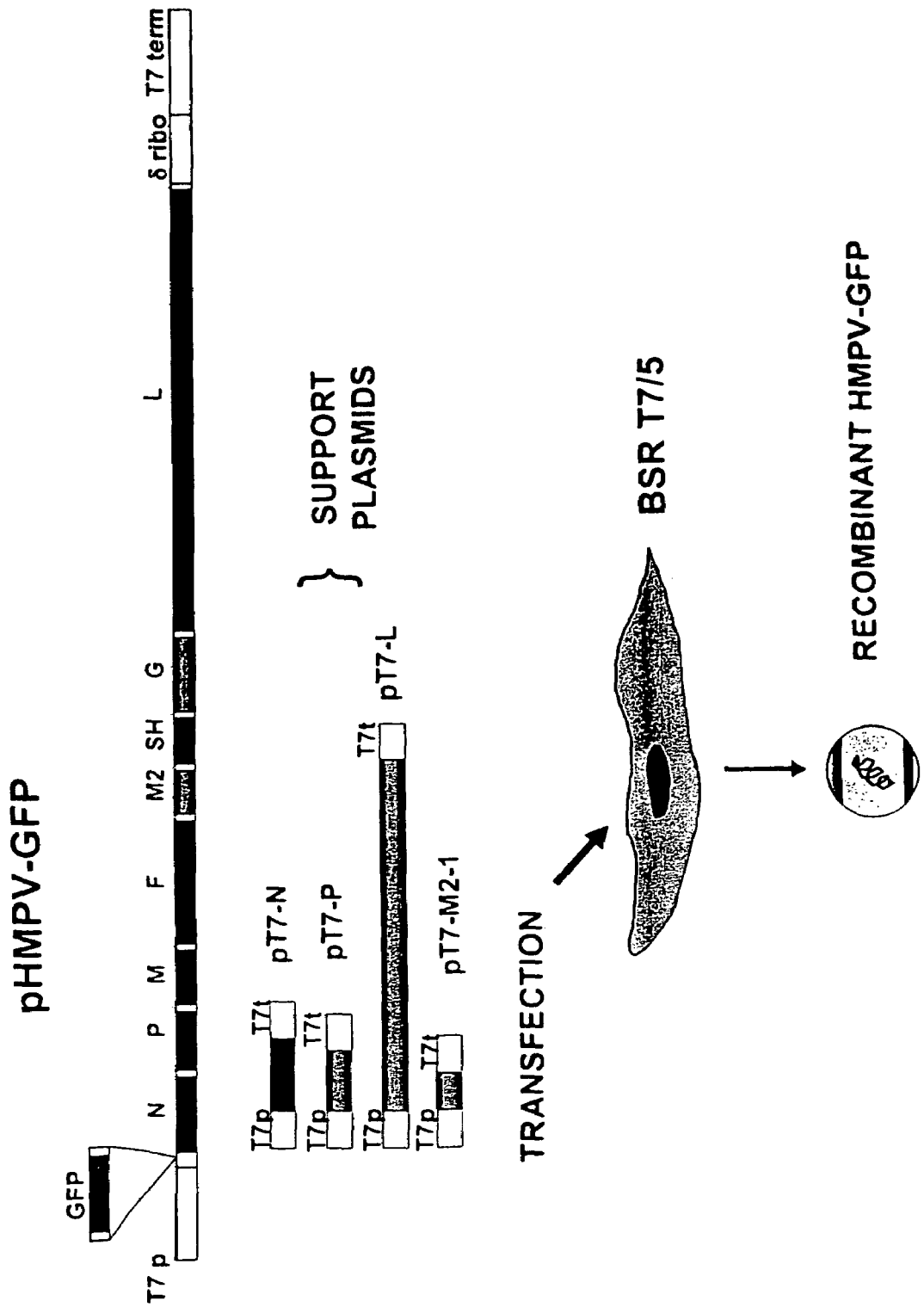

To test the ability to recover recombinant HMPV that lacked the GFP gene, plasmid expressing the HMPV antigenome depicted in FIG. 11 but lacking the GFP insert was transfected into BRS T7/5 cells together with N, P, M2-1 and L support plasmids. The recovery of recombinant HMPV was confirmed by the detection of viral antigen in single cells and in foci by indirect immunofluorescence assay as described above.

Figure 13:
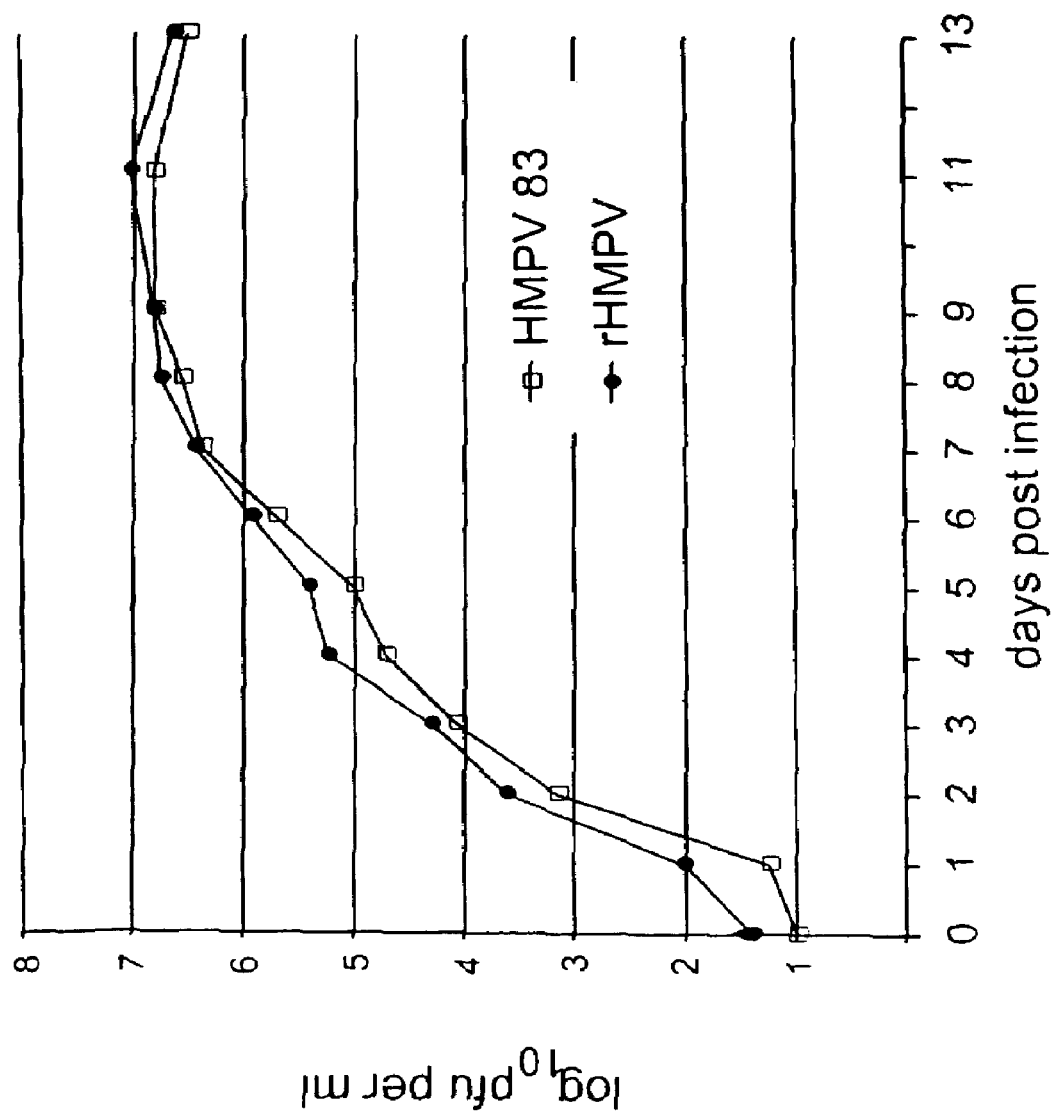

The recovered recombinant HMPV strain 83 was compared to the biologically-derived strain 83 isolate with regard to the efficiency of multi-cycle replication in vitro. LLC-MK2 cells were inoculated with 0.01 plaque forming units (PFU) per cell and incubated at 32° C. in the presence of 5 µg/ml trypsin. Aliquots of the medium were taken at 24 h intervals and flash frozen. The aliquots were subsequently diluted in medium containing fresh trypsin and analyzed in parallel by plaque assay to determine the infectivity titer. As shown in FIG. 13, the recombinant HMPV replicated efficiently over the 10 day period tested. The efficiency of replication of rHMPV was essentially indistinguishable from that of its biologically-derived counterpart. The ability to recover a wild type-like virus entirely from cloned cDNA showed that the sequences used to construct these cDNAs are fully functional, and thus define an authentic, functional, prototype wild type HMPV and its encoded proteins. This is noteworthy, since these viruses exhibit a high frequency of mutation (and thus a sequence cannot be assumed to be functional). The rHMPV antigenomic cDNA had been sequenced in its entirety following construction, as noted above, with the result that its sequence was confirmed to be exactly as designed. Thus, this experiment established (i) the exact genomic sequence of a prototypic HMPV, and (ii) conditions for recovering cloned cDNAs representing this sequence. This verified prototypic system provides the basis for the expedited recovery of other strains of HMPV, as well as for the systematic modification of HMPV via changes introduced into the cloned cDNA intermediate. Finally, the ability to precisely reconstruct a wild type recombinant HMPV indicates the robustness and precision of the methods disclosed herein. This is further demonstrated by the ability to recovery numerous engineered derivatives described in subsequent examples.

Figure 14:
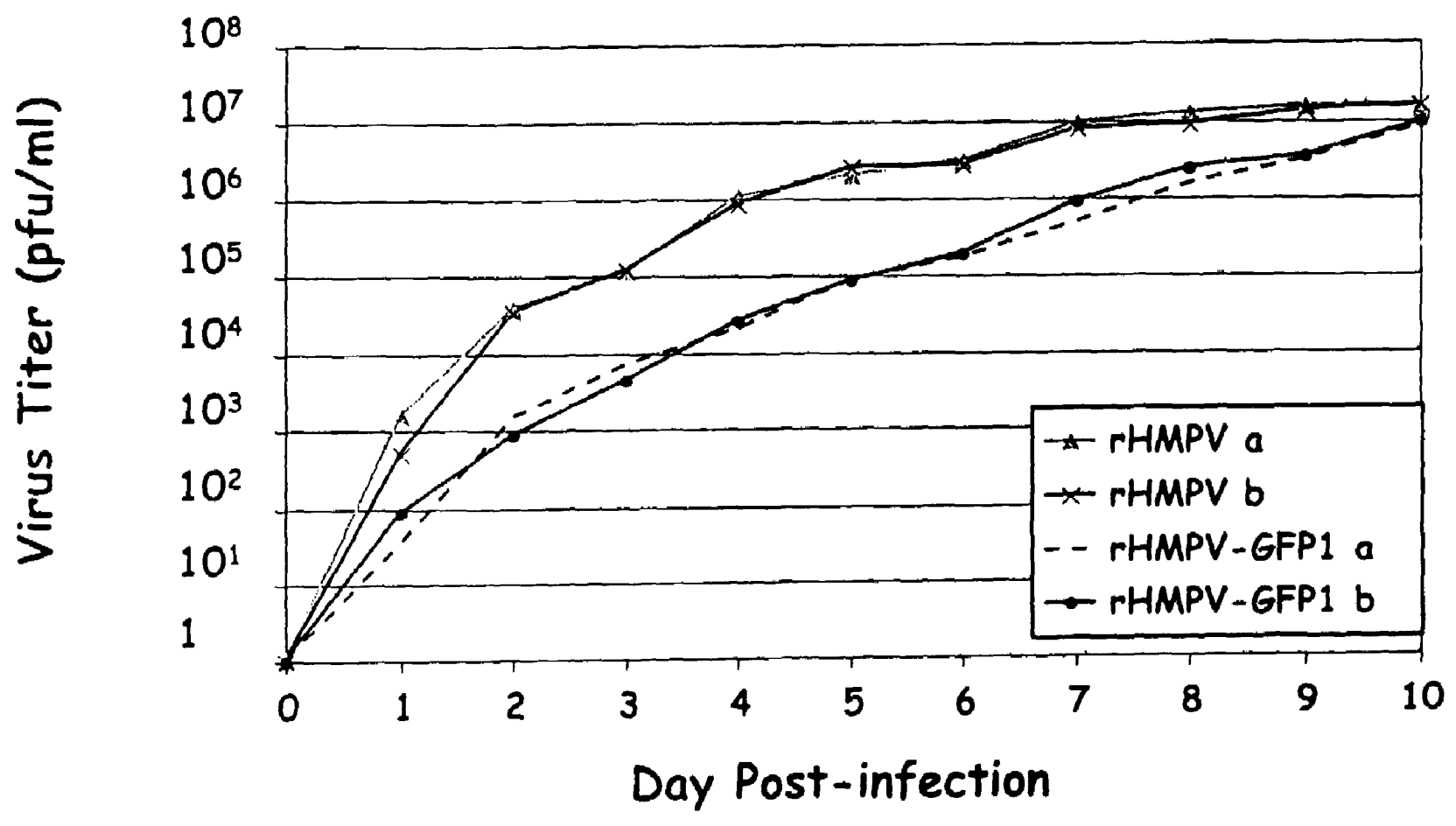

Next, recombinant HMPV-GFP was compared to rHMPV with regard to the efficiency of multi-cycle growth in vitro to evaluate the effect of the addition of a transcription cassette. As shown in FIG. 14, rHMPV-GFP replicated over the tested 10-day period with an efficiency that, at times, was reduced more than 10-fold compared to rHMPV. However, at the end of the 10 day period the final titers were very similar. Thus, a foreign insert can be accommodated by HMPV without a drastic effect on in vitro replication, such that a recombinant virus containing such an insert can be feasibly manufactured. It also is possible that such an insert will prove to be attenuated in vivo, as can now be expeditiously determined in experiments employing experimental animals that were identified as supporting HMPV replication in experiments described in a subsequent Example.

Example 3

The Development of Recombinant HMPV Derivatives Containing Pre-Determined Mutations Specifying Desired Phenotypic Changes The ability to produce infectious rHMPV from cDNA provides the basis for the planned introduction of mutations into infectious HMPV to develop recombinant viral candidates possessing desirable characteristics for use in immunogenic compositions, such as temperature-sensitivity, cold adaptation, host range restriction, improved replication in vitro, reduced reactogenicity, increased safety, increased antigen expression, increased genetic or phenotypic stability, broader immunogenic coverage, increased immunogenicity, and attenuation. Mutations might be devised that have advantages in other applications as well, such as to yield increased antigen expression and/or to facilitate preparation of purified viral protein. Each antigenome can be assayed for the ability to direct the recovery of infectious virus, and recovered mutant viruses can be evaluated for in vitro affects on growth and cytopathogenicity, temperature sensitivity, plaque morphology, and other characteristics. Appropriate mutant viruses can then be evaluated for growth efficiency, antigen expression, temperature sensitivity, plaque morphology, cytopathogenesis, attenuation, pathogenicity, tropism, genetic and phenotypic stability, immunogenicity, safety, and protective efficacy in cell culture and predictive animal models for HMPV activity in human subjects, including mice, hamsters, cotton rats, and non-human primates, as well as in clinical studies.

Figure 15:
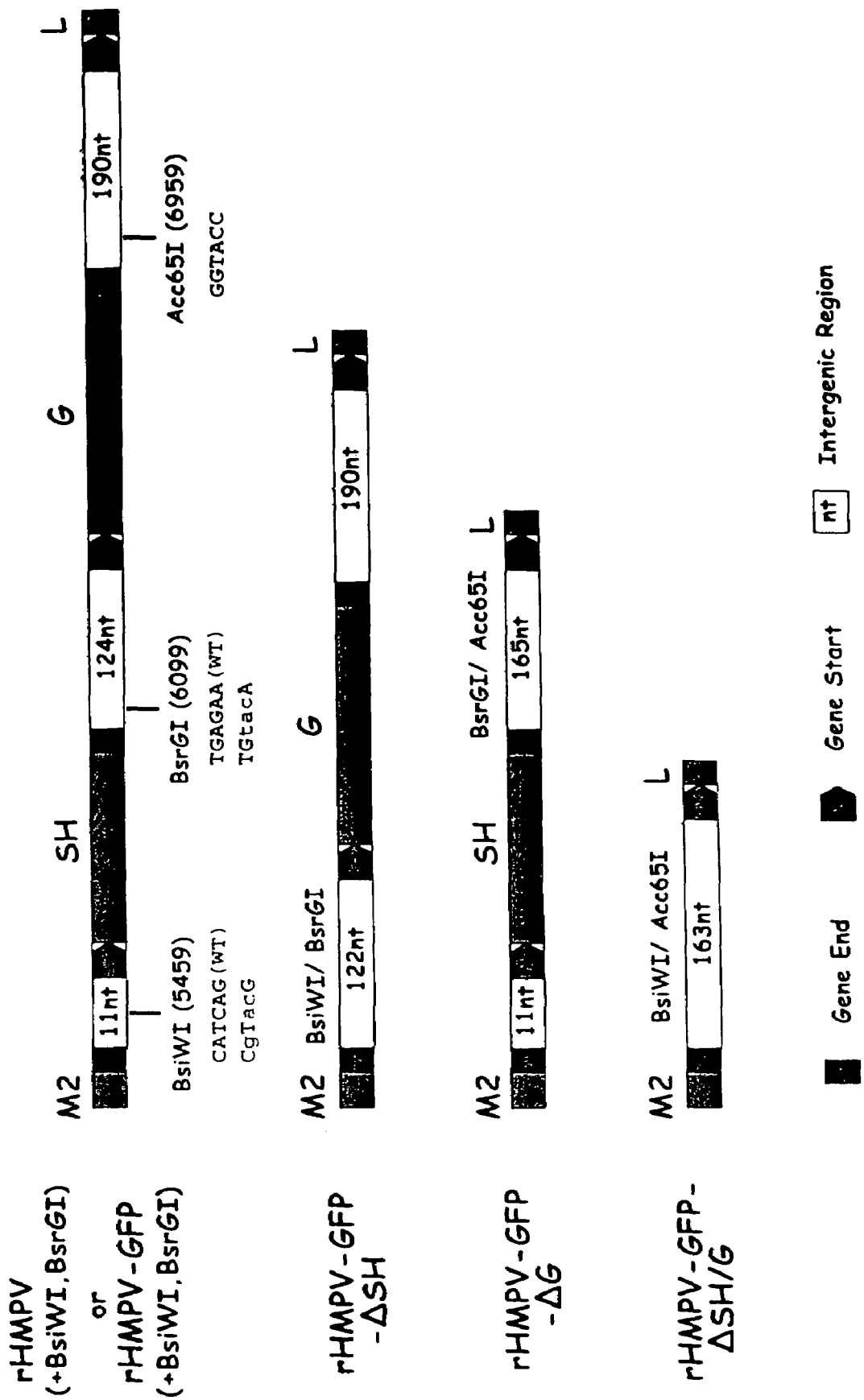

One type of desirable mutation involves the deletion of sequence from the HMPV genome. For example, each of the HMPV genes or ORFs or parts thereof can be systematically deleted either in its entirety or in part, either alone or in combination with other genes or ORFs, to obtain virus with improved properties, particularly for use within immunogenic compositions. Exemplary genes or ORFs include the SH, G, M2-2 and M2-1 ORFs, but can involve any gene or ORF or genome region or part thereof, including non-ORF sequences such as noncoding genes or extragenic regions or cis-acting signals in whole or in part. As an example of the strategy of deleting entire genes, antigenomic cDNAs were designed in which the putative SH and G ORFs, each with their surrounding-set of putative GS and GE signals, were deleted singly or together (FIG. 15). To make these constructs, the wild type GFP was modified to insert BsiWI and BsrGI sites at positions 5459 and 6099 (numbered relative to the complete antigenome exclusive of GFP, a convention that will be followed throughout this document). These positions are within the M2-SH and SH-G intergenic regions, respectively. Cleavage at either of these two sites creates the overhang GTAC, which also is the case for the naturally-occurring Acc65I site located at position 6959, within the G-L intergenic region (FIG. 15). Thus, the presence of these three compatible restriction sites flanking the SH and G genes facilitate deletion of either or both genes by cleavage with the appropriate pairs of enzymes followed by religation. This resulted in cDNAs encoding rHMPV-GFP antigenomes that lacked the SH (ΔSH) or G (ΔG) genes or both (ΔSH/G). Each antigenomic cDNA was evaluated for the ability to direct the recovery of infectious virus in BSR-T7 cells in the presence of the N, P, L and M2-1 support plasmids. In each case, infectious virus was readily and successfully recovered.

Figure 16:
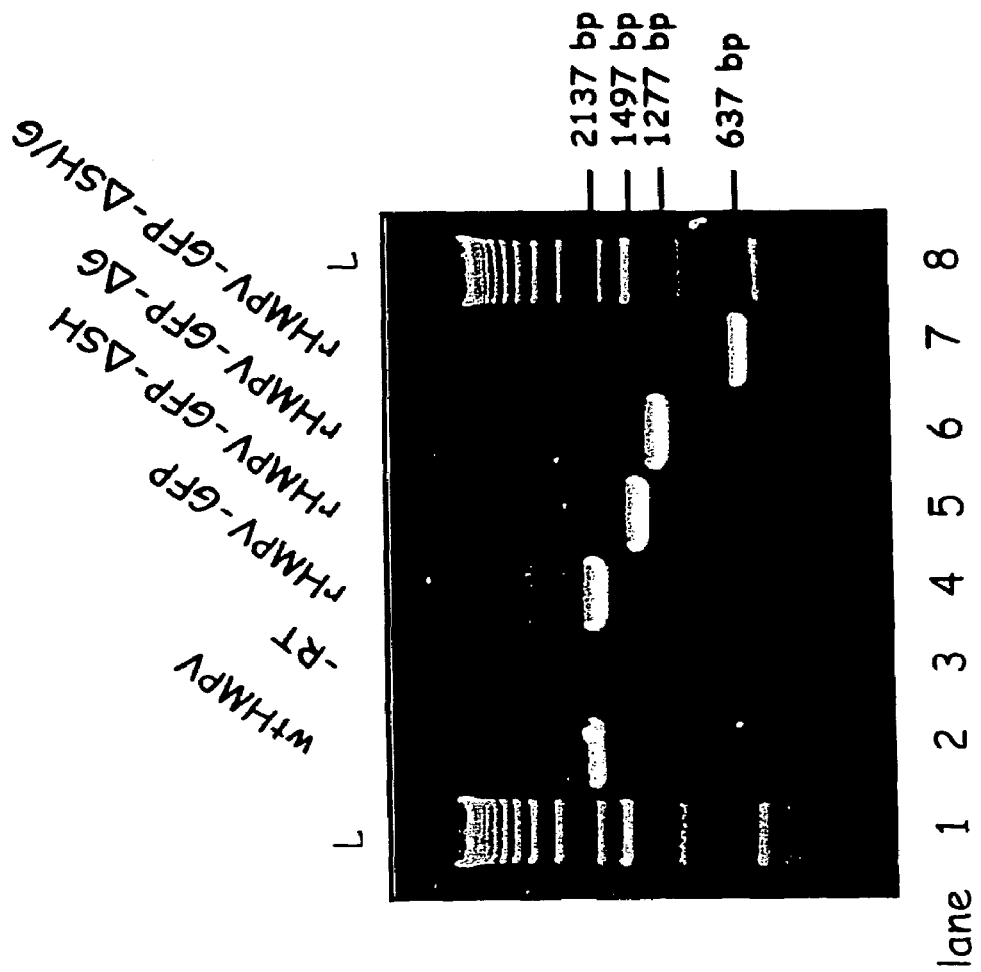

These could then be evaluated with regard to kinetics and efficiency of growth in vitro and in experimental animals to define advantageous properties including attenuation. The presence of the expected deletion in each virus was confirmed by RT-PCR analysis of the SH-G region of each recovered genome, as shown in FIG. 16. Also, limited nucleotide sequencing of the RT-PCR products confirmed the sequences at the junctions of the deletions.

Figure 17A:
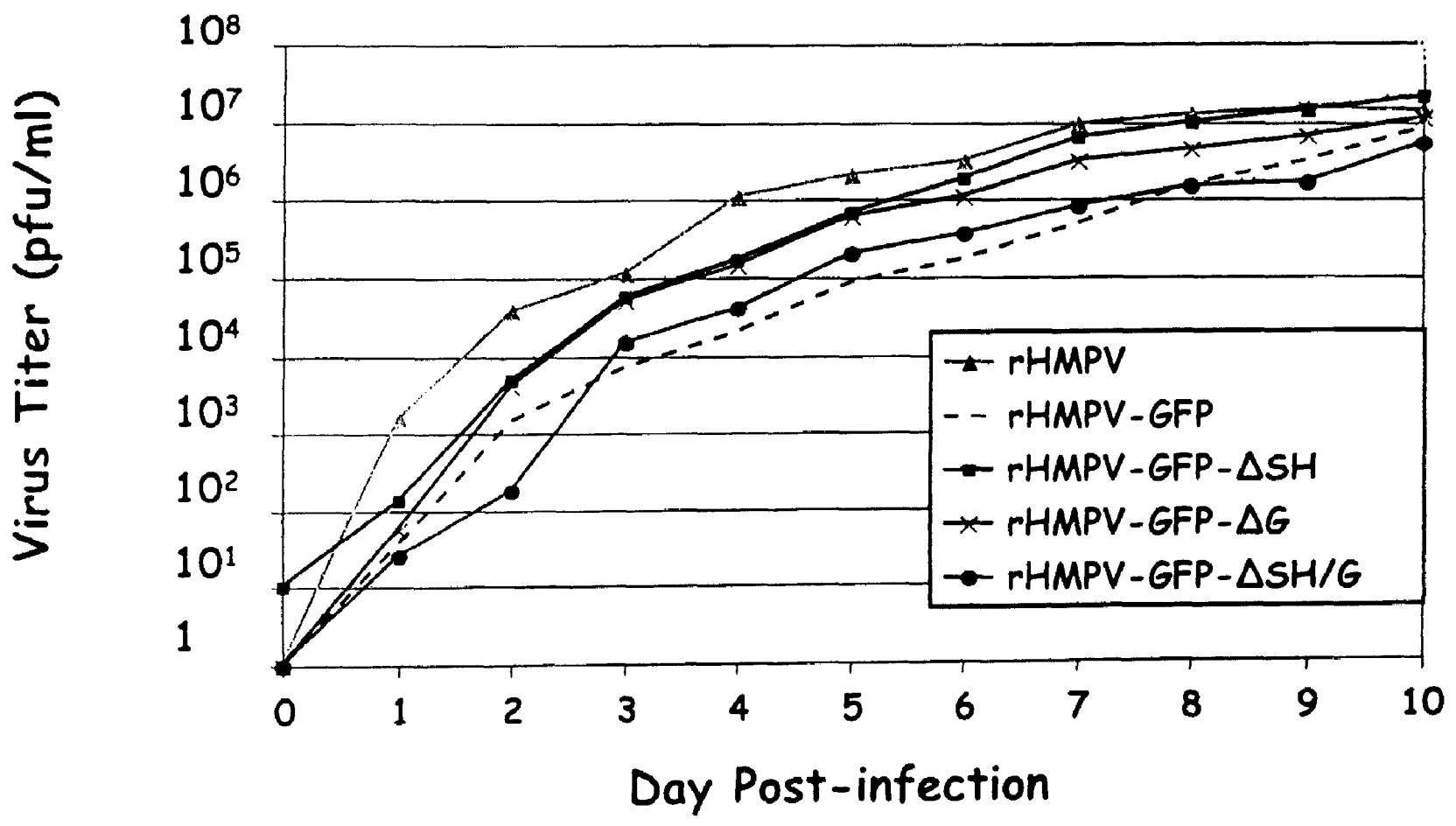

The rHMPV-GFPΔSH, ΔG and ΔSH/G mutants were compared with rHMPV-GFP and rHMPV with regard to the efficiency of multi-cycle replication LLC-MK2 cells following infection with an input of 0.01 PFU per cell (FIG. 17A). In this experiment, the gene-deletion mutants contained the GFP marker gene and thus should be compared to rHMPV-GFP. Remarkably, rHMPV-GFP containing the deletion of a single gene, either SH or G, replicated 3- to 10-fold more efficiently than rHMPV-GFP alone. Thus, these genes are not essential for replication in vitro and, indeed, their loss improved replicative fitness in vitro. This may reflect a growth advantage due to the shorter length of the genome and loss of a transcriptional unit, although it also is possible that the absence of the SH or G protein might somehow improve growth. This can readily be investigated by the methods disclosed herein by ablating translation of SH and/or G by making nucleotide substitutions that remove translational start codons and introduce termination codons, thereby ablating expression of the protein while maintaining the gene number, the genome length, and the number of transcribed mRNAs. rHMPV-GFP lacking both SH and G replicated with an efficiency similar to that of complete rHMPV-GFP, suggesting as one interpretation that whatever gain might be made from deleting genes and shortening the genome was counteracted by a slight loss of replicative fitness due to the absence of both SH and G. Thus, production of an HMPV immunogenic composition might be improved by deletion of SH or G, but deletion of both might not be optimal. Also, deletion of either gene might increase the ability of rHMPV to accommodate one or more added foreign genes. Given the efficient replication of these viruses in vitro, it will now be possible to evaluate the effects of these gene deletions on HMPV replication, immunogenicity, and pathogenesis in experimental animals and human volunteers.

A second, parallel set of ΔSH, ΔG, and ΔSH/G mutants was made in an rHMPV strain 83 backbone lacking the GFP marker gene. Each of the viruses from this second set of mutants was readily recovered and propagated in vitro. These could be evaluated with regard to kinetics and efficiency of growth in vitro and in experimental animals to define advantageous properties including immunogenicity and attenuation. While the presence of the GFP gene can facilitate characterization of mutant viruses in vitro and in vivo, the GFP, gene preferably would not be included in candidates for developing immunogenic compositions. Hence, it is advantageous to be able to expeditiously produce mutants with or without GFP, or both, as appropriate.

Figure 17B:
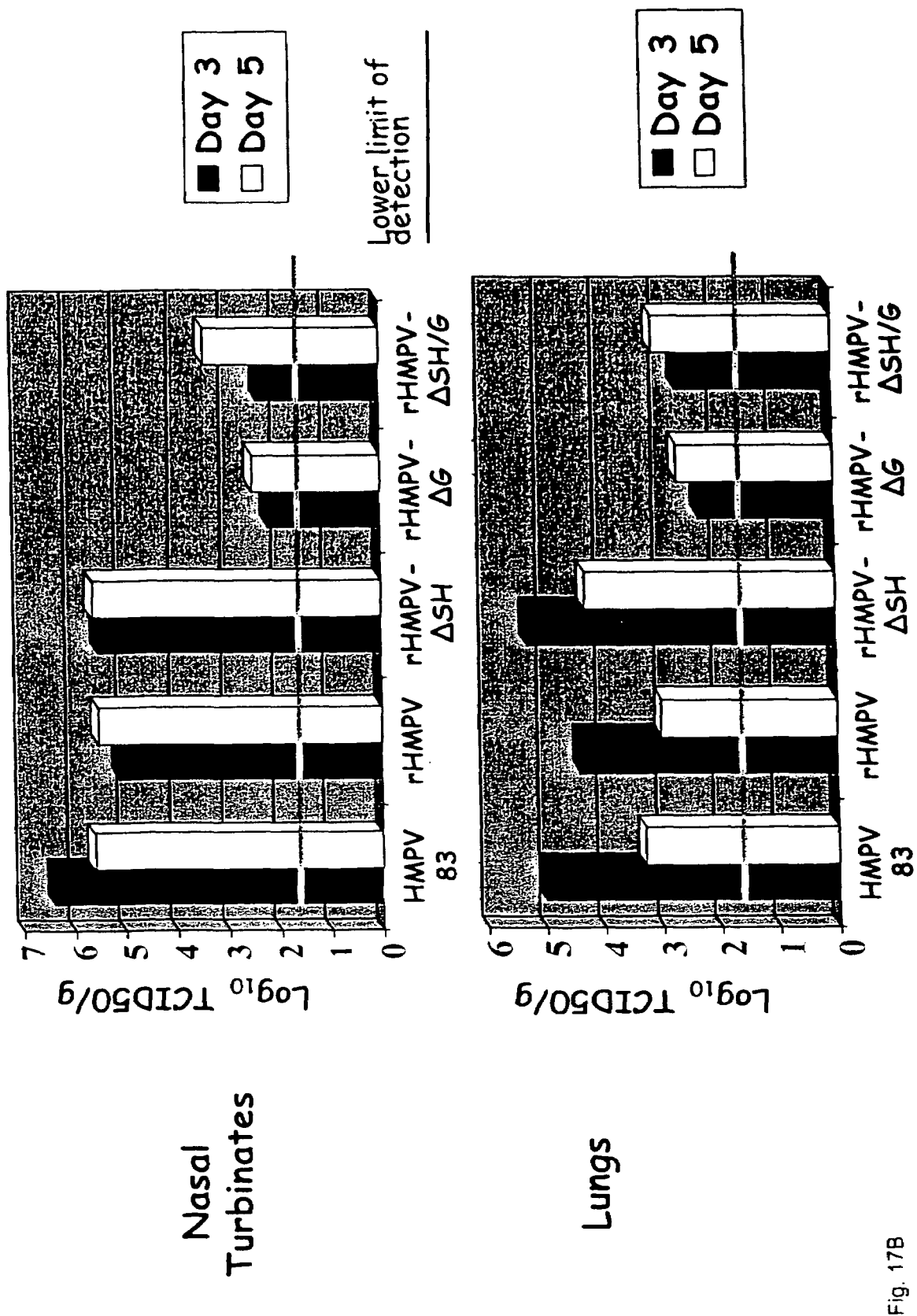
FIG. 17B is a graph illustrating the efficiency of replication of biologically-derived HMPV83 and recombinantly-derived rHMPV, rHMPVΔSH, rHMPVΔG, and rHMPVΔSH/G in the upper (nasal turbinates) and lower (lungs) respiratory tract of Golden Syrian hamsters. Animals in groups of 12 were infected intranasally with the following viruses at a dose of $5.0 \times 10^5$ TCID$_{50}$ per animal in 0.1 ml: biologically derived HMPV83, rHMPV, rHMPVΔSH, and rHMPVΔSH/G, and the following virus at $1.6 \times 10^5$ TCID$_{50}$ per animal in 0.1 ml: rHMPVΔG. Six animals from each group were sacrificed on days 3 and 5 and the nasal turbinates and lungs were recovered and analyzed by limiting dilution to determine the viral titer. This showed that the rHMPV replicated in vivo with an efficiency similar to that of its biologically-derived parent (HMPV83), that the replication of the rHMPVΔSH virus was not significantly reduced, and that the replication of the rHMPVΔG and ΔSH/G viruses were strongly reduced, although virus replication was detectable in each case.

The set of rHMPVΔSH and ΔG viruses lacking the GFP marker gene were evaluated for replication in vivo (FIG. 17B). Golden Syrian hamsters were infected intranasally with biologically-derived HMPV83, rHMPV, rHMPVΔSH, rHMPVΔG, or rHMPVΔSH/G. Six animals from each group were sacrificed three or five days later and the nasal turbinates and lungs were harvested, homogenized, and analyzed by limiting dilution to determine the viral titers (FIG. 17B). There were several instances where differences in titer were observed between days 3 and 5, the most notable being the higher titers of HMPV 83, rHMPV and rHMPVΔSH in the lungs on day 3 versus day 5. However, in general the titers for the two days followed a consistent pattern. Recombinantly-derived HMPV replicated in vivo with an efficiency similar to that of its biologically-derived parent HMPV83. Thus, rHMPV appeared to have wild type-like growth properties in vivo as well as in vitro and represents a suitable starting point for developing attenuated derivatives as candidate vaccines.

Interestingly, the replication of HMPV was not significantly reduced by deletion of the SH gene (FIG. 17B). Indeed, the ΔSH virus replicated marginally better than its wild type counterpart, perhaps due to the shorter genome length and reduced gene number. In contrast, deletion of the G gene resulted in a 2.9 (day 5) to 3.2 (day 3) $\log_{10}$ decrease in replication in the nasal turbinates, and a 0.3 (day 5) to 2.3 (day 3) $\log_{10}$ decrease in the lungs. The rHMPVΔSH/G double-deletion virus exhibited a similar marked reduction in virus titer. Thus, these mutant viruses are highly attenuated in vivo.

Figure 17C:
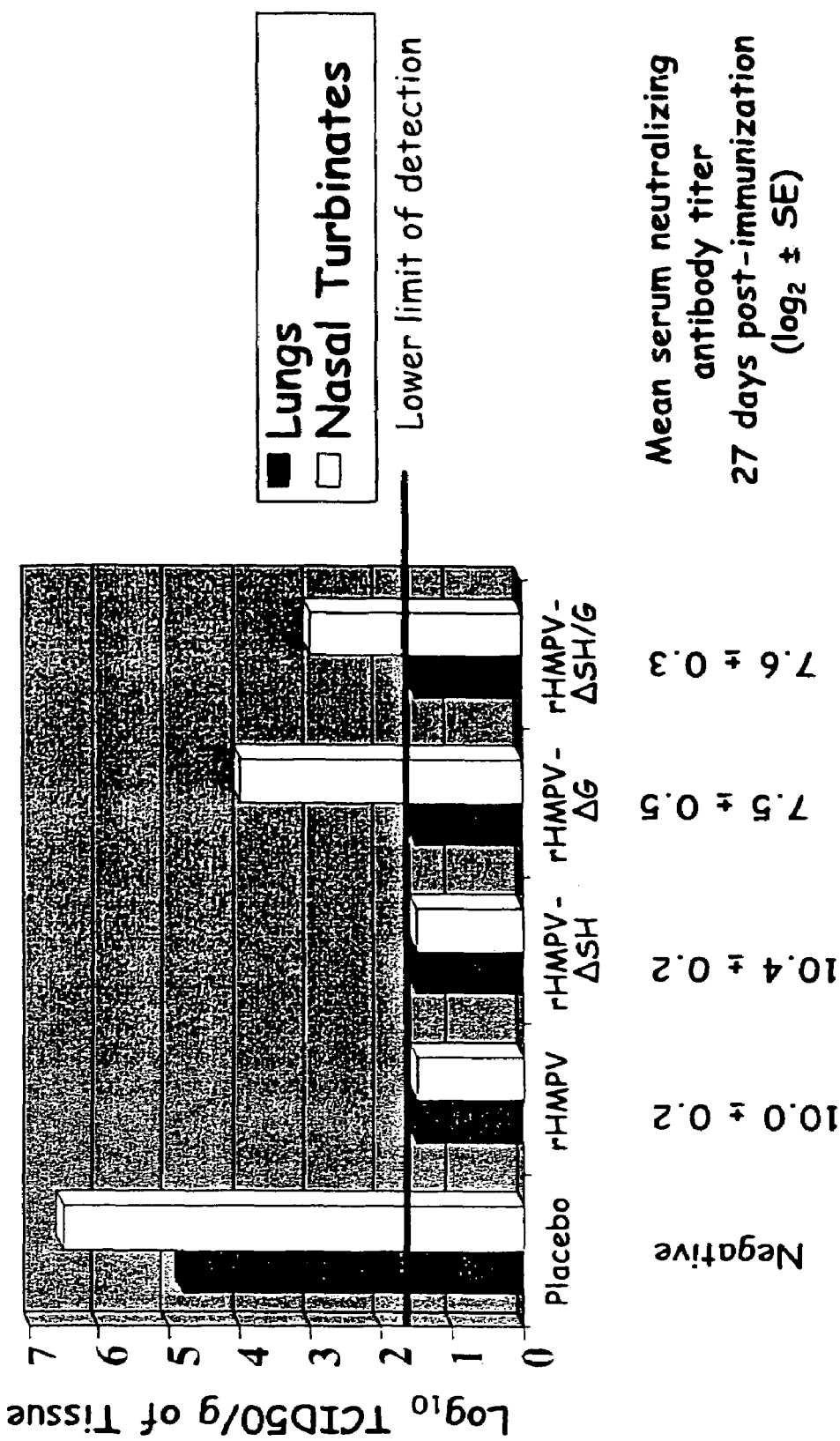
FIG. 17C is a graph illustrating the protective efficacy of immunization with the indicated HMPV deletion mutant viruses. Golden Syrian hamsters in groups of 6 were infected as described in FIG. 17B and, 27 days later, serum samples were taken and analyzed to determine the titers of HMPV-neutralizing serum antibodies. These titers are shown at the bottom. The animals were then challenged on day 28 by the intranasal instillation of $5.0 \log_{10}$ TCID$_{50}$ per animal of biologically-derived wild type HMPV83. Three days later, the animals were sacrificed and the nasal turbinates and lungs were harvested, homogenized, and analyzed by limiting dilution to determine virus titers. This showed that there was no detectable replication of the challenge virus in animals that has received rHMPV or rHMPVΔSH, whereas animals that initially had received rHMPVΔG or rHMPVΔSH/G had no detectable challenge virus replication in the lungs and had reduced replication in the nasal turbinates compared to the control that had not been previously infected.

In order to evaluate possible immunogenicity and protective efficacy, the rHMPV, rHMPVΔSH, rHMPVΔG and rHMPVΔSH/G viruses were administered intranasally to additional hamsters (FIG. 17C). Serum samples were taken 27 days later and analyzed for the ability to neutralize HMPV infectivity in vitro (FIG. 17C). This showed that the highly attenuated ΔG and ΔSH/G viruses induced high titers of HMPV-neutralizing serum antibodies even though they were highly attenuated. On day 28 post immunization, the animals were challenged intranasally with wild type HMPV, and the animals were sacrificed three days later and nasal turbinates and lungs were harvested and virus titers were determined by limiting dilution (FIG. 17C). This showed that no challenge virus replication could be detected in animals that had been infected with rHMPV or rHMPVΔSH. Interestingly, animals that had been infected with rHMPVΔG or rHMPVΔSH/G also did not have detectable challenge virus replication in the lungs, and only a low level of challenge virus replication was detected in the nasal turbinates. Thus, despite their strongly attenuated nature, the rHMPVΔG and rHMPVΔSH/G viruses were immunogenic and highly protective against HMPV challenge. These viruses represent promising vaccine candidates. In particular, it was remarkable that deletion of the G gene would yield a promising vaccine candidate, since the G protein is presumed to be an attachment protein important in initiating infection, and the corresponding deletion in HRSV yielded a virus that did not replicate in mice (Teng et al, Virology 289, 283-296, 2001) and was over attenuated in humans (Karron et al., Proc. Natl. Acad. Sci. USA 94: 13961-13966).

The deletion or otherwise modification of intergenic regions of HMPV offers an important strategy for achieving improved phenotypic properties. For example, the intergenic regions of HMPV strain 83 range in length from 2 nt (N/P) to 190 nt (G/L). Previous work with RSV indicated that plaque size was decreased if a single intergenic region was longer than 100 nt in length (Bukreyev et al., J. Virol. 74:11017-26, 2000). Two of the naturally-occurring intergenic regions of HMPV strain 83 are greater than 100 nt in length, namely SH/G (124 nt) and G/L (190 nt). Thus, reducing the length of these or other intergenic regions offers a strategy to improve replication in vitro, while increasing intergenic length offers a strategy for attenuating the virus, as desired.

Figure 18A:
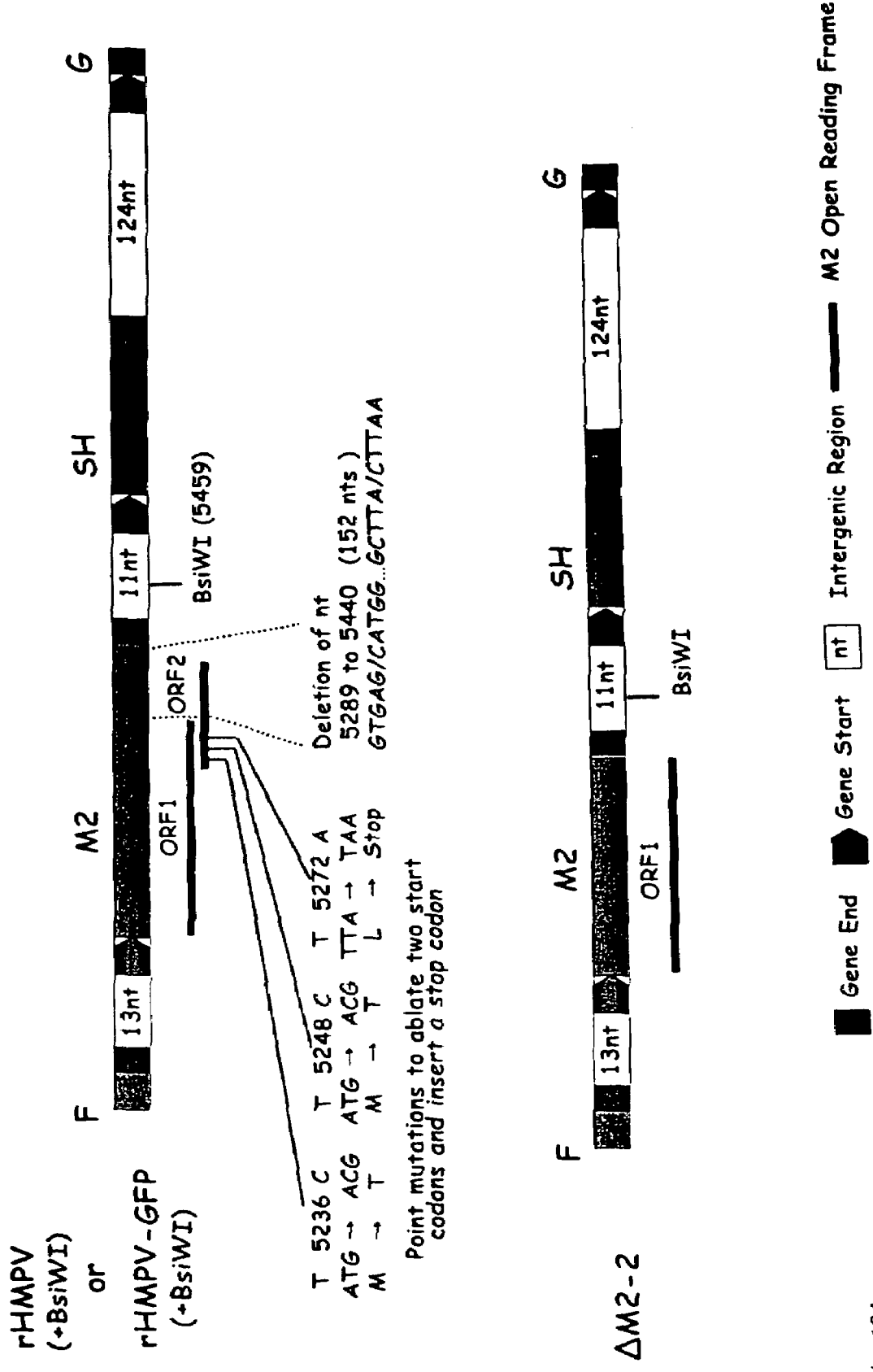
FIG. 18A is a diagram illustrating ablation of the putative M2-2 ORF in infectious rHMPV and rHMPV-GFP (strain 83), each containing an introduced BsiWI site. The region of the antigenomic cDNA clone containing the putative M2-1 and M2-2 ORF is illustrated, with each ORF depicted by a solid horizontal line. Two nucleotide substitutions were made at positions 5236 and 5248 (SEQ ID NO: 1; numbered according to the complete antigenomic cDNA exclusive of GFP) that ablate two potential translation initiation codons for the M2-2 ORF. A third substitution was made at position 5272 (SEQ ID NO: 1) that introduces an in-frame stop codon. In addition, nucleotides 5289-5440 (SEQ ID NO: 1) were deleted, removing most of the M2-2 ORF. The ΔM2-2 mutant was successfully recovered in both the rHMPV and rHMPV-GFP backbones and designated rHMPVΔM2-2 and rHMPV-GFPΔM2-2, respectively.
Figure 18B:
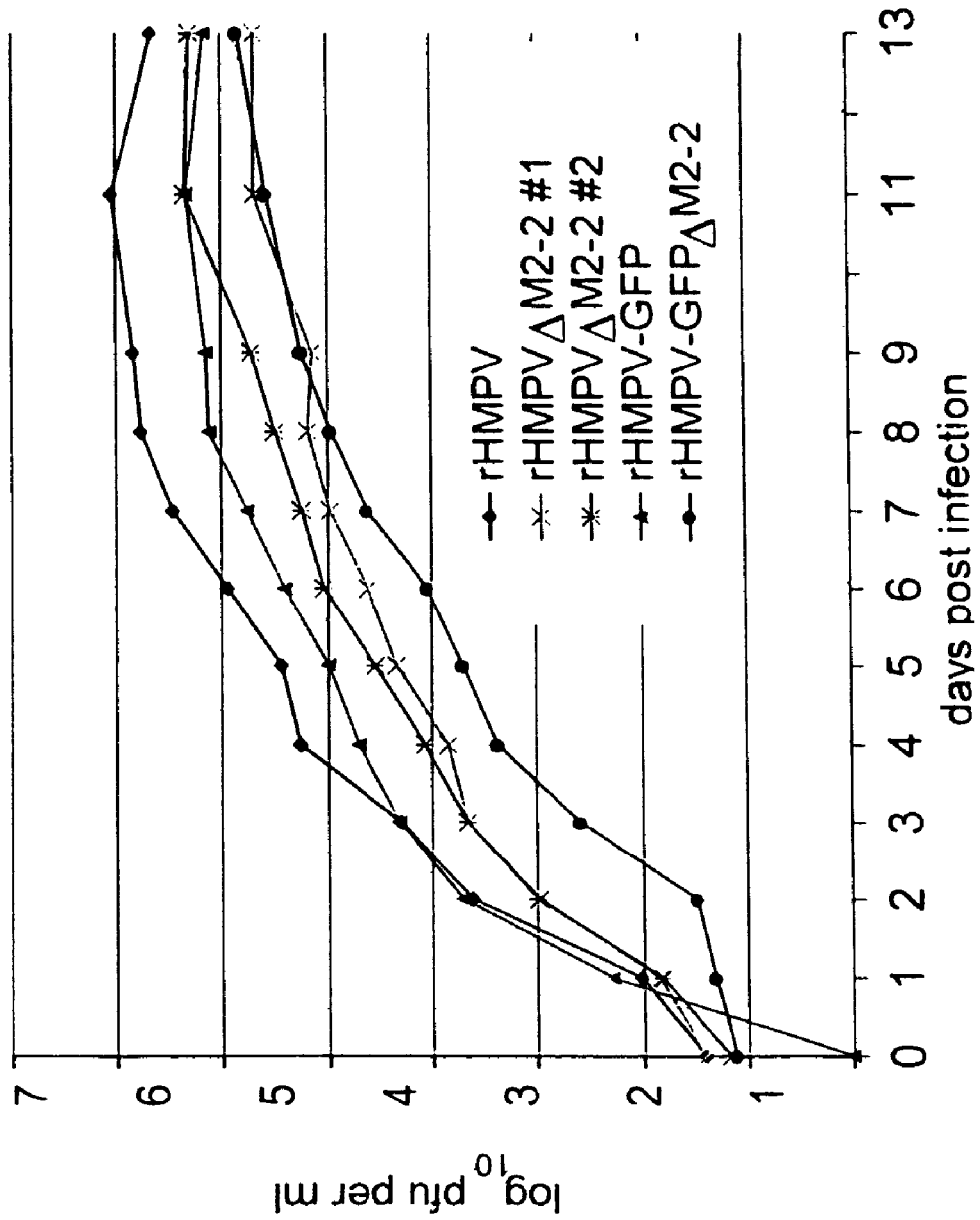
FIG. 18B is a graph illustrating evaluation of multi-step growth kinetics of the recovered viruses in vitro. The rHMPVΔM2-2 and rHMPV-GFPΔM2-2 viruses were compared with rHMPV and rHMPV-GFP with regard to multi-step growth kinetics and yield in LLC-MK2 cells as described above for FIG. 13. rHMPVΔM2 clones #1 and #2 represent virus derived independently from two sister cDNA clones.
Figure 18C:
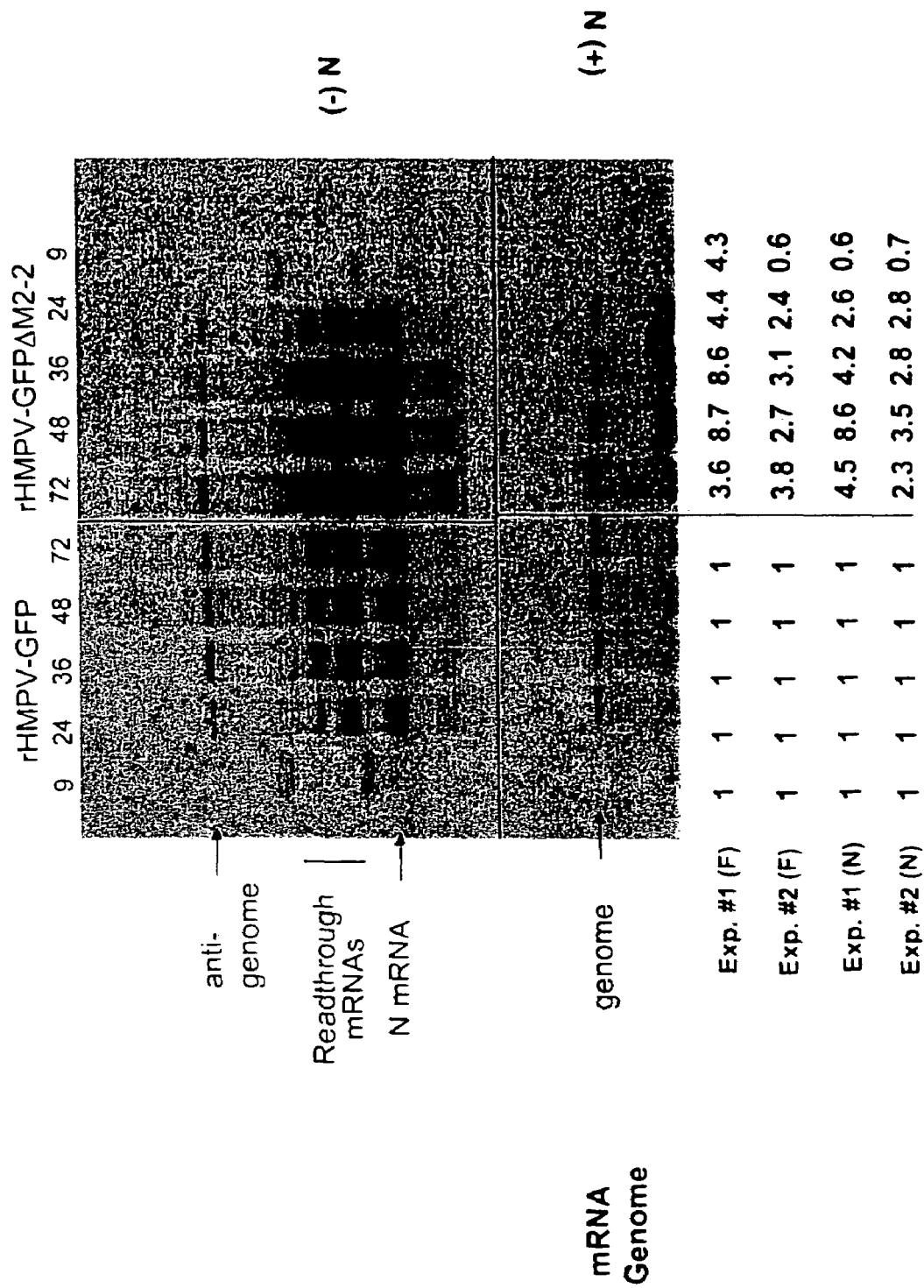
FIG. 18C is a digitized image of a nylon membrane illustrating Northern blot analysis of intracellular RNAs expressed by rHMPV-GFP and rHMPV-GFPΔM2-2. Replicate monolayers of LLC-MK2 cells were infected at an MOI of 3 PFU per cell with either virus as indicated and incubated at 32° C. Monolayers were harvested at 9, 24, 36, 48, and 72 h post infection as indicated and processed for purification of intracellular RNA. The RNA preparations were analyzed by Northern blot hybridization with strand-specific riboprobes representing the N gene: the upper panels detect hybridization with the negative-sense probe and thus represent antigenome and N-related mRNA, as indicated, and the bottom panels detect hybridization of a replicate set of gel lanes (that had been transferred in parallel onto the same membrane, which was then cut and the replicate sets hybridized separately) with positive-sense riboprobe and represent genome. Beneath the Northern blot are calculations from four experiments involving hybridization with a probe specific for N or for F, as indicated. In each experiment, the amount of total N-related or F-related mRNA for each time point was divided by the amount of antigenome from a replicate gel lane (that had been transferred in parallel onto the same membrane, which was then cut and the replicas hybridized separately). Then, each time point for the rHMPV-GFPΔM2-2 virus was normalized relative to the corresponding time point for rHMPV-GFP as 1.0. Thus, this provides a comparison of the efficiency of mRNA expression for the ΔM2-2 mutant compared to wild type HMPV.

As another example, recombinant HMPV was recovered in which the M2-2 ORF was silenced (FIG. 18A). The proposed M2-1 ORF initiates at nucleotide position 4724 and terminates at position 5287. The proposed M2-2 ORF potentially initiates at positions 5235 or 5247 and terminates at 5450, and thus overlaps the M2-1 ORF. To create a mutant HMPV in which the M2-2 ORF is silenced, single nucleotide substitutions were introduced at positions 5236 and 5248, which removed the two potential translational start codons without changing the amino acid coding assignment in the overlapping M2-1 ORF (FIG. 18A). A third nucleotide substitution was made at position 5272, which introduced a translational stop codon into the M2-2 ORF. In addition, nucleotides 5289-5440 were deleted, which deleted most of the M2-2 ORF. These changes were introduced into the wild type rHMPV antigenomic cDNA as well as into the rHMPV-GFP antigenomic cDNA. In each case, the ΔM2-2 virus was recovered successfully from cDNA. The rHMPVΔM2-2 and rHMPV-GFPΔM2-2 viruses were compared to their respective parents, rHMPV and rHMPV-GFP, with regard to multi-step growth kinetics in vitro (FIG. 18B). This showed that each ΔM2-2 virus replicated somewhat less efficiently than its rHMPV-GFP parent at many of the time points, although by the end of the experiment at 13 hours, the titers were very similar. These mutations are of interest for vaccine design, since they do not greatly affect growth in vitro (which is necessary for vaccine manufacture) and are likely attenuating in vivo. They are evaluated in the hamster model noted in FIGS. 17B and C, and described more completely in a subsequent Example below. Northern blot hybridization was then used to monitor the synthesis of intracellular RNA by the ΔM2-2 virus. As shown in FIG. 18C, the synthesis of genome and antigenome by the ΔM2-2 virus was not greatly different than that of wild type HMPV. However, the ΔM2-2 virus directed a level of mRNA synthesis that, when normalized to the amount of genome from replicate gel lanes, was up to 8.7-fold that of wild type HMPV. The up-regulation of protein synthesis without a concomitant increase in virus replication would be highly desirable for a vaccine virus. This phenotype resembles, but is not identical to, that of the ΔM2-2 mutant of human RSV. For RSV, the ΔM2-2 mutant exhibited a delay in the accumulation of mRNA that was not observed here, and exhibited a delay and reduction in the accumulation of genome and antigenome that also was not observed for HMPV. Further unanticipated differences between the HMPV and RSV are described herein, namely the ability to disrupt the HMPV M2-1 ORF, or to delete M2-1 and M2-2 altogether, without loss of viral viability for HMPV whereas either mutation was lethal for RSV.

Figure 20:
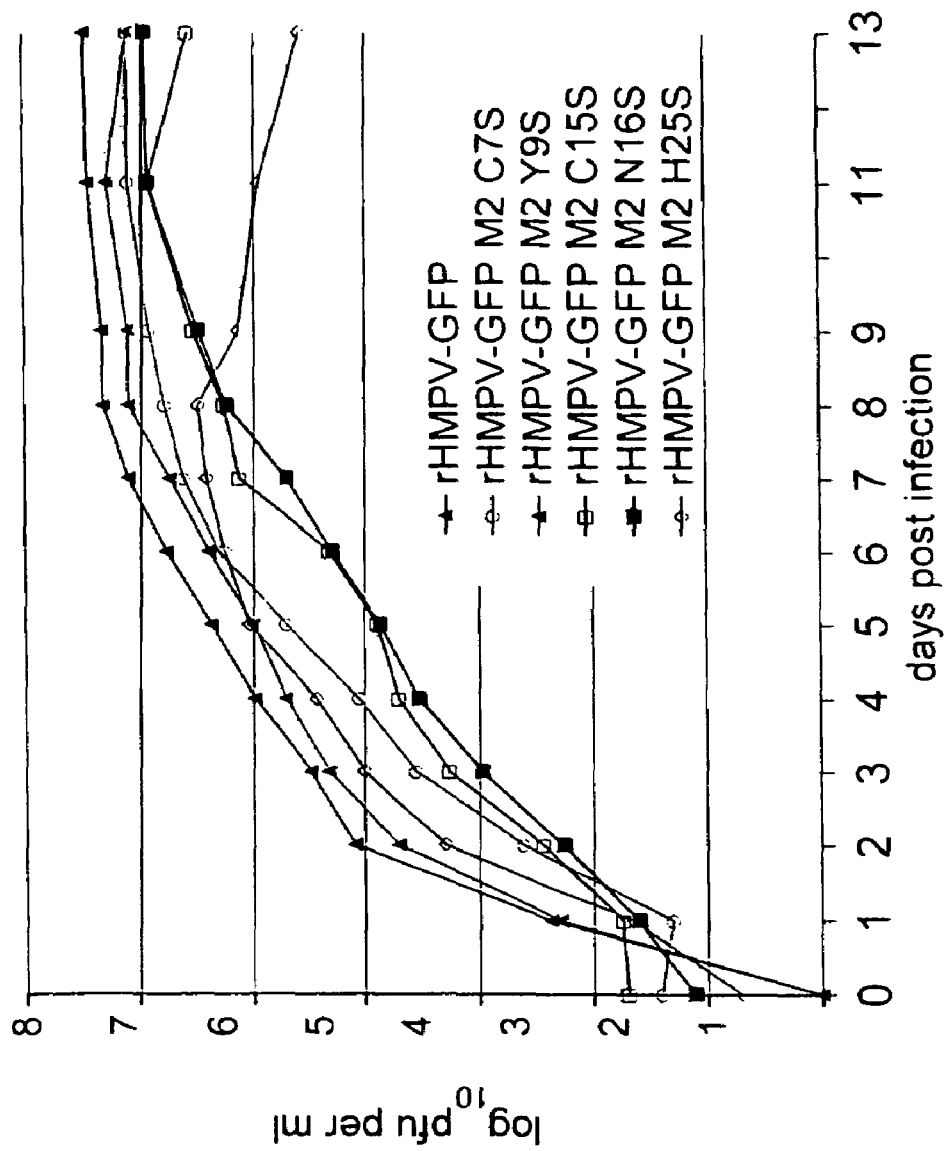
FIG. 20 is a graph illustrating multi-step growth of derivatives of rHMPV-GFP containing mutations in the Cys3-His1 motif of the M2-1 ORF, compared to rHMPV-GFP and rHMPV, performed in LLC-MK2 cells as described above for FIG. 13. The mutants involve single amino acid point mutations in the Cys3-His1 motif: C7S, Y9S, C15S, N16S and H25S. The mutations were introduced into rHMPV-GFP, and thus rHMPV-GFP is the "wild type" or parental equivalent for comparison.

In another application, illustrated in FIG. 19, a series of single amino acid substitutions was introduced into the cysteine-histidine motif present in the predicted M2-1 protein of rHMPV-GFP. This "Cys3-His1" motif consists of three cysteine residues at M2-1 amino acid positions 7, 15, and 21, and a histidine residue at position 25 (FIG. 19). This motif is exactly conserved in RSV and other pneumoviruses. In RSV, the integrity of this motif is essential for the transcriptional processivity and anti-termination function of M2-1, and is essential for the recovery of infectious recombinant virus (Hardy and Wertz J. Virol. 74:5880-5885, 2000; Tang et al., J. Virol. 75:11328-11335, 2001). The amino acid substitutions introduced into the M2-1 protein of rHMPV-GFP were as follows: Cysteine-7-Serine (C7S), Cysteine-15-Serine (C15S), and Histidine-25-Serine (H25S). As controls, two additional mutants were made involving amino acids that are found in the vicinity of the motif but are not considered to be part of the motif: Tyrosine-9-Serine (Y6S) and Asparagine-25-Serine (N25S). Each of these mutants was readily recovered as infectious virus. The C7S, Y19S, C15S, N16S, H25S and ΔM2-1 mutants of rHMPV-GFP were evaluated for multi-cycle growth in LLC-MK2 cells in parallel with rHMPV and rHMPV-GFP, as shown in FIG. 20. The mutants exhibited a range of growth efficiency relative to the rHMPV-GFP parent, with the Y9S mutant replicating more efficiently, the C7S mutant replicating comparably, and the others replicating somewhat less efficiently. Nonetheless, with the exception of the H25S mutant, the final titers at 13 days were mostly comparable to that of the rHMPV-GFP parent.

In another mutation involving the M2-1 ORF of rHMPV-GFP, the ATG translational start site was changed to a TAG termination codon, as shown in FIG. 21, resulting in the mutant designated rHMPV-GFPΔM2-1. The next ATG codon is located far down the ORF, at codon 134 out of 187 codons, and hence this mutation should ablate synthesis of M2-1. In this same mutant, additional termination codons were introduced closely downstream in each of the three reading frames to further preclude possible ribosomal entry and passage down the ORF. The HMPV-GFP-ΔM2-1 mutant was readily recovered as infectious virus.

The ability to rapidly and effectively recover this panel of mutants in the M2-1 ORF was a further demonstration that the cDNA-based recovery system is a robust method for expeditiously developing rHMPV variants bearing predetermined changes. The finding that a number of these mutants replicated more efficiently that their direct parent rHMPV-GFP suggests that such mutants would be valuable for use in immunogenic compositions, since improved replication in vitro would greatly facilitate the production of rHMPV and also might be an improved source of HMPV antigen for a protein-based immunogenic composition. In these embodiments, rHMPV-GFP was used as a parent because the expression of the GFP marker facilitates in vitro characterization. These forms also can be directly evaluated in experimental animals, and the presence of the marker would facilitate analysis of possible effects on virus localization in vivo. In addition, non-GFP versions can readily be generated, as was done above for the ΔSH, ΔG and ΔSH/G viruses, which would be appropriate for clinical evaluation. The finding that the Cys3His1 motif, and the M2-1 ORF altogether, are not required for efficient growth in vitro was completely unanticipated, particularly since with the Cys3-His1 motif and M2-1 protein were previously shown to be essential for the recovery of infectious RSV (Tang et al., J. Virol. 75:11328-11335, 2001). In addition, it was independently confirmed that mutations in the Cys3-His1 motif of RSV, or silencing the M2-1 ORF of RSV, prevented the recovery of recombinant RSV. Although the Cys3-His1 motif is not required for efficient HMPV replication in vitro, it is reasonable to anticipate that this motif and this protein have been conserved in HMPV for functional reasons and do contribute to some aspect of HMPV replication or interaction with its host. Thus, it is reasonable to anticipate that some of these mutations will be found to be attenuating in vivo and useful for inclusion in a live attenuated HMPV immunogenic composition.

Figure 22A:
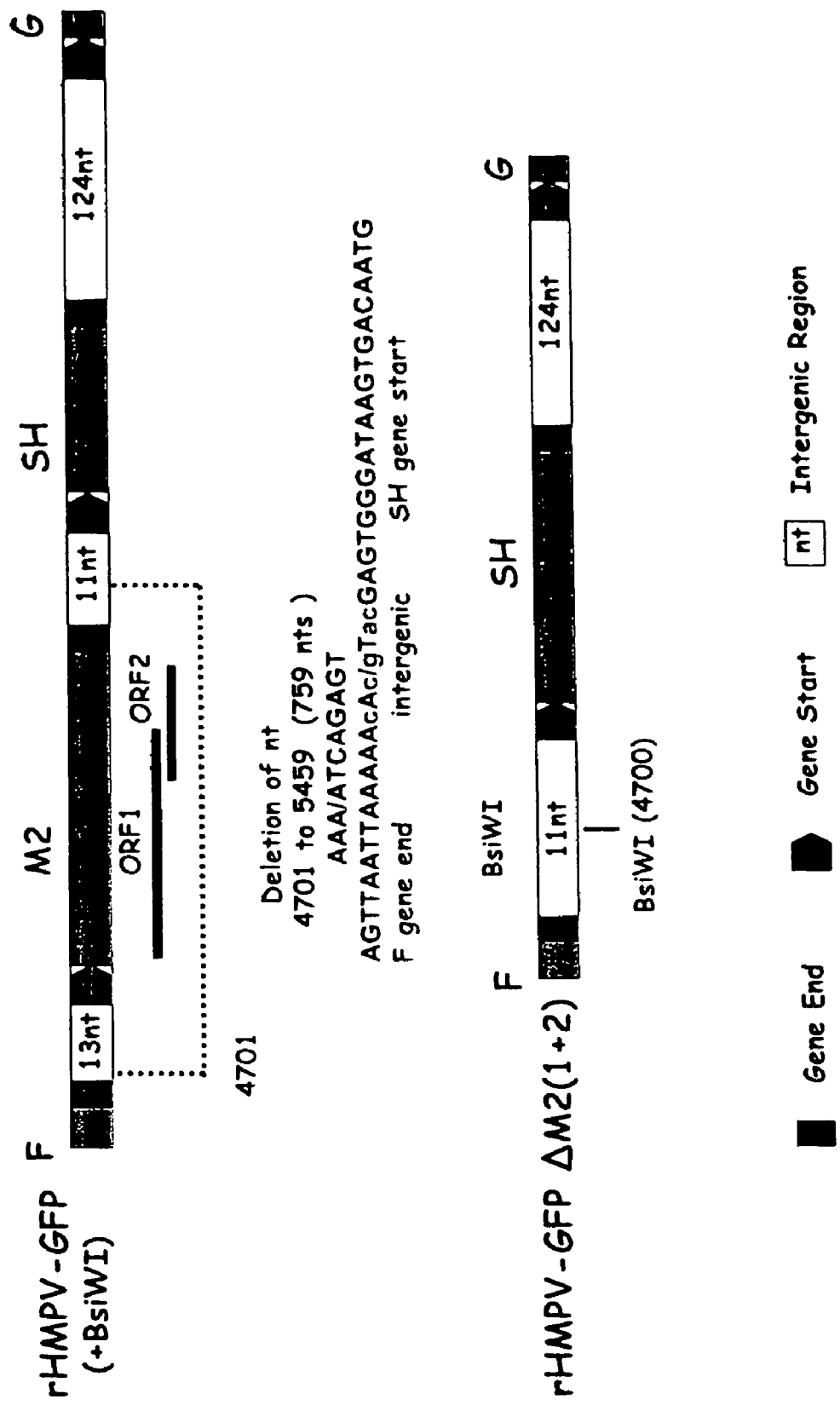
FIG. 22A is a diagram illustrating deletion of the complete M2 gene in infectious rHMPV-GFP (strain 83) containing an introduced BsiWI site. The region of the antigenomic cDNA clone containing the putative M2-1 and M2-2 ORF is illustrated, with each ORF depicted by a solid horizontal line. Nucleotides 4701 to 5459 (SEQ ID NO: 1), representing a total of 759 nucleotides, were deleted, resulting in the mutant rHMPV-GFP-ΔM2(1+2). This mutant was successfully recovered as infectious recombinant virus.
Figure 22B:
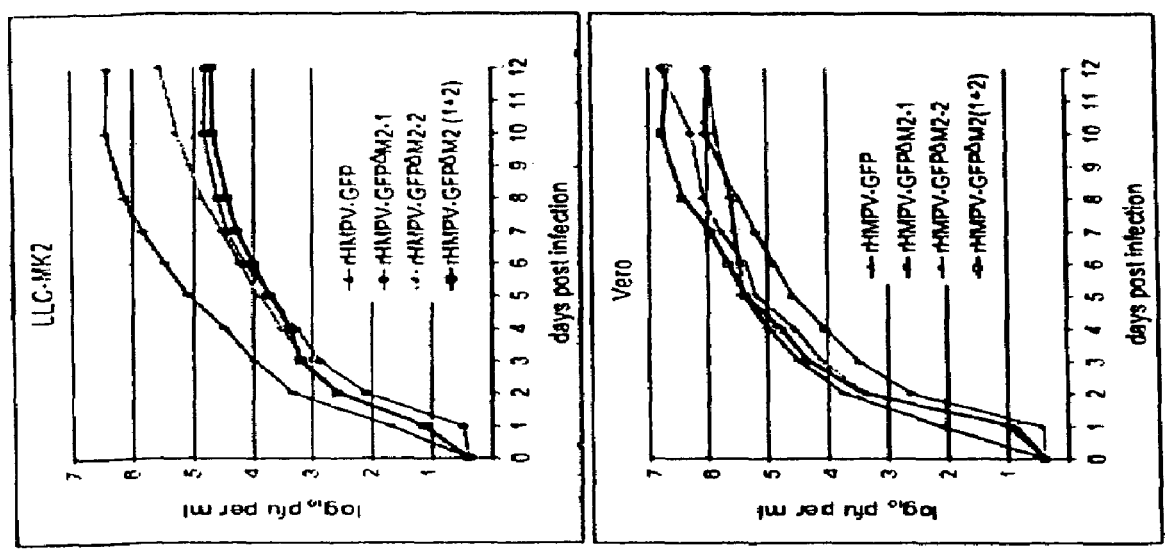
FIG. 22B is a graph illustrating a comparison of the efficiency of growth of viruses with alterations in the coding of M2-1 and/or M2-2 proteins in LLC-MK2 cells (upper panel), which are competent for expressing type I interferons versus Vero cells (lower panel), which lack the interferon structural genes. Cells were infected with 0.01 PFU per cell and incubated at 32° C. in the presence of 5 µg/ml trypsin. Aliquots were taken at 24 h intervals, flash-frozen, and viral titers were measured by plaque assay and immunostaining with convalescent serum from hamsters that had been infected with HMPV.

In another exemplary embodiment the HMPV M2 gene was deleted altogether from rHMPV-GFP, including its GS and GE signals and both the M2-1 and M2-2 ORFs (FIG. 22A). The resulting rHMPV-GFP-ΔM2(1+2) virus was readily recovered and propagated in vitro. The ΔM2-2, ΔM2-1, and ΔM2(1+2) viruses were compared with wild type HMPV with regard to the efficiency of multi-cycle replication in LLC-MK2 and Vero cells (FIG. 22B, upper and lower panels, respectively). This experiment was performed with versions of the viruses that express GFP in order to facilitate visualization of growth but the expression of GFP was not otherwise relevant to the experiment. In LLC-MK2 cells, each of the M2 mutant viruses replicated more than 10-fold less efficiently than wild type. In contrast, in Vero cells each of the M2 deletion viruses grew to a final titer that equaled or exceeded that of wild type HMPV. One of the important differences between LLC-MK2 and Vero cells is that the latter lack the structural genes for type 1 interferon. Thus, this result suggested that that the M2 deletion viruses were more sensitive to interferon than wild type HMPV. In addition, the observation that the M2 deletion viruses replicated efficiently in Vero cells is important, since this is a cell substrate that is acceptable for preparing vaccines for humans.

To directly evaluate the interferon-sensitivity of the M2 deletion viruses, Vero cells were pre-treated overnight with a range of concentrations of type 1 interferon in order to induce an antiviral state. The ability of the ΔM2(1+2) and ΔM2-2 viruses to replicate was evaluated in the interferon-treated cells compared to wild type HMPV and wild type HRSV. Each of the viruses used in this experiment expressed GFP for the purpose of monitoring the infections, but the presence of GFP was not otherwise relevant to the results. Cell monolayers were infected at an moi of 1 PFU per cell (or a multiplicity of infection (moi) of 0.01 in the case of RSV, reflecting its more efficient growth) and incubated for 4 days. Control monolayers were mock-interferon-treated, infected and processed in parallel. The media supernatants were harvested and analyzed by plaque assay to determine virus titers. The fold reduction between each interferon-treated culture and its corresponding mock-interferon-treated control was calculated and is shown in FIG. 22C. Thus, the replication of wild type rHMPV-GFP were reduced from 5-fold to 1680-fold by increasing amounts of interferon, compared to mock-interferon-treated controls. In comparison, the ΔM2(1+2) and ΔM2-2 viruses were more sensitive and were reduced 19-fold and 13-fold, respectively at the lowest concentration and were completely inhibited at the highest concentration. Viruses that exhibit increased sensitivity to interferon typically are attenuated in vivo. Thus, these results suggest that these viruses are candidates to be attenuated derivatives.

Another exemplary embodiment of the current disclosure involves changing gene order to achieve attenuation, increase antigen expression, or achieve some other desirable phenotype. In a subsequent Example, the F protein of HMPV is identified as a major protective antigen, and the G and SH are also identified as virion surface proteins, which makes them likely protective antigens. In the wild type gene order, SH, G and F are located at gene positions 6, 7 and 4, respectively. It is anticipated that HMPV transcription will exhibit a polar gradient, in which promoter-proximal genes are expressed more efficiently than downstream ones. Thus, placement of putative protective antigen genes such as SH, G, and F proximal to the promoter, either singly, as a pair, or as a triplet, will result in more efficient expression. In this application, the genes can be moved to this position from their wild type location, such that the virus retains a single copy of each, or the genes can be inserted as a second copy, such that the virus now expresses two copies of one or more of the HMPV protective antigens. The change in gene expression due to the relocation of genes or to the addition of a second copy can have other desirable effects, such as increased or decreased growth in vitro or in vivo.

Figure 23A:
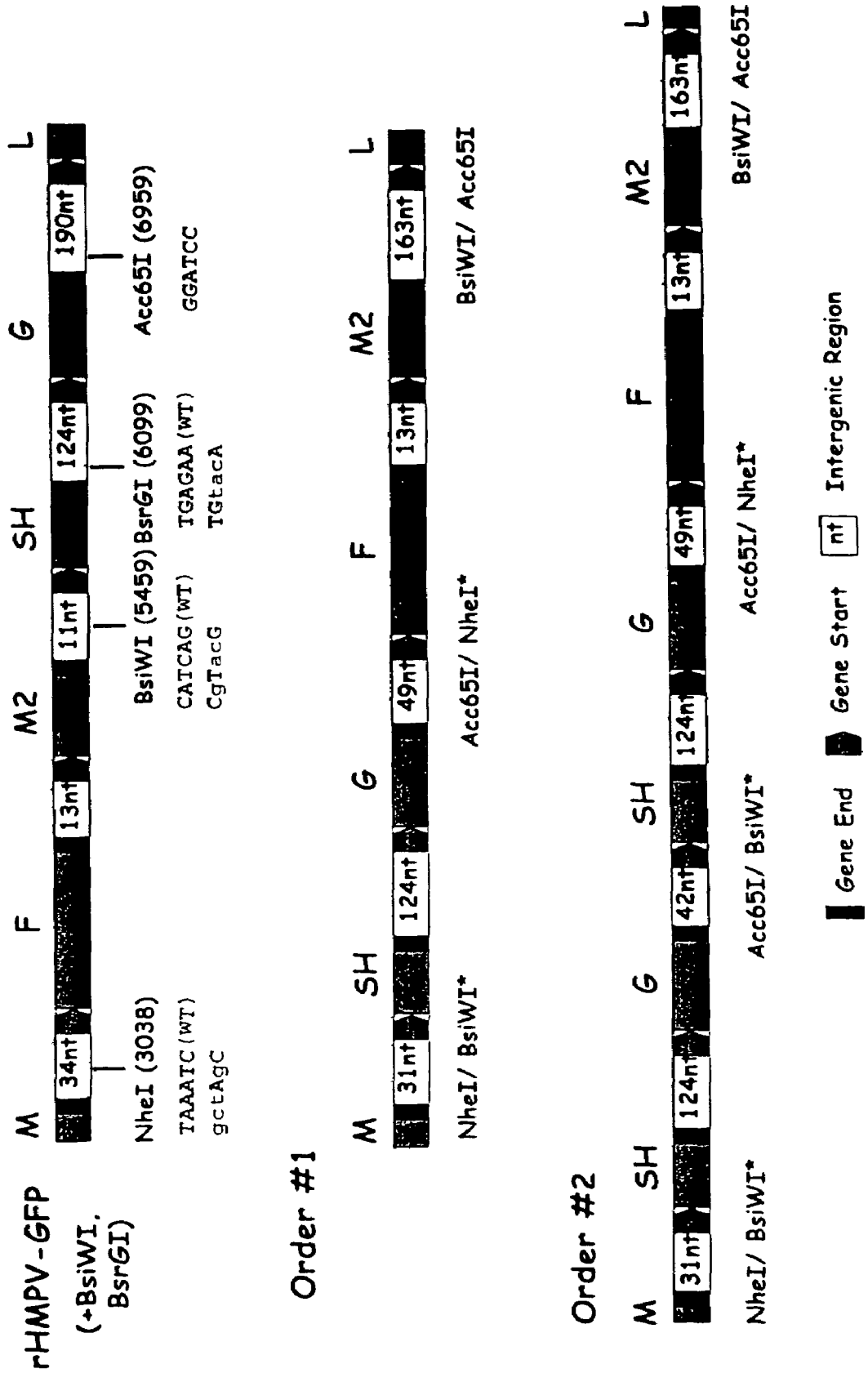
FIG. 23A is a diagram illustrating the construction of two rearrangements of the genes of rHMPV-GFP (strain 83). The wild type gene order is shown on top for the M-L region of the rHMPV-GFP antigenomic cDNA clone. The restriction sites shown are the ones introduced as illustrated above in FIGS. 7 and 15 (the restriction sites are numbered according to the position of the first residue in the wild type HMPV sequence, SEQ ID NO: 1, exclusive of GFP), and were used to rearrange the order if the putative SH and G gene pair. Religations involving NheI were not compatible with the other sites and necessitated fill-in of each end followed by blunt end ligation. Two examples of gene rearrangements are shown: in the mutant called "Order 1", the positions of the SH-G gene pair and the F-M2 gene pair were swapped, resulting in a local gene order that mimics that of RSV, namely M-SH-G-F-M2-L. This mutant was successfully recovered as infectious virus. In a subsequent mutant, "Order 2", the same RSV-like gene order was achieved, but the SH-G gene pair was duplicated.
Figure 23B:
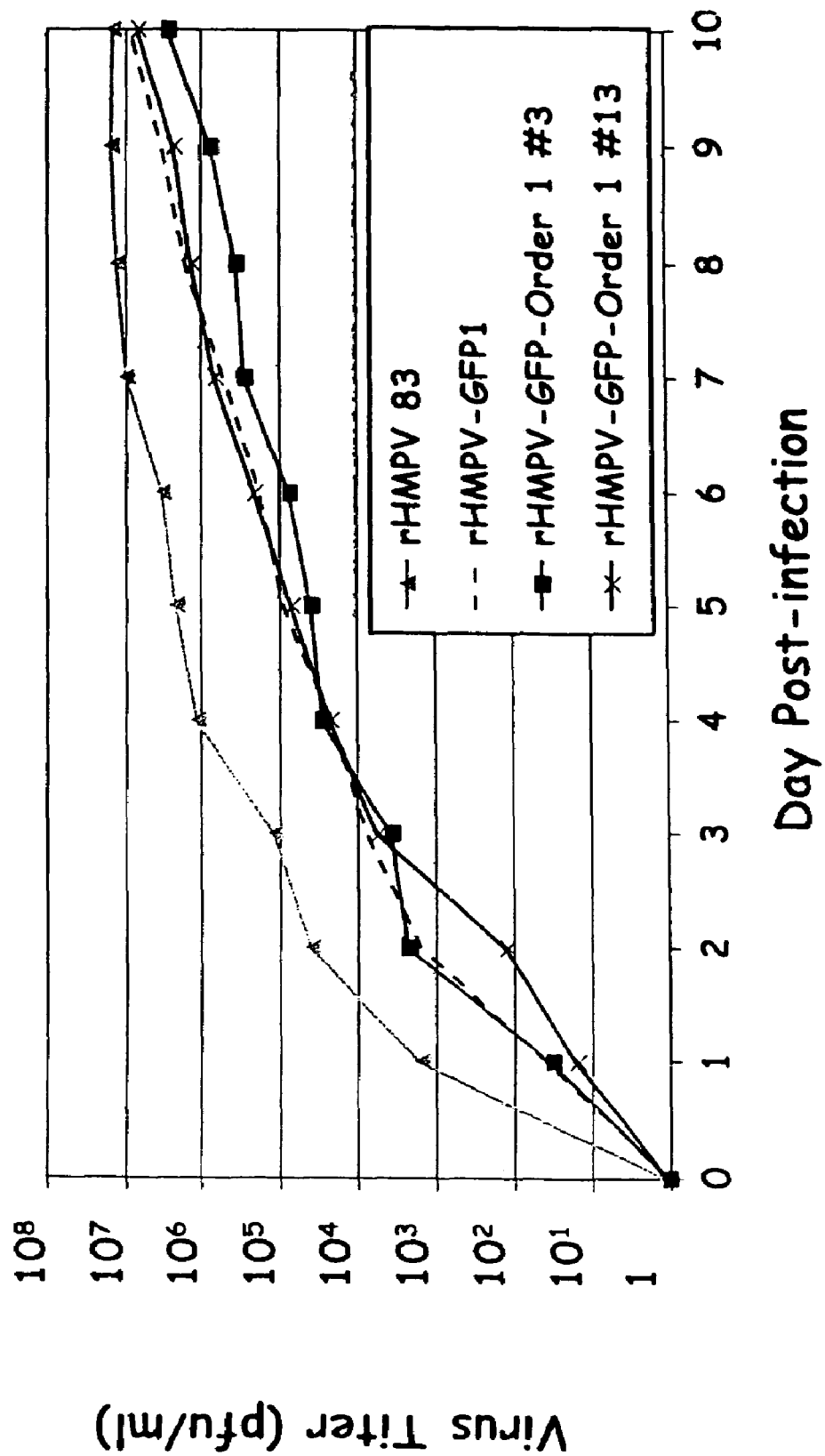
FIG. 23B is a graph illustrating the multi-step growth kinetics of one of these mutants, rHMPV-GFP-Order #1 compared to its direct parent rHMPV-GFP, as well as rHMPV, performed as described above for FIG. 13. Clones #3 and #13 represent viruses derived independently from two sister cDNA clones.

Exemplifying this strategy of "shifting" gene position for developing HMPV derivatives with improved properties, the position of the SH-G gene pair was altered in rHMPV-GFP (FIG. 23A). In one construct, designated "Order #1", the SH-G gene pair was moved from its position following the M2 gene to a position preceding the F gene. This results in a gene order in that region of the genome that mimics that of RSV, namely: M-SH-G-F-M2-L. Hence, the positions of four genes were altered in "Order 1", namely SH and G (each moved upstream by two positions) and F and M2 (each moved downstream by two positions). Accordingly, any gene or combination of genes can be moved within the genome, obtaining changes in gene expression that can provide desirable phenotypes including increased antigen expression, improved growth in vitro, and attenuation. As shown in FIG. 23B, the kinetics and magnitude of replication of the mutant called RSV Order #1 was indistinguishable from that of its direct parent rHMPV-GFP. This showed that changes in gene order can readily be achieved, resulting in infectious virus that replicates efficiently in vitro and can be evaluated for desirable properties such as attenuation or improved antigen expression in vivo.

Figure 24A:
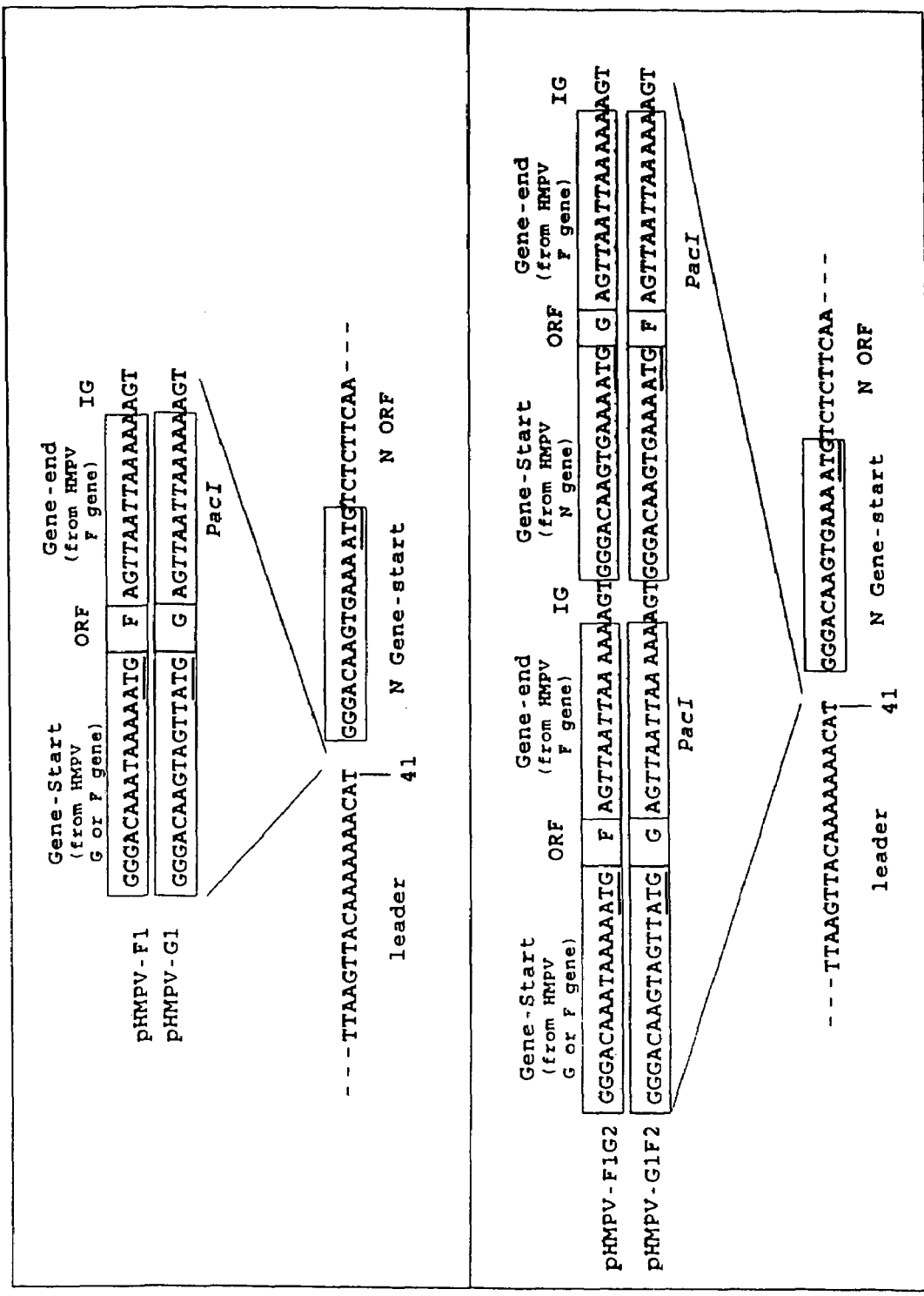
FIG. 24A is a diagram illustrating shifting of the F and/or G genes of HMPV (strain 83) from their natural positions as the fourth and seventh genes, respectively, to promoter-proximal positions 1 or 2. As illustrated in the upper box, the putative F and G ORFs were engineered to be flanked by putative GS (bases 3054-3069 and 6219-6234 of SEQ ID NO: 1, respectively) and GE (bases 4685-4697 of SEQ ID NO: 1) signals and inserted individually into the HMPV antigenomic cDNA clone. Sequence representing part of the 3' leader region (bases 23-41 of SEQ ID NO: 1) and the putative N GS signal and beginning of the putative N ORF (bases 42-66 of SEQ ID NO: 1) is shown. Note that the choice of transcription signals and insertion site was the same as for the rHMPV-GFP construct shown above in FIG. 9, and places the inserted gene as the first in the gene order. As illustrated in the lower box, the putative F and G ORFs were inserted as a pair, in the order G1-F2 or its converse F1-G2, using the same transcription signals and insertion site as in the single-gene rearrangements. Infectious virus was successfully recovered from each of the constructs. These viruses were designated rHMPV−F1, −G1, −F1G2, and G1F2, with the number indicating the position of the gene in the gene order. In the virus designation, the "−" symbol preceding the shifted gene indicates that the shifted gene was removed from its normal position in the gene order.
Figure 24B:
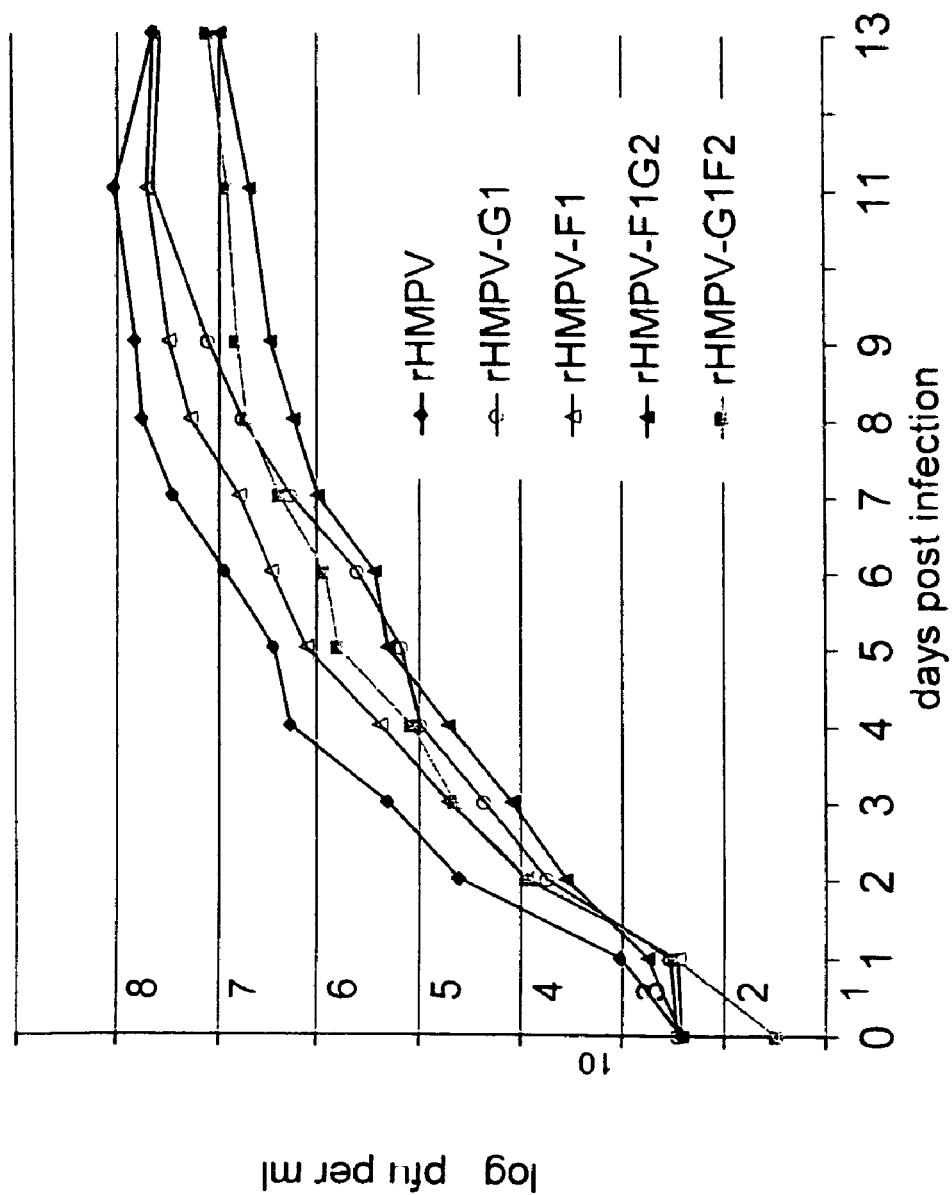
FIG. 24B is a graph illustrating multi-cycle growth kinetics of the recovered viruses in vitro. The recovered rHMPV−G1, F1, F1G2, and G1F2 viruses were compared to their rHMPV parent with regard to multi-step growth in LLC-MK2 cells as described above for FIG. 13.

As another permutation shown in FIG. 23A, the SH-G pair was moved to be upstream of the F gene in rHMPV-GFP, and a second copy of the pair was inserted, resulting in the construct "Order #2". Thus, this construct contains two copies of the SH and G genes, which are potential protective antigens. In this case, the F-M2 gene pair has been moved a total of four positions downstream relative to the viral promoter, and the L gene is now two positions further downstream compared to the parental wild type HMPV. Yet another strategy of "gene shifting" involves moving the presumed protective antigen G and F genes from their normal positions as the $7^{th}$ and $4^{th}$ genes, respectively, in the HMPV gene map to promoter-proximal positions. Each gene can be moved individually or as a pair, as shown in FIG. 24A. In the case of the constructs shown in FIG. 24A, the promoter-proximal insertion site will be the same as was used for insertion of the GFP transcription cassette to make the rHMPV-GFP construct (FIG. 9), from which efficient expression has been demonstrated. While these represent preferred signals and insertion sites, other signals and insertion sites can readily be evaluated and used by the methods of this current disclosure. Preferred insertion sites would be ones in proposed intergenic regions or regions of genes that are outside of the ORFs and putative transcription signals and thus more likely to accommodate engineering without affecting HMPV replication. A subsequent Example provides identification of genome regions that are poorly conserved between divergent strains of HMPV, suggesting that they are less likely to be essential, which provides further guidance to identify preferred insertion sites. The transcription cassette should preferably be designed so that, following its insertion into the antigenomic cDNA clone, the inserted ORF is flanked by a set of GS and GE signals and each gene is the backbone similarly is flanked by a set of transcription signals. In the gene-shift constructs shown in FIG. 24A, insertion of the G and/or F gene into a promoter proximal position was accompanied by deletion of the corresponding copy from the normal antigenome position: in instances where G was shifted to the first or second position, nucleotides 6101-6960 were deleted to delete G from its natural location, and in instances where F was shifted, nucleotides 3053-4710 were deleted to delete the naturally-occurring copy of F. Analysis of the multi-step growth kinetics of these viruses in vitro (FIG. 24B) showed that each replicated somewhat less efficiently than the wild type parent, although the Final titers of the single-gene shift mutants (rHMPV–G1 and F1) were identical to that of the rHMPV parent, while the double-gene shift mutants were only slightly lower.

Figure 25A:
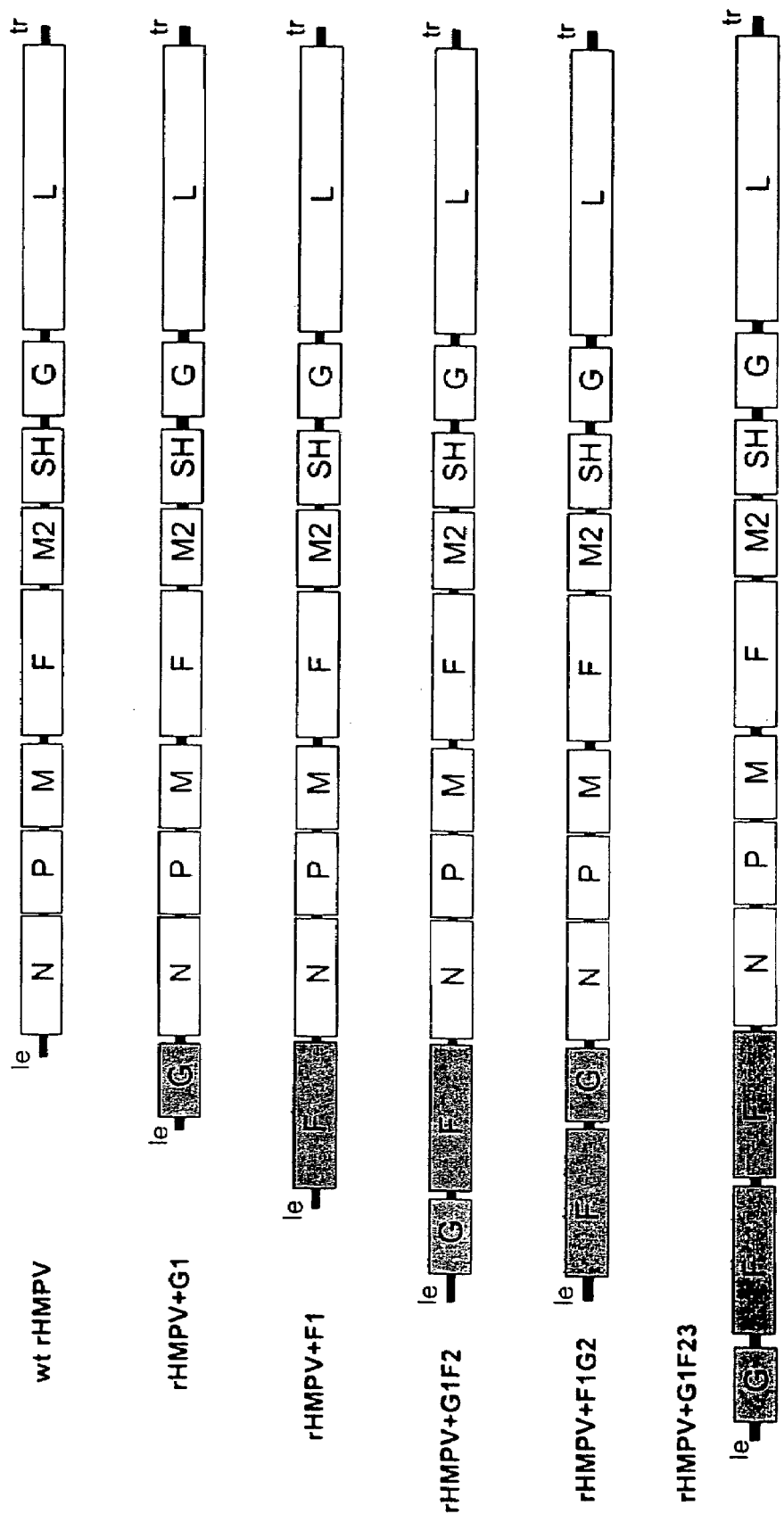
FIG. 25A is a diagram showing representations of rHMPV in which one or more extra copies of the F and/or G gene was placed in promoter proximal positions 1, 2 or 3 in addition to the F and/or G gene present in the normal genome position. The G or F genes were inserted individually into promoter proximal position 1 (rHMPV+G1 or +F 1), or were inserted as a pair into positions 1 and 2 in each of the two possible orders (rHMPV+G1F2 or +F1G2), or were inserted as the pair G1F2 with an additional copy of F in the third position (rHMPV+G1F2,3). The detailed structure of the gene insertions were as shown in FIG. 24A. In the designations, the "+" symbol before the named gene or genes indicates that it/they were additional to the one or ones in the normal position. The added genes are shaded.
Figure 25B:
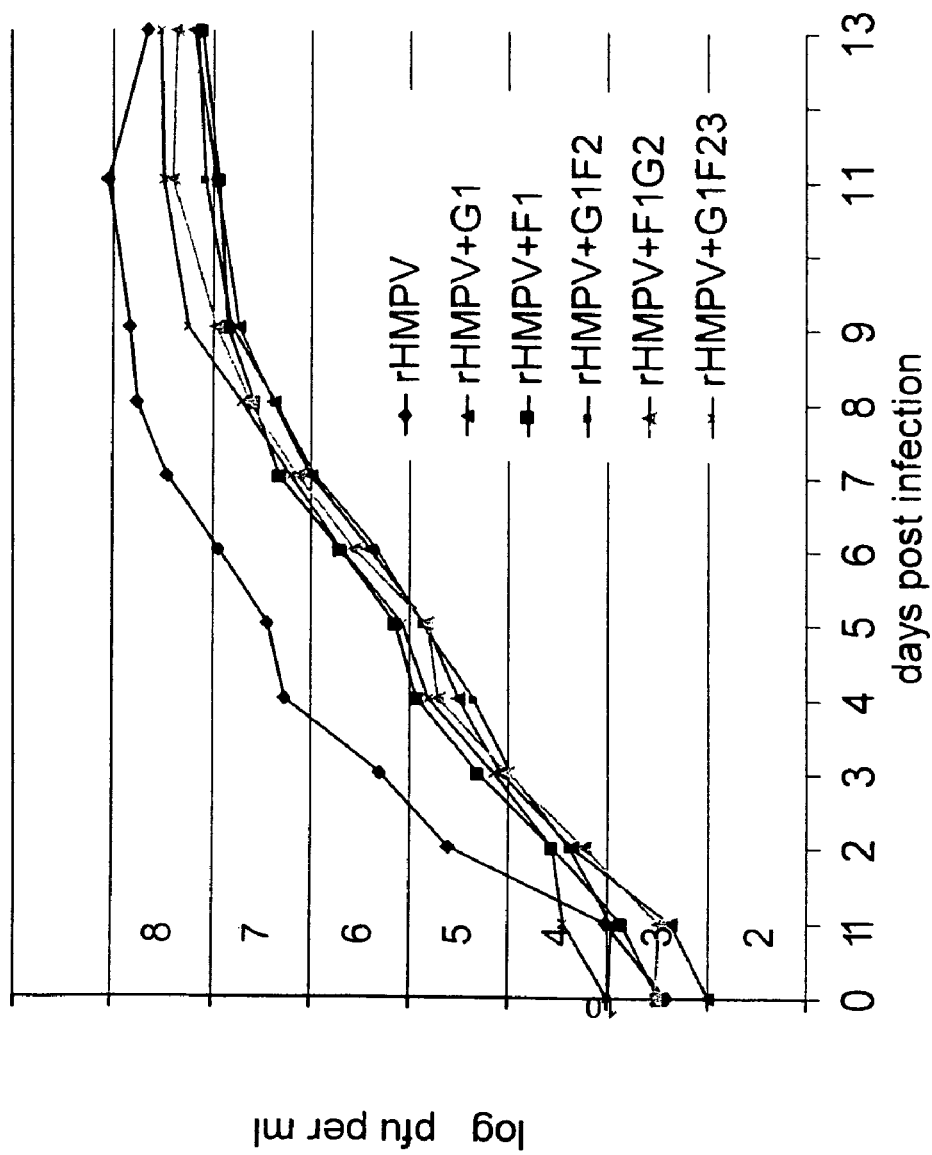
FIG. 25B is a graph illustrating multi-cycle growth kinetics in vitro. The recovered viruses were compared to their rHMPV parent and to rHMPV-GFP with regard to multi-step growth in LLC-MK2 cells as described above for FIG. 13.

A further set of exemplary viruses were constructed in which the G and F genes were inserted into the promoter proximal positions, but the copies of the genes in their natural positions were left undisturbed, as shown in FIG. 25A. Thus, rHMPV+G1 and +F1 contains two copies of the indicated gene (note that the symbol "+" in the designation indicates that the genes were added rather than "shifted"). Similarly, rHMPV+G1F2 and +F1G2 contained an additional copy each of G and F in the indicated position, and rHMPV+G1F2F3 contained an additional copy of G and two additional copies of F in the indicated positions. Interestingly, the multi-cycle growth kinetics of these viruses were somewhat reduced compared to their rHMPV parent (FIG. 25B), but among themselves the various addition mutations grew with similar kinetics. Thus, while the addition of one gene was somewhat attenuating, as had also been observed with GFP, the further addition of one or two more genes had little effect, even in the case of the relatively large F gene. The level of replication in this particular experiment had not plateaued, and the final virus yields were not determined. In these particular constructs, the added genes were of the same virus strain. However, it also should be feasible to incorporate one or more genes from a different strain, such as one possessing antigenic differences. Thus, for example, a rHMPV+G1F2 virus could be made that expresses F and G pairs representing two different strains, resulting in a single bivalent recombinant virus that would elicit a broader immune response.

The presence and intactness of the additional genes in the genome of recovered rHMPV+G1F23 were investigated by RT-PCR performed on total RNA from recovered virus following three passages in Vero cells. RT-PCR was performed with a forward primer hybridizing to the HMPV leader region and a reverse primer hybridizing to N sequence, which yielded a single, major band of approximately 4.1 kb, the appropriate size to contain the tandem G1F2F3 supernumerary genes (not shown). The sequence of the supernumerary G1F2F3 genes could not be determined directly by RT-PCR consensus sequencing of viral RNA because primers specific to G or F would prime on each of the two copies of G and three copies of F, precluding analysis of each gene individually. Therefore, the supernumerary genes were first amplified by RT-PCR in three separate, overlapping segments. The first RT-PCR segment used a forward (positive-sense) primer (which also served as the RT primer) from the leader region and a reverse primer from the F gene (840 nt downstream of the F GS signal): although this latter primer would prime on each copy of F, priming from the promoter-proximal copy (F2, numbered as in rHMPV+G1F23) would be the most efficient in combination with this forward primer, and yielded a ~1.6 kb fragment that contained the leader, the G1 gene, and about 840 bp of the F2 gene, and was purified by gel electrophoresis for sequence analysis. The second segment was amplified by RT-PCR with an RT/forward primer located about 670 nt downstream of the F GS, and a reverse primer located 554 nt downstream of the F GS: although the forward primer would prime in all three copies of F and the reverse primer in all three copies of F, priming in F2 and F3 would be the only combination to result in successful amplification of a PCR fragment (~1.5 kb) that contained the downstream 978 bp part of the F2 gene, and a 554 bp upstream part of F3, and was purified by gel electrophoresis for sequence analysis. The third fragment was generated with an RT/forward primer from the upstream end of F (14 nt downstream the F GS signal) and a reverse primer from the upstream end of N: the forward primer would prime in all three copies of F, but priming in F3 would be the most efficient and would yield a ~1.75 kb product that contained most of the F3 gene, and 120 bp of the N gene, and was purified by gel electrophoresis for sequence analysis. This provided an RT-PCR consensus sequence of the G1F-2F3 supernumerary genes that was free of mutations, and all GS/GE signals and intergenic sequences were correct, indicating that these added genes were stably recovered in recombinant virus.

Figure 25C:
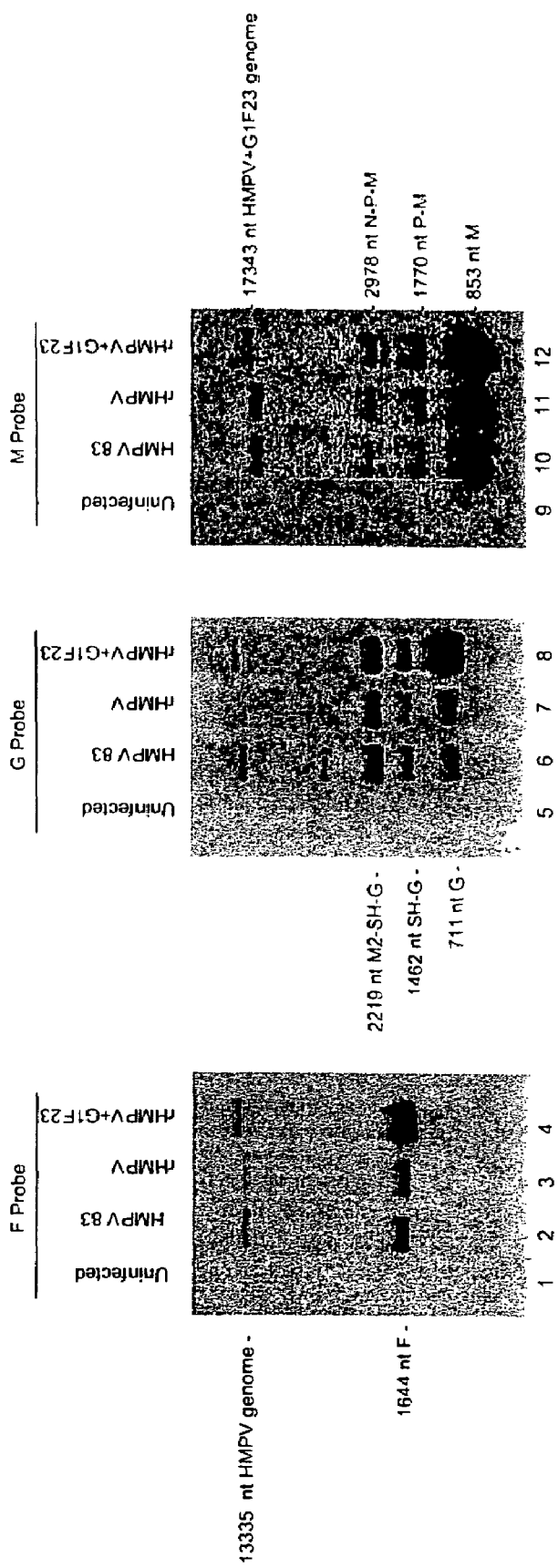
FIG. 25C is a digitized image of a nylon membrane illustrating Northern blot analysis of intracellular mRNAs expressed by rHMPV+G1F23. LLC-MK2 cells were mock-infected (lanes 1, 5 and 9) or infected at an MOI of 3 PFU per cell with HMPV83 (lanes 2, 6 and 10), rHMPV (lanes 3, 7 and 11), or rHMPV+G1F23 (lanes 4, 8 and 12). Three days later, total intracellular RNA was isolated, electrophoresed on 1% agarose-formaldehyde gels, transferred to charged nylon and analyzed by hybridization to double-stranded $^{32}$P-labeled DNA probe specific to the F (lanes 1-4) G (lanes 5-8), or M (lanes 9-12) gene. The identities and calculated sizes of individual RNA species are indicated.

To determine the effect of the gene additions on viral gene expression, cells were mock-infected or infected with biologically-derived HMPV83, rHMPV, or rHMPV+G1F23, and total intracellular RNA was isolated three days later and subjected to Northern blot analysis with double stranded probes to the F, G or M genes (FIG. 25C). The F probe detected a major band of the appropriate size to be the 1644-nt F mRNA, as well as a fainter band of genome and antigenome, which in the case of rHMPV+G1F23 would be 4008 nt larger compared to HMPV83 or rHMPV due to the presence of the three added gene copies (FIG. 25C, lane 4). There were only trace amounts of readthrough mRNAs detected with the F probe. Phosphorimager analysis indicated that the amount of genome plus antigenome for rHPMV+G1F23 compared to HMPV83 and rHMPV was 0.9 and 0.5, respectively (corrected for the two extra copies of the F gene present in rHMPV+G1F23). In comparison, the relative amount of F mRNA for rHMPV+G1F23 compared to HMPV83 and rHMPV was 6 in each case. Normalized to the respective value of genome plus antigenome, this corresponded to a 6.6- to 12-fold higher level of F mRNA for rHMPV+G1F23 compared to HMPV83 and rHMPV.

Northern blot analysis with the G probe detected, for each of the three viruses, a band of the appropriate size to be the 711-nt G mRNA as well as bands corresponding to SH-G and M-SH-G readthrough mRNAs and a band corresponding to antigenome and genome RNAs (FIG. 25C, lanes 6, 7 and 8). Phosphorimager analysis indicated that the amount of genome plus antigenome for rHMPV+G1F23 compared to HMPV83 and rHMPV was 1.0 and 0.5, respectively (corrected for the extra copy of the G gene present in rHMPV+G1F23), values very similar to that observed with the F probe noted above. In comparison the relative amount of G mRNA for rHMPV–G1F23 compared to HMPV83 and rHMPV was 14-fold and 15-fold, respectively. This would correspond to a 14- to 30-fold higher level of G mRNA for rHMPV+G1F23 compared to HMPV83 and rHMPV. Thus, the expression of the G and F genes by the rHMPV+G1F23 virus indeed was greatly increased.

Yet another strategy for designing improved immunogenic compositions against HMPV is to modify the ORFs encoding protective antigens so that the codon usage is consistent with efficient translation. Specifically, for many of the codons in a given ORF, the degeneracy of the genetic code allows for more that one choice of codon without changing the amino acid coding assignment. In a number of cases, specific codon choices have been shown to be associated with efficient translation while, conversely, other codon choices are associated with decreased efficiency of translation. Thus, the ORFs encoding HMPV antigens can be re-engineered to contain codon choices consistent with efficient translation. This can be done for ORFs in their natural genome positions as well as for ORFs that have been shifted or for heterologous ORFs that have been inserted.

Another exemplary embodiment of the current disclosure involves using a single attenuated HMPV backbone to make immunogenic compositions against more than one HMPV strain, subgroup or serotype. In this application, the protective antigen genes of an attenuated derivative of HMPV, such as strain 83, are replaced singly or in toto by the corresponding genes of a heterologous HMPV. Provided that most of the attenuating mutations of the attenuated parent HMPV lie in genes other than the protective antigen genes, this results in a chimeric virus in which the attenuated backbone of the parent bears the protective antigens of the heterologous strain. This chimeric virus can then be administered on its own, or can be combined with the original parent to make a two-virus bivalent immunogenic composition against the two viruses. This process can be repeated for additional heterologous strains as necessary.

Yet another exemplary embodiment of the current disclosure involves the addition of one or more transcription cassettes encoding one or more foreign ORFs, as exemplified in Example II by GFP. In this application, the foreign gene is placed under the control of HMPV transcription signals and is inserted into the genome in a location that does not interfere with virus viability, such as an intergenic region or a gene noncoding region. In this way, a variety of foreign proteins can be expressed, such as ones encoding protective antigens of heterologous pathogens, or immunomodulatory molecules.

Figure 27:
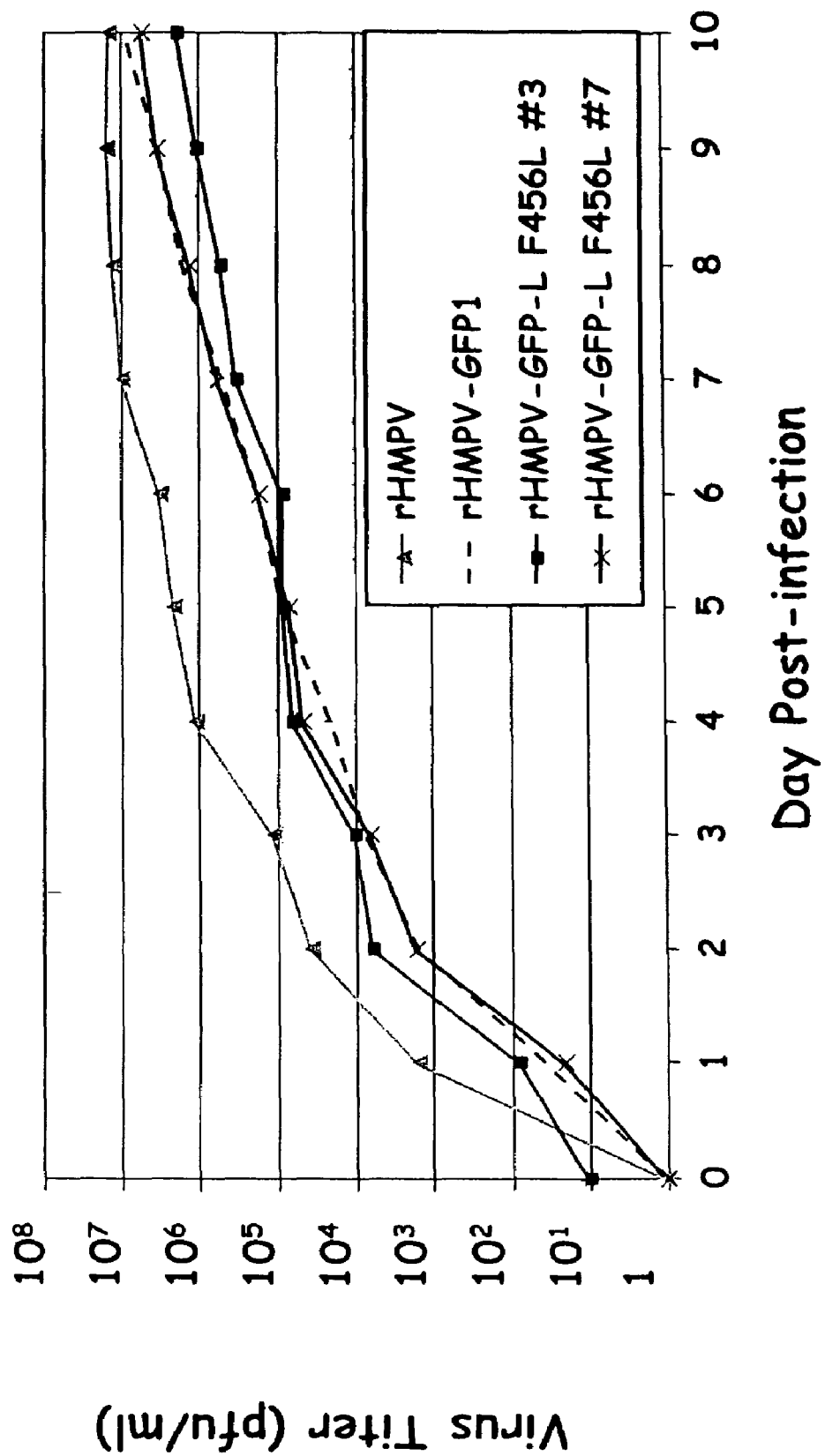
FIG. 27 is a graph illustrating multi-step growth of rHMPV-GFP containing the F456L mutation (see FIG. 26A), compared to rHMPV, performed in LLC-MK2 cells as described above for FIG. 13. Clones #3 and #7 represent viruses derived independently from two sister cDNA clones.

In yet another exemplary embodiment, rHMPV-GFP was recombinantly modified to incorporate a Phenylalanine to Leucine mutation at amino acid position 456 in the L protein, a mutation designated F456L. This particular mutation was suggested by amino acid sequence alignment as corresponding to a position that encodes attenuating mutations in other, heterologous mutant nonsegmented negative stranded RNA viruses. The sequence alignment in FIG. 26A shows a phenylalanine-521 to Leucine (F521L) substitution in the L protein specified by a mutation in the L gene of an RSV cold-passage temperature-sensitive (cpts) mutant cpts530 (Juhasz et al, J. Virol. 71:5814-9, 1999). The wild type F521 residue in the RSV sequence is exactly conserved among other mononegaviruses examined and, in particular, is present in HMPV. It should be noted that the amino acid position of the corresponding residue is not the same in each L protein, reflecting differences in length as well as small deletions and insertions elsewhere in the various individual molecules. Thus, the corresponding residue is F456 in HMPV. From this comparative mapping analysis, the F456 residue in HMPV is identified as a target for either an identical, conservative, or even non-conservative amino acid substitution (for example, substitution of the F456 residue by a leucine, or by a conservative or non-conservative amino acid as compared to leucine). In this particular Example, the F456L mutation was introduced into rHMPV-GFP and was readily recovered in a recombinant virus, designated rHMPV-GFP-F456L. As shown in FIG. 27, this mutant replicated in vitro with an efficiency that was indistinguishable from that of its direct parent, rHMPV-GFP, a characteristic that is important for efficient viral recovery, evaluation and manufacture. Thus, this mutant is an excellent candidate for further evaluation to determine its phenotypic characteristics in vitro and in vivo. Further description of this general strategy, including discussion of FIGS. 26B-26F and 28, is provided above, along with other strategies for the expeditious design of attenuated derivatives based on the methods of this current disclosure.

Yet another strategy for making live attenuated vaccine candidates is the "Jennerian" approach, which involves the use of a mammalian or avian virus to immunize against an antigenically related human virus. This approach is named after Edward Jenner's successful use of cowpox as the initial vaccine against smallpox in humans. This approach is based on the idea that a virus that has evolved to replicate efficiently in its natural animal host often will replicate inefficiently and thus be attenuated in the non-natural human host, reflecting a host range restriction. Such a host range restriction typically is a very stable phenotype, being the aggregate effect of the many nucleotide and amino acid sequence differences between the animal and human viral counterpart. A phenotype that is based on many loci would be refractory to drift.

Other examples of "Jennerian" vaccines include the use of bovine rotavirus or bovine PIV as candidate vaccines against the respective human viruses. This can involve using the animal virus as it is provided by nature, as illustrated by the use of bovine PIV directly as a vaccine (Karron et al., Pediatr Infect Dis J 15:650-654, 1996). Alternatively, the virus can be modified so that some of the genes are derived from the animal virus and some from the human virus. In such a case, it is preferable to have the major protective antigens be derived from the human virus, such that the immunity that is induced will be maximally effective against the human virus, and one or more other genes be derived from the animal virus such that they confer host range restriction. One such situation involves chimeras between human and bovine parainfluenza type3 viruses: in one case, the attenuated bovine backbone was modified so that the protective HN and F antigen genes were replaced by those of the human virus, thus combining the attenuated bovine viral backbone with the antigenic determinants of the human virus (Schmidt et al., J. Virol. 74: 8922-8929, 2000), and in a second case the human virus was attenuated by replacing a single gene, that of the nucleocapsid N protein, with that of its bovine viral counterpart (Bailly et al., J. Virol. 74:3188-3195, 2000). Surprisingly, each of these bovine/human chimeric viruses was satisfactorily attenuated and immunogenic in rodent and nonhuman primates, and both are being prepared for clinical trials.

FIG. 30A illustrates chimeric HMPV vaccine candidates that were constricted by individually replacing the N, P or M ORFs of HMPV with the corresponding ORFs from APV subtype C. At the amino acid level, the N, P and M genes of HMPV and APV-C are 90, 69, and 89% identical, respectively. For comparison, the N protein of bovine parainfluenza type 3 virus, whose substitution into the human PIV backbone provided a promising vaccine candidate, also was within this range, being 85% identical with its human viral counterpart. Furthermore, there are A, B and D subtypes of APV that are less closely related to HMPV, providing a source of additional replacements ORFs whose greater degree of divergence might provide a higher degree of attenuation.

FIG. 30 Panels B, C and D illustrate the construction of chimeric N (Part B), P (Part C), and M (Part D) genes. In each panel, the upper sequence is that of a cDNA containing the native N, P or M HMPV gene, and the bottom sequence of each panel is a cDNA in which the HMPV ORF has been replaced by its APV counterpart. Both the native HMPV and chimeric HMPV/APV cDNAs have been constructed to be flanked by restriction recognition sites for enzymes (BbsI, BsmBI, BfuAI, as indicated) that cleave on the inner side of each recognition sequence to yield 4-nt overhangs. Since the actual cut site of these particular enzymes are not sequence specific, the cut sites can be designed to have the native HMPV sequence. This makes it possible to ligate the N, P and M genes together in a single step, as in FIG. 30E. Any combination of HMPV and HMPV/APV genes can be ligated. For example, ligation of HMPV/APV N with HMPV P and HMPV M would yield a virus in which the N ORF alone was derived from APV. Single, double, or triple ORF replacements can readily be made. This represents one strategy for introducing attenuating host range mutations, namely a strategy in which the backbone is derived from HMPV and one or more individual ORFs from APV are introduced. An alternative strategy that also can be achieved by the methods of this current disclosure involves starting with a full length APV genome and replacing the putative protective antigen genes, namely G, F and SH, by their HMPV counterparts in whatever combination is desired. This would combine the antigenic determinants of HMPV with the attenuated backbone of APV.

Example 4

Analysis of Genetic Diversity Between Distinct Antigenic Subgroups of HMPV for Development of Improved Immunogenic Compositions When van den Hoogen et al. first described the isolation of HMPV, they proposed that there was significant diversity among the various isolates (also called strains) and noted that "it is tempting to speculate that these subgroups of hMPV isolates represent different serotypes of hMPV" (Nat. Med. 7:719-24, 2001). "Serotype" means that there would be insignificant antigenic cross-reactivity between HMPV subgroups following a primary immunization, and would necessitate the development of a separate vaccine for each. Even if the HMPV subgroups do exhibit antigenic cross reactivity, it could be that sufficient antigenic diversity exists such that neutralization and protection across subgroups is significantly reduced compared to within a subgroup, and it might be necessary to have both such subgroups included in an effective immunogenic composition against HMPV. Sequence diversity also was reported by Peret et al., albeit following analysis of a small segment of the genome who proposed that there may be two "major groups or lineages" of HMPV (J. Infect. Dis. 185:1660-3, 2002). This also is supported by recent sequence analysis of the N, P, M and F genes of a number of HMPV isolates (Bastien et al., Virus Res. 93:51-62, 2003). The extent of sequence and antigenic diversity among circulating HMPV strains is of considerable importance to epidemiology, viral detection, and development of immunogenic compositions. Strains 83 and 00-1 as described herein are members of one of the proposed subgroups, and therefore a third strain was analyzed (75) that represents the second subgroup. Comparison of the three strains provided a measure of the degree of genetic diversity between subgroups (strain 83 or 00-1 versus 75) or within a subgroup (strain 83 versus 75).

A complete consensus sequence (FIGS. 39A-39D) was determined for the genome of strain 75 using the general procedures described in Example 1 above for strain 83. In this analysis, the sequence of the genomic termni of strain 75 were determined by 3' and 5' RACE as described in Example, 1. Whereas strain 83 had yielded an unambiguous sequence for its entirety, strain 75 yielded a sequence in which a number of positions in the SH and G genes contained a mixture of two assignments. This suggested that the isolate was a mixture of two or more viruses that likely reflected quasispecies variants, either present in the original clinical sample or arising during in vitro passage. Analysis of cloned RT-PCR products spanning the SH and G genes produced two closely related sets of sequence that likely represented two different viruses. To obtain a sequence that could be unambiguously attributed to a single replication-competent HMPV 75 virus, the isolate was subjected to biological cloning by plaque isolation. Eight independent plaque-purified preparations yielded identical consensus sequences in the region of SH and G that was consistent with that of one of the two groups of cloned cDNA sequences. This sequence appears to represent the major constituent and was taken to be HMPV 75.

Figure 29:
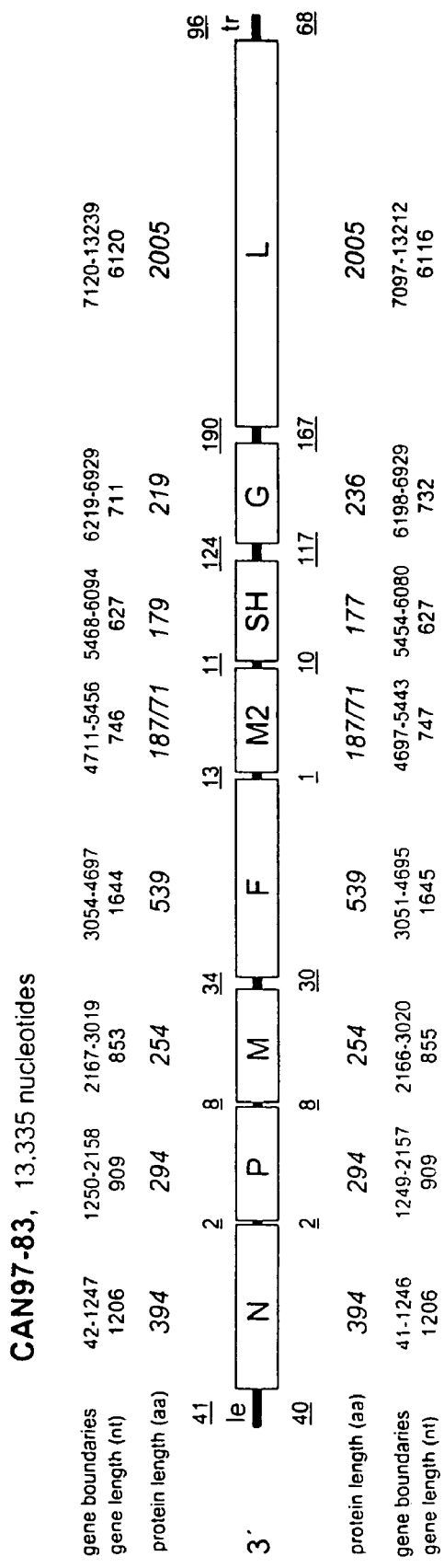
FIG. 29 is a diagrammatic representation of the genome structure of biologically-derived HMPV strains 83 and CAN98-75 (hereafter referred to as 75 or CAN75), representing the two proposed genetic HMPV subgroups and thus illustrating the diversity that must be considered in designing an HMPV immunogenic composition. Individual genes are indicated by boxes, with gene lengths and boundaries within the complete genomic sequence given in nucleotides together with the unmodified amino acid length (italics) of the deduced protein (in the case of M2, two predicted proteins, M2-1 and M2-2). The nucleotides lengths of the extragenic 3' leader, 5' trailer and intergenic regions are underlined.

The genome of strain 75 is 13, 280 nucleotides in length, compared to 13,335 for strain 83 and an estimated length of 13,378 for strain 00-1. The gene maps of strains 83 and 75, showing the cross-subgroup comparison, are shown in FIG. 29. Overall, the two genomes shared 80% nucleotide identity, compared to 81% between the A2 and B1 strains of RSV representing the two RSV antigenic subgroups A and B, respectively (Genbank accession numbers M74568 and AF013254, respectively). Similarly, the nucleotide sequence of isolate 75 (FIGS. 39A-39D) was 80% identical to that of isolate 00-1 (excluding the regions for which sequence was unavailable for 00-1), representing a second cross-subgroup comparison. The sequences of isolate 83 (FIGS. 37A-37D) and 00-1, representing an intra-subgroup comparison, were 92% identical. As will be detailed further herein, the level of divergence between the two HMPV subgroups bears considerable similarity to that between the two antigenic subgroups of RSV. This finding was unpredicted and is of considerable value because there is extensive information on the significance of RSV diversity for epidemiology and development of immunogenic compositions, and this provides a very useful context for consideration of the divergence between HMPV subgroups, particularly since the overall magnitude is similar. As will be noted herein, there were some differences between the diversity of HMPV versus RSV, but even here RSV provides a useful benchmark for evaluating these differences.

For most genera of the Paramyxovirus family, there is a "rule of six" whereby the nucleotide length of each genome is an even multiple of six (Kolakofsky et al., J. Virol. 72:891-899, 1998). In many cases, the placement of cis-acting signals relative to hexamer spacing also follows a conserved pattern. However, HMPV replication and gene expression do not appear to be ruled by a phasing requirement based on the following observations: (i) the sequences for the three available isolates differ in length, as mentioned above; (ii) no integer from 2 to 9 is evenly divisible into each of the three genomes, and (iii) there was no apparent pattern of phasing for the gene boundaries within or between isolates. The absence of a phasing requirement also is suggested by the ability to recover a number of recombinant viral mutants possessing a wide variety of lengths, as shown in previous Examples. The absence of such a requirement was unpredicted, and will greatly facilitate the construction of recombinant HMPVs.

The availability of complete genome sequences representing the two HMPV genetic subgroups provides an opportunity to examine the relatedness of the proposed HMPV transcription signals between subgroups. This is illustrated in FIG. 31, which compares the putative GS, GE and intergenic sequences between the two subgroups. The GS and GE signals exhibited extensive sequence identity among the difference genes and between the two subgroups, and a number of residues were exactly conserved in all sequences. In contrast, the intergenic regions exhibited only 48% identity between subgroups, and non-coding gene regions that were not part of the putative GS and GE signal exhibited only 54% identity. This sharp distinction in the pattern of sequence identity, combined with the functional analysis for transcription activity illustrated by the the GFP expression cassette in Example II above, provides guidance and an experimental method for a clear delineation of these important cis-acting sequences. Conversely, the identification of regions such as the intergenic regions and the non-translated, non-signal gene regions points out areas where the likelihood is increased that modifications involved in gene insertions, gene rearrangements and other genetic engineering would be tolerated, providing guidance that will facilitate production of recombinant viruses for use in immunogenic compositions.

The conserved sequence at the up-stream end of each gene, which would include the GS signal, consists of 16 nucleotides, consensus: GGGACAAnTnnnAATG (FIG. 31). One unusual feature of the GS signal of all HMPV isolates sequenced to date is the presence of ATG at positions 14-16 (FIGS. 8 and 31), which initiates the major ORF. In the SH gene of strains 75 and 00-1, there is an additional upstream ATG at GS positions 8-10: however, this start site is unlikely to be used because of its unfavorable sequence context. The methods of the current disclosure allow for a determination to be made whether the ATG at positions 14-16 is a functional element of the HMPV GS signal or whether the conserved spacing of this translational start site plays some other role in gene expression. This can readily be accomplished using either complete recombinant virus or the minigenome system. The downstream end of each HMPV gene is delineated by the putative 12- to 15-nucleotide GE motif (consensus: AGTTAtnnnAAAAA), consisting of (in positive sense) a highly conserved AGTTA pentamer, followed by a poorly conserved A/T-rich trinucleotide followed by a tract of 4 to 7 A residues. A sequence that resembles the GE motif also is present near the downstream end of the HMPV leader region (FIG. 31), and the methods of the current disclosure will clarify whether this functions like a GE signal.

FIG. 32 shows the percent nucleotide identity and amino acid sequence identity between the two HMPV subgroups (strain 83 versus 75) and within a subgroup (strain 83 versus 00-1) for the various individual ORFs and their encoded proteins. With regard to nucleotide sequence identity between the two subgroups, the HMPV ORFS shared 81-87% nucleotide identity except for SH and G, which were substantially more divergent (69% and 59% identity, respectively). This pattern resembled that of the two subgroups of HRSV, for which the percent nucleotide identity for the various ORFs was 81-85% identical except for the more divergent M2-2, SH and G ORFs (69%, 77%, and 67% identity, respectively; FIG. 32). As noted above, the intergenic regions and the noncoding gene regions (exclusive of GS and GE signals) were 48% and 54% identical, respectively, between subgroups, compared to values of 42% and approximately 50%, respectively, for RSV (Johnson et al., J. Gen. Virol. 69:2901-2906, 1988). Thus, the coding sequence for HMPV G was only marginally more conserved than HMPV noncoding gene sequence in general (59% versus 54%). Extensive nucleotide sequence divergence for the ORFs encoding the SH protein and, in particular, the G protein also was observed between two strains of the same subgroup (strain 83 versus 00-1, FIG. 32).

FIG. 32 also shows the amino acid sequence relatedness of the various HMPV proteins between the two subgroups (strain 83 versus strain 75), and within a subgroup (strain 83 versus 00-1). With regard to the total proteome, the HMPV subgroups shared 90% amino acid sequence identity, compared to 88% identity between the RSV subgroups. With regard to individual proteins, the most conserved HMPV proteins were N, M, F, M2-1, and L (≧94% identity between subgroups), followed by P and M2-2 (85%-89%), followed by the divergent SH (59%) and G (37%) proteins. SH and G are the only ones for which the percent relatedness at the amino acid level was less than at the nucleotide level, suggesting that amino acid substitutions were preferentially retained.

The pattern of HMPV sequence diversity between subgroups has general similarities to that of RSV (FIG. 32). For RSV, the "internal" virion proteins and the F protein constituted a group of highly conserved species, while the M2-2, SH and G proteins were more divergent. Three differences between HMPV and RSV were particularly noteworthy: (i) the HMPV M2-2 protein was markedly more conserved (89% amino acid identity between subgroups) than its RSV counterpart (61%); (ii) the HMPV F protein also was more conserved than was the case for RSV (95% identity between subgroups versus 89%); and (iii) the HMPV SH and G proteins were markedly more divergent than their RSV counterparts (59% and 37%, identity between subgroups, respectively, compared to 72% and 55%, respectively). FIG. 32 also compares the HMPV proteins within a subgroup (strain 83 versus 00-1). For most of the proteins, the percent amino acid identity was very high (≦95%), with the SH and G proteins being more divergent (85% and 70% identity, respectively). The value of 70% sequence identity for G within an HMPV subgroup is much lower that the value of 91% reported for RSV G from the analysis of seven subgroup B strains (Sullender et al., J. Virol. 65:5425-5434, 1991). Thus, the HMPV SH protein and, in particular, the G protein were markedly more divergent within and between subgroups than was the case for their HRSV counterparts. This finding was unpredicted and is important because it indicates these antigens would be ones for which it will be important to have both subgroups represented in an immunogenic composition once they are identified as significant protective antigens. A test for evaluating whether or not an HMPV protein is a protective antigen is presented below.

It was also surprising to find that the HMPV M2-2 ORF and protein exhibited a high level of identity between the two putative subgroups, since M2-2 of RSV is poorly conserved (FIG. 32). In the case of RSV, the M2-2 protein was identified as a functional gene product by the observation that disruption of its ORF in infectious recombinant virus resulted in altered virus growth and RNA synthesis (Bermingham and Collins, Proc. Natl. Acad. Sci. USA 96:11259-11264, 1999; Jin et al., J. Virol. 74:74-78, 2000). As noted above, rHMPV in which the M2-2 ORF has rendered nonfunctional remains viable in vitro, although its phenotype remains to be fully defined. The high level of sequence conservation for the M2-2 ORF between HMPV subgroups suggests that it encodes a significant product, the absence of which might prove to be attenuating and useful in immunogenic compositions. The RSV M2-2 ORF is expressed by a ribosomal stop-restart mechanism, whereby ribosomes that exit the M2-1 ORF apparently double back and initiate translation at the overlapping M2-2 ORF (Ahmadian et al., EMBO J. 19:2681-2689). For the HMPV M2-2 ORF, there are two possible methionyl translational start sites located 38 and 50 nucleotides upstream of the translational termination codon of the M2-1 ORF. These two sites are exactly conserved among all three strains compared here, and are embedded in highly conserved sequence. This is another example where the availability of the cross-subgroup comparison is useful for identifying structural features that are of potential significance, and whose possible functional roles can be tested using complete recombinant virus or minigenomes by the methods of this current disclosure.

The HMPV F, SH and G proteins appear to correspond to the three RSV surface glycoproteins F, SH and G, although there was clear sequence relatedness between HMPV and HRSV counterparts only for F (33% amino acid identity). For RSV, G and F are the only significant neutralization antigens and are the major protective antigens. The HMPV F protein is identified as a neutralization and protective antigen of HMPV in an Example below. The status of the remaining HMPV proteins as potential neutralization and protective antigens can be determined by the same method. The RSV F protein has a high degree of antigenic relatedness between subgroups (Johnson et al., J. Virol. 61:3163-3166), consistent with its sequence relatedness (FIG. 32), and is the major contributor to HRSV cross-subgroup neutralization and protection. For HMPV F, amino acid sequence identity between subgroups was even higher than for RSV, and it is reasonable to anticipate that this similarly will make a substantial contribution to cross-neutralization and cross-protection between the HMPV subgroups. Conversely, the high degree of divergence of the G protein between and within HMPV subgroups likely will compromise its contribution to cross-neutralization and cross-protection to an even greater degree than is the case for RSV.

FIG. 33 shows amino acid sequence alignments between and within a subgroup for the SH (FIG. 33A) and G (FIG. 33B) proteins. The HMPV SH protein, like its RSV counterpart, is predicted to be a type II glycoprotein that is inserted in the plasma membrane by a hydrophobic signal/anchor sequence located near its amino terminus (FIG. 33A, boxed sequence), with a cytoplasmic amino terminus and an extracellular carboxy terminus. The SH proteins of strains 75, 83, and 00-1 varied in length (177, 179, and 183 amino acids, respectively; FIG. 33A) and were considerably longer than their 64- or 65-amino acid counterparts in RSV. The predicted extracellular domain has 2-4 motifs for N-linked glycosylation, one of which is conserved in all three isolates, as well as 3 or 4 potential sites for O-glycosylation (Hansen et al., Glycoconj. J. 15:115-130, 1998) that are clustered within residues 75-81 in all three isolates (FIG. 33A). In addition, the SH proteins of the three isolates contain 9 or 10 cysteine residues, which are mostly in the extracellular domain, 9 of which are conserved among all three strains. The differences in length and amino acid sequence between the SH proteins of the different isolates were concentrated in the extracellular domain.

The HMPV G protein (FIG. 33B) also is a type II surface protein, bearing a general resemblance (but no significant sequence relatedness) to the G protein of RSV. The amino acid lengths of the G proteins of strains 75, 83, and 00-1 were 236, 219, and 236, considerably shorter than their 289- to 299-amino acid counterparts in RSV. The HMPV G protein, like its RSV counterpart, contains a high percentage of serine plus threonine residues (32-35% for the three isolates, compared to a data base average of 13%) and a somewhat elevated level of proline residues (7-8.5%, compared to an average of 5%). Strains 83, −75 and 00-1 had 1, 4 and 4, respectively, potential acceptor sites for N-linked glycosylation in the ectodomain. Each HMPV G protein contained more than 40 predicted acceptor sites for O-linked carbohydrate (not shown): by analogy to RSV it is likely that not all of these are used, and usage might be heterogeneous. The serine, threonine, proline residues and the predicted sites for O-linked sugars were concentrated in the predicted extracellular domain, suggesting that this region has a long, extended, heavily glycosylated "mucin-like" structure, as is thought to be the case for RSV.

The HMPV G protein also resembles that of RSV in having most of the amino acid divergence localized to the extracellular domain (FIG. 33B). Specifically, the cytoplasmic and transmembrane domains combined were 64% and 96% identical between and within subgroups, respectively, compared to the remarkably low values for the extracellular domain of 25% and 61% identity between and within subgroups. For comparison, the value of 25% amino acid sequence identity is comparable to that observed for the attachment hemagglutinin-neuraminidase protein of PIVs from different genera, such as Genus Paramyxovirus versus Genus Rubulavirus or Avulavirus, and is substantially lower than the value of 42-66% identity observed for the influenza A hemagglutinin glycoprotein between subtypes H1, H2 and H3.

The HMPV G protein lacks several of the prominent features of its RSV counterpart. HMPV G lacks the conserved 13-amino acid domain in the RSV G extracellular domain that is exactly conserved among all RSV strains and is partially conserved in bovine RSV (Johnson et al., Proc. Natl. Acad. Sci. USA 84:5625-5629, 1987; Teng and Collins, J. Virol. 76:6164-6171, 2002). Indeed, the HMPV G ectodomain did not contain more than 3 adjacent amino acids conserved among all three isolates. HMPV G also lacks the four conserved, closely-spaced cysteine residues in HRSV G that partially overlap the 13-amino acid conserved domain, form a cystine noose, and include a CX3C chemokine motif (Tripp et al., Nat. Immunol. 2:732-738 2001). The three HMPV G proteins in FIG. 33B each contained only 1 or 2 cysteine residues, with the only conserved one being at the inner face of the cytoplasmic domain, representing a potential acceptor site for fatty acid acylation. HMPV G also lacks a counterpart to the second methionyl translational start codon in the HRSV G ORF, which gives rise to a secreted form and is conserved between HRSV subgroups (Roberts et al. J. Virol. 68:45384546, 1994). Only isolate CAN75 has an appropriately located potential counterpart (methionine-43), and it is the fourth rather than the second methionyl residue. Thus, comparison of sequence features whose presence or absence is consistent across subgroups helps guide the identification of structural features as possible targets for mutational analysis and construction of chimeric recombinant viruses for use in immunogenic compositions according to the methods of this current disclosure.

The high level of divergence in HMPV SH and G proteins is consistent with the idea that there is a preference for retaining amino acid changes in these proteins. It is particularly noteworthy that the divergence was concentrated in the extracellular domain of each protein (FIG. 33A, B). A codon-by-codon examination of the nucleotide coding sequences for the extracellular domains of F, G and SH ORFs indicated that 75% of the codons containing a single nucleotide change were associated with amino acid substitutions, compared to 50% for SH and 7% for F. Based on the findings herein, it is suggested that the extraordinary frequency of amino acid substitution per nucleotide substitution in HMPV G (and to a lesser extent SH) reflects two factors: (i) selective pressure for amino acid change, which might come from host immunity, and (ii) the ability of the protein to tolerate substitution, which might be due to its proposed extended, unfolded nature. In contrast, HMPV F appears to resemble HRSV F, which is one of the more highly conserved proteins despite its status as a major HRSV neutralization and protective antigen. This likely reflects functional and structural constraints on amino acid substitution in this folded, globular glycoprotein. The time scale of nucleotide and amino acid substitution for HMPV is not known, but it was noted that, for HRSV, it is difficult to detect antigenic drift and thus the differences probably reflect a slow accumulation over years. These findings indicate that diversity in SH and G is an important consideration for HMPV epidemiology, virus detection, and development of effective immunogenic compositions.

In conclusion, the present Example defines the amount genetic diversity that exists between the two proposed HMPV genetic subgroups and shows that, overall, the diversity between subgroups is similar in magnitude to that observed between the well-characterized RSV antigenic subgroups, although certain specific differences were observed. By comparing the two divergent HMPV subgroups, the identification of transcription signal motifs was further substantiated. Conversely, the identification of poorly-conserved regions such as the non-signal, non-protein-coding gene regions and the intergenic regions provides guidance in selecting these sites as being likely to be amenable to genetic manipulation. Importantly, the F glycoprotein was shown to be highly conserved between the two subgroups, which highlights the usefulness of this surface protein for incorporation in recombinant HMPV and chimeric recombinant HMPV of the current disclosure for production of broadly cross-reactive immunogenic compositions. Conversely, the other two viral surface proteins, SH and G, were demonstrated to be highly divergent between the subgroups, and will therefore be employed within recombinant HMPV and chimeric recombinant HMPV to contribute to subgroup-specific, rather than cross-subgroup, immunity (although they will often be used in multivalent immunogenic compositions as described herein above). The diversity of the two genetic subgroups at the antigenic level is characterized herein, and the importance of the F protein as a major neutralization and protective antigen is demonstrated.

Example 5

The Use of Experimental Animals to Evaluate HMPV Infectivity and Immunogenicity

Generation of Hamster Polyclonal Anti-HMPV Antibodies to the 75 and 83 Strains

To demonstrate that HMPV is infectious in a rodent animal model and can elicit an immune response characterized by production of HMPV-specific antibodies in the model host, three groups of 8- to 10-week-old golden Syrian hamsters (*Mesocricetus auratus*) were infected intranasally (IN) with approximately $10^3$-$10^4$ TCID$_{50}$ of: a mixture of HMPV strains 75 and 83, HMPV 75 alone, or HMPV 83 alone. As described in the previous Example, strains 75 and 83 (also referred to as CAN75 and CAN83, respectively) represent the two genetic subgroups of HMPV and thus provide an evaluation of the biological characteristics of viruses from each subgroup and, in particular, give a measurement of the antigenic diversity between subgroups. Serum samples were collected on day 28 or 44 post-immunization and examined for their ability to detect HMPV infected monkey kidney cells (LLC-MK2) by indirect immunofluorescence. LLC-MK2 cells grown in OptiMEM (Invitrogen GIBCO) on glass slides were infected with a mixture of HMPV strains 75 and 83, strain 75 alone, or strain 83 alone, and were incubated at 32° C. in OptiMEM medium with 5 μg/ml trypsin. At approximately 70 hours post-infection the cells were fixed and permeabilized with 3% formaldehyde and 0.1% Triton-X100 in PBS, as described previously (Skiadopoulos and McBride, J. Virol. 70:1117-24, 1996). Indirect immunofluorescence was performed with pooled hamster sera from animals that had been inoculated with HMPV 75+83, and fluorescein (FITC)-conjugated goat anti-Syrian Hamster IgG antibodies (Jackson ImmunoResearch Laboratories, Inc, West Grove, Pa.) were used for indirect immunofluorescence. As a control, serum from an adult human seropositive for HMPV was also used to detect HMPV infected cells in a comparable indirect immunofluorescence assay. Immunofluorescence was detected and images were collected on a Leica TCS-SP2 (Leica Microsystems, Mannheim, Germany). Images were processed using the Leica TCS-NT/SP software (version 1.6.587), Imaris 3.1.1 (Bitplane AG, Zurich Switzerland), and Adobe Photoshop 5.5 (Adobe systems). Both the human serum and the serum from hamsters infected with HMPV strains 75 and 83 were able to detect LLC-MK2 cells infected with either HMPV strain 75 or 83, demonstrating that IN-administered HMPV is infectious and immunogenic in hamsters. Sera from animals that received strain 75 alone or strain 83 alone were further analyzed as described herein.

Generation of Rabbit Polyclonal Antibodies to HMPV Strains 75 and 83

Specific pathogen free rabbits (Harlan Sprague Dawley) were surgically implanted with sterilized plastic wiffle balls and were immunized by injection of approximately $10^5$ TCID$_{50}$ of HMPV strain 75 or 83 into the wiffle ball, as described previously (Clemons et al., Lab. Anim. Sci. 42:307-11, 1992). Fluid present in the chambers was collected on day 29, and the animals received two boosts by injection of HMPV preparations that had been purified and concentrated by centrifugation in sucrose gradient following conventional procedures: the first boost was on day 29 and the second was on day 57. Fluid present in the chambers was collected again on day 71. These sera were analyzed as described herein.

Virus Titration and Serum Antibody Infectivity Neutralization Assays

Viral titer was quantified by serial 10-fold dilutions of virus applied to LLC-MK2 monolayer cultures on 96-well plates that were then incubated for 7 days at 37° C. in OptiMEM medium with 5 μg/ml added trypsin, as described previously (Newman et al., Virus Genes 24:77-92, 2002). Virus infected monolayers were detected by incubation with hamster polyclonal antiserum, which had been raised by IN infection with a mixture of strains 75 and 83 as described above, followed by a second antibody consisting of peroxidase-conjugated rabbit anti-Syrian hamster IgG. Bound antibody-antigen complexes were detected by immunoperoxidase staining achieved with ECL chromogenic substrate.

The susceptibility of HMPV to neutralization by HMPV-specific antiserum was determined using an endpoint dilution neutralization assay performed with heat inactivated hamster, rabbit or chimpanzee sera. The hamster and rabbit sera were prepared as described above. The chimpanzee sera were from 31 caged animals, as described further herein. Briefly, replicate aliquots each containing approximately 100-200 TCID$_{50}$ of HMPV 75 or 83 were mixed with aliquots from a dilution series prepared from a heat-inactivated serum sample and incubated at 37° C. for 1 hr. The virus-antiserum mixtures were then transferred to LLC-MK2 monolayers in 96-well plates and the cells were incubated for 1 hour at 32° C. The monolayers were washed two times with OptiMEM to remove serum and were overlaid with OptiMEM supplemented with 5 μg/ml added trypsin. The cells were then incubated for 7 days at 32° C. and infected monolayers were detected by immunoperoxidase staining with the polyclonal hamster anti-HMPV 75+83 antiserum and peroxidase-conjugated rabbit anti-Syrian hamster IgG and ECL chromogenic substrate, as described above. The neutralization titer is read as the highest dilution of antibody at which the cultures were 50% reduced for infection. This assay was used to determine the HMPV neutralization titer of serum from infected animals, and also was used to screen animals to determine whether they had previously been exposed to HMPV.

With the availability of the HMPV-GFP virus, the neutralization assay can now be simplified. In this case, replicate aliquots of HMPV-GFP virus (approximately 100-200 TCID$_{50}$) would be mixed with aliquots of a dilution series of serum as above, incubated for 1 hour at 32° C., and transferred to LLC-MK2 cells. The cells would be washed to remove serum, overlaid with OptiMEM supplemented with 5 μg/ml added trypsin, and incubated for 7 days at 32° C. Infected cells could be visualized directly by fluorescent microscopy. The neutralization endpoint would be indicated by the appearance of green fluorescence, indicative of infection.

Many of the details of this assay can be varied as necessary, such as the period of incubation of HMPV-GFP and antibody, the choice of cell substrate, and the period of incubation of the cells. In particular, the use of HMP-GFP means that the cells can be monitored by fluorescent microscopy to select an optimal time at which to read the assay. The efficiency of virus titration was compared by visualization of GFP versus immunostaining and found to be identical. However, detection by GFP was easier because the progression of the virus infection can be monitored and the plates read at an optimal time. In contrast, immunostaining can only be done once, and the timing is determined by estimating cytopathology by eye, which is more qualitative and not as precise. A further advantage is that GFP can be read directly, whereas immunostaining is a multi-step, time-consuming process requiring antibodies and development reagents. Furthermore, the washing steps need in immunostaining frequently result in damage to or removal of the cell monolayer, which can complicate or ruin the assay. Thus, using rHMPV-GFP as an indicator virus for antibody titration (or evaluation of antiviral agents) provides a better method for titration.

Evaluation of the Antigenic Relatedness of Strains 83 and 75

As described in the previous Example, it has been suggested that HMPV isolates can be segregated into two genetic subgroups (van den Hoogen et al., Nat. Med. 7:719-24; Peret et al., J. Infect. Dis. 185:1660-3, 2002). The previous Example described in detail the level of genetic diversity between the two proposed subgroups. The present Example (and also Example VI) describes the amount of antigenic difference between the two subgroups. The extent of antigenic diversity among circulating HMPV strains is of considerable importance to epidemiology and for development of effective immunogenic compositions.

The antigenic relatedness between strains 75 and 83 was investigated by a cross neutralization study. As described above, antiserum was raised in rabbits by parenteral immunization of gradient-purified HMPV 75 or 83 followed by a boost of the same material, with serum obtained following each step. In addition, as described above, hamsters were infected IN with strain 75 or 83 and sera were obtained. These individual sera were assayed for the ability to neutralize both strain 75 and 83. Thus, this would compare the ability of antibodies from an animal exposed to either strain to neutralize the infectivity of the homologous strain versus its ability to neutralize the heterologous strain. If extensive antigenic differences exit, each serum should be much less effective in neutralizing the heterologous strain compared to the homologous strain.

As shown in Table 1, hamsters were immunized by intranasal infection with strain 83 or 75 and the sera were collected on day 44 and evaluated for the ability to neutralize each strain in vitro. Of the eleven animals that were infected with strain 75, there was no consistent pattern in which the homologous 75 strain was neutralized more efficiently than the heterologous 83 strain: four animals neutralized the homologous strain more efficiently (up to 3.0 $\log_2$ difference, with animal 2164 exhibiting the greatest difference), but one (animal 2168) showed no difference and the remainder neutralized the homologous strain less efficiently (up to 3.0 $\log_2$ difference, animal 2174). Conversely, all ten animals infected with strain 83 yielded sera that neutralized the homologous 83 strain more efficiently than the heterologous 75 strain, with a difference ranging from 0.4 $\log_2$ (animal 2203) to 3.4 $\log_2$ (animal 2201). Thus, each of the HMPV strains representing the two heterologous subgroups induced antibodies that efficiently neutralized the homologous and heterologous viruses, although antibodies from animals infected with strain 83 appeared to be somewhat less effective in neutralizing the heterologous versus the homologous virus.

Also as shown in Table 1, rabbits were immunized with either strain of HMPV and then boosted with the same strain, and post-primary immunization and post-boost sera were collected and tested for the ability to neutralize the homologous and heterologous subgroup virus. The initial immunization of rabbits resulted in sera that had relatively low neutralizing titers against either strain of HMPV, with titers in the range of $\leq 4.3$ $\log_2$ to 8.4 $\log_2$. With these primary sera, there was no consistent difference between the efficiency of neutralization of the homologous versus the heterologous strain. Following the boost, the titers were substantially higher, in the range of 6.9 $\log_2$ to 11.4 $\log_2$, and in most cases the neutralization titer against the homologous strain was greater than against the heterologous strain. However, the difference was relatively modest, ranging from either no difference to a (difference of 2.6 $\log_2$. For example, animal R030, which had been immunized and boosted with strain 75, had a titer of 11.4 $\log_2$ against the homologous strain 75 and a titer of 9.9 $\log_2$ against the heterologous strain 83, corresponding to a 1.5 $\log_2$ difference. The other rabbit (R031) that was immunized and boosted with strain 75 yielded serum that neutralized the homologous strain 75 four times (2.0 $\log_2$) more efficiently than the heterologous strain 83. In the converse situation, with animals (R032 and R033) that had been immunized and boosted with strain 83, the titers following the boost either showed no difference for the heterologous versus homologous strain (animal R03), or showed 0.5 $\log_2$ higher homologous versus heterologous titer (animal R033). Thus, out of the eight post-immunization and post-boost rabbit sera, one had a lower homologous versus heterologous titer, three had no difference, and four had a greater homologous versus heterologous titer, with the greatest difference being 2.6 $\log_2$. This indicates a trend towards greater homologous versus heterologous reactivity, but the inconsistent nature of the pattern and the low magnitude is consistent with the interpretation that the two strain exhibit a very high degree of cross-neutralization in vitro. Thus, the high degree of antigenic relatedness observed with post-infection hamster sera was confirmed with rabbit sera both upon initial immunization and following a boost.

The high degree of antigenic cross-reactivity observed in vitro indicates that at least one major HMPV neutralization antigen or major epitope is conserved between the HMPV subgroups. The genetic analysis presented in the previous Example showed that, of the three HMPV surface proteins F, SH and G, the F glycoprotein was highly conserved between subgroups. In contrast, the SH and G glycoproteins were highly variable and neither protein had no more than three contiguous conserved amino acid in the extracellular domain, suggesting that conserved antigenic sites would be rare or nonexistent. The HMPV neutralization and protective antigens had yet been identified previously. In the case of RSV, the F and G surface proteins are the only significant neutralization antigens and the major protective antigens (Connors et al., J. Virol. 65:1634-1637 1991), and in the case of the human PIVs the two surface proteins F and HN also are the neutralization and major protective antigens. A subsequent Example (Example VI) will illustrate identification of a major HMPV neutralization and protective antigen effective in conferring protection against infection with either genetic subgroup.

TABLE 1

Homologous and heterologous HMPV antibody responses in rodents following immunization with HMPV strain CAN75 or CAN83

| Rodent species and number | Immunizing virus[a,b] | Serum-neutralizing antibody titer[c] (recip. $log_2$) against: CAN75 | CAN83 |
|---|---|---|---|
| Hamsters | | | |
| 2163 | CAN75 | 8.9 | 6.9 |
| 2164 | CAN75 | 8.3 | 5.3 |
| 2165 | CAN75 | 7.9 | 5.9 |
| 2169 | CAN75 | 9.9 | 10.4 |
| 2170 | CAN75 | 8.4 | 7.3 |
| 2166 | CAN75 | 8.4 | 8.9 |
| 2167 | CAN75 | 8.9 | 9.9 |
| 2168 | CAN75 | 8.4 | 8.4 |
| 2173 | CAN75 | 9.9 | 12.7 |
| 2174 | CAN75 | 9.4 | 12.4 |
| 2175 | CAN75 | 9.9 | 11.9 |
| 2201 | CAN83 | 7.3 | 10.7 |
| 2202 | CAN83 | 8.4 | 11.3 |
| 2203 | CAN83 | 10.9 | 11.3 |
| 2204 | CAN83 | 7.9 | 10.3 |
| 2205 | CAN83 | 7.9 | 10.3 |
| 2206 | CAN83 | 8.9 | 11.7 |
| 2207 | CAN83 | 7.9 | 10.3 |
| 2208 | CAN83 | 8.9 | 11.7 |
| 2209 | CAN83 | 9.9 | 12.3 |
| 2210 | CAN83 | 8.9 | 10.3 |
| Rabbits | | | |
| R030 | CAN75 | ≦4.3[d] | 5.9[d] |
| R030 (p.b.) | CAN75 | 11.4[e] | 9.9[e] |
| R031 | CAN75 | ≦4.3[d] | ≦4.3[d] |
| R031 (p.b.) | CAN75 | 11.4[e] | 9.4[e] |
| R032 | CAN83 | ≦4.3[d] | 6.9[d] |
| R032 (p.b.) | CAN83 | 6.9[e] | 6.9[e] |
| R033 | CAN83 | 8.4[d] | 8.4[d] |
| R033 (p.b.) | CAN83 | 8.4[e] | 8.9[e] |

[a]Hamsters were inoculated intranasally with $10^4$ $TCID_{50}$ of the indicated strain of HMPV.
[b]Rabbits were immunized parenterally with $10^5$ $TCID_{50}$ on day 0 with the indicated strain of HMPV, and were boosted on day 28 with $10^7$ $TCID_{50}$ of gradient-purified virus of the same strain of HMPV.
[c]Hamster neutralizing antibody titer, day 44 post-immunization serum. All animals had pre-immunization neutralizing antibody titers of ≦1.0.
[d]Rabbit neutralizing antibody titer, day 28 post-immunization. All animals had pre-immunization neutralizing antibody titers of ≦1.0.
[e]Rabbit neutralizing antibody titer post-boost, day 70 following the initial immunization. All animals had pre-immunization neutralizing antibody titers of ≦1.0.
p.b.: post-boost

Prevalence of HMPV Serum Antibodies in Chimpanzees

Thirty-one captive chimpanzees (pan troglodytes) were screened for the presence of serum neutralizing antibodies to HMPV strain 75 or 83, using an in vitro infectivity neutralization assay with HMPV strain 75 or strain 83 as the antigen, (Table 2). Nineteen animals (61%) were found to be seropositive for either one or both HMPV strains. Serum neutralizing antibody titers to HMPV strain 75 ranged from undetectable (≦1.0 $log_2$) to ≧9.6 $log_2$. Serum neutralizing antibody titers to HMPV strain 83 ranged from ≦1.0 $log_2$ to 8.6 $log_2$. Twelve animals (39%) did not have detectable HMPV-75 neutralizing titers: these 12 animals also were seronegative to strain 83. Four additional animals were seropositive to strain 75 but seronegative to strain 83. These four animals had very low neutralizing antibody titers (2.6-4.0 $log_2$), and their specificity is provisional. The prevalence of HMPV antibodies in chimpanzees indicates that these animals can become readily infected with HMPV in captivity, most likely from their human handlers. It also is possible, and indeed likely, that there is animal-to-animal transmission. The ability of these animals to be infected by contact from humans or other animals is a strong indication of permissiveness to HMPV. The finding that very few animals were seropositive for only one of the two strains suggests that these strains are highly related antigenically in primates and likely represent only a single HMPV serotype.

TABLE 2

Prevalence of HMPV-neutralizing antibodies in chimpanzee sera

| Sample number | Chimpanzee ID No. | Serum neutralization titer (recip. $log_2$) to indicated HMPV strain[1] 75 | 83 |
|---|---|---|---|
| 1 | 99A005 | 6.6 | 4.6 |
| 2 | A0A001 | 7.0 | 5.6 |
| 3 | A0A002 | 5.6 | 4.0 |
| 4 | A1A005 | 1.0 | ≦1.0 |
| 5 | A1A007 | ≦1.0 | ≦1.0 |
| 6 | A1A001 | 2.6 | 3.6 |
| 7 | A1A002 | 5.6 | 3.6 |
| 8 | A1A003 | 3.6 | ≦1.0 |
| 9 | A1A006 | ≦1.0 | ≦1.0 |
| 10 | A0A006 | 4.0 | ≦1.0 |
| 11 | A0A007 | 4.6 | 3.6 |
| 12 | A0A005 | 2.6 | ≦1.0 |
| 13 | A0A009 | 3.6 | ≦1.0 |
| 14 | AOA003 | 7.6 | 4.6 |
| 15 | 99A004 | 7.6 | 6.6 |
| 16 | A2A001 | ≦1.0 | ≦1.0 |
| 17 | A2A004 | ≦1.0 | ≦1.0 |
| 18 | A2A006 | ≦1.0 | ≦1.0 |
| 19 | A2A009 | ≦1.0 | ≦1.0 |
| 20 | A2A011 | 6.0 | 4.6 |
| 21 | A2A013 | 6.6 | 4.0 |
| 22 | A2A014 | 6.6 | 5.6 |
| 23 | 98A008 | 8.6 | 6.0 |
| 24 | 99A001 | 8.0 | 5.0 |
| 25 | 99A002 | 8.0 | 6.6 |
| 26 | 99A003 | 9.6 | 8.6 |
| 27 | A1A010 | ≦1.0 | ≦1.0 |
| 28 | A1A012 | ≦1.0 | ≦1.0 |
| 29 | A1A013 | ≦1.0 | ≦1.0 |
| 30 | A2A007 | ≦1.0 | ≦1.0 |
| 31 | A2A008 | ≦1.0 | ≦1.0 |
| Control serum (pre)2 | | ≦1.0 | ≦1.0 |
| Control serum (post)3 | | 8.3 | 8.3 |

[1]Numbers in parentheses are the titers expressed as the reciprocal dilution $log_2$.
2. pre-immune serum from hamsters before inoculation with both HMPV 75 and 83.
3. Post-immunization serum obtained from hamsters following inoculation with both HMPV 75 and 83.

HMPV Infection of Chimpanzees and Monkeys: Virus Replication, Immunogenicity and Effect of Previous Exposure to HMPV The ability of HMPV strains 75 and 83 to infect chimpanzees identified as seropositive or seronegative by the HMPV neutralization assay described above was evaluated. As shown in Table 3, eight animals were organized into four groups (two animals per group): group 1 was seronegative for strain 75 and 83. Group 2 and group 4 were seropositive for both strains. Group 3 was seronegative for 83 and had low or no detectable neutralization titers to strain 75. Groups 1 and 2 were administered strain 75, and groups 3 and 4 were administered strain 83. The animals were inoculated intranasally (IN) and intratracheally (IT) with 1 ml per site of $1\times10^{5.2}$ $TCID_{50}$/ml of the indicated virus. Administration was by both the intranasal (IN) and intratracheal (IT) routes to provide the opportunity for the virus to replicate at each site (Hall et al., Virus Res. 22:173-84, 1992; Crow et al., Vaccine 12:783-790, 1994). Animals were housed and specimens collected as previously described (Durbin et al., J. Infect. Dis. 179:1345-51, 1999; Skiadopoulos et al., Virology 260:125-35, 1999). The animals were observed clinically for 16 days post-inoculation. Nasopharyngeal swabs were collected on days 1 to 10 and 12 post-infection and tracheal lavages were collected on days 2, 4, 6, 8, 10, and 12 post-infection. Each of the four seronegative animals (groups 1 and 3) had nasal discharge on days 7, 8, 9 and 10 post-infection. As a precautionary measure, groups 1 and 3 were started on penicillin on day 8, because of evidence of congestion and noise in the lungs. One of the animals in group 1 had thick mucus in the day 8 post-infection TL sample and had decreased appetite. The seropositive animals (groups 2 and 4) showed no signs of illness throughout the course of the study. Thus, HMPV seronegative chimpanzees can develop illness following infection with the 75 and 83 HMPV strains demonstrating that these viruses are infectious and virulent in chimpanzees. Since the recombinant HMPV strain 83 virus differs from its biologically-derived parent by only four nucleotide differences involved in creating the NheI marker in the M/F intergenic region (FIG. 7), it is also considered a "wild type" virus in terms of genomic and phenotypic characteristics. Importantly, animals that were seropositive to both strains were protected from disease following challenge with either strain. This appears to be the first observation demonstrating the feasibility of immunizing against HMPV: since natural exposure protects against disease, it is reasonable to expect immunization with an appropriate immunogenic composition comprising a recombinant HMPV of the current disclosure will elicit a desired immune response as well. These results indicate that serum neutralizing antibody titers of 4.6 (animal AOA003) to 7.0 (animal AOA001) $\log_{10}$ are sufficient to confer protection from HMPV disease. Results obtained with chimpanzees are particularly relevant given the close evolutionary relationship between chimpanzees and humans.

all of the animals in these groups exhibited clinical disease signs in response to infection, the mean peak titers of virus recovered from the nasopharyngeal swabs ranged from 1.9 to 3.2 $\log_{10}$, and the titers from the tracheal lavage were 1.8 to 2.0 $\log_{10}$. The swabs and lavages from animals in groups 2 and 4, which were seropositive to HMPV, either lacked detectable HMPV or had a very low titer (1.5 $\log_{10}$). Thus, the lack of disease signs correlated with a reduced or undetectable level of virus shedding. The apparent incongruity between the low level of HMPV shedding in the presence of disease symptoms might reflect difficulty in retrieving infectious virus from secretions, possibly due to inactivation by host immune factors or a high level of cell-association of HMPV in the epithelial cells lining the respiratory tract of the chimpanzees. Since the chimpanzee is so closely related to humans, this raises the possibility that detection of HMPV in human secretions might also be inefficient. The inability to detect substantial HMPV shedding was unexpected, since RSV is known to be labile and cell-associated in vitro, but nonetheless is shed from RSV infected chimpanzees presenting with RSV-associated illness at a level that is 100 to 1000-fold greater than was the case for HMPV-infected chimpanzees (Belshe et al., J. Med. Virol. 1:157-162, 1977). Alternatively, the level of HMPV replication in chimpanzees may indeed be low, but infection may trigger immune- or chemokine-mediated pathology resulting in development of disease symptoms (Glass et al., Curr. Opin. Allergy Clin. Immunol. 3:467-473).

Serum samples taken four to six weeks post infection contained high levels of serum neutralizing antibodies for every experimental group, with no clear difference between animals that had been seronegative or seropositive prior to the experimental infection. The post-immunization titers ranged from 7.4 to 10.2 $\log_{10}$, considerably higher than the range of 4.6 to 7.0 $\log_{10}$ that was associated with protection from clinical disease. Interesting, in this small sample there was no evidence of antigenic differences between strains 75 and 83. Specifically, seronegative animals that were immunized with either strain (groups 1 and 3) developed antibodies with titers

TABLE 3

Infection of chimpanzees with HMPV

| Group | Chimpanzee ID No. | Serum neutralization titer to HMPV strain: 75 | 83 | HMPV administered[1] | clinical signs (day post-infection) rhinorrhea | cough |
|---|---|---|---|---|---|---|
| 1 | A1A005 | ≦1.0 | ≦1.0 | 75 | 6, 7, 8, 9, 10, 12 | |
|   | A1A007 | ≦1.0 | ≦1.0 |    | 7, 8, 9, 10 | |
| 2 | 99A005 | 6.6 | 4.6 | 75 | | |
|   | A0A001 | 7.0 | 5.6 |    | | |
| 3 | A1A006 | ≦1.0 | ≦1.0 | 83 | 7, 8, 9, 10 | |
|   | A0A005 | 2.6 | ≦1.0 |    | 7, 8, 9, 10 | 5 |
| 4 | AOA003 | 7.6 | 4.6 | 83 | | |
|   | 99A004 | 7.6 | 6.6 |    | | |

[1]The animals were inoculated intranasally (IN) and intratracheally (IT) with 1 ml per site of $10^{5.2}$ TCID$_{50}$/ml of HMPV strain 75 or strain 83.

The virus titers in the nasopharyngeal swabs and tracheal lavages taken from the HMPV-infected chimpanzees described in Table 3 were determined by an end point dilution assay with viral infectivity detected by immunostaining. As shown in Table 4, the chimpanzees shed relatively low levels of virus. This was particularly noteworthy for the animals in group 1, which were seronegative for both strains, and group 3, which was seronegative for strain 83: animals even though that were somewhat higher against strain 83 than against strain 83, irrespective of the immunizing virus.

The animals that were seronegative for the strain used in the primary infection were next challenged with the heterologous HMPV strain. As shown in Table 4, both groups of animals were completely protected from cross-challenge, indicating that previous infection by one HMPV lineage protects chimpanzees from subsequent infection by the heterologous lineage. Thus, in the experimental animal that most closely resembles the human, immunity induced by an HMPV strain representing either genetic subgroup protected against infection with an HMPV strain from the heterologous subgroup.

It also was of interest to investigate the replication and immunogenicity of HMPV 75 and 83 in monkeys, which are more plentiful, less expensive and easier to house than chimpanzees. Twenty-two rhesus macaques and twenty African green monkeys were screened for serum neutralizing antibodies to HMPV, and each animal was seronegative to HMPV (≦1.0 $log_2$). This limited sampling suggested that these two species of monkeys are not readily infected with HMPV by exposure in captivity. Four animals of each species were infected and intratracheally with $10^{5.2}$ $TCID_{50}$ of either HMPV strain CAN75 or CAN83. Four animals of each species were infected and intratracheally with $10^{5.2}$ $TCID_{50}$ of either HMPV strain CAN75 or CAN83 at each site, and nasopharyngeal swab samples were taken at days 1 to 10 and 12 post-infection, and tracheal lavage samples were taken at days 2, 4, 6, 8, 10 and 12 post-infection (Table 5). The samples were assayed for virus titer by end point dilution. Illness did not develop in any of the monkeys. The infected rhesus monkeys had very low titers of virus, ranging from 0.9 to 2.6 $log_{10}$ $TCID_{50}$ (Table 5). Furthermore, the post-immunization titers of serum neutralizing antibodies were also relatively low, ranging from 6.3 to 8.4 $log_2$. Thus, rhesus monkeys support the replication of HMPV, but the level of replication is low.

Infected African green monkeys (Table 5) shed titers of HMPV ranging from 2.2 to 4.9 $log_{10}$ $TCID_{50}$, and developed serum neutralizing antibody titers that ranged from 9.4 to 10.9 $log_2$. The time course of HMPV replication in samples collected from the nasopharynx and the trachea of the African green monkeys is shown in FIG. 35, and indicates that virus shedding occurred over a broad window of more than six days. These data showed that African green monkeys are permissive for HMPV replication and, in particular, represent a suitable primate host in which to evaluate the replication and immunogenicity of rHMPV derivatives for use in immunogenic compositions. In particular, the highest titers of virus and antibody were obtained with strain 83, which is the one represented by recombinant HMPV of this current disclosure. In this regard, the ability to monitor HMPV replication tip to almost 5 $log_{10}$ with concomitant immunogenicity provides a wide window for assessing effects on replication and immunogenicity due to the incorporation of attenuating mutations.

Thirty days following the first infection, the African green monkeys were challenged with the heterologous HMPV strain (Table 5). Both groups of animals were completely protected from cross-challenge, indicating that previous infection by one HMPV lineage confers resistance to subsequent infection by the heterologous strain. These data indicate that African green monkeys represent a suitable primate host in which to evaluate the protective efficacy of HMPV immunogenic compositions.

The studies described above provide data on the primary antibody response to strain 75 or 83 in seronegative animals, and describe the ability of the resulting antibodies to neutralize the homologous versus heterologous subgroup virus. These data were analyzed statistically by the Archetti-Horsfall formula (Archetti and Horsfall, J. Exp. Med. 92:441-462, 1950) to determine the degree of antigenic relatedness based on in vitro neutralization. Each species was calculated separately, showing that the percent relatedness of the two HMPV subgroups was 48%, 64% and 99%, respectively, based on the data from hamsters, Rhesus monkeys and African green monkeys, respectively. This compares with a value of 25% and 31% for the two subgroups of RSV, based on analysis of animal and human sera, respectively (Johnson et al. J. Virol. 61:3163-3166, 1987; Hendry et al., J. Infect. Dis. 157:640-647, 1988). These data indicate that the two HMPV genetic subgroups are highly related antigenically and do not represent distinct serotypes or, likely, not even significant antigenic subgroups. This high degree of relatedness for the two HMPV subgroups is based on in vitro neutralization, and thus needs to be taken with some caution, since cross-neutralization in vitro might be mediated by a single highly conserved antigen, whereas cross-protection in vivo might require the contribution of more than a single antigen, or might be augmented by the inclusion of additional antigens. Nonetheless, the present findings provide the first indication that the genetic diversity of HMPV can readily be accommodated by an HMPV vaccine, and that such a vaccine might need to represent only a single HMPV strain.

TABLE 4

Level Of Replication, Immunogenicity And Cross-Protection Of HMPV Strains CAN75 And CAN83 In Chimpanzees

| Group | Virus | Serostatus at time | Pre-immunization serum neutralization titer[d] to: | | Level of virus replication[e] in: | | Post-immunization (day 28) serum neutralization titer[d] to: | | Level of challenge virus replication[f] in: | |
|---|---|---|---|---|---|---|---|---|---|---|
| no.[a] | administered | of inoculation | CAN75 | CAN83 | NP swab | TL | CAN75 | CAN83 | NP swab | TL |
| 1 | CAN75 | negative[b] | ≦1.0 ± 0.0 | ≦1.0 ± 0.0 | 1.9 ± 0.4 | 2.0 ± 0.8 | 8.7 ± 0.3 | 10.2 ± 0.3 | ≦0.5 ± 0.0 | ≦0.5 ± 0.0 |
| 2 | CAN83 | negative[b] | 3.8 ± 1.5 | ≦1.0 ± 0.0 | 3.2 ± 0.5 | 1.8 ± 0.3 | 8.9 ± 1.0 | 10.2 ± 0.3 | ≦0.5 ± 0.0 | ≦0.5 ± 0.0 |
| 3 | CAN75 | positive[c] | 6.8 ± 0.2 | 5.1 ± 0.5 | 1.5 ± 0.0 | ≦0.5 ± 0.0 | 7.4 ± 0.5 | 9.2 ± 0.2 | nd | nd |
| 4 | CAN83 | positive[c] | 7.6 ± 0.0 | 5.6 ± 1.0 | ≦0.5 ± 0.0 | 1.5 ± 0.3 | 8.4 ± 1.5 | 10.2 ± 0.2 | nd | nd |

[a]Animals in groups of two were inoculated IN and intratracheally (IT) with $10^{5.2}$ $TCID_{50}$ of the indicated virus in a 1 ml inoculum at each site.
[b]Chimpanzees in this group were seronegative (mean antibody titer of <1:4) for the homologous infecting HMPV strain at the start of the study.
[c]Chimpanzees in this group were seropositive (mean antibody titer of >1:20) for the homologous infecting HMPV strain at the start of the study.
[d]Serum neutralization antibody titer to the indicated virus is expressed as the mean reciprocal $log_2$ ± standard error.
[e]Level of virus replication is expressed as the mean of the peak virus titers ($log_{10}$ $TCID_{50}$/ml ± standard error) for the animals in each group irrespective of sampling day. The NP titers on day 0 were ≦0.5 $log_{10}$ $TCID_{50}$/ml. The lower limit of detection is 1.0 $log_{10}$ $TCID_{50}$/ml. A value of ≦0.5 $log_{10}$ $TCID_{50}$/ml is assigned to samples with no detectable virus.
[f]On day 35, animals were challenged IN and IT with $10^{5.2}$ $TCID_{50}$ of the heterologous strain of HMPV in a 1 ml inoculum at each site. Level of virus replication is expressed as the mean of the peak virus titers ($log_{10}$ $TCID_{50}$/ml ± standard error) for the animals in each group irrespective of sampling day. The NP titers on day 0 were ≦0.5 $log_{10}$ $TCID_{50}$/ml. The lower limit of detection is 1.0 $log_{10}$ $TCID_{50}$/ml.
nd: not done

TABLE 5

Level Of Replication, Immunogenicity And Cross-Protection Of HMPV Strains CAN75 And CAN83 In Two Species Of Monkeys

| Primate species | No. of animals | Virus inoculum[a] | Level of virus replication[b] in: | | Post-immunization (day 28) serum neutralization titer[c] to: | | Percent antigenic relatedness[d] | Level of challenge virus replication[e] in: | |
|---|---|---|---|---|---|---|---|---|---|
| | | | NP swab | TL | CAN75 | CAN83 | | NP swab | TL |
| Rhesus | 4 | CAN75 | 1.3 ± 0.1 | 0.9 ± 0.2 | 6.4 ± 0.6 | 7.2 ± 0.3 | 64 | nd | nd |
| Rhesus | 4 | CAN83 | 1.6 ± 0.1 | 2.6 ± 0.3 | 6.3 ± 0.1 | 8.4 ± 0.3 | | nd | nd |
| African Green | 4 | CAN75 | 2.6 ± 0.5 | 3.2 ± 0.4 | 9.4 ± 0.3 | 10.8 ± 0.4 | 99 | 1.4 ± 0.1 | 0.8 ± 0.1 |
| African Green | 4 | CAN83 | 2.2 ± 0.2 | 4.9 ± 0.1 | 9.5 ± 0.5 | 10.9 ± 0.4 | | 0.6 ± 0.1 | 0.9 ± 0.2 |

[a]Animals were inoculated IN and intratracheally (IT) with $10^{5.2}$ TCID$_{50}$ of the indicated virus in a 1 ml inoculum at each site.
[b]The level of virus replication is expressed as the mean of the peak virus titers ($\log_{10}$ TCID$_{50}$/ml ± standard error) for the animals in each group irrespective of sampling day. Virus titrations were performed on LLC-MK2 cells. The lower limit of detection is 1.0 $\log_{10}$ TCID$_{50}$/ml. A value of $\leq 0.5$ $\log_{10}$ TCID$_{50}$/ml is assigned to samples with no detectable virus.
[c]Mean serum neutralization antibody titer to the indicated HMPV strain is expressed as the mean reciprocal $\log_2$ ± standard error. All animals were seronegative for both strains of HMPV at the start of the study (that is, day 0 reciprocal neutralization titer of $\leq 1.0 \log_2$).
[d]Percent antigenic relatedness was calculated using the formula of Archetti and Horsfall.
[e]On day 30, animals were challenged IN and IT with $10^{5.2}$ TCID$_{50}$ of the heterologous virus in a 1 ml inoculum at each site. Level of virus replication is expressed as the mean of the peak virus titers ($\log_{10}$ TCID$_{50}$/ml ± standard error) for the animals in each group irrespective of sampling day. The lower limit of detection is 1.0 $\log_{10}$ TCID$_{50}$/ml.
nd: not done Development of a Small Animal Model of HMPV Replication The evaluation of HMPV and rHMPV derivatives is further facilitated by the availability of a small animal model for evaluating replication and immunogenicity in vivo. Hamsters were infected intranasally with $10^6$ TCID$_{50}$ of either strain 83 or 75, and animals were sacrificed on days 3, 4, 5, 6 or 7 and the nasal turbinates and lungs were harvested and assayed for virus titer. As shown in Table 6, each virus replicated to a peak titer greater than 6 $\log_{10}$ in the nasal turbinates and 3.6 to 4.4 $\log_{10}$ in the lower respiratory tract. Thus, hamsters were permissive for both subgroup strains. As shown in Table 1 (and in Table 7), infection with strain 83 induced serum neutralizing antibody titers of 10.3 to 12.3 $\log_{10}$ against the homologous strain, and infection with strain 75 induced titers of 7.9 to 9.9 $\log_{10}$ against the homologous strain. The basis for the apparent lower immunogenicity of strain 75 is not known, although this finding will need to be confirmed in a further study in which virus replication and immunogenicity are measured for each strain in the same study. The present data show that hamsters are relatively permissive for HMPV replication and provide a convenient small animal model for evaluating HMPV replication and immunogenicity.

The hamster model was used to evaluate cross-protection between the two HMPV genetic subgroups, as had also been investigated in chimpanzees as shown in Table 4. Groups of hamsters were infected with either strain of HMPV or with L15 diluent as a negative control. After 6 weeks the hamsters were challenged with either strain of HMPV and the level of pulmonary challenge virus replication in the respiratory tract on day 4 was determined, as described above. As shown in Table 7, previous infection by either HMPV strain induced a high level of protection against the homologous and heterologous HMPV strain in the upper respiratory tract. The lower respiratory tract was completely protected from challenge with either strain. In addition, sera were collected 31 days following the first infection and assayed to determine the neutralizing titer against each strain (Table 7). The results were very similar to those shown previously in Table 1: infection with CAN83 induced antibodies that were modestly more effective in neutralizing the homologous versus heterologous strain, but antibodies induced by infection with CAN75 neutralized the homologous and heterologous strains with similar efficiencies. These cross-protection data and reciprocal-neutralization assays indicated that CAN83 and CAN75 are antigenically highly related.

TABLE 6

DAILY LEVEL OF REPLICATION OF HMPV STRAINS CAN75 AND CAN83 IN THE UPPER AND LOWER RESPIRATORY TRACT OF INFECTED HAMSTERS

| | | Mean virus titer ($\log_{10}$ TCID$_{50}$/g ± S.E.) on day[b]: | | | | |
|---|---|---|---|---|---|---|
| Virus inoculum[a] | Tissue | 3 | 4 | 5 | 6 | 7 |
| HMPV-CAN83 | Nasal turbinates | 6.0 ± 0.5 | 5.7 ± 0.3 | 5.1 ± 0.3 | 3.7 ± 1.2 | 1.7 ± 0.5 |
| | Lungs | 3.6 ± 1.0 | 3.1 ± 0.3 | 3.0 ± 0.3 | $\leq$1.5 ± 0.0 | $\leq$1.5 ± 0.0 |

TABLE 6-continued

DAILY LEVEL OF REPLICATION OF HMPV STRAINS CAN75 AND CAN83 IN THE UPPER AND LOWER RESPIRATORY TRACT OF INFECTED HAMSTERS

| Virus inoculum[a] | Tissue | Mean virus titer ($\log_{10}$ TCID$_{50}$/g ± S.E.) on day[b]: | | | | |
|---|---|---|---|---|---|---|
| | | 3 | 4 | 5 | 6 | 7 |
| HMPV-CAN75 | Nasal turbinates | 6.6 ± 0.4 | 6.4 ± 0.4 | 6.4 ± 0.6 | 5.2 ± 0.5 | 4.2 ± 0.7 |
| | Lungs | 4.4 ± 0.6 | 4.3 ± 0.7 | 3.3 ± 0.2 | ≤1.5 ± 0.0 | ≤1.5 ± 0.0 |

[a]Hamsters in groups of 30 animals were inoculated intranasally with $10^6$ TCID$_{50}$ of the indicated virus.
[b]Nasal turbinates and lung tissues from six animals from each group where harvested on days 3 through 7 post-infection. Virus present in tissue homogenates was quantified by serial dilution on LLC-MK2 monolayers at 32° C. Infected cultures were detected with hamster anti-HMPV antibodies and immunoperoxidase staining. Mean virus titer for each group of hamsters is expressed as $\log_{10}$ TCID$_{50}$/gram ± standard error, S.E.

TABLE 7

Hamsters Infected With HMPV Strain CAN83 Or CAN75 Are Protected Against Challenge With The Homologous And Heterologous HMPV Strains

| Animal immunized with[a] | Mean serum-neutralizing antibody titer[b] (reciprocal log$_2$) against: | | Mean virus titer ($\log_{10}$ TCID$_{50}$/g) in nasal turbinates of hamsters administered the indicated challenge virus[c]: | |
|---|---|---|---|---|
| | CAN75 | CAN83 | CAN75 | CAN83 |
| CAN83 | 9.2 ± 0.2 | 10.4 ± 0.3 | 2.0 ± 0.2 | 1.7 ± 0.2 |
| CAN75 | 10.9 ± 0.2 | 7.7 ± 0.2 | ≤1.5 ± 0.0 | 2.4 ± 0.5 |
| L15 medium | ≤1.0 ± 0.0 | ≤1.0 ± 0.0 | 5.3 ± 0.1 | 5.6 ± 0.2 |

[a]Hamsters in groups of 12 were immunized by IN infection with $10^{5.5}$ TCID$_{50}$ of the indicated virus or mock-infected with L15 medium.
[b]Sera were collected 2–3 days before and 31 days following the first infection, and the neutralizing titer against each of the two strains was determined. The pre-infection anti-HMPV serum titers were ≤1.0 (reciprocal log$_2$) for all animals in the study.
[c]On day 42, six hamsters from each group were challenged IN with $10^{5.5}$ TCID$_{50}$ of CAN83 and the remaining six were challenged with CAN75. Nasal turbinates and lungs were harvested four days later, and the virus titer was determined on LLC-MK2 cells. The mean virus titer for each group of hamsters is expressed as $\log_{10}$ TCID$_{50}$/gram of nasal turbinate ± standard error.

Example 6

Construction of a Human Parainfluenza Type 1 Virus (HPIV1) that Induces Neutralizing Antibodies and Protective Efficacy Against Both HMPV Genetic Subgroups To examine the ability of the HMPV F protein alone to induce serum neutralizing antibodies and to confer protection against HMPV challenge, a recombinant HPIV1 expressing the CAN83 F protein (rHPIV1-F$_{83}$) was recovered in vitro from an HPIV1 antigenomic cDNA containing the CAN83 F protein ORF inserted upstream of the HPIV1 N gene and flanked by HPIV1 GS and GE transcription signals (FIG. 36A). Expression of the F protein was confirmed by indirect immunofluorescence of infected cells (FIG. 36 B). Thus, rHPIV1-F$_{83}$ would express all of the proteins of HPIV1 as well as the F protein of HMPV.

Groups of hamsters were immunized with CAN83, wild type rHPIV1, rHPIV1-F$_{83}$ or with L15 medium, and 33 days later sera were collected and tested for the ability to neutralize the CAN75 and CAN83 strains. As shown in Table 8, sera from animals immunized with CAN83 or rHPIV1-F$_{83}$ efficiently neutralized both strains of virus. In each case, neutralization of the homologous CAN83 strain was somewhat more efficient than for the heterologous CAN75 strain. The mean neutralization titer of sera from rHPIV1-F$_{83}$-infected animals was 1.2 log$_2$ lower than that observed from CAN83-infected animals, which corresponds well with the lower titer of rHPIV1 replication in hamsters in this experiment compared to CAN83. Thus, when adjusted for the level of virus replication, the rHPIV1-F$_{83}$ vector, expressing only a single CAN83 antigen, was as efficient in inducing CAN83-neutralizing antibodies as CAN83 itself.

Fifty days following immunization, the animals were challenged by intranasal infection with rHPIV1, CAN75 or CAN83. As shown in Table 8, animals previously infected with rHPIV1-F$_{83}$ had a 125-fold and 158-fold reduction in the upper respiratory tract in the level of replication of the CAN75 and CAN83 challenge virus, respectively. Animals were completely protected in the lower respiratory tract. The rHPIV1-F$_{83}$ virus also protected against HPIV1 challenge, indicating that this virus was able to protect against the three respiratory tract pathogens, namely CAN75, CAN83 and HPIV1. This method also can now be used to determine the relative contribution of each of the other HMPV proteins to the induction of neutralizing antibodies and resistance to challenge virus replication. Importantly, these findings identify the F protein of HMPV as a major neutralization and protective antigen. Furthermore, the F protein of the CAN83 strain induced neutralizing antibodies and protection that were effective against both CAN83 and CAN75. This highlights the importance of this specific antigen in developing vaccines effective against all strains of HMPV.

TABLE 8

A Recombinant HPIV1 Expressing The CAN83 F Protein (RHPIV1-F$_{83}$)
Equally Protects Hamsters Against Challenge With HMPV Subgroup CAN75
And CAN83 As Well As Against HPIV1

| Virus inoculum[a] | Mean serum neutralization titer ($\log_2$) to indicated virus[b]: | | | Mean level of replication of the indicated challenge virus in the nasal turbinates[c] | | |
|---|---|---|---|---|---|---|
| | rHPIV1 | CAN75 | CAN83 | rHPIV1 | CAN75 | CAN83 |
| L15 medium | $\leq 1.0 \pm 0.0$ | $\leq 1.0 \pm 0.0$ | $\leq 1.0 \pm 0.0$ | $4.9 \pm 0.3$ | $5.0 \pm 0.2$ | $6.1 \pm 0.3$ |
| CAN83 | $\leq 1.0 \pm 0.0$ | $8.3 \pm 0.2$ | $9.8 \pm 0.2$ | $4.6 \pm 0.1$ | $1.5 \pm 0.0$ | $1.5 \pm 0.0$ |
| rHPIV1 wt | $6.1 \pm 0.3$ | $\leq 1.0 \pm 0.0$ | $\leq 1.0 \pm 0.0$ | $2.0 \pm 0.2$ | $4.4 \pm 0.2$[d] | $5.8 \pm 0.2$[e] |
| rHPIV1-F$_{83}$ | $4.7 \pm 0.2$ | $6.0 \pm 0.3$ | $8.6 \pm 0.2$ | $1.9 \pm 0.2$ | $2.9 \pm 0.3$[d] | $3.9 \pm 0.1$[e] |

[a]Groups of 18 hamsters were infected IN with $10^5$ TCID$_{50}$ of the indicated virus or with L15 medium as a negative control.
[b]Thirty-three days following the first infection, sera were collected and assayed to determine the neutralization titers against HPIV1, CAN75 and CAN83. 50 days following the first infection, six hamsters from each group were challenged IN with $10^5$ TCID$_{50}$ of the indicated virus and the nasal turbinates were harvested after four days.
[c]Virus present in the tissue homogenates was quantified and is expressed as the mean $\log_{10}$ TCID$_{50}$/g for each group ± standard error.
[d]Statistically significant difference between indicated values; $p < 0.01$ (unpaired t-test).
[e]Statistically significant difference between indicated values; $p < 0.0001$ (unpaired t-test)

Example 7

Construction of HMPV Recombinant Virus Expressing Protective Antigens for Both Putative Antigenic Subgroups of HMPV As described above, different strains of HMPV can exhibit genetic diversity, especially in the SH and G proteins, and there appear to be two major genetic subgroups. The preceding Example identified the HMPV F protein as a major neutralization and protective antigen effective against both subgroups. This, it is a preferred antigen for including in an HMPV vaccine. The preceding Examples showed that it is possible to achieve a high degree of protective immunity against both genetic subgroups by infection with a single HMPV from either subgroup. Furthermore, the F protein was identified as a major neutralization and protective antigen effective against both subgroups. However, it may be that optimal immunogenicity and protective efficacy will be achieved by including the SH or G protein from either or both subgroups, or by including F protein from both subgroups. In addition, the available information indicates that HMPV is a significant cause of serious respiratory tract disease early in life, approximately coincident with RSV and the PIVs. Thus, an immunogenic composition against HMPV likely would be administered at approximately the same time in life (optionally in a combinatorial formulation or coordinate immunization protocol for infants, and certain adult subjects) as immunogenic compositions directed against RSV and the PIVs. Accordingly, certain aspects of the current disclosure provide for broad coverage of an HMPV immunogenic composition, yielding increased effectiveness against multiple, antigenically-distinct strains. It is also advantageous in certain embodiments to decrease the number of separate viruses that must be administered: an immunogenic composition comprised of multiple separate viruses is more difficult to develop and formulate since each virus must be verified to be safe and immunogenic separately and in combination, and issues such as viral interference can complicate formulation. The methods of the current disclosure offer a flexibility and versatility in design of immunogenic compositions that addressees these and related problems.

Figure 34:
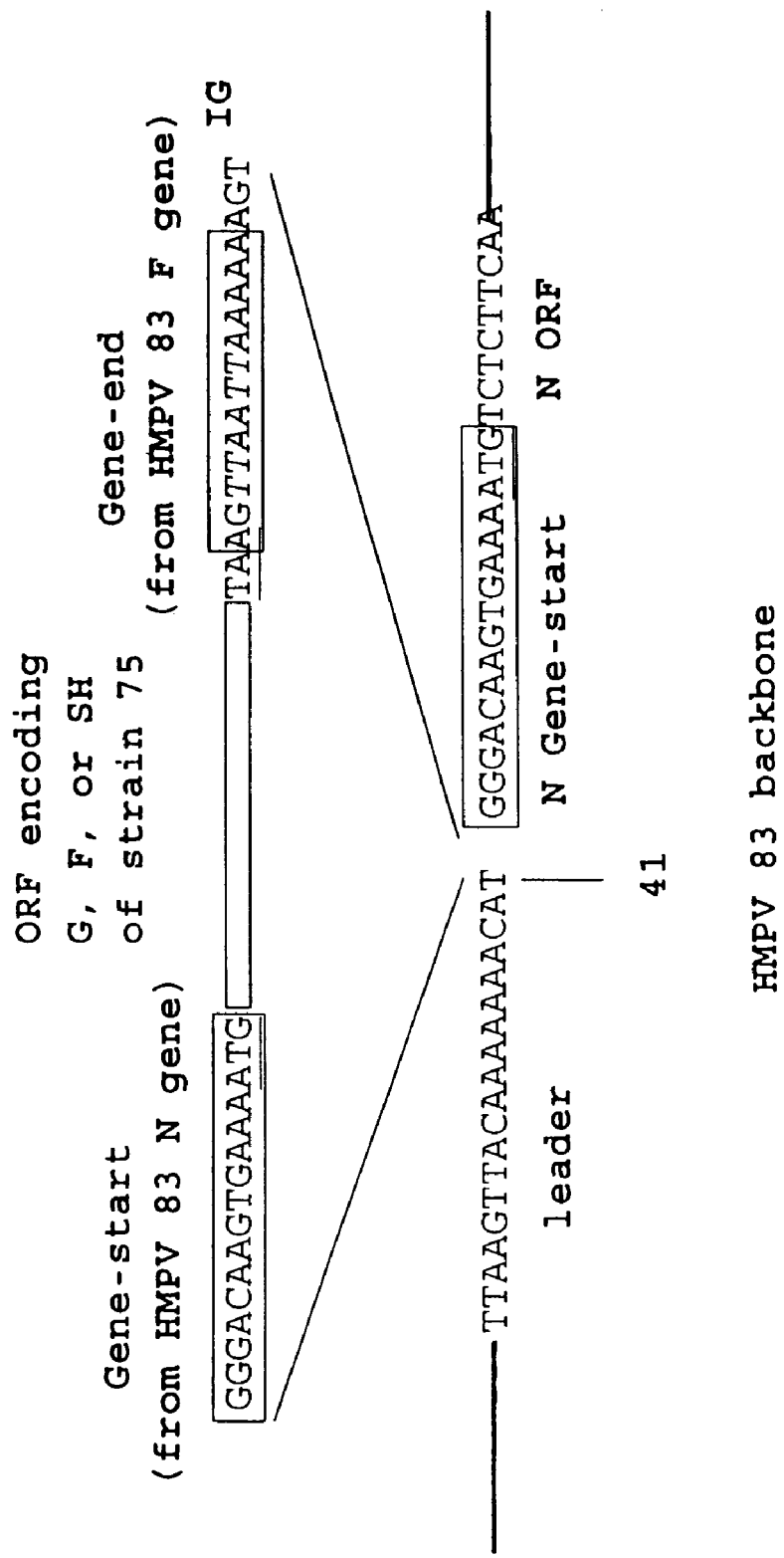
FIG. 34 is a diagram illustrating the design of a chimeric HMPV virus bearing antigens specific to HMPV strains that represent two different antigenic subgroups of HMPV. The strain 83 antigenomic cDNA clone was used as the backbone (sequence representing part of the 3' leader region (bases 23-41 of SEQ ID NO: 1) and the putative N GS signal and beginning of the putative N ORF (bases 42-66 of SEQ ID NO: 1) is shown), and a transcription cassette was designed that consists of the ORF encoding the putative G, F, or SH surface proteins of strain 75 under the control of transcription signals from strain 83 (which including bases 42-57 of SEQ ID NO: 1, representing the conserved putative N GS signal, and bases 4685-4697 of SEQ ID NO: 1, representing the putative F GE signal). This transcription cassette is then inserted into the strain 83 backbone at a promoter-proximal site. This strategy for constructing a bivalent immunogenic construct employs the same strain 83 transcription signals and insertion site as shown for the HMPV-GFP construct in FIG. 9.
Figure 35:
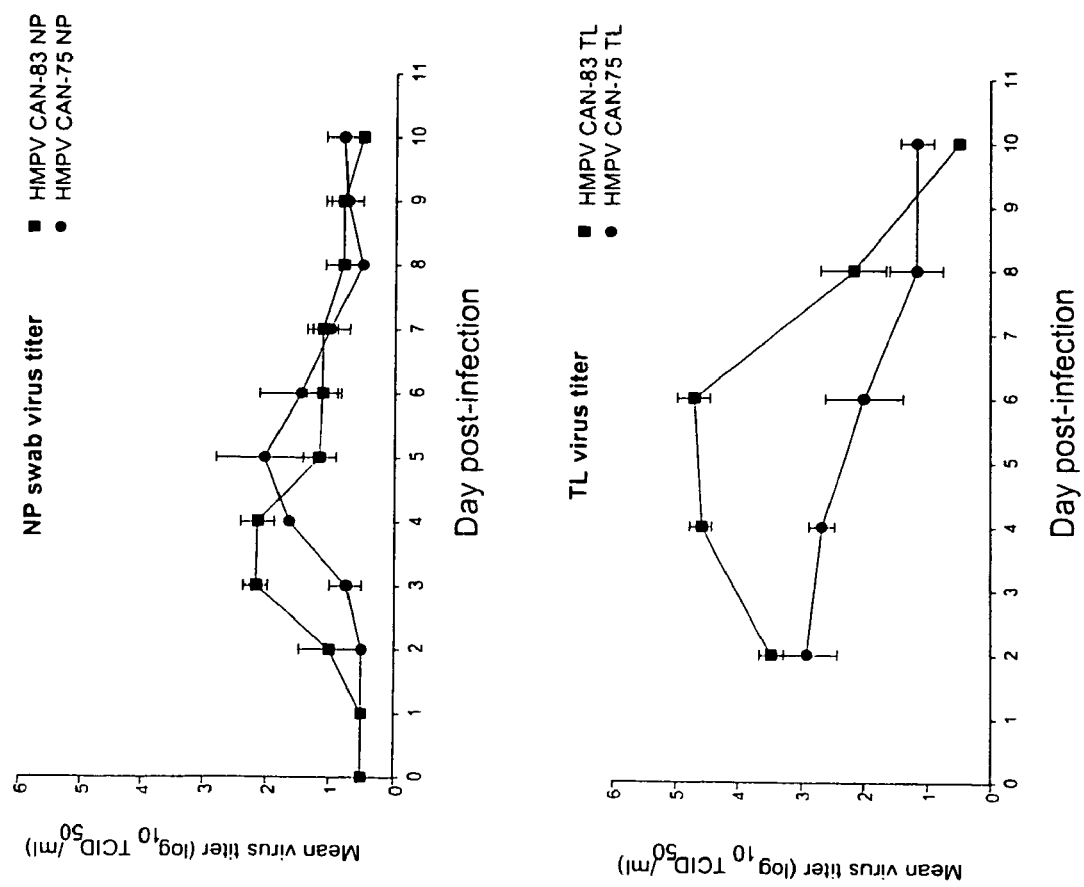
FIG. 35 is a graph illustrating the daily level of replication of HMPV strains 75 and 83 in the upper and lower respiratory tract of African green monkeys. Mean daily virus titers in the nasopharyngeal (upper panel) or tracheal lavage (lower panel) specimens obtained on the indicated day post-inoculation from animals infected simultaneously by the intranasal and intratracheal routes with 105 TCID50 of the indicated virus: strain 75 (●), strain 83 (■).

In one exemplary strategy, one or more ORFs each encoding a heterologous, immunogenic protein or antigenic determinant (for example, fragment or epitope) thereof can be engineered into transcription cassettes and inserted into the genome of HMPV. For example, as illustrated in FIG. 34, an ORF encoding the G, F or SH surface protein of HMPV strain 75 is engineered to be flanked by GS and GE signals from strain 83, and is inserted into the HMPV strain 83 backbone. This results in a chimeric virus that contains an additional gene and expresses all of the genes of strain 83 as well as a surface protein antigen of strain 75. This chimeric virus therefore expresses antigens representing both HMPV antigenic subgroups. This addresses the need to broaden coverage of immunogenic compositions, as well as meeting the need to minimize the number of separate viruses that must be included in such compositions. A preferred heterologous strain HMPV gene for insertion into an HMPV backbone would be the F gene, since F has been directly identified as a major HMPV neutralization and protective antigen. A second preferred gene is the G gene, since its encoded protein appears to be highly divergent between HMPV strains, exhibiting only 70% amino acid identity between strain 00-1 and 83 compared to 98% identify for the F protein. Similarly, the SH protein is a third preferred gene for insertion into chimeric virus, since it also is relatively divergent and exhibits 85% sequence identity between strains 00-1 and 83. The example illustrated in FIG. 34 employed the same transcription signals and genome insertion site that was used for expression of GFP. However, the methods of the current disclosure allow other signals or insertion sites to be tested. Also, the Example of FIG. 34 involved an ORF from a heterologous strain of HMPV, but the same strategy can be applied to other heterologous ORFs, such as ones from RSV, HPIV1, 2 or 3, other heterologous viruses or pathogens, and other molecules such as immunomodulatory proteins such as granulocyte-macrophage colony stimulating factor. In this way, an HMPV backbone can be used to create additional viruses bearing the surface proteins of heterologous, non-HMPVs. Chimeric viruses of the current disclosure can then be administered on

Example 8

Methods of Screening for Compounds that Inhibit HMPV

The current disclosure demonstrates that expression of the N, P, L and M2-1 proteins alone are sufficient to direct HMPV transcription and RNA replication. This was documented in two ways. First, expression of these proteins was sufficient to direct transcription and RNA replication of a cDNA-encoded mini-replicon derived from the HMPV genome and carrying a reporter gene. Second, expression of these proteins was sufficient to launch the rescue of complete infectious HMPV from a cDNA-encoded antigenome. The antigenome is by definition the complement of the genome and is not able to serve as the direct template for transcription. Hence, both RNA replication and transcription must have occurred under the direction of the supplied proteins in order for a productive infection to be launched, indicating that N, P, L, and M2-1 are sufficient to direct all phases of HMPV RNA synthesis. Therefore, the current disclosure provides novel and readily practiced methods for screening, identifying, designing, and characterizing compounds that inhibit one or more activities of HMPV (for example, transcription, translation, growth, infectivity, virulence, immunogenicity, etc.)

In addition, the current disclosure provides new, facilitated methods of monitoring infection by complete HMPV which provide for the screening, identification and design of antiviral compounds that act at any stage in the HMPV replicative cycle. The current disclosure also provides methods for identifying the viral targets of antiviral compounds, thereby providing for improved design of compounds effective in inhibiting HMPV.

Potential antiviral compounds effective against HMPV include monoclonal or polyclonal antibodies obtained by biological or recombinant methods, peptides or protein fragments (Lambert et al., Proc. Natl. Acad. Sci. USA 93:2186-2191, 1996), sugar derivatives, polyionic polymers, antisense RNA, double stranded RNAs capable of meditating RNA interference RNA (RNAi) (Bitko and Barik, BMC Mirco. 1:34-44, 2001), and small molecule compounds (De Clercq, Antimicrob. Agents 7:193-202, 1996; Prince, Ex. Opin. Invest. Drugs 10: 197-308, 2002). In general, the methods will apply to any antiviral compounds capable of inhibiting HMPV in solution, in cell extracts, in cell culture, and in vivo. Antiviral compounds can act, for example, by inhibiting attachment, penetration (fusion), RNA synthesis, and virion assembly, and in other cases their specific target of action may not be fully elucidated (De Clercq, Antimicrob. Agents 7:193-202, 1996; Prince, Ex. Opin. Invest. Drugs 10:197-308, 2002). Antiviral agents also can act by enhancing the host immune response, such as by stimulating the interferon-mediated antiviral state (Player et al., Proc. Natl. Acad. Sci. USA 95:8874-9, 1998). In addition, an antiviral agent can be combined with an anti-inflammatory agent to effect a further reduction in disease (Prince et al., J. Infect. Dis. 182:1326-1330, 2000).

In one embodiment of the current disclosure, rHMPV-GFP is used to screen antiviral compounds. In one exemplary strategy, rHMPV-GFP) is treated with a test compound or library of compounds (for example, a compound or library of compounds prospectively including one or more antiviral agents) and compared with mock-treated control rHMPV-GFP for the ability to infect cells. Following a period of absorption, the inoculum containing the potential antiviral compound can be removed by washing if desired. Infectivity is typically assayed by observation or measurement of a detectable label or signal whose presence or level of expression or detection is correlated with one or more activities of HMPV, for example as indicated by the development of green fluorescence due to expression of the GFP marker gene by recombinant HMPV-GFP, a method that can be monitored in living cells without compromising sterility over the course of the infection. Alternatively, the antiviral agent can be included in the medium overlay for the duration of the infection. Alternatively, infection can be initiated in the absence of the compound, which can be subsequently added. In addition to identifying compounds capable of inhibiting one or more activities of HMPV, these assays can give an indication of the mode of action of a compound, such as whether it acts by directly neutralizing virus, or inhibiting subsequent gene expression, or inhibiting viral spread. While GFP is provided as an exemplary label or marker, a wide range of useful "reporter sequences" (for example, reporter genes) and other sequences that direct expression of detectable labels and markers are known in the art and can be readily employed as detectable "signal" agents whose presence, level of activity or expression correlate with one or more selected activities of HMPV. Exemplary alternative markers and/or labels in this context include, inter alia, chloramphenicol acetyl transferase, luciferase, secreted alkaline phosphatase, and a large number of other known reporter sequences routinely used in the art. This provides the ability to design a reporter virus or subviral construct that will be useful in a variety of high throughput screening protocols.

Within related aspects of the current disclosure, the availability of rHMPV variants that each lack one or more of the viral ORFs, as described above, provides particularly useful tools and methods to identify possible viral targets of antiviral compounds. For example, if a compound inhibits the infectivity of complete HMPV, it will be tested (for example, for its efficacy and/or target gene or protein specificity) against a panel of rHMPV lacking various genes, such as the ΔSH, ΔG, ΔSH/G, and ΔM2-2 variants mentioned previously. An alternative and complementary method of identifying targets for an antiviral compound involves forcing the virus to grow in the presence of the compound (present at minimal or suboptimal inhibitory concentrations if necessary). Under these conditions, it is expected that a large panel of useful variants will emerge that have developed increased resistance to the subject inhibitory compound. Sequence analysis of such variants can identify mutations that are potentially responsible for the increased resistance. By the methods of this current disclosure, mutations suspected of conferring increased resistance can be introduced individually or in combinations into rHMPV, and the resistant rHMPV expressing a convenient reporter gene such as GFP will provide yet additional tools and methods to facilitate other phases of HMPV control and antiviral development. For example, the introduction of mutations identified in resistant viruses provides a method of directly confirming that they confer resistance and thus distinguishes them from adventitious mutation that occur during passage. This provides direct identification of viral genes involved in drug resistance, and is an important tool for further drug development. As another example, as noted above, HMPV-GFP can be used to assay quickly and accurately to detect antibodies to HMPV. This can be advantageous in studies to develop monoclonal or polyclonal antibodies capable of neutralizing HMPV as immunoprophylaxic or therapeutic agents. This also has applications in epidemiologic studies for example to determine the serostatus of individuals in a population. Furthermore, it provides a facilitated method to monitor changes in the level of HMPV antibodies in experimental animals or clinical subjects, such as in response to experimental immunogenic compositions, or in situations were the efficacy of an antiviral compound is being evaluated. Also, the expression of a reporter gene such as GFP provides a useful marker to detect and quantify HMPV infection and immunity in individuals, including experimental animals, thereby providing an assay for viral disease detection, tropism and/or to identify and evaluate additional antiviral agents.

In other embodiments of the current disclosure, rHMPV expressing a convenient reporter gene can be readily employed within screening compositions and methods based on cell-free in vitro assays. For example, a nucleocapsid preparation can be made from cells infected with rHMPV expressing a reporter gene, such as alkaline phosphatase or some other sensitively-detected enzyme or marker. Replicate in vitro assays can be constructed and used to screen compounds for antiviral activity in a high throughput format designed to detect the expressed reporter gene. This can be based on the expression of a convenient reporter gene or, alternatively, can be based on the detection of RNA representing the marker gene or one or more HMPV genes. For example, mRNA produced in such an in vitro reaction mixture can be captured in situ by matrix-bound oligodT and, following washing to remove the reaction mixture, the resulting hybrids can be detected by secondary hybridization with probes tagged with reporter enzymes or ligands. Such assays can be further modified to specifically target, for example, products of RNA replication or read-through of gene junctions as a measure of altered transcription.

The identification of the N, P, L, and optionally, M2-1 as proteins useful and/or sufficient to direct HMPV transcription and RNA replication provides additional new methods for screening compounds for anti-viral activity. In one embodiment, these four proteins can be expressed intracellularly together with a mini-replicon that encodes a reporter gene, resulting in reconstituted HMPV transcription and RNA. This can be used to screen for compounds, particularly those that are effective against HMPV transcription, RNA replication, and nucleotide assembly and function. Alternatively, the N, P, L, and M2-1 proteins can be expressed at high levels, using recombinant baculovirus, vaccinia virus, bacteria or any other suitable expression system, and purified to use in reconstituted assays such as in vitro RNA synthesis, protein-protein interactions, or protein-RNA interactions. Alternatively, the N, P, L and M2-1 proteins can be tagged recombinantly by the incorporation of, for example, a hexa-Histindine tag or an epitope recognized by a monoclonal antibody, such as the well known FLAG tag (Nilsson et al., Prot. Exp. Pur. 11: 1-16, 1997). These provide the basis for purification of these components by affinity chromatography, facilitating the development of in vitro assays. In addition, when such tagged genes are expressed from the context of infection by recombinant HMPV, it provides a method of isolating and identifying possible cellular and viral binding partners. Such binding partners can be identified by a variety of methods. For example, in some cases, binding partners will be present in sufficient quantity that they can be visualized by gel electrophoresis and identified by conventional methods of protein sequencing. Low abundance binding partners can be identified from complex mixtures by mass spectrometric methods coupled with trypsin cleavage and protein sequencing. The identification of viral and cellular binding partners provides additional information to guide the development of compounds that inhibit HMPV.

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the claims below.

We claim:

1. An attenuated, replication competent recombinant human metapneumovirus (rHMPV), comprising a recombinant HMPV genome or antigenome of SEQ ID NO: 1 or SEQ ID NO: 2, comprising one or more attenuating nucleotide modifications including a partial or complete deletion of the rHMPV M2-2 ORF or one or more nucleotide substitutions that ablates expression of the rHMPV M2-2 ORF, and a major nucleocapsid (N) protein, a nucleocapsid phosphoprotein (P), and a large polymerase protein (L) of a HMPV.

2. The rHMPV of claim 1, wherein the recombinant HMPV genome or antigenome further comprises a detectable heterologous sequence encoding a polypeptide.

3. The rHMPV of claim 2, wherein the detectable heterologous sequence encodes a reporter.

4. The rHMPV of claim 3, wherein the reporter comprises green fluorescent protein (GFP).

5. The rHMPV of claim 2, wherein the detectable heterologous sequence is operably linked to a HMPV gene transcription start signal and to a HMPV gene end signal.

6. The rHMPV claim 1, wherein the one or more attenuating nucleotide modifications comprises one or more nucleotide substitutions that ablates expression of a rHMPV M2-2 ORF.

7. The rHMPV of claim 6, wherein the one or more nucleotide substitutions that ablates expression of the rHMPV M2-2 ORF comprises one or more nucleotide substitutions that ablates one or more potential translation initiation codons of the rHMPV M2-2 ORF or introduces one or more in-frame stop codons into the rHMPV M2-2 ORF.

8. The rHMPV of claim 7, that demonstrates a ten-fold or more reduction in growth in the presence of interferon, but is not attenuated when growing in the absence of interferon.

* * * * *

SEQUENCE LISTING

```
<160> NUMBER OF SEQ ID NOS: 36

<210> SEQ ID NO 1
<211> LENGTH: 13335
<212> TYPE: DNA
<213> ORGANISM: human metapneumovirus

<400> SEQUENCE: 1
acgcgaaaaa aacgcgtata aattaagtta caaaaaaaca tgggacaagt gaaaatgtct      60
cttcaaggga ttcacctgag tgatctatca tacaagcatg ctatattaaa agagtctcag     120
tatacaataa agagagatgt aggcacaaca acagcagtga caccctcatc attgcaacaa     180
gaaataacac tattgtgtgg agaaattcta tatgctaagc atgctgatta caaatatgct     240
gcagaaatag gaatacaata tattagcaca gctctaggat cagagagagt acagcagatt     300
ctaagaaact caggcagtga agtccaagtg gtttttaacca gaacgtactc cttggggaaa     360
gttaaaaaca acaaaggaga agatttacag atgttagaca tacacggagt agagaaaagc     420
tgggtggaag agatagacaa agaagcaaga aaaacaatgg caactttgct taaagaatca     480
tcaggcaata ttccacaaaa tcagaggcct tcagcaccag acacacctat aatcttatta     540
```

```
tgtgtaggtg ccttaatatt taccaaacta gcatcaacta tagaagtggg attagagacc    600
acagtcagaa gagctaaccg tgtactaagt gatgcactca aaagataccc taggatggac    660
ataccaaaaa tcgctagatc tttctatgat ttatttgaac aaaaagtgta ttacagaagt    720
ttgttcattg agtatggcaa agcattaggc tcatcctcta caggcagcaa agcagaaagt    780
ttattcgtta atatattcat gcaagcttac ggtgctggtc aaacaatgct gaggtgggga    840
gtcattgcca ggtcatctaa caatataatg ttaggacatg tatctgtcca agctgagtta    900
aaacaagtca cagaagtcta tgacctggtg cgagaaatgg ccctgaatc tgggctccta     960 catttaaggc aaagcccaaa agctggactg ttatcactag ccaattgtcc caactttgca   1020
agtgttgttc tcggcaatgc ctcaggctta ggcataatag gtatgtatcg cgggagagtg   1080
ccaaacacag aactattttc agcagcagaa agctatgcca agagtttgaa agaaagcaat   1140
aaaattaact tttcttcatt aggactcaca gatgaagaaa agaggctgc agaacacttt    1200 ctaaatgtga gtgacgacag tcaaaatgat tatgagtaat aaaaaagtg ggacaagtca    1260 aaatgtcatt ccctgaagga aaagatattc ttttcatggg taatgaagcg gcaaaattgg   1320
cagaagcttt ccaaaaatca ttaagaaaac ctagtcataa aagatctcaa tctattatag   1380
gagaaaaagt gaacactgta tctgaaacat ggaattacc tactatcagt agacctacca    1440
aaccgaccat attgtcagag ccgaagttag catggacaga caaggtggg gcaatcaaaa    1500 ctgaagcaaa gcaaacaatc aaagttatgg atcctattga agaagaagag tttactgaga   1560 aagggtgct gccctccagt gatgggaaaa ctcctgcaga aaagaagttg aaaccatcaa    1620
ccaatactaa aaagaaggtc tcatttacac caaatgaacc aggaaaatac acaaagttgg   1680
agaaagatgc tctagacttg ctttcagaca atgaagaaga agatgcagaa tcctcaatct   1740
taaccttcga agaaagagat acttcatcat taagcattga agccagacta gaatcgattg   1800
aggagaaatt aagcatgata ttagggctat taagaacact caacattgct acagcaggac   1860
ccacagcagc aagagatggg atcagagatg caatgattgg cataagggag gaactaatag   1920
cagacataat aaaagaagcc aagggaaaag cagcagaaat gatggaagaa gaaatgaacc   1980
agcggacaaa ataggaaac ggtagtgtaa aattaactga aaaggcaaag gagctcaaca    2040
aaattgttga agacgagagc acaagtggtg aatccgaaga agaagaagaa ctaaaagaca   2100
cacaggaaaa taatcaagaa gatgacattt accagttaat tatgtagttt aataaaaata   2160
aaaaatggga caagtgaaaa tggagtccta tctggtagac acctatcaag gcatcccta    2220 cacagcagct gttcaagttg atctagtaga aaaggacctg ttacctgcaa gcctaacaat   2280
atggttcccc ctgtttcagg ccaatacacc accagcagtt ctgcttgatc agctaaagac   2340
tctgactata actactctgt atgctgcatc acaaagtggt ccaatactaa aagtgaatgc   2400
atcggcccag ggtgcagcaa tgtctgtact tcccaaaaag tttgaagtca atgcgactgt   2460
agcacttgac gaatatagca aattagaatt tgacaaactt acagtctgtg aagtaaaaac   2520
agtttactta acaaccatga aaccatatgg gatggtatca agtttgtga gctcggccaa    2580 accagttggc aaaaaacac atgatctaat cgcattatgc gattttatgg atctagaaaa    2640
gaacacacca gttacaatac cagcattttat caaatcagtt tctatcaagg agagtgaatc   2700
agccactgtt gaagctgcaa taagcagtga agcagaccaa gctctaacac aagccaaaat   2760
tgcaccttat gcgggactga tcatgattat gaccatgaac aatcccaaag gcatattcaa   2820
gaagcttgga gctgggaccc aagttatagt agaactagga gcatatgtcc aggctgaaag   2880
cataagtaaa atatgcaaga cttggagcca tcaaggaaca agatatgtgc tgaagtccag   2940
```

```
ataacagcca agcaacctga ccaagaacta ccaactctat tctatagact aaaaagtcgc    3000
cattttagtt atataaaaat caagttagaa taagaattaa atcaatcaag aacgggacaa    3060
ataaaaatgt cttggaaagt ggtgatcatt ttttcattgc taataacacc tcaacacggt    3120
cttaaagaga gctacctaga agaatcatgt agcactataa ctgagggata tcttagtgtt    3180
ctgaggacag gttggtatac caacgttttt acattagagg tgggtgatgt agaaaacctt    3240
acatgttctg atggacctag cctaataaaa acagaattag atctgaccaa aagtgcacta    3300
agagagctca aaacagtctc tgctgaccaa ttggcaagag aggaacaaat tgagaatccc    3360
agacaatcta ggtttgttct aggagcaata gcactcggtg ttgcaacagc agctgcagtc    3420
acagcaggtg ttgcaattgc caaaaccatc cggcttgaga gtgaagtcac agcaattaag    3480
aatgccctca aaacgaccaa tgaagcagta tctacattgg ggaatggagt tcgagtgttg    3540
gcaactgcag tgagagagct gaaagacttt gtgagcaaga atttaactcg tgcaatcaac    3600
aaaaacaagt gcgacattga tgacctaaaa atggccgtta gcttcagtca attcaacaga    3660
aggtttctaa atgttgtgcg gcaattttca gacaatgctg gaataacacc agcaatatct    3720
ttggacttaa tgacagatgc tgaactagcc agggccgttt ctaacatgcc gacatctgca    3780
ggacaaataa aattgatgtt ggagaaccgt gcgatggtgc gaagaaaggg gttcggaatc    3840
ctgatagggg tctacgggag ctccgtaatt tacatggtgc agctgccaat ctttggcgtt    3900
atagacacgc cttgctggat agtaaaagca gcccttctt gttccggaaa aaagggaaac    3960
tatgcttgcc tcttaagaga agaccaaggg tggtattgtc agaatgcagg gtcaactgtt    4020
tactacccaa atgagaaaga ctgtgaaaca agaggagacc atgtcttttg cgacacagca    4080
gcgggaatta atgttgctga gcaatcaaag gagtgcaaca tcaacatatc cactacaaat    4140
tacccatgca aagtcagcac aggaagacat cctatcagta tggttgcact gtctcctctt    4200
ggggctctgg ttgcttgcta caaggagta agctgttcca ttggcagcaa cagagtaggg    4260
atcatcaagc agctgaacaa gggttgctcc tatataacca accaagatgc agacacagtg    4320
acaatagaca acactgtata tcagctaagc aaagttgagg gtgaacagca tgttataaaa    4380
ggcagaccag tgtcaagcag ctttgatcca atcaagtttc ctgaagatca attcaatgtt    4440
gcacttgacc aagtttttga gaacattgaa acagccagg ccttggtaga tcaatcaaac    4500
agaatcctaa gcagtgcaga gaaagggaat actggcttca tcattgtaat aattctaatt    4560
gctgtccttg gctctagcat gatcctagtg agcatcttca ttataatcaa gaaaacaaag    4620
aaaccaacgg gagcacctcc agagctgagt ggtgtcacaa acaatggctt cataccacac    4680
agttagttaa ttaaaaataa aataaaattt gggacaaatc ataatgtctc gcaaggctcc    4740
atgcaaatat gaagtgcggg gcaaatgcaa cagaggaagt gagtgtaagt ttaaccacaa    4800
ttactggagt tggccagata gatacttatt aataagatca aactatctat aaatcagct    4860 tttaaggaac actgatagag ctgatggcct atcaataata tcaggcgcag gcagagaaga    4920
cagaacgcaa gattttgttc taggttccac caatgtggtt caaggttata ttgatgataa    4980
ccaaagcata acaaaagctg cagcctgcta cagtctacac aacataatca agcaactaca    5040
agaagttgaa gttaggcagg ctagagatag caaactatct gacagcaagc atgtggcact    5100
ccataactta atcttatctt acatggagat gagcaaaact cccgcatctt taatcaacaa    5160
tctcaaaaga ctgccgagag aaaaactgaa aaaattagca aagctgataa ttgacttatc    5220
agcaggcgct gacaatgact cttcatatgc cctgcaagac agtgaaagca ttaatcaagt    5280
```

```
gcagtgagca tggtcctgtt ttcattacta tagaggttga tgaaatgata tggactcaaa    5340
aagaattaaa agaagctttg tccgatggga tagtgaagtc tcacaccaac atttacaatt    5400
gttatttaga aaacatagaa attatatatg tcaaggctta cttaagttag taaaaacaca    5460
tcagagtggg ataagtgaca atgataacat tagatgtcat taaaagtgat gggtcttcaa    5520
aaacatgtac tcacctcaaa aaaataatca aagaccattc tggtaaagtg cttattgcac    5580
ttaagttaat attagcttta ctaacatttt tcacaataac aatcactata aattacataa    5640
aagtagaaaa caatctacaa atatgccagt caaaaactga atcagacaaa gaagactcac    5700
catcaaatac cacatccgtc acaaccaaga ccactctaga ccatgatata acacagtatt    5760
ttaaaagatt aattcaaagg tatacagatt ctgtaataaa caaggacaca tgctggaaaa    5820
taagcagaaa tcaatgcaca aatataacaa catataaatt tttatgcttt aaacctgagg    5880
actcaaaaat caacagttgt gatagactga cagatctatg cagaaacaaa tcaaaatcag    5940
cagctgaagc atatcataca gtagaatgcc attgcatata cacaattgag tggaagtgct    6000
atcaccactc aatagattaa acccaatctt gaatgttaaa actagactag gatccgtcta    6060
agactatcag ttcaatagtt tagttatttt aaaatatttg agaataggta agtttctatg    6120
gcacttcata gcaataggta ataattaaca gcttaattat aattaaaaca ttatttaaaa    6180
tcgtaactat ttaatttaca aagtaaaaac aaaaatatgg gacaagtagt tatggaggtg    6240
aaagtagaga acattcgagc aatagacatg ctcaaagcaa gagtgaaaaa tcgtgtggca    6300
cgtagcaaat gctttaaaaa tgcttcttta atcctcatag gaataactac actgagtata    6360
gctctcaata tctatctgat cataaactac acaatacaaa aaacctcatc tgaatcagaa    6420
caccacacca gctcaccacc cacagaatcc aacaaggaag cttcaacaat ctccacagac    6480
aacccagaca tcaatccaaa ctcacagcat ccaactcaac agtccacaga aaaccccaca    6540
ctcaaccccg cagcatcagt gagcccatca gaaacagaac cagcatcaac accagacaca    6600
acaaaccgcc tgtcctccgt agacaggtcc acagcacaac caagtgaaag cagaacaaag    6660
acaaaaccga cagtccacac aagaaacaac ccaagcacag cttccagtac acaatcccca    6720
ccacgggcaa caacgaaggc aatccgcaga gccaccactt tccgcatgag cagcacagga    6780
aaaagaccaa ccacaacatc agtccagtcc gacagcagca ccacaaccca aaatcatgaa    6840
gaaacaggtt cagcgaaccc acaggcatct gtaagcacaa tgcaaaacta gcacaccaac    6900
aatataaaac caaattagtt aacaaaaaat acgagatagc tctaaagtaa acatgtagg    6960 taccaacaat caagaaacca aaagacaact cacaatctcc ctaaaacagc aacgacacca    7020
tgtcagcttt gctcaaatct ctctgggaga acttttgcc cacatactaa caacatcaca    7080
accatctcaa gaaaagaaac tgggcaaaac agcatccaag agacaaatag caatggatcc    7140
tcttaatgaa tccactgtta atgtctatct ccctgattcg taccttaaag gagtaatttc    7200
ttttagtgaa actaatgcaa ttggttcatg tctcttaaaa agaccctact taaaaaatga    7260
caacactgca aaagttgcca tagagaatcc tgttattgag catgtgagac tcaaaaatgc    7320
agtcaattct aaaatgaaaa tatcagatta caaggtagta gagccagtaa acatgcaaca    7380
tgaaataatg aagaatgtac acagttgtga gctcacacta ttgaaacagt ttttaacaag    7440
gagtaaaaac attagcactc tcaaattgaa tatgatatgt gattggctgc aattaaagtc    7500
tacatcagat gataccctcaa tcctaagttt catagatgta gaatttatac ctagttgggt    7560
aagcaactgg tttagtaatt ggtacaatct caataagtta atttggaat tcagaagaga    7620 ggaagtaata agaaccggtt caatcttatg caggtcattg ggtaaattag ttttttattgt    7680
```

```
atcatcatat ggatgtatcg tcaagagcaa caaaagcaaa agagtgagct tcttcacata    7740
caatcaactg ttaacatgga agatgtgat gttaagtaga tttaatgcga atttttgtat    7800
atgggtaagc aatagtctga atgaaaatca ggaagggcta gggttgagaa gtaatctgca    7860
aggtatgtta actaataaac tatatgaaac tgtagattat atgctaagct tatgttgcaa    7920
tgaaggtttc tcacttgtga aagagttcga aggttttatt atgagtgaga tccttaggat    7980
tactgaacat gctcaattca gtactagatt tagaaatact ttattgaatg gattaacaga    8040
tcaattaaca aaattaaaaa ataaaaacag actcagagtt catagtaccg tattagaaaa    8100
taatgattat ccaatgtatg aagttgtact taaattatta ggagatactt tgagatgtat    8160
caaattatta atcaataaaa acttagagaa tgctgcagaa ttatactata tattcagaat    8220
ttttggtcat ccaatggtag atgaaagaga tgcaatggat gctgtcaaat taaacaatga    8280
aatcacaaaa atcctaaggt tggagagctt gacagaacta agaggggcat tcatattaag    8340
gattatcaaa ggatttgtgg acaacaacaa aaggtggccc aaaattaaaa acttaaaagt    8400
gcttagcaaa agatggacta tgtacttcaa agctaaaaat taccccagtc aactcgaatt    8460
aagtgaacaa gactttctag agcttgctgc aatacaattt gaacaagagt tttctgttcc    8520
tgaaaaaacc aatcttgaga tggtattaaa tgacaaagcc atatcacctc ctaaaagatt    8580
aatatggtct gtgtatccaa agaattactt acctgagacg ataaaaaatc gatatttaga    8640
agaaactttc aatgcgagtg atagtctcaa aacaagaaga gtactagagt actatttaaa    8700
agataataaa tttgatcaaa aggaacttaa aagttatgta gttagacaag aatatttaaa    8760
cgataaggag cacattgtct cattaactgg aaaagaaaga gaattaagtg taggtagaat    8820
gtttgctatg caaccaggaa aacagcgaca aatacaaata ttggcagaaa aattgttagc    8880
tgataacatt gtacctttct tcccggaaac cttaacaaag tatggtgatc tagatcttca    8940
gagaataatg gaaatcaaat cagaactttc ttctatcaaa accagaagaa atgatagtta    9000
taataattac attgcaagag catccatagt aacagatttg agcaagttca accaagcctt    9060
tagatatgaa actacagcga tctgtgcgga tgtagcagac gaattacatg gaacacaaag    9120
cttattctgt tggttacatc ttatcgttcc tatgactaca atgatatgtg cctatagaca    9180
tgcaccacca gaaacaaaag gtgaaatga tatagataag atagaagagc aaagtggtct    9240
atatagatat cacatgggcg gtattgaagg atggtgtcaa aaactctgga caatggaagc    9300
tatatcttta ttggatgttg tatctgtaaa gacacggtgt caaatgacat ctttattaaa    9360
cggtgacaac caatcaatag atgtaagtaa accagtcaag ttatctgaag gtttagatga    9420
agtgaaggca gattatcgct tagcagtaaa aatgctaaaa gaataagag atgcatacag    9480 aaatataggc cataaactta agaaggggaa acatatata tcaagggatc ttcagtttat    9540
aagcaaggtg attcaatctg aaggagtgat gcatcctacc cctataaaaa aggtcttgag    9600
agtaggacca tggataaaca caatattaga tgacattaaa actagtgctg agtcaatagg    9660
gagtctatgt caagaattag aattaggggg agaaagcata atagttagtc tgatattaag    9720
aaacttctgg ctgtataact tatacatgca tgaatcaaag caacatcctt tggcagggaa    9780
acagttattc aaacaactaa ataaaacatt aacatcagtg cagagatttt ttgaaattaa    9840
aagggaaaat gaggtagtag atctatggat gaacatacca atgcaatttg gaggaggaga    9900
tccagtagtc ttctatagat cttttctatag aaggacccct gatttttta ctgaggcaat    9960 cagccatgta gatattctgt taaaaatatc agctaacata aaaatgaaa cgaaagtaag   10020
```

-continued

```
tttcttcaaa gccttactat caatagaaaa aaatgaacgt gctacactga caacactaat    10080
gagagatcct caagctgttg gatcagaacg acaagcaaaa gtaacaagtg acatcaatag    10140
aacagcagtt accagtatct taagtctttc cccaaatcaa cttttcagtg atagtgctat    10200
acactacagc agaaatgaag aagaagtggg aatcattgca gaaaacataa cacctgttta    10260
tcctcatggg ctgagagtat tatatgaatc attgcccttt cacaaagctg aaaaagttgt    10320
aaacatgata tcagggacaa aatctataac caacttatta cagagaacat ccgctattaa    10380
tggtgaagat attgacaggg ctgtatctat gatgttggag aatctaggat tattatctag    10440
aatattgtca gtagttgttg atagtataga aattccaatc aaatctaatg gtaggctgat    10500
atgttgtcaa atctctagga ctttaagaga gacatcatgg aataatatgg aaatagttgg    10560
agtaacatct cctagcatca ctacatgtat ggatgtcata tatgcaacta gttctcattt    10620
gaaagggata attatagaaa agttcagcac tgacagaact acaaggggtc aaagaggtcc    10680
aaaaagccct tgggtagggt cgagtactca agagaaaaaa ttagtacctg tttataacag    10740
acaaattctc tcaaaacaac aaagagaaca gctagaagca attggaaaaa tgagatgggt    10800
gtataaaggg acaccaggct tgcgacgatt actcaacaag atctgtcttg ggagtttagg    10860
cattagctac aaatgtgtaa aacctttatt acctaggttt atgagtgtaa atttcttaca    10920
tagattatct gtcagtagta gacctatgga attcccagca tcagttccag cttatagaac    10980
aacaaattac catttcgaca ctagtcctat taatcaagca ctaagtgaga gatttgggaa    11040
tgaagatatt aacttggtct tccaaaatgc aatcagctgt ggaattagca taatgagtgt    11100
agtagaacaa ttaacaggta gaagcccaaa acagttagtt ttaataccc aattagaaga    11160 aatagacatt atgccaccac cagtgtttca agggaaattc aattataaat tagtagataa    11220
gataacttct gatcaacata tctttagtcc ggacaaaata gatatgttaa cactagggaa    11280
aatgctcatg cccactataa aaggtcagaa aacagatcag ttcttaaata agagagaaaa    11340
ttatttccat ggaaacaatc ttattgagtc tttatcagca gcattagcat gtcattggtg    11400
tgggatatta acagaacaat gcatagaaaa taatattttc aagaaagact ggggtgacgg    11460
gtttatatca gatcatgctt ttatggactt caaaatattc ctatgtgtct ttaaaactaa    11520
acttttatgt agttggggat ctcaagggaa aaacattaaa gatgaagata tagtagatga    11580
atcaatagat aaaattgttaa ggattgacaa tacttttgg agaatgttca gcaaagttat    11640
gtttgaacca aaggttaaga aaaggataat gttatatgat gtaaaattcc tatcactagt    11700
aggctacata gggtttaaga actggtttat agagcagttg agatcagctg aattgcatga    11760
aataccttgg attgtcaatg ccgaaggtga tttggttgag atcaagtcaa ttaaaatcta    11820
tttgcaactg atagaacaaa gcttattttt aagaataact gttttgaact atacagatat    11880
ggcacatgct ctcacacgat taatcagaaa gaagttaatg tgtgataatg cactgttaac    11940
cccaattcca tccccaatgg ttaacttaac tcaagttatt gatcccacaa cacaattaga    12000
ttacttcccc aagataacat tcgaaaggct aaaaaattat gacacaagtt caaattatgc    12060
taaagggaag ctaacaagaa attacatgat actattgcca tggcagcatg ttaatagata    12120
taactttgtc tttagttcta ctggatgtaa agttagtctg aaaacatgta ttggaaaact    12180
tatgaaagac ctaaatccta agtttttgta ctttattgga gaaggagcag gaaattggat    12240
ggccagaaca gcatgtgaat atcctgatat taaatttgta tatagaagtc tgaaagatga    12300
ccttgatcat cattatccctc tggaatacca gagagtgata ggtgaattaa gcagaatcat    12360
agatagtggt gaaggacttt caatggaaac aacagacgca actcaaaaaa ctcattggga    12420
```

```
tttgatacac agggtaagca aagatgcttt attaataact ttatgtgatg cagaatttaa      12480
ggacagagat gattttttta agatggtaat tctatggaga aacatgtat tatcatgcag       12540 aatttgcact acttatggga cggacctcta tttattcgca aagtatcatg ctaaagactg      12600
caatgtaaaa ttaccttttt tgtgagatc agttgctact ttcattatgc agggtagtaa       12660
gctgtcaggt tcagaatgct acatactctt aacactaggc caccacaaca gtttaccttg      12720
ccatggagaa atacaaaatt ctaagatgaa aatagcagtg tgtaatgatt tttatgctgc      12780
aaaaaaactc gacaataaat caattgaagc taattgtaaa tcacttttgt cagggctaag      12840
aatacctata aataagaagg aactagatag acagagaaga ttattaacac tacaaagcaa      12900
tcattcttct gtagcaacag ttggcggtag caagatcata gagtctaagt ggttaacaaa      12960
caaagcaagt acaataattg attggttaga acatatttta aattctccaa agggcgaatt      13020
aaattatgat tttttgaag cattggagaa cacttaccct aatatgatta aactaataga      13080
taacttaggg aatgcagaga ttaaaaaact gatcaaagta acaggataca tgcttgtaag      13140
taaaaaatga aaaatgatga agatgacaaa atagatgaca acttcatact attctaaatt      13200
aattatttga ttatgcaatt atatgatagt taattaaaat taaaaattaa aaatcaaaag      13260
ttaaaattta aaacctatca ttaagtttat taaaaataag aaattataat tgaatgtata      13320
cggttttttt gccgt                                                      13335

<210> SEQ ID NO 2
<211> LENGTH: 13280
<212> TYPE: DNA
<213> ORGANISM: human metapneumovirus

<400> SEQUENCE: 2
acgcgaaaaa aacgcgtata aattaaattc caaacaaaac gggacaaata aaaatgtctc       60
ttcaagggat tcacctaagt gatctgtcat ataaacatgc tatattaaaa gagtctcaat      120
acacaataaa aagagatgta ggcaccacaa ctgcagtgac accttcatca ttgcagcaag      180
agataacact tttgtgtgga gagattcttt acactaaaca tactgattac aaatatgctg      240
cagagatagg gatacaatat atttgcacgg ctctaggatc agaaagagta caacagattt      300
taagaaattc aggcagtgaa gttcaggtgg ttctaaccaa gacatactct ttagggaaag      360
gtaaaaatag taaggggaa gagttgcaaa tgttagatat acatggagtg gaaaagagtt       420
gggtagaaga aatagacaaa gaggcaagaa aaacaatggt gactttgcta aaggaatcat      480
caggtaacat cccacaaaac cagaggcctt cagcaccaga caccaata tttttattat        540 gtgtaggtgc tttaatattc actaaactag catcaacaat agaagttgga ctagagacta      600
cagttagaag agctaacaga gtgctaagtg atgcgctcaa aagataccct agggtagata      660
taccgaagat tgctagatct ttctatgaac tatttgagca gaaagtgtat tacaggagtc      720
tattcattga gtatgggaaa gctttaggct catcttcaac aggaagcaaa gcagaaagtt      780
tgtttgtaaa tatatttatg caagcttatg gagccggtca acaatgcta aggtggggtg       840 tcattgccag atcatctaac aacataatgc taggacatgt gtctgtgcaa gctgaattga       900
agcaagttac agaggtttat gatttggtga gagaaatggg tcctgaatct gggcttttac       960
atctaagaca aagtccaaag gcaggactgt atcgttggc caattgcccc gattttgcta       1020
gtgttgttct tggtaatgct tcaggtctag gtataatcgg aatgtacaga ggaagagtgc      1080
caaacacaga gctatttct gcagcagaaa gttatgccag aagcttaaaa gaaagcaaca      1140
```

```
aaatcaactt ctcctcatta gggctcacag acgaagaaaa agaagctgca gaacacttct    1200
taaacatgag tgatgacaat caagatgatt atgagtaatt aaaaaactgg gacaagtcaa    1260
aatgtcattc cctgaaggaa aagatatcct gttcatgggt aatgaagcag caaaaatagc    1320
agaagctttc cagaaatcac taaaaagatc aggtcacaaa agaacccagt ctattgtagg    1380
ggaaaaagta acactatat cagaaactct agagctacct accatcagca aacctgcacg    1440
atcatctaca ctgctagagc caaaattggc atgggcagac agcagcagag ccaccaaaac    1500
cacagaaaaa caaacaacca aaacaacaga tcctgttgaa aagaggaac tcaatgaaaa     1560 gaagatatca ccttccagtg atgggaagac tcccgcagag aaaaaatcaa aatctccaac    1620
caatgtaaaa aagaaagttt ccttcacatc aaatgaacca gggaaatata ccaaactaga    1680
aaaagatgcc ctagatttgc tctcagacaa tgaggaagaa gacgcagagt cctcaatctt    1740 aaccttgaa gagagagaca catcatcact aagcattgag gctagactag aatcaataga     1800
agagaagcta agcatgatat taggactgct tcgtacactt aacattgcaa cagcaggacc    1860
aacggctgca agagatggaa tcagagatgc aatgattggt ataagagaag aactaatagc    1920
agaaataata aaagaagcaa agggaaaagc agctgaaatg atggaagagg aaatgaatca    1980
aaggtcaaaa ataggtaatg gcagtgtaaa actaaccgag aaggcaaaag aacttaataa    2040
aattgttgaa gacgagagca caagcggtga atcagaagaa gaagaagaac caaagaaac    2100 tcaggataac aatcaaggag aagatattta ccagttaatc atgtagttta ataaaaataa    2160
acaatgggac aagtcaagat ggagtcctat ctagtggaca cttatcaagg cattccctac    2220
acagctgctg ttcaagttga tctggtagaa aaagacttac taccagcaag tttgacaata    2280
tggtttcctc tattccaagc caacacacca ccagcggttt tgctcgatca gctaaagacc    2340
ttgacaataa caactctgta tgctgcatca cagaatggtc caatactcaa ggtaaatgca    2400
tcagctcagg gtgctgctat gtctgtactt cccaaaaaat tcgaagtaaa tgcaactgtg    2460
gcacttgatg aatacagcaa acttgacttt gacaagttaa cggtttgcga tgttaaaaca    2520
gtttatttga caaccatgaa accatatggg atggtgtcaa aatttgtgag ttcagccaaa    2580
tcagttggca acaagacaca tgatctaatt gcactgtgtg acttcatgga cctagagaaa    2640
aatatacctg tgacaatacc agcattcata aagtcagttt caatcaaaga gagtgagtca    2700
gccactgttg aagctgcaat aagcagtgag gccgaccaag cattaacaca agccaaaatt    2760
gcaccctatg caggactaat catgatcatg accatgaaca atccaaaagg tatattcaag    2820
aaactaggag ctggaacaca agtgatagta gagctagggg catatgttca agccgagagc    2880
atcagcagga tctgcaagag ctggagtcac caaggaacaa gatatgtact aaaatccaga    2940
taaaaataac tgtcctaatc aataattgct tatataatct taaagatcaa tgagcttatt    3000
attatagtta tataaaaaaa tttagaacta ggaaggtatt aatagaaagc gggacaagta    3060
aaaatgtctt ggaaagtgat gattatcatt tcgttactca taacacctca gcacggacta    3120
aaggaaagtt atttagaaga atcatgtagt actataactg aaggatatct cagtgtttta    3180
agaacaggtt ggtacaccaa tgtctttaca ttagaagttg gtgatgttga aaatcttaca    3240
tgtactgatg gacctagctt aatcaaaaca gaacttgacc taaccaaaag tgctctaaga    3300
gaactcaaaa cagtttctgc tgatcagtta gcgagagaag aacaaattga aaatcccaga    3360
caatcaaggt ttgtcctagg tgcaatagct cttggtgttg ccacagcagc agcagtcaca    3420
gcaggcattg cgatagccaa aaccataagg cttgagagtg aagtgaatgc aatcaaaggt    3480
gctctcaaaa caaccaatga ggcagtatcc acactaggaa atggagtgcg agtcctagcc    3540
```

```
accgcagtaa gagagctgaa agaatttgtg agcaaaaacc tgactagtgc aattaacaag   3600
aacaaatgtg acattgctga tctgaagatg gctgtcagct tcagtcaatt caacagaaga   3660
ttcctaaatg ttgtgcggca gttttcagac aatgcaggga taacaccagc aatatcattg   3720
gacctaatga ctgatgctga gctggccaga gctgtatcat acatgccaac atctgcagga   3780
cagataaaac taatgttaga gaaccgtgca atggtgagga gaaaaggatt tggaatcttg   3840 atagggtct acggaagctc cgtgatttac atggtccagc tgccgatctt tggtgtcata    3900
gatacacctt gttggataat caaggcagct ccctcttgtt cagaaaaaga tggaaactat   3960
gcttgcctcc taagagagga tcaagggtgg tattgtaaaa atgcaggatc cactgtttac   4020
tacccaaata aaaagactg cgaaacaaga ggtgatcatg ttttttgtga cacagctgca    4080
gggatcaatg ttgctgagca atcaagagaa tgcaacatca acatatctac aaccaactac   4140
ccatgcaaag tcagcacagg aagacaccct atcagcatgg ttgcactatc acctctcggt   4200
gctttggtgg cttgctacaa aggggttagc tgttcaattg gcagtaatcg ggttggaata   4260
atcaaacaac tacctaaagg ctgctcatac ataactaacc aggacgcaga cactgtaaca   4320
attgacaaca ctgtgtatca actaagcaaa gttgagggtg aacagcatgt aataaaaggg   4380
agaccagttt caagcagttt cgatccaatc aagtttcctg aggatcagtt caatgttgcg   4440
cttgatcaag tctttgaaag cattgaaaac agtcaagcac tagtgaccaa gtcaaacaaa   4500
attctgaaca gtgcagaaaa aggaaacact ggcttcatta ttgtaataat tttgattgct   4560
gttcttgggt taaccatgat ttcagtgagc atcatcatca taatcaaaaa acaaggaaa   4620 cccacagggg cacctccaga gctgaatggt gttaccaacg gcggtttat accgcatagt   4680 tagttaatta aaaaatggga caaatcatca tgtctcgtaa agctccatgc aaatatgaag   4740
tacggggcaa gtgcaacagg ggaagtgagt gcaaattcaa ccacaattac tggagttggc   4800
ctgataggta tttattgtta agatcaaatt atctcttgaa tcagctttta agaaacactg   4860
ataaggctga tggtttgtca ataatatcag gagcaggtag agaagacagg actcaagact   4920
ttgttcttgg ttctactaat gtggttcaag ggtacattga tgacaatcaa ggaataacaa   4980
aggctgcagc ttgctatagt ctacataaca taataaaaca gctacaagaa atagaagtaa   5040
gacaggccag agataataag ctttctgaca gcaaacatgt ggcacttcac aacttgatat   5100
tatcctatat ggagatgagc aaaactcctg catccctgat taataaccta agaaactac   5160 caagagaaaa actgaaaaaa ttagcgaaat taataattga tttatcagca ggaactgata   5220
atgactcttc atatgccttg caagacagtg aaagcactaa tcaagtgcag taagcatggt   5280
cccaaattca tcaccataga ggcagatgat atgatatgga cacacaaaga attaaaagag   5340
acactgtctg atgggatagc aaaatcacac accaatattt acagttgtta tttagaaaat   5400
atagaaataa tatatgttaa agcttactta agttagtaaa aaataaatag aatgggataa   5460
atgacaatga aaacattaga tgtcataaaa agtgacggat cctcagaaac atgtaatcaa   5520
ctcaaaaaaa taataaaaaa acactcaggt aaattgctta ttgcatcaaa accgacattg   5580
gccttattga cgtccttcac agtaacaatt actgtcaact atacaaaagt agaaaataat   5640
ttgcaggcat gtcaattaaa aaatgaatca gacaaaaagg acacaaagct aaataccaca   5700
tcaacaacaa tcagacccat tcctgatcta aatgcagtac agtacctgaa aaggctgatt   5760
cagaaacaca ccaactctgt cacaaaagac agagatacct gttggagaat acacacgaat   5820
caatgcacaa atataaaaat atataagttc ttatgttttg ggtctatgaa ttcaacaaat   5880
```

```
acagactgtg aagaaccaac agttctatgc gacaaaaagt caaaaaccat gacagaaaaa   5940
cataggaaag cagagtgtca ccgtccacat acaaccgagt ggtggtgcca ttatctttaa   6000
gagaaaactc agttttcaac attaaaatca gaacaaatca tatctagatc tattaatata   6060
atagtctagt tatttaaaaa ctctaaatat tgtctagact tcacaacacc ctgcggtcat   6120
atgcaataat caatggtcaa accactgttg caaacccacc tataatacaa tcactgagta   6180
atacaaaaca agaaaatggg acaagtggcc atggaagcaa gagtggagaa cattcgggca   6240
atagacatgt tcaaagcaaa gatgaaaaac cgtataagaa gtagcaagtg ccatagaaat   6300
gctacactga tccttattgg atcaacagca ccaagtatgg cactcaacac ccttttaatc   6360
attgatcatg caacatcaaa aaacatgacc aaagtggaac actgtgtcaa catgccgccg   6420
gtagaaccaa gcaagaagac cccaatgacc tctgcagcag acccaaacac caaacccaat   6480
ccacagcagg caacacagct gaccacagag gattcaacat ctctagcagc aaccctagag   6540
gaccatctac acacagggac aactccaaca ccagatgcaa cagtctccca gcaaaccaca   6600
gacgagcaca caacactgct gagatcaacc aacagacaga ccacccaaac aaccgcagag   6660
aaaaagccaa ccgagcaac aaccaaaaaa gaaaccacaa ctcgaaccac aagcacagct   6720
gcaacccaaa cactcaacac caccaaccaa actagcaatg gaagagaggc aaccacaaca   6780
tctgccagat ccagaaacaa tgccacaact caaagcagcg atcaaacaac ccaggcagca   6840
gacccaagct cccaatcaca acatacacag aaaagcacaa caacaacaca caacacagac   6900
acatcttctc caagtagtta acaaaaaaac tataaaataa ccatgaaaac caaaaaacta   6960
gaaaagttaa tttgaactca gaaaagaaca caaacactat atgaattgtt tgagcgtata   7020
tactaatgaa atagcatctg tttgtgcatc aataatacca tcattattta agaaataaga   7080
agaagctaaa attcaaggga caaataacaa tggatccgtt ttgtgaatcc actgtcaatg   7140
tctatcttcc tgattcatat ctcaaaggag taatatcttt cagtgaaacc aatgcaattg   7200
gctcatgcct tttgaaaaga ccctatctta aaaaagataa cactgctaaa gttgctgtag   7260
aaaaccctgt tgttgaacat gtcagactta gaaatgcagt catgaccaaa atgaagatat   7320
cagattataa agtggttgaa ccaattaata tgcagcatga aataatgaaa aatatacaca   7380
gttgtgagct cacattatta aaacaattct taacaagaag taaaaacatt agctccctaa   7440
aattaagtat gatatgtgat tggttacagt aaaatccac ctcagataac acatcaattc    7500
ttaattttat agatgtggag tttataccg tttgggtgag caattggttt agtaactggt    7560
ataatctcaa taaattaatc ttagagttta gaagagagga agtaataaga actggttcaa   7620
ttttatgcag atcactaggc aagttagttt tcattgtatc atcttatggg tgtgtagtaa   7680
aaagcaacaa aagtaaaaga gtaagttttt tcacatataa ccaactgtta acatggaaag   7740
atgtgatgtt aagtaggttc aatgcaaact tttgtatatg ggtaagtaac aacctgaaca   7800
aaaatcaaga aggactagga tttagaagta atctacaagg tatgttaact aataaattat   7860
atgaaactgt tgattatatg ttaagtctat gtagcaatga agggttctca ctagtgaaag   7920
agttcgaagg ctttattatg agtgaaattc ttaaaattac tgagcatgct caattcagta   7980
ctaggtttag gaatacttta ttaaatgggt tgactgaaca attatcaatg ttgaaagcta   8040
aaaacagatc tagagttctt ggcactatat tagaaaacaa tgattacccc atgtatgaag   8100
tagtacttaa attattaggg gacactttga aaagtataaa attattaatt aacaagaatt   8160
tagaaaatgc tgcagaatta tattatatat tcagaatttt tggacaccct atggtagatg   8220
agagggaagc aatggatgct gttaaattaa ataatgagat tacaaaaatt cttaaactgg   8280
```

```
agagcttaac agaactaaga ggagcattta tactaagaat tataaaaggg tttgtagata    8340
ataataaaag atggcctaaa attaagaatt taaaagtgct cagtaaaaga tgggttatgt    8400
atttcaaagc taaaagttac cctagccaac ttgagctaag tgtacaagat tttttagaac    8460
ttgctgcagt acaattcgaa caggaatttt ctgtccctga aaaaccaat cttgagatgg     8520 tattaaatga taaagcaata tctccaccaa aaaagttaat atggtcggta tatccaaaaa   8580
attatctacc tgaaattata aaaatcaat atttagaaga ggtcttcaat gcaagtgaca    8640
gtcaaagaac gaggagagtc ttagaatttt acttaaaaga ttgcaaattt gatcaaaaag   8700
acctcaaacg ttatgtaact aaacaagagt atctaaatga caaagaccac attgtctcat   8760
taactgggaa agaagagaa ttaagtgtag gcaggatgtt tgcaatgcaa cctggcaaac   8820
aaagacaaat acagatacta gccgagaaac ttttagctga taatattgta cccttttcc    8880 cagaaacttt aacaaagtat ggtgacttgg atctccaaag aattatggaa atgaaatcag   8940
aactttcttc cattaaaact aggaagaatg atagttacaa caattatat gcaagagcct    9000 ccatagtaac agacctaagt aaattcaatc aagcctttag atatgaaacc acagctatct   9060
gcgcagacgt agcagatgag ttacatggca cgcaaagctt attttgttgg ttacatctta   9120
ttgttcccat gaccacaatg atatgtgcat acagacatgc accaccagaa acaaaggggg   9180
agtatgatat agacaaaata gaagagcaaa gtgggctata cagataccat atgggaggga   9240
ttgaagggtg gtgtcagaag ttatggacaa tggaggcgat atccttgtta gatgtagtat   9300
ctgttaagac tcgttgtcag atgacctctc tattaaacgg agacaatcaa tcaatagatg   9360
tcagtaaacc agtaaaattg tctgaaggta tagatgaagt aaaagcagat tatagcttag   9420
caattaaaat gcttaaagag ataagagatg cctataaaa cattggccat aaactcaaag   9480
aaggtgaaac atatatatca agagatcttc aatttataag taaggtgatt caatctgagg   9540
gggtcatgca tcctacccc ataaaaaaga tattaagggg aggtccctgg ataaatacaa    9600
tactagatga cattaaaact agtgcagaat caatagggag tctgtgtcaa gaactagagt   9660
tcagaggaga aagtatacta gttagcttga tattaaggaa ttttctggctg tataacttat   9720 acatgcatga gtcaaaacag catccgttag ctggaaaaca actgttaaa caattgaaca    9780 aaacactaac atctgtgcaa agattttttg agctgaagaa agaaaatgat gtggttgacc   9840
tatggatgaa ataccaatg cagtttggag ggggagaccc agtagttttt tacagatctt    9900
tttacagaag gactcctgat ttcttgactg aagcaatcag ccatgtggat ttactgttaa   9960
aagtttcaaa caatattaaa atgagactaa agatacgatt ctttaaagcc ttattatcta  10020
tagaaaagaa tgaacgtgct acattaacaa cactaatgag agaccccag gcggtaggat   10080 cggaaagaca agctaaggta acaagtgata taaatagaac agcagttact agcatactga  10140
gtctatctcc gaatcagcta ttttgtgata gtgctataca ctatagcaga aatgaagaag   10200
aagtagggat cattgcagac aacataacac ctgtttatcc tcacggattg agagtgctct   10260
atgaatcact acctttcat aaggctgaaa aggttgtcaa tatgatatca ggtacaaagt    10320
ctataactaa cctattgcag agaacatctg ctatcaatgg tgaagatatt gatagagcag  10380
tgtctatgat gttagagaac ttaggggttgt tatctaggat attgtcagta ataattaata  10440
gtatagaaat accaattaag tccaatggca gattgatatg ctgtcaaatt tctaagactt  10500
tgagagaaaa atcatggaac aatatggaaa tagtaggagt gacatctcca agtattgtaa   10560
catgtatgga tgttgtgtat gcgactagtt ctcatttaaa aggaataatt attgaaaaat   10620
```

```
tcagtactga caagaccaca agaggtcaga ggggaccaaa aagcccttgg gtaggatcaa    10680
gcactcaaga gaaaaaatta gttcctgttt ataacagaca aattctttca aaacaacaaa    10740
aagagcaact ggaagcaata ggaaaaatga ggtgggtgta taaaggaact ccagggctaa    10800
gaagattgct caataagatt tgcataggaa gtttaggtat tagctataaa tgtgtaaaac    10860
ctctattacc aagatttatg agtgtaaact tcttacatag gttatctgtt agtagcagac    10920
ccatggaatt cccagcttct gttccagctt ataggacaac aaattaccac tttgacacta    10980
gtccaatcaa ccaagcatta agtgagaggt tcgggaacga agacattaat ctagtgttcc    11040
aaaatgcaat cagctgcgga attagtataa tgagtgttgt agaacagtta actggtagaa    11100
gcccaaaaca attagtctta atcccccaat tagaagagat agatattatg ccccctcctg    11160
tatttcaagg aaaattcaat tataaactag ttgataaaat aacctccgat caacacatct    11220
tcagtcctga caaaatagac atattaacac tagggaagat gcttatgcct actataaaag    11280
gtcaaaaaac tgatcagttc ttaaataaga gagaaaacta tttccatgga aataatttaa    11340
ttgaatcttt atctgcagca cttgcatgcc attggtgtgg aatattaaca gaacagtgtg    11400
tagaaaacaa tatctttagg aaagactggg gtgatgggtt catatcagat catgccttca    11460
tggatttcaa gatatttcta tgtgtattta aaaccaaact tttatgtagt tggggatccc    11520
aagggaaaaa tgtaaaagat gaagatataa tagatgaatc cattgacaaa ttattaagaa    11580
ttgacaacac tttttggaga atgttcagca aagtcatgtt tgaatcaaag gtcaaaaaaa    11640
gaataatgtt atatgatgta aaattcctat cattagtagg ttatatagga tttaaaaact    11700
ggtttataga gcagttaaga gtagtagaat tgcatgaagt accctggatt gtcaatgctg    11760
aaggggagct agttgaaatt aaaccaatca aaatttattt gcagttaata gaacaaagtc    11820
tatctttaag aataactgtt ttgaattata cagacatggc acatgctctt acacgattaa    11880
ttaggaagaa attgatgtgt gataatgcac tctttaatcc aagttcatca ccaatgttta    11940
gtctaactca agttattgat cctacaacac agctagacta ttttcctaag gtaatatttg    12000
aaaggttaaa aagttatgac accagttcag actacaacaa agggaagtta acaagaaatt    12060
acatgacatt attaccatgg cagcacgtaa acaggtataa ttttgtcttt agttcaacag    12120
gatgtaaaat cagcttgaag acatgcatcg ggaaattgat aaaggactta aaccctaagg    12180
ttctttactt tattggagaa ggagcaggta actggatggc aagaacagca tgtgagtatc    12240
ctgacataaa atttgtatat aggagtttaa aggatgatct tgatcaccat tacccattag    12300
aatatcaaag ggtaataggt gatttaaata gagtaataga tggtggtgaa ggattatcaa    12360
tggagaccac agatgcaact caaaagactc attgggactt gatacacaga ataagtaaag    12420
atgctttatt gataacattg tgtgatgcag aattcaaaaa cagagatgat ttctttaaaa    12480
tggtaattct ttggagaaaa catgtattat catgtagaat ctgtacagct tatggaacag    12540
atctttactt atttgcaaag tatcatgcga cggactgcaa tataaagtta ccattttttg    12600
taaggtctgt agctactttt attatgcaag gaagcaaatt gtcaggatca gaatgttaca    12660
tactttttaac attaggtcat cacaataatc tgccatgtca cggagaaata caaaattcca    12720
aaatgagaat agcagtgtgt aatgatttcc atgcctcaaa aaaactagac aacaaatcaa    12780
ttgaagcaaa ctgcaaatct cttctatcag gattaagaat accaataaac aaaaaagagt    12840
taaatagaca aagaaactg ttaacactac aaagcaatca ttcttccata gcaacagttg    12900
gcggaagtaa gattatagaa tccaaatggt taaagaataa agcaagtaca ataattgatt    12960
ggttagagca tatcttgaat tctccaagag gtgaattaaa ctatgatttc tttgaagcat    13020
```

| | |
|---|---|
| tagagaacac atatcccaat atgatcaagc ttatagataa cctgggaaat gcagagataa | 13080 |
| aaaaactaat caaagttacc gggtatatgc ttgtgagtga gaagtaataa taataataat | 13140 |
| aatcaaccat aatctcacac aactgagaaa atgatcatct aacagtttaa ttgaccatta | 13200 |
| gttaattaaa aattataaat tagtaactaa ttgataaaaa ataagaaatt gaaattgaat | 13260 |
| gtatacggtt tttttgccgt | 13280 |

<210> SEQ ID NO 3
<211> LENGTH: 14083
<212> TYPE: DNA
<213> ORGANISM: Artificial Sequence
<220> FEATURE:
<223> OTHER INFORMATION: HMPV strain 83 with GFP inserted prior to N
      gene.

<400> SEQUENCE: 3
acgcgaaaaa aacgcgtata aattaagtta caaaaaaaca tgggacaagt gaaaatggtg 60
agcaagggcg aggagctgtt caccggggtg gtgcccatcc tggtcgagct ggacggcgac 120
gtaaacggcc acaagttcag cgtgtccggc gagggcgagg gcgatgccac ctacggcaag 180
ctgaccctga agttcatctg caccaccggc aagctgcccg tgccctggcc caccctcgtg 240
accaccctga cctacggcgt gcagtgcttc agccgctacc ccgaccacat gaagcagcac 300
gacttcttca agtccgccat gcccgaaggc tacgtccagg agcgcaccat cttcttcaag 360
gacgacggca actacaagac ccgcgccgag gtgaagttcg agggcgacac cctggtgaac 420
cgcatcgagc tgaagggcat cgacttcaag gaggacggca acatcctggg gcacaagctg 480
gagtacaact acaacagcca caacgtctat atcatggccg acaagcagaa gaacggcatc 540
aaggtgaact tcaagatccg ccacaacatc gaggacggca gcgtgcagct cgccgaccac 600
taccagcaga acacccccat cggcgacggc cccgtgctgc tgcccgacaa ccactacctg 660
agcacccagt ccgccctgag caaagacccc aacgagaagc gcgatcacat ggtcctgctg 720
gagttcgtga ccgccgccgg gatcactctc ggcatggacg agctgtacaa gtaagttaat 780
taaaaaagtg ggacaagtga aaatgtctct tcaagggatt cacctgagtg atctatcata 840
caagcatgct atattaaaag agtctcagta tacaataaag agagatgtag gcacaacaac 900
agcagtgaca ccctcatcat tgcaacaaga aataacacta ttgtgtggag aaattctata 960
tgctaagcat gctgattaca aatatgctgc agaaatagga atacaatata ttagcacagc 1020
tctaggatca gagagagtac agcagattct aagaaactca ggcagtgaag tccaagtggt 1080
tttaaccaga acgtactcct tggggaaagt taaaaacaac aaaggagaag atttacagat 1140
gttagacata cacggagtag agaaaagctg ggtggaagag atagacaaag aagcaagaaa 1200
aacaatggca actttgctta aagaatcatc aggcaatatt ccacaaaatc agaggccttc 1260
agcaccagac acacctataa tcttattatg tgtaggtgcc ttaatattta ccaaactagc 1320
atcaactata gaagtgggat tagagaccac agtcagaaga gctaaccgtg tactaagtga 1380
tgcactcaaa agatacccta ggatggacat accaaaaatc gctagatctt tctatgattt 1440
atttgaacaa aaagtgtatt acagaagttt gttcattgag tatggcaaag cattaggctc 1500
atcctctaca ggcagcaaag cagaaagttt attcgttaat atattcatgc aagcttacgg 1560
tgctggtcaa acaatgctga ggtggggagt cattgccagg tcatctaaca atataatgtt 1620
aggacatgta tctgtccaag ctgagttaaa acaagtcaca gaagtctatg acctggtgcg 1680
agaaatgggc cctgaatctg ggctcctaca tttaaggcaa agcccaaaag ctggactgtt 1740

-continued

```
atcactagcc aattgtccca actttgcaag tgttgttctc ggcaatgcct caggcttagg      1800
cataataggt atgtatcgcg ggagagtgcc aaacacagaa ctattttcag cagcagaaag      1860
ctatgccaag agtttgaaag aaagcaataa aattaacttt tcttcattag gactcacaga      1920
tgaagaaaaa gaggctgcag aacactttct aaatgtgagt gacgacagtc aaaatgatta      1980
tgagtaatta aaaagtgggg acaagtcaaa atgtcattcc ctgaaggaaa agatattctt      2040
ttcatgggta atgaagcggc aaaattggca gaagctttcc aaaaatcatt aagaaaacct      2100
agtcataaaa gatctcaatc tattatagga gaaaaagtga acactgtatc tgaaacattg      2160
gaattaccta ctatcagtag acctaccaaa ccgaccatat tgtcagagcc gaagttagca      2220
tggacagaca aaggtggggc aatcaaaact gaagcaaagc aaacaatcaa agttatggat      2280
cctattgaag aagaagagtt tactgagaaa agggtgctgc cctccagtga tgggaaaact      2340
cctgcagaaa agaagttgaa accatcaacc aatactaaaa agaaggtctc atttacacca      2400
aatgaaccag gaaaatacac aaagttggag aaagatgctc tagacttgct ttcagacaat      2460
gaagaagaag atgcagaatc ctcaatctta accttcgaag aaagagatac ttcatcatta      2520
agcattgaag ccagactaga atcgattgag gagaaattaa gcatgatatt agggctatta      2580
agaacactca acattgctac agcaggaccc acagcagcaa gagatgggat cagagatgca      2640
atgattggca taagggagga actaatagca gacataataa aagaagccaa gggaaaagca      2700
gcagaaatga tggaagaaga atgaaccag cggacaaaaa taggaaacgg tagtgtaaaa      2760
ttaactgaaa aggcaaagga gctcaacaaa attgttgaag acgagagcac aagtggtgaa      2820
tccgaagaag aagaagaact aaaagacaca caggaaaata atcaagaaga tgacatttac      2880
cagttaatta tgtagtttaa taaaaataaa aaatgggaca agtgaaaatg gagtcctatc      2940
tggtagacac ctatcaaggc atcccttaca cagcagctgt tcaagttgat ctagtagaaa      3000
aggacctgtt acctgcaagc ctaacaatat ggttccccct gtttcaggcc aatacaccac      3060
cagcagttct gcttgatcag ctaaagactc tgactataac tactctgtat gctgcatcac      3120
aaagtggtcc aatactaaaa gtgaatgcat cggcccaggg tgcagcaatg tctgtacttc      3180
ccaaaaagtt tgaagtcaat gcgactgtag cacttgacga atatagcaaa ttagaatttg      3240
acaaacttac agtctgtgaa gtaaaaacag tttacttaac aaccatgaaa ccatatggga      3300
tggtatcaaa gtttgtgagc tcggccaaac cagttggcaa aaaacacat gatctaatcg      3360 cattatgcga ttttatggat ctagaaaaga acacaccagt tacaatacca gcatttatca      3420
aatcagtttc tatcaaggag agtgaatcag ccactgttga agctgcaata agcagtgaag      3480
cagaccaagc tctaacacaa gccaaaattg caccttatgc gggactgatc atgattatga      3540
ccatgaacaa tcccaaaggc atattcaaga agcttggagc tgggacccaa gttatagtag      3600
aactaggagc atatgtccag gctgaaagca taagtaaaat atgcaagact tggagccatc      3660
aaggaacaag atatgtgctg aagtccagat aacagccaag caacctgacc aagaactacc      3720
aactctattc tatagactaa aaagtcgcca ttttagttat ataaaaatca agttagaata      3780
agaatgctag caatcaagaa cgggacaaat aaaaatgtct tggaaagtgg tgatcatttt      3840
ttcattgcta ataacacctc aacacggtct taaagagagc tacctagaag aatcatgtag      3900
cactataact gagggatatc ttagtgttct gaggacaggt tggtatacca acgttttac      3960 attgaggtg ggtgatgtag aaaacctac atgttctgat ggacctagcc taataaaaac      4020
agaattagat ctgaccaaaa gtgcactaag agagctcaaa acagtctctg ctgaccaatt      4080
```

```
ggcaagagag gaacaaattg agaatcccag acaatctagg tttgttctag gagcaatagc   4140
actcggtgtt gcaacagcag ctgcagtcac agcaggtgtt gcaattgcca aaaccatccg   4200
gcttgagagt gaagtcacag caattaagaa tgccctcaaa acgaccaatg aagcagtatc   4260
tacattgggg aatggagttc gagtgttggc aactgcagtg agagagctga aagactttgt   4320
gagcaagaat ttaactcgtg caatcaacaa aaacaagtgc gacattgatg acctaaaaat   4380
ggccgttagc ttcagtcaat tcaacagaag gtttctaaat gttgtgcggc aattttcaga   4440
caatgctgga ataacaccag caatatcttt ggacttaatg acagatgctg aactagccag   4500
ggccgtttct aacatgccga catctgcagg acaaataaaa ttgatgttgg agaaccgtgc   4560
gatggtgcga agaaagggt tcggaatcct gatagggtc tacgggagct ccgtaattta   4620
catggtgcag ctgccaatct tggcgttat agacacgcct tgctggatag taaaagcagc   4680
ccctt cttgt tccggaaaaa agggaaacta tgcttgcctc ttaagagaag accaagggtg   4740
gtattgtcag aatgcagggt caactgttta ctacccaaat gagaaagact gtgaaacaag   4800
aggagaccat gtcttttgcg acacagcagc gggaattaat gttgctgagc aatcaaagga   4860
gtgcaacatc aacatatcca ctacaaatta cccatgcaaa gtcagcacag aagacatcc   4920
tatcagtatg gttgcactgt ctcctcttgg ggctctggtt gcttgctaca aaggagtaag   4980
ctgttccatt ggcagcaaca gagtagggat catcaagcag ctgaacaagg gttgctccta   5040
tataaccaac caagatgcag acacagtgac aatagacaac actgtatatc agctaagcaa   5100
agttgagggt gaacagcatg ttataaaagg cagaccagtg tcaagcagct ttgatccaat   5160
caagtttcct gaagatcaat tcaatgttgc acttgaccaa gttttttgaga acattgaaaa   5220
cagccaggcc ttggtagatc aatcaaacag aatcctaagc agtgcagaga agggaatac   5280
tggcttcatc attgtaataa ttctaattgc tgtccttggc tctagcatga tcctagtgag   5340
catcttcatt ataatcaaga aaacaaagaa accaacggga gcacctccag agctgagtgg   5400
tgtcacaaac aatggcttca taccacacag ttagttaatt aaaaataaaa taaaatttgg   5460
gacaaatcat aatgtctcgc aaggctccat gcaaatatga agtgcggggc aaatgcaaca   5520
gaggaagtga gtgtaagttt aaccacaatt actggagttg gccagataga tacttattaa   5580
taagatcaaa ctatctatta aatcagcttt taaggaacac tgatagagct gatggcctat   5640
caataatatc aggcgcaggc agagaagaca gaacgcaaga ttttgttcta ggttccacca   5700
atgtggttca aggttatatt gatgataacc aaagcataac aaaagctgca gcctgctaca   5760
gtctacacaa cataatcaag caactacaag aagttgaagt taggcaggct agagatagca   5820
aactatctga cagcaagcat gtggcactcc ataacttaat cttatcttac atggagatga   5880
gcaaaactcc cgcatcttta atcaacaatc tcaaaagact gccgagagaa aaactgaaaa   5940
aattagcaaa gctgataatt gacttatcag caggcgctga caatgactct tcatatgccc   6000
tgcaagacag tgaaagcatt aatcaagtgc agtgagcatg tcctgttttt cattactata   6060
gaggttgatg aaatgatatg gactcaaaaa gaattaaaag aagctttgtc cgatgggata   6120
gtgaagtctc acaccaacat ttacaattgt tatttagaaa acatagaaat tatatatgtc   6180
aaggcttact taagttagta aaaacacatc agagtgggat aagtgacaat gataacatta   6240
gatgtcatta aaagtgatgg gtcttcaaaa acatgtactc acctcaaaaa aataatcaaa   6300
gaccattctg gtaaagtgct tattgcactt aagttaatat tagctttact aacatttttc   6360
acaataacaa tcactataaa ttacataaaa gtagaaaaca atctacaaat atgccagtca   6420
aaaactgaat cagacaaaga agactcacca tcaaatacca catccgtcac aaccaagacc   6480
```

```
actctagacc atgatataac acagtatttt aaaagattaa ttcaaaggta tacagattct   6540
gtaataaaca aggacacatg ctggaaaata agcagaaatc aatgcacaaa tataacaaca   6600
tataaatttt tatgctttaa acctgaggac tcaaaaatca acagttgtga tagactgaca   6660
gatctatgca gaaacaaatc aaaatcagca gctgaagcat atcatacagt agaatgccat   6720
tgcatataca caattgagtg gaagtgctat caccactcaa tagattaaac ccaatcttga   6780
atgttaaaac tagactagga tccgtctaag actatcagtt caatagttta gttattttaa   6840
aatatttgag aataggtaag tttctatggc acttcatagc aataggtaat aattaacagc   6900
ttaattataa ttaaaacatt atttaaaatc gtaactattt aatttacaaa gtaaaaacaa   6960
aaatatggga caagtagtta tggaggtgaa agtagagaac attcgagcaa tagacatgct   7020
caaagcaaga gtgaaaaatc gtgtggcacg tagcaaatgc tttaaaaatg cttctttaat   7080
cctcatagga ataactacac tgagtatagc tctcaatatc tatctgatca taaactacac   7140
aatacaaaaa acctcatctg aatcagaaca ccacaccagc tcaccaccca cagaatccaa   7200
caaggaagct tcaacaatct ccacagacaa cccagacatc aatccaaact cacagcatcc   7260
aactcaacag tccacagaaa accccacact caaccccgca gcatcagtga gcccatcaga   7320
aacagaacca gcatcaacac cagacacaac aaaaccgcctg tcctccgtag acaggtccac   7380
agcacaacca agtgaaagca gaacaaagac aaaaccgaca gtccacacaa gaaacaaccc   7440
aagcacagct tccagtacac aatccccacc acgggcaaca acgaaggcaa tccgcagagc   7500
caccactttc cgcatgagca gcacaggaaa aagaccaacc acaacatcag tccagtccga   7560
cagcagcacc acaacccaaa atcatgaaga aacaggttca gcgaacccac aggcatctgt   7620
aagcacaatg caaaactagc acaccaacaa tataaaacca aattagttaa caaaaaatac   7680
gagatagctc taaagtaaaa catgtaggta ccaacaatca agaaaccaaa agacaactca   7740
caatctccct aaaacagcaa cgacaccatg tcagctttgc tcaaatctct ctgggagaaa   7800
cttttgccca catactaaca acatcacaac catctcaaga aaagaaactg gcaaaacag   7860
catccaagag acaaatagca atggatcctc ttaatgaatc cactgttaat gtctatctcc   7920
ctgattcgta ccttaaagga gtaatttctt ttagtgaaac taatgcaatt ggttcatgtc   7980
tcttaaaaag accctactta aaaaatgaca acactgcaaa agttgccata gagaatcctg   8040
ttattgagca tgtgagactc aaaaatgcag tcaattctaa aatgaaaata tcagattaca   8100
aggtagtaga gccagtaaac atgcaacatg aaataatgaa gaatgtacac agttgtgagc   8160
tcacactatt gaaacagttt ttaacaagga gtaaaaacat tagcactctc aaattgaata   8220
tgatatgtga ttggctgcaa ttaaagtcta catcagatga tacctcaatc ctaagtttca   8280
tagatgtaga atttatacct agttgggtaa gcaactggtt tagtaattgg tacaatctca   8340
ataagttaat tttggaattc agaagagagg aagtaataag aaccggttca atcttatgca   8400
ggtcattggg taaattagtt tttattgtat catcatatgg atgtatcgtc aagagcaaca   8460
aaagcaaaag agtgagcttc ttcacataca atcaactgtt aacatggaaa gatgtgatgt   8520
taagtagatt taatgcgaat ttttgtatat gggtaagcaa tagtctgaat gaaaatcagg   8580
aagggctagg gttgagaagt aatctgcaag gtatgttaac taataaacta tatgaaactg   8640
tagattatat gctaagctta tgttgcaatg aaggtttctc acttgtgaaa gagttcgaag   8700
gtttttattat gagtgagatc cttaggatta ctgaacatgc tcaattcagt actagattta   8760
gaaatacttt attgaatgga ttaacagatc aattaacaaa attaaaaaat aaaacagac   8820
```

```
tcagagttca tagtaccgta ttagaaaata atgattatcc aatgtatgaa gttgtactta    8880
aattattagg agatactttg agatgtatca aattattaat caataaaaac ttagagaatg    8940
ctgcagaatt atactatata ttcagaattt ttggtcatcc aatggtagat gaaagagatg    9000
caatggatgc tgtcaaatta aacaatgaaa tcacaaaaat cctaaggttg gagagcttga    9060
cagaactaag aggggcattc atattaagga ttatcaaagg atttgtggac aacaacaaaa    9120
ggtggcccaa aattaaaaac ttaaaagtgc ttagcaaaag atggactatg tacttcaaag    9180
ctaaaaatta ccccagtcaa ctcgaattaa gtgaacaaga cttctagag cttgctgcaa     9240 tacaatttga acaagagttt tctgttcctg aaaaaaccaa tcttgagatg gtattaaatg    9300
acaaagccat atcacctcct aaaagattaa tatggtctgt gtatccaaag aattacttac    9360
ctgagacgat aaaaaatcga tatttagaag aaactttcaa tgcgagtgat agtctcaaaa    9420
caagaagagt actagagtac tatttaaaag ataataaatt tgatcaaaag gaacttaaaa    9480
gttatgtagt tagacaagaa tatttaaacg ataaggagca cattgtctca ttaactggaa    9540
aagaaagaga attaagtgta ggtagaatgt ttgctatgca accaggaaaa cagcgacaaa    9600
tacaaatatt ggcagaaaaa ttgttagctg ataacattgt acctttcttc ccggaaacct    9660
taacaaagta tggtgatcta gatcttcaga gaataatgga aatcaaatca gactttctt    9720 ctatcaaaac cagaagaaat gatagttata ataattacat tgcaagagca tccatagtaa    9780
cagatttgag caagttcaac caagccttta gatatgaaac tacagcgatc tgtgcggatg    9840
tagcagacga attacatgga acacaaagct tattctgttg gttacatctt atcgttccta    9900
tgactacaat gatatgtgcc tatagacatg caccaccaga aacaaaggt gaatatgata    9960 tagataagat agaagagcaa agtggtctat atagatatca catgggcggt attgaaggat    10020
ggtgtcaaaa actctggaca atggaagcta tatctttatt ggatgttgta tctgtaaaga    10080
cacggtgtca aatgacatct ttattaaacg gtgacaacca atcaatagat gtaagtaaac    10140
cagtcaagtt atctgaaggt ttagatgaag tgaaggcaga ttatcgctta gcagtaaaaa    10200
tgctaaaaga aataagagat gcatacagaa atataggcca taaacttaaa gaaggggaaa    10260
catatatatc aagggatctt cagtttataa gcaaggtgat tcaatctgaa ggagtgatgc    10320
atcctacccc tataaaaaag gtcttgagag taggaccatg gataaacaca atattagatg    10380 acattaaaaac tagtgctgag tcaatagga gtctatgtca agaattagaa tttaggggag    10440
aaagcataat agttagtctg atattaagaa acttctggct gtataactta tacatgcatg    10500
aatcaaagca acatcctttg gcagggaaac agttattcaa acaactaaat aaaacattaa    10560
catcagtgca gagatttttt gaaattaaaa gggaaaatga ggtagtagat ctatggatga    10620
acataccaat gcaatttgga ggaggagatc cagtagtctt ctatagatct ttctataaa    10680 ggaccccctga tttttaact gaggcaatca gccatgtaga tattctgtta aaaatatcag    10740
ctaacataaa aaatgaaacg aaagtaagtt tcttcaaagc cttactatca atagaaaaaa    10800
atgaacgtgc tacactgaca acactaatga gagatcctca agctgttgga tcagaacgac    10860
aagcaaaagt aacaagtgac atcaatgaaa cagcagttac cagtatctta agtctttccc    10920
caaatcaact tttcagtgat agtgctatac actacagcag aaatgaagaa gaagtgggaa    10980
tcattgcaga aaacataaca cctgtttatc ctcatgggct gagagtatta tatgaatcat    11040 tgcccttttca caaagctgaa aaagttgtaa acatgatatc agggacaaaa tctataacca    11100
acttattaca gagaacatcc gctattaatg gtgaagatat tgacagggct gtatctatga    11160
tgttggagaa tctaggatta ttatctagaa tattgtcagt agttgttgat agtatagaaa    11220
```

```
ttccaatcaa atctaatggt aggctgatat gttgtcaaat ctctaggact ttaagagaga   11280
catcatggaa taatatggaa atagttggag taacatctcc tagcatcact acatgtatgg   11340
atgtcatata tgcaactagt tctcatttga aagggataat tatagaaaag ttcagcactg   11400
acagaactac aaggggtcaa agaggtccaa aaagcccttg ggtagggtcg agtactcaag   11460
agaaaaaatt agtacctgtt tataacagac aaattctctc aaaacaacaa agagaacagc   11520
tagaagcaat tggaaaaatg agatgggtgt ataaagggac accaggcttg cgacgattac   11580
tcaacaagat ctgtcttggg agtttaggca ttagctacaa atgtgtaaaa cctttattac   11640
ctaggtttat gagtgtaaat ttcttacata gattatctgt cagtagtaga cctatggaat   11700
tcccagcatc agttccagct tatagaacaa caaattacca tttcgacact agtcctatta   11760
atcaagcact aagtgagaga tttgggaatg aagatattaa cttggtcttc caaaatgcaa   11820
tcagctgtgg aattagcata atgagtgtag tagaacaatt aacaggtaga agcccaaaac   11880
agttagtttt aatacccccaa ttagaagaaa tagacattat gccaccacca gtgtttcaag   11940
ggaaattcaa ttataaatta gtagataaga taacttctga tcaacatatc tttagtccgg   12000
acaaaataga tatgttaaca ctagggaaaa tgctcatgcc cactataaaa ggtcagaaaa   12060
cagatcagtt cttaaataag agagaaaatt atttccatgg aaacaatctt attgagtctt   12120
tatcagcagc attagcatgt cattggtgtg ggatattaac agaacaatgc atagaaaata   12180
atattttcaa gaaagactgg ggtgacgggt ttatatcaga tcatgctttt atggacttca   12240
aaatattcct atgtgtcttt aaaactaaac ttttatgtag ttggggatct caagggaaaa   12300
acattaaaga tgaagatata gtagatgaat caatagataa attgttaagg attgacaata   12360 cttttttggag aatgttcagc aaagttatgt ttgaaccaaa ggttaagaaa aggataatgt   12420
tatatgatgt aaaattccta tcactagtag gctacatagg gtttaagaac tggtttatag   12480
agcagttgag atcagctgaa ttgcatgaaa taccttggat tgtcaatgcc gaaggtgatt   12540
tggttgagat caagtcaatt aaaatctatt tgcaactgat agaacaaagc ttattttaa    12600 gaataactgt tttgaactat acagatatgg cacatgctct cacacgatta atcagaaaga   12660
agttaatgtg tgataatgca ctgttaaccc caatttcatc cccaatggtt aacttaactc   12720
aagttattga tccacaacaa caattagatt acttccccaa gataacattc gaaaggctaa   12780
aaaattatga cacaagttca aattatgcta aagggaagct aacaagaaat tacatgatac   12840
tattgccatg gcagcatgtt aatagatata actttgtctt tagttctact ggatgtaaag   12900
ttagtctgaa aacatgtatt ggaaaactta tgaaagacct aaatcctaaa gttttgtact   12960
ttattggaga aggagcagga aattggatgg ccagaacagc atgtgaatat cctgatatta   13020
aatttgtata tagaagtctg aaagatgacc ttgatcatca ttatcctctg gaataccaga   13080
gagtgatagg tgaattaagc agaatcatag atagtggtga aggactttca atggaaacaa   13140
cagacgcaac tcaaaaaact cattgggatt tgatacacag ggtaagcaaa gatgctttat   13200
taataacttt atgtgatgca gaatttaagg acagagatga ttttttaag atggtaattc    13260 tatggagaaa acatgtatta tcatgcagaa tttgcactac ttatgggacg gacctctatt   13320
tattcgcaaa gtatcatgct aaagactgca atgtaaaatt accttttttt gtgagatcag   13380
ttgctacttt cattatgcag ggtagtaagc tgtcaggttc agaatgctac atactcttaa   13440
cactaggcca ccacaacagt ttaccttgcc atggagaaat acaaaattct aagatgaaaa   13500
tagcagtgtg taatgatttt tatgctgcaa aaaaactcga caataaatca attgaagcta   13560
```

```
attgtaaatc acttttgtca gggctaagaa tacctataaa taagaaggaa ctagatagac    13620
agagaagatt attaacacta caaagcaatc attcttctgt agcaacagtt ggcggtagca    13680
agatcataga gtctaagtgg ttaacaaaca aagcaagtac aataattgat tggttagaac    13740
atattttaaa ttctccaaag ggcgaattaa attatgattt ttttgaagca ttggagaaca    13800
cttaccctaa tatgattaaa ctaatagata acttagggaa tgcagagatt aaaaaactga    13860
tcaaagtaac aggatacatg cttgtaagta aaaatgaaa aatgatgaag atgacaaaat     13920
agatgacaac ttcatactat tctaaattaa ttatttgatt atgcaattat atgatagtta    13980
attaaaatta aaaattaaaa atcaaaagtt aaaatttaaa acctatcatt aagtttatta    14040
aaaataagaa attataattg aatgtatacg gttttttgc cgt                       14083
```

<210> SEQ ID NO 4
<211> LENGTH: 187
<212> TYPE: PRT
<213> ORGANISM: human metapneumovirus

<400> SEQUENCE: 4

```
Met Ser Arg Lys Ala Pro Cys Lys Tyr Glu Val Arg Gly Lys Cys Asn
1               5                   10                  15

Arg Gly Ser Glu Cys Lys Phe Asn His Asn Tyr Trp Ser Trp Pro Asp
            20                  25                  30

Arg Tyr Leu Leu Ile Arg Ser Asn Tyr Leu Leu Asn Gln Leu Leu Arg
        35                  40                  45

Asn Thr Asp Arg Ala Asp Gly Leu Ser Ile Ile Ser Gly Ala Gly Arg
    50                  55                  60

Glu Asp Arg Thr Gln Asp Phe Val Leu Gly Ser Thr Asn Val Val Gln
65                  70                  75                  80

Gly Tyr Ile Asp Asp Asn Gln Ser Ile Thr Lys Ala Ala Ala Cys Tyr
                85                  90                  95

Ser Leu His Asn Ile Ile Lys Gln Leu Gln Glu Val Glu Val Arg Gln
            100                 105                 110

Ala Arg Asp Ser Lys Leu Ser Asp Ser Lys His Val Ala Leu His Asn
        115                 120                 125

Leu Ile Leu Ser Tyr Met Glu Met Ser Lys Thr Pro Ala Ser Leu Ile
    130                 135                 140

Asn Asn Leu Lys Arg Leu Pro Arg Glu Lys Leu Lys Lys Leu Ala Lys
145                 150                 155                 160

Leu Ile Ile Asp Leu Ser Ala Gly Ala Asp Asn Asp Ser Ser Tyr Ala
                165                 170                 175

Leu Gln Asp Ser Glu Ser Ile Asn Gln Val Gln
            180                 185
```

<210> SEQ ID NO 5
<211> LENGTH: 179
<212> TYPE: PRT
<213> ORGANISM: human metapneumovirus

<400> SEQUENCE: 5

```
Met Ile Thr Leu Asp Val Ile Lys Ser Asp Gly Ser Ser Lys Thr Cys
1               5                   10                  15

Thr His Leu Lys Lys Ile Ile Lys Asp His Ser Gly Lys Val Leu Ile
            20                  25                  30

Ala Leu Lys Leu Ile Leu Ala Leu Leu Thr Phe Phe Thr Ile Thr Ile
        35                  40                  45
```

```
Thr Ile Asn Tyr Ile Lys Val Glu Asn Asn Leu Gln Ile Cys Gln Ser
    50                  55                  60
Lys Thr Glu Ser Asp Lys Glu Asp Ser Pro Ser Asn Thr Thr Ser Val
 65                  70                  75                  80
Thr Thr Lys Thr Thr Leu Asp His Asp Ile Thr Gln Tyr Phe Lys Arg
                 85                  90                  95
Leu Ile Gln Arg Tyr Thr Asp Ser Val Ile Asn Lys Asp Thr Cys Trp
                100                 105                 110
Lys Ile Ser Arg Asn Gln Cys Thr Asn Ile Thr Thr Tyr Lys Phe Leu
                115                 120                 125
Cys Phe Lys Pro Glu Asp Ser Lys Ile Asn Ser Cys Asp Arg Leu Thr
    130                 135                 140
Asp Leu Cys Arg Asn Lys Ser Lys Ser Ala Ala Glu Ala Tyr His Thr
145                 150                 155                 160
Val Glu Cys His Cys Ile Tyr Thr Ile Glu Trp Lys Cys Tyr His His
                165                 170                 175
Ser Ile Asp

<210> SEQ ID NO 6
<211> LENGTH: 219
<212> TYPE: PRT
<213> ORGANISM: human metapneumovirus

<400> SEQUENCE: 6

Met Glu Val Lys Val Glu Asn Ile Arg Ala Ile Asp Met Leu Lys Ala
 1               5                  10                  15
Arg Val Lys Asn Arg Val Ala Arg Ser Lys Cys Phe Lys Asn Ala Ser
                20                  25                  30
Leu Ile Leu Ile Gly Ile Thr Thr Leu Ser Ile Ala Leu Asn Ile Tyr
             35                  40                  45
Leu Ile Ile Asn Tyr Thr Ile Gln Lys Thr Ser Ser Glu Ser Glu His
    50                  55                  60
His Thr Ser Ser Pro Pro Thr Glu Ser Asn Lys Glu Ala Ser Thr Ile
 65                  70                  75                  80
Ser Thr Asp Asn Pro Asp Ile Asn Pro Asn Ser Gln His Pro Thr Gln
                 85                  90                  95
Gln Ser Thr Glu Asn Pro Thr Leu Asn Pro Ala Ala Ser Val Ser Pro
                100                 105                 110
Ser Glu Thr Glu Pro Ala Ser Thr Pro Asp Thr Thr Asn Arg Leu Ser
                115                 120                 125
Ser Val Asp Arg Ser Thr Ala Gln Pro Ser Glu Ser Arg Thr Lys Thr
    130                 135                 140
Lys Pro Thr Val His Thr Arg Asn Asn Pro Ser Thr Ala Ser Ser Thr
145                 150                 155                 160
Gln Ser Pro Pro Arg Ala Thr Thr Lys Ala Ile Arg Arg Ala Thr Thr
                165                 170                 175
Phe Arg Met Ser Ser Thr Gly Lys Arg Pro Thr Thr Thr Ser Val Gln
                180                 185                 190
Ser Asp Ser Ser Thr Thr Thr Gln Asn His Glu Glu Thr Gly Ser Ala
    195                 200                 205
Asn Pro Gln Ala Ser Val Ser Thr Met Gln Asn
    210                 215

<210> SEQ ID NO 7
<211> LENGTH: 2005
```

```
<212> TYPE: PRT
<213> ORGANISM: human metapneumovirus

<400> SEQUENCE: 7
```

| | | | | | | | | | | | | | | |
|---|---|---|---|---|---|---|---|---|---|---|---|---|---|---|
|Met|Asp|Pro|Leu|Asn|Glu|Ser|Thr|Val|Asn|Val|Tyr|Leu|Pro|Asp|Ser|
|1| | | |5| | | | |10| | | | |15|

Tyr Leu Lys Gly Val Ile Ser Phe Ser Glu Thr Asn Ala Ile Gly Ser
                20                  25                  30

Cys Leu Leu Lys Arg Pro Tyr Leu Lys Asn Asp Asn Thr Ala Lys Val
            35                  40                  45

Ala Ile Glu Asn Pro Val Ile Glu His Val Arg Leu Lys Asn Ala Val
 50                  55                  60

Asn Ser Lys Met Lys Ile Ser Asp Tyr Lys Val Val Glu Pro Val Asn
 65                  70                  75                  80

Met Gln His Glu Ile Met Lys Asn Val His Ser Cys Glu Leu Thr Leu
                 85                  90                  95

Leu Lys Gln Phe Leu Thr Arg Ser Lys Asn Ile Ser Thr Leu Lys Leu
                100                 105                 110

Asn Met Ile Cys Asp Trp Leu Gln Leu Lys Ser Thr Ser Asp Asp Thr
                115                 120                 125

Ser Ile Leu Ser Phe Ile Asp Val Glu Phe Ile Pro Ser Trp Val Ser
130                 135                 140

Asn Trp Phe Ser Asn Trp Tyr Asn Leu Asn Lys Leu Ile Leu Glu Phe
145                 150                 155                 160

Arg Arg Glu Glu Val Ile Arg Thr Gly Ser Ile Leu Cys Arg Ser Leu
                165                 170                 175

Gly Lys Leu Val Phe Ile Val Ser Ser Tyr Gly Cys Ile Val Lys Ser
                180                 185                 190

Asn Lys Ser Lys Arg Val Ser Phe Phe Thr Tyr Asn Gln Leu Leu Thr
                195                 200                 205

Trp Lys Asp Val Met Leu Ser Arg Phe Asn Ala Asn Phe Cys Ile Trp
                210                 215                 220

Val Ser Asn Ser Leu Asn Glu Asn Gln Glu Gly Leu Gly Leu Arg Ser
225                 230                 235                 240

Asn Leu Gln Gly Met Leu Thr Asn Lys Leu Tyr Glu Thr Val Asp Tyr
                245                 250                 255

Met Leu Ser Leu Cys Cys Asn Glu Gly Phe Ser Leu Val Lys Glu Phe
                260                 265                 270

Glu Gly Phe Ile Met Ser Glu Ile Leu Arg Ile Thr Glu His Ala Gln
                275                 280                 285

Phe Ser Thr Arg Phe Arg Asn Thr Leu Leu Asn Gly Leu Thr Asp Gln
290                 295                 300

Leu Thr Lys Leu Lys Asn Lys Asn Arg Leu Arg Val His Ser Thr Val
305                 310                 315                 320

Leu Glu Asn Asn Asp Tyr Pro Met Tyr Glu Val Val Leu Lys Leu Leu
                325                 330                 335

Gly Asp Thr Leu Arg Cys Ile Lys Leu Leu Ile Asn Lys Asn Leu Glu
                340                 345                 350

Asn Ala Ala Glu Leu Tyr Tyr Ile Phe Arg Ile Phe Gly His Pro Met
                355                 360                 365

Val Asp Glu Arg Asp Ala Met Asp Ala Val Lys Leu Asn Asn Glu Ile
                370                 375                 380

Thr Lys Ile Leu Arg Leu Glu Ser Leu Thr Glu Leu Arg Gly Ala Phe
385                 390                 395                 400

```
Ile Leu Arg Ile Ile Lys Gly Phe Val Asp Asn Asn Lys Arg Trp Pro
                405                 410                 415
Lys Ile Lys Asn Leu Lys Val Leu Ser Lys Arg Trp Thr Met Tyr Phe
            420                 425                 430
Lys Ala Lys Asn Tyr Pro Ser Gln Leu Glu Leu Ser Glu Gln Asp Phe
        435                 440                 445
Leu Glu Leu Ala Ala Ile Gln Phe Glu Gln Phe Ser Val Pro Glu
    450                 455                 460
Lys Thr Asn Leu Glu Met Val Leu Asn Asp Lys Ala Ile Ser Pro Pro
465                 470                 475                 480
Lys Arg Leu Ile Trp Ser Val Tyr Pro Lys Asn Tyr Leu Pro Glu Thr
                485                 490                 495
Ile Lys Asn Arg Tyr Leu Glu Glu Thr Phe Asn Ala Ser Asp Ser Leu
            500                 505                 510
Lys Thr Arg Arg Val Leu Glu Tyr Tyr Leu Lys Asp Asn Lys Phe Asp
        515                 520                 525
Gln Lys Glu Leu Lys Ser Tyr Val Val Arg Gln Glu Tyr Leu Asn Asp
    530                 535                 540
Lys Glu His Ile Val Ser Leu Thr Gly Lys Glu Arg Glu Leu Ser Val
545                 550                 555                 560
Gly Arg Met Phe Ala Met Gln Pro Gly Lys Gln Arg Gln Ile Gln Ile
                565                 570                 575
Leu Ala Glu Lys Leu Leu Ala Asp Asn Ile Val Pro Phe Phe Pro Glu
            580                 585                 590
Thr Leu Thr Lys Tyr Gly Asp Leu Asp Leu Gln Arg Ile Met Glu Ile
        595                 600                 605
Lys Ser Glu Leu Ser Ser Ile Lys Thr Arg Arg Asn Asp Ser Tyr Asn
    610                 615                 620
Asn Tyr Ile Ala Arg Ala Ser Ile Val Thr Asp Leu Ser Lys Phe Asn
625                 630                 635                 640
Gln Ala Phe Arg Tyr Glu Thr Thr Ala Ile Cys Ala Asp Val Ala Asp
                645                 650                 655
Glu Leu His Gly Thr Gln Ser Leu Phe Cys Trp Leu His Leu Ile Val
            660                 665                 670
Pro Met Thr Thr Met Ile Cys Ala Tyr Arg His Ala Pro Pro Glu Thr
        675                 680                 685
Lys Gly Glu Tyr Asp Ile Asp Lys Ile Glu Glu Gln Ser Gly Leu Tyr
    690                 695                 700
Arg Tyr His Met Gly Gly Ile Glu Gly Trp Cys Gln Lys Leu Trp Thr
705                 710                 715                 720
Met Glu Ala Ile Ser Leu Leu Asp Val Val Ser Val Lys Thr Arg Cys
                725                 730                 735
Gln Met Thr Ser Leu Leu Asn Gly Asp Asn Gln Ser Ile Asp Val Ser
            740                 745                 750
Lys Pro Val Lys Leu Ser Glu Gly Leu Asp Glu Val Lys Ala Asp Tyr
        755                 760                 765
Arg Leu Ala Val Lys Met Leu Lys Glu Ile Arg Asp Ala Tyr Arg Asn
    770                 775                 780
Ile Gly His Lys Leu Lys Glu Gly Glu Thr Tyr Ile Ser Arg Asp Leu
785                 790                 795                 800
Gln Phe Ile Ser Lys Val Ile Gln Ser Glu Gly Val Met His Pro Thr
                805                 810                 815
```

-continued

```
Pro Ile Lys Lys Val Leu Arg Val Gly Pro Trp Ile Asn Thr Ile Leu
            820                 825                 830

Asp Asp Ile Lys Thr Ser Ala Glu Ser Ile Gly Ser Leu Cys Gln Glu
            835                 840                 845

Leu Glu Phe Arg Gly Glu Ser Ile Ile Val Ser Leu Ile Leu Arg Asn
850                 855                 860

Phe Trp Leu Tyr Asn Leu Tyr Met His Glu Ser Lys Gln His Pro Leu
865                 870                 875                 880

Ala Gly Lys Gln Leu Phe Lys Gln Leu Asn Lys Thr Leu Thr Ser Val
                885                 890                 895

Gln Arg Phe Phe Glu Ile Lys Arg Glu Asn Glu Val Val Asp Leu Trp
            900                 905                 910

Met Asn Ile Pro Met Gln Phe Gly Gly Gly Asp Pro Val Val Phe Tyr
            915                 920                 925

Arg Ser Phe Tyr Arg Arg Thr Pro Asp Phe Leu Thr Glu Ala Ile Ser
930                 935                 940

His Val Asp Ile Leu Leu Lys Ile Ser Ala Asn Ile Lys Asn Glu Thr
945                 950                 955                 960

Lys Val Ser Phe Phe Lys Ala Leu Leu Ser Ile Glu Lys Asn Glu Arg
                965                 970                 975

Ala Thr Leu Thr Thr Leu Met Arg Asp Pro Gln Ala Val Gly Ser Glu
            980                 985                 990

Arg Gln Ala Lys Val Thr Ser Asp  Ile Asn Arg Thr Ala  Val Thr Ser
            995                 1000                1005

Ile Leu  Ser Leu Ser Pro Asn  Gln Leu Phe Ser Asp  Ser Ala Ile
    1010                1015                1020

His Tyr  Ser Arg Asn Glu Glu  Glu Val Gly Ile Ile  Ala Glu Asn
    1025                1030                1035

Ile Thr  Pro Val Tyr Pro His  Gly Leu Arg Val Leu  Tyr Glu Ser
    1040                1045                1050

Leu Pro  Phe His Lys Ala Glu  Lys Val Val Asn Met  Ile Ser Gly
    1055                1060                1065

Thr Lys  Ser Ile Thr Asn Leu  Leu Gln Arg Thr Ser  Ala Ile Asn
    1070                1075                1080

Gly Glu  Asp Ile Asp Arg Ala  Val Ser Met Met Leu  Glu Asn Leu
    1085                1090                1095

Gly Leu  Leu Ser Arg Ile Leu  Ser Val Val Val Asp  Ser Ile Glu
    1100                1105                1110

Ile Pro  Ile Lys Ser Asn Gly  Arg Leu Ile Cys Cys  Gln Ile Ser
    1115                1120                1125

Arg Thr  Leu Arg Glu Thr Ser  Trp Asn Asn Met Glu  Ile Val Gly
    1130                1135                1140

Val Thr  Ser Pro Ser Ile Thr  Thr Cys Met Asp Val  Ile Tyr Ala
    1145                1150                1155

Thr Ser  Ser His Leu Lys Gly  Ile Ile Ile Glu Lys  Phe Ser Thr
    1160                1165                1170

Asp Arg  Thr Thr Arg Gly Gln  Arg Gly Pro Lys Ser  Pro Trp Val
    1175                1180                1185

Gly Ser  Ser Thr Gln Glu Lys  Lys Leu Val Pro Val  Tyr Asn Arg
    1190                1195                1200

Gln Ile  Leu Ser Lys Gln Gln  Arg Glu Gln Leu Glu  Ala Ile Gly
    1205                1210                1215

Lys Met  Arg Trp Val Tyr Lys  Gly Thr Pro Gly Leu  Arg Arg Leu
```

```
                 1220               1225               1230
Leu Asn Lys Ile Cys Leu Gly Ser Leu Gly Ile Ser Tyr Lys Cys
    1235                1240                1245

Val Lys Pro Leu Leu Pro Arg Phe Met Ser Val Asn Phe Leu His
    1250                1255                1260

Arg Leu Ser Val Ser Ser Arg Pro Met Glu Phe Pro Ala Ser Val
    1265                1270                1275

Pro Ala Tyr Arg Thr Thr Asn Tyr His Phe Asp Thr Ser Pro Ile
    1280                1285                1290

Asn Gln Ala Leu Ser Glu Arg Phe Gly Asn Glu Asp Ile Asn Leu
    1295                1300                1305

Val Phe Gln Asn Ala Ile Ser Cys Gly Ile Ser Ile Met Ser Val
    1310                1315                1320

Val Glu Gln Leu Thr Gly Arg Ser Pro Lys Gln Leu Val Leu Ile
    1325                1330                1335

Pro Gln Leu Glu Glu Ile Asp Ile Met Pro Pro Val Phe Gln
    1340                1345                1350

Gly Lys Phe Asn Tyr Lys Leu Val Asp Lys Ile Thr Ser Asp Gln
    1355                1360                1365

His Ile Phe Ser Pro Asp Lys Ile Asp Met Leu Thr Leu Gly Lys
    1370                1375                1380

Met Leu Met Pro Thr Ile Lys Gly Gln Lys Thr Asp Gln Phe Leu
    1385                1390                1395

Asn Lys Arg Glu Asn Tyr Phe His Gly Asn Asn Leu Ile Glu Ser
    1400                1405                1410

Leu Ser Ala Ala Leu Ala Cys His Trp Cys Gly Ile Leu Thr Glu
    1415                1420                1425

Gln Cys Ile Glu Asn Asn Ile Phe Lys Lys Asp Trp Gly Asp Gly
    1430                1435                1440

Phe Ile Ser Asp His Ala Phe Met Asp Phe Lys Ile Phe Leu Cys
    1445                1450                1455

Val Phe Lys Thr Lys Leu Leu Cys Ser Trp Gly Ser Gln Gly Lys
    1460                1465                1470

Asn Ile Lys Asp Glu Asp Ile Val Asp Glu Ser Ile Asp Lys Leu
    1475                1480                1485

Leu Arg Ile Asp Asn Thr Phe Trp Arg Met Phe Ser Lys Val Met
    1490                1495                1500

Phe Glu Pro Lys Val Lys Arg Ile Met Leu Tyr Asp Val Lys
    1505                1510                1515

Phe Leu Ser Leu Val Gly Tyr Ile Gly Phe Lys Asn Trp Phe Ile
    1520                1525                1530

Glu Gln Leu Arg Ser Ala Glu Leu His Glu Ile Pro Trp Ile Val
    1535                1540                1545

Asn Ala Glu Gly Asp Leu Val Glu Ile Lys Ser Ile Lys Ile Tyr
    1550                1555                1560

Leu Gln Leu Ile Glu Gln Ser Leu Phe Leu Arg Ile Thr Val Leu
    1565                1570                1575

Asn Tyr Thr Asp Met Ala His Ala Leu Thr Arg Leu Ile Arg Lys
    1580                1585                1590

Lys Leu Met Cys Asp Asn Ala Leu Leu Thr Pro Ile Ser Ser Pro
    1595                1600                1605

Met Val Asn Leu Thr Gln Val Ile Asp Pro Thr Thr Gln Leu Asp
    1610                1615                1620
```

```
Tyr Phe Pro Lys Ile Thr Phe Glu Arg Leu Lys Asn Tyr Asp Thr
    1625                1630                1635

Ser Ser Asn Tyr Ala Lys Gly Lys Leu Thr Arg Asn Tyr Met Ile
    1640                1645                1650

Leu Leu Pro Trp Gln His Val Asn Arg Tyr Asn Phe Val Phe Ser
    1655                1660                1665

Ser Thr Gly Cys Lys Val Ser Leu Lys Thr Cys Ile Gly Lys Leu
    1670                1675                1680

Met Lys Asp Leu Asn Pro Lys Val Leu Tyr Phe Ile Gly Glu Gly
    1685                1690                1695

Ala Gly Asn Trp Met Ala Arg Thr Ala Cys Glu Tyr Pro Asp Ile
    1700                1705                1710

Lys Phe Val Tyr Arg Ser Leu Lys Asp Asp Leu Asp His His Tyr
    1715                1720                1725

Pro Leu Glu Tyr Gln Arg Val Ile Gly Glu Leu Ser Arg Ile Ile
    1730                1735                1740

Asp Ser Gly Glu Gly Leu Ser Met Glu Thr Thr Asp Ala Thr Gln
    1745                1750                1755

Lys Thr His Trp Asp Leu Ile His Arg Val Ser Lys Asp Ala Leu
    1760                1765                1770

Leu Ile Thr Leu Cys Asp Ala Glu Phe Lys Asp Arg Asp Asp Phe
    1775                1780                1785

Phe Lys Met Val Ile Leu Trp Arg Lys His Val Leu Ser Cys Arg
    1790                1795                1800

Ile Cys Thr Thr Tyr Gly Thr Asp Leu Tyr Leu Phe Ala Lys Tyr
    1805                1810                1815

His Ala Lys Asp Cys Asn Val Lys Leu Pro Phe Phe Val Arg Ser
    1820                1825                1830

Val Ala Thr Phe Ile Met Gln Gly Ser Lys Leu Ser Gly Ser Glu
    1835                1840                1845

Cys Tyr Ile Leu Leu Thr Leu Gly His His Asn Ser Leu Pro Cys
    1850                1855                1860

His Gly Glu Ile Gln Asn Ser Lys Met Lys Ile Ala Val Cys Asn
    1865                1870                1875

Asp Phe Tyr Ala Ala Lys Lys Leu Asp Asn Lys Ser Ile Glu Ala
    1880                1885                1890

Asn Cys Lys Ser Leu Leu Ser Gly Leu Arg Ile Pro Ile Asn Lys
    1895                1900                1905

Lys Glu Leu Asp Arg Gln Arg Arg Leu Leu Thr Leu Gln Ser Asn
    1910                1915                1920

His Ser Ser Val Ala Thr Val Gly Gly Ser Lys Ile Ile Glu Ser
    1925                1930                1935

Lys Trp Leu Thr Asn Lys Ala Ser Thr Ile Ile Asp Trp Leu Glu
    1940                1945                1950

His Ile Leu Asn Ser Pro Lys Gly Glu Leu Asn Tyr Asp Phe Phe
    1955                1960                1965

Glu Ala Leu Glu Asn Thr Tyr Pro Asn Met Ile Lys Leu Ile Asp
    1970                1975                1980

Asn Leu Gly Asn Ala Glu Ile Lys Lys Leu Ile Lys Val Thr Gly
    1985                1990                1995

Tyr Met Leu Val Ser Lys Lys
    2000                2005
```

-continued

<210> SEQ ID NO 8
<211> LENGTH: 177
<212> TYPE: PRT
<213> ORGANISM: human metapneumovirus

<400> SEQUENCE: 8

```
Met Lys Thr Leu Asp Val Ile Lys Ser Asp Gly Ser Ser Glu Thr Cys
1               5                   10                  15

Asn Gln Leu Lys Lys Ile Ile Lys Lys His Ser Gly Lys Leu Leu Ile
            20                  25                  30

Ala Ser Lys Pro Thr Leu Ala Leu Leu Thr Ser Phe Thr Val Thr Ile
        35                  40                  45

Thr Val Asn Tyr Thr Lys Val Glu Asn Asn Leu Gln Ala Cys Gln Leu
    50                  55                  60

Lys Asn Glu Ser Asp Lys Lys Asp Thr Lys Leu Asn Thr Thr Ser Thr
65                  70                  75                  80

Thr Ile Arg Pro Ile Pro Asp Leu Asn Ala Val Gln Tyr Leu Lys Arg
                85                  90                  95

Leu Ile Gln Lys His Thr Asn Ser Val Thr Lys Asp Arg Asp Thr Cys
            100                 105                 110

Trp Arg Ile His Thr Asn Gln Cys Thr Asn Ile Lys Ile Tyr Lys Phe
        115                 120                 125

Leu Cys Phe Gly Ser Met Asn Ser Thr Asn Thr Asp Cys Glu Glu Pro
    130                 135                 140

Thr Val Leu Cys Asp Lys Lys Ser Lys Thr Met Thr Glu Lys His Arg
145                 150                 155                 160

Lys Ala Glu Cys His Arg Pro His Thr Thr Glu Trp Trp Cys His Tyr
                165                 170                 175

Leu
```

<210> SEQ ID NO 9
<211> LENGTH: 236
<212> TYPE: PRT
<213> ORGANISM: human metapneumovirus

<400> SEQUENCE: 9

```
Met Glu Ala Arg Val Glu Asn Ile Arg Ala Ile Asp Met Phe Lys Ala
1               5                   10                  15

Lys Met Lys Asn Arg Ile Arg Ser Ser Lys Cys His Arg Asn Ala Thr
            20                  25                  30

Leu Ile Leu Ile Gly Ser Thr Ala Pro Ser Met Ala Leu Asn Thr Leu
        35                  40                  45

Leu Ile Ile Asp His Ala Thr Ser Lys Asn Met Thr Lys Val Glu His
    50                  55                  60

Cys Val Asn Met Pro Pro Val Glu Pro Ser Lys Lys Thr Pro Met Thr
65                  70                  75                  80

Ser Ala Ala Asp Pro Asn Thr Lys Pro Asn Pro Gln Gln Ala Thr Gln
                85                  90                  95

Leu Thr Thr Glu Asp Ser Thr Ser Leu Ala Ala Thr Leu Glu Asp His
            100                 105                 110

Leu His Thr Gly Thr Thr Pro Thr Pro Asp Ala Thr Val Ser Gln Gln
        115                 120                 125

Thr Thr Asp Glu His Thr Thr Leu Leu Arg Ser Thr Asn Arg Gln Thr
    130                 135                 140

Thr Gln Thr Thr Ala Glu Lys Lys Pro Thr Arg Ala Thr Thr Lys Lys
```

-continued 145                 150                 155                 160
Glu Thr Thr Thr Arg Thr Thr Ser Thr Ala Ala Thr Gln Thr Leu Asn
                165                 170                 175

Thr Thr Asn Gln Thr Ser Asn Gly Arg Glu Ala Thr Thr Thr Ser Ala
            180                 185                 190

Arg Ser Arg Asn Asn Ala Thr Thr Gln Ser Ser Asp Gln Thr Thr Gln
        195                 200                 205

Ala Ala Asp Pro Ser Ser Gln Ser Gln His Thr Gln Lys Ser Thr Thr
    210                 215                 220

Thr Thr His Asn Thr Asp Thr Ser Ser Pro Ser Ser
225                 230                 235

<210> SEQ ID NO 10
<211> LENGTH: 183
<212> TYPE: PRT
<213> ORGANISM: human metapneumovirus

<400> SEQUENCE: 10

Met Ile Thr Leu Asp Val Ile Lys Ser Asp Gly Ser Ser Lys Thr Cys
1               5                   10                  15

Thr His Leu Lys Lys Ile Ile Lys Asp His Ser Gly Lys Val Leu Ile
            20                  25                  30

Val Leu Lys Leu Ile Leu Ala Leu Leu Thr Phe Leu Thr Val Thr Ile
        35                  40                  45

Thr Ile Asn Tyr Ile Lys Val Glu Asn Asn Leu Gln Ile Cys Gln Ser
    50                  55                  60

Lys Thr Glu Ser Asp Lys Lys Asp Ser Ser Ser Asn Thr Thr Ser Val
65                  70                  75                  80

Thr Thr Lys Thr Thr Leu Asn His Asp Ile Thr Gln Tyr Phe Lys Ser
                85                  90                  95

Leu Ile Gln Arg Tyr Thr Asn Ser Ala Ile Asn Ser Asp Thr Cys Trp
            100                 105                 110

Lys Ile Asn Arg Asn Gln Cys Thr Asn Ile Thr Thr Tyr Lys Phe Leu
        115                 120                 125

Cys Phe Lys Ser Glu Asp Thr Lys Thr Asn Asn Cys Asp Lys Leu Thr
    130                 135                 140

Asp Leu Cys Arg Asn Lys Pro Lys Pro Ala Val Gly Val Tyr His Ile
145                 150                 155                 160

Val Glu Cys His Cys Ile Tyr Thr Val Lys Trp Lys Cys Tyr His Tyr
                165                 170                 175

Pro Thr Asp Glu Thr Gln Ser
            180

<210> SEQ ID NO 11
<211> LENGTH: 236
<212> TYPE: PRT
<213> ORGANISM: human metapneumovirus

<400> SEQUENCE: 11

Met Glu Val Lys Val Glu Asn Ile Arg Thr Ile Asp Met Leu Lys Ala
1               5                   10                  15

Arg Val Lys Asn Arg Val Ala Arg Ser Lys Cys Phe Lys Asn Ala Ser
            20                  25                  30

Leu Val Leu Ile Gly Ile Thr Thr Leu Ser Ile Ala Leu Asn Ile Tyr
        35                  40                  45

Leu Ile Ile Asn Tyr Lys Met Gln Lys Asn Thr Ser Glu Ser Glu His

```
                50                  55                  60
His Thr Ser Ser Ser Pro Met Glu Ser Ser Arg Glu Thr Pro Thr Val
 65                  70                  75                  80

Pro Thr Asp Asn Ser Asp Thr Asn Ser Ser Pro Gln His Pro Thr Gln
                 85                  90                  95

Gln Ser Thr Glu Gly Ser Thr Leu Tyr Phe Ala Ala Ser Ala Ser Ser
            100                 105                 110

Pro Glu Thr Glu Pro Thr Ser Thr Pro Asp Thr Thr Asn Arg Pro Pro
        115                 120                 125

Phe Val Asp Thr His Thr Thr Pro Pro Ser Ala Ser Arg Thr Lys Thr
130                 135                 140

Ser Pro Ala Val His Thr Lys Asn Asn Pro Arg Thr Ser Ser Arg Thr
145                 150                 155                 160

His Ser Pro Pro Arg Ala Thr Thr Arg Thr Ala Arg Arg Thr Thr Thr
                165                 170                 175

Leu Arg Thr Ser Ser Thr Arg Lys Arg Pro Ser Thr Ala Ser Val Gln
            180                 185                 190

Pro Asp Ile Ser Ala Thr Thr His Lys Asn Glu Glu Ala Ser Pro Ala
        195                 200                 205

Ser Pro Gln Thr Ser Ala Ser Thr Thr Arg Ile Gln Arg Lys Ser Val
    210                 215                 220

Glu Ala Asn Thr Ser Thr Thr Tyr Asn Gln Thr Ser
225                 230                 235

<210> SEQ ID NO 12
<211> LENGTH: 2005
<212> TYPE: PRT
<213> ORGANISM: human metapneumovirus

<400> SEQUENCE: 12

Met Asp Pro Leu Asn Glu Ser Thr Val Asn Val Tyr Leu Pro Asp Ser
 1               5                  10                  15

Tyr Leu Lys Gly Val Ile Ser Phe Ser Glu Thr Asn Ala Ile Gly Ser
             20                  25                  30

Cys Leu Leu Lys Arg Pro Tyr Leu Lys Asn Asp Asn Thr Ala Lys Val
         35                  40                  45

Ala Ile Glu Asn Pro Val Ile Glu His Val Arg Leu Lys Asn Ala Val
     50                  55                  60

Asn Ser Lys Met Lys Ile Ser Asp Tyr Lys Ile Val Glu Pro Val Asn
 65                  70                  75                  80

Met Gln His Glu Ile Met Lys Asn Val His Ser Cys Glu Leu Thr Leu
                 85                  90                  95

Leu Lys Gln Phe Leu Thr Arg Ser Lys Asn Ile Ser Thr Leu Lys Leu
            100                 105                 110

Asn Met Ile Cys Asp Trp Leu Gln Leu Lys Ser Thr Ser Asp Asp Thr
        115                 120                 125

Ser Ile Leu Ser Phe Ile Asp Val Glu Phe Ile Pro Ser Trp Val Ser
    130                 135                 140

Asn Trp Phe Ser Asn Trp Tyr Asn Leu Asn Lys Leu Ile Leu Glu Phe
145                 150                 155                 160

Arg Lys Glu Glu Val Ile Arg Thr Gly Ser Ile Leu Cys Arg Ser Leu
                165                 170                 175

Gly Lys Leu Val Phe Val Val Ser Ser Tyr Gly Cys Ile Val Lys Ser
            180                 185                 190
```

-continued

```
Asn Lys Ser Lys Arg Val Ser Phe Phe Thr Tyr Asn Gln Leu Leu Thr
        195                 200                 205

Trp Lys Asp Val Met Leu Ser Arg Phe Asn Ala Asn Phe Cys Ile Trp
    210                 215                 220

Val Ser Asn Ser Leu Asn Glu Asn Gln Glu Gly Leu Gly Leu Arg Ser
225                 230                 235                 240

Asn Leu Gln Gly Ile Leu Thr Asn Lys Leu Tyr Glu Thr Val Asp Tyr
                245                 250                 255

Met Leu Ser Leu Cys Cys Asn Glu Gly Phe Ser Leu Val Lys Glu Phe
            260                 265                 270

Glu Gly Phe Ile Met Ser Glu Ile Leu Arg Ile Thr Glu His Ala Gln
        275                 280                 285

Phe Ser Thr Arg Phe Arg Asn Thr Leu Asn Gly Leu Thr Asp Gln
    290                 295                 300

Leu Thr Lys Leu Lys Asn Lys Asn Arg Leu Arg Val His Gly Thr Val
305                 310                 315                 320

Leu Glu Asn Asn Asp Tyr Pro Met Tyr Glu Val Leu Lys Leu Leu
                325                 330                 335

Gly Asp Thr Leu Arg Cys Ile Lys Leu Leu Ile Asn Lys Asn Leu Glu
            340                 345                 350

Asn Ala Ala Glu Leu Tyr Tyr Ile Phe Arg Ile Phe Gly His Pro Met
        355                 360                 365

Val Asp Glu Arg Asp Ala Met Asp Ala Val Lys Leu Asn Asn Glu Ile
    370                 375                 380

Thr Lys Ile Leu Arg Trp Glu Ser Leu Thr Glu Leu Arg Gly Ala Phe
385                 390                 395                 400

Ile Leu Arg Ile Ile Lys Gly Phe Val Asp Asn Asn Lys Arg Trp Pro
                405                 410                 415

Lys Ile Lys Asn Leu Lys Val Leu Ser Lys Arg Trp Thr Met Tyr Phe
            420                 425                 430

Lys Ala Lys Ser Tyr Pro Ser Gln Leu Glu Leu Ser Glu Gln Asp Phe
        435                 440                 445

Leu Glu Leu Ala Ala Ile Gln Phe Glu Gln Glu Phe Ser Val Pro Glu
    450                 455                 460

Lys Thr Asn Leu Glu Met Val Leu Asn Asp Lys Ala Ile Ser Pro Pro
465                 470                 475                 480

Lys Arg Leu Ile Trp Ser Val Tyr Pro Lys Asn Tyr Leu Pro Glu Lys
                485                 490                 495

Ile Lys Asn Arg Tyr Leu Glu Glu Thr Phe Asn Ala Ser Asp Ser Leu
            500                 505                 510

Lys Thr Arg Arg Val Leu Glu Tyr Tyr Leu Lys Asp Asn Lys Phe Asp
        515                 520                 525

Gln Lys Glu Leu Lys Ser Tyr Val Val Lys Gln Glu Tyr Leu Asn Asp
    530                 535                 540

Lys Asp His Ile Val Ser Leu Thr Gly Lys Glu Arg Glu Leu Ser Val
545                 550                 555                 560

Gly Arg Met Phe Ala Met Gln Pro Gly Lys Gln Arg Gln Ile Gln Ile
                565                 570                 575

Leu Ala Glu Lys Leu Leu Ala Asp Asn Ile Val Pro Phe Phe Pro Glu
            580                 585                 590

Thr Leu Thr Lys Tyr Gly Asp Leu Asp Leu Gln Arg Ile Met Glu Ile
        595                 600                 605

Lys Ser Glu Leu Ser Ser Ile Lys Thr Arg Arg Asn Asp Ser Tyr Asn
```

```
                610                 615                 620
Asn Tyr Ile Ala Arg Ala Ser Ile Val Thr Asp Leu Ser Lys Phe Asn
625                 630                 635                 640

Gln Ala Phe Arg Tyr Glu Thr Thr Ala Ile Cys Ala Asp Val Ala Asp
                645                 650                 655

Glu Leu His Gly Thr Gln Ser Leu Phe Cys Trp Leu His Leu Ile Val
                660                 665                 670

Pro Met Thr Thr Met Ile Cys Ala Tyr Arg His Ala Pro Pro Glu Thr
                675                 680                 685

Lys Gly Glu Tyr Asp Ile Asp Lys Ile Glu Gln Ser Gly Leu Tyr
690                 695                 700

Arg Tyr His Met Gly Gly Ile Glu Gly Trp Cys Gln Lys Leu Trp Thr
705                 710                 715                 720

Met Glu Ala Ile Ser Leu Leu Asp Val Val Ser Val Lys Thr Arg Cys
                725                 730                 735

Gln Met Thr Ser Leu Leu Asn Gly Asp Asn Gln Ser Ile Asp Val Ser
                740                 745                 750

Lys Pro Val Lys Leu Ser Glu Gly Leu Asp Glu Val Lys Ala Asp Tyr
                755                 760                 765

Ser Leu Ala Val Lys Met Leu Lys Glu Ile Arg Asp Ala Tyr Arg Asn
                770                 775                 780

Ile Gly His Lys Leu Lys Glu Gly Glu Thr Tyr Ile Ser Arg Asp Leu
785                 790                 795                 800

Gln Phe Ile Ser Lys Val Ile Gln Ser Glu Gly Val Met His Pro Thr
                805                 810                 815

Pro Ile Lys Lys Ile Leu Arg Val Gly Pro Trp Ile Asn Thr Ile Leu
                820                 825                 830

Asp Asp Ile Lys Thr Ser Ala Glu Ser Ile Gly Ser Leu Cys Gln Glu
                835                 840                 845

Leu Glu Phe Arg Gly Glu Ser Ile Ile Val Ser Leu Ile Leu Arg Asn
                850                 855                 860

Phe Trp Leu Tyr Asn Leu Tyr Met His Glu Ser Lys Gln His Pro Leu
865                 870                 875                 880

Ala Gly Lys Gln Leu Phe Lys Gln Leu Asn Lys Thr Leu Thr Ser Val
                885                 890                 895

Gln Arg Phe Phe Glu Ile Lys Lys Glu Asn Glu Val Val Asp Leu Trp
                900                 905                 910

Met Asn Ile Pro Met Gln Phe Gly Gly Asp Pro Val Val Phe Tyr
                915                 920                 925

Arg Ser Phe Tyr Arg Arg Thr Pro Asp Phe Leu Thr Glu Ala Ile Ser
930                 935                 940

His Val Asp Ile Leu Leu Arg Ile Ser Ala Asn Ile Arg Asn Glu Ala
945                 950                 955                 960

Lys Ile Ser Phe Phe Lys Ala Leu Leu Ser Ile Glu Lys Asn Glu Arg
                965                 970                 975

Ala Thr Leu Thr Thr Leu Met Arg Asp Pro Gln Ala Val Gly Ser Glu
                980                 985                 990

Arg Gln Ala Lys Val Thr Ser Asp Ile Asn Arg Thr Ala Val Thr Ser
                995                 1000                1005

Ile Leu Ser Leu Ser Pro Asn Gln Leu Phe Ser Asp Ser Ala Ile
        1010                1015                1020

His Tyr Ser Arg Asn Glu Glu Glu Val Gly Ile Ile Ala Asp Asn
        1025                1030                1035
```

-continued

```
Ile Thr Pro Val Tyr Pro His Gly Leu Arg Val Leu Tyr Glu Ser
    1040            1045                1050

Leu Pro Phe His Lys Ala Glu Lys Val Val Asn Met Ile Ser Gly
    1055            1060                1065

Thr Lys Ser Ile Thr Asn Leu Leu Gln Arg Thr Ser Ala Ile Asn
    1070            1075                1080

Gly Glu Asp Ile Asp Arg Ala Val Ser Met Met Leu Glu Asn Leu
    1085            1090                1095

Gly Leu Leu Ser Arg Ile Leu Ser Val Val Val Asp Ser Ile Glu
    1100            1105                1110

Ile Pro Thr Lys Ser Asn Gly Arg Leu Ile Cys Cys Gln Ile Ser
    1115            1120                1125

Arg Thr Leu Arg Glu Thr Ser Trp Asn Asn Met Glu Ile Val Gly
    1130            1135                1140

Val Thr Ser Pro Ser Ile Thr Thr Cys Met Asp Val Ile Tyr Ala
    1145            1150                1155

Thr Ser Ser His Leu Lys Gly Ile Ile Ile Glu Lys Phe Ser Thr
    1160            1165                1170

Asp Arg Thr Thr Arg Gly Gln Arg Gly Pro Lys Ser Pro Trp Val
    1175            1180                1185

Gly Ser Ser Thr Gln Glu Lys Lys Leu Val Pro Val Tyr Asn Arg
    1190            1195                1200

Gln Ile Leu Ser Lys Gln Gln Arg Glu Gln Leu Glu Ala Ile Gly
    1205            1210                1215

Lys Met Arg Trp Val Tyr Lys Gly Thr Pro Gly Leu Arg Arg Leu
    1220            1225                1230

Leu Asn Lys Ile Cys Leu Gly Ser Leu Gly Ile Ser Tyr Lys Cys
    1235            1240                1245

Val Lys Pro Leu Leu Pro Arg Phe Met Ser Val Asn Phe Leu His
    1250            1255                1260

Arg Leu Ser Val Ser Ser Arg Pro Met Glu Phe Pro Ala Ser Val
    1265            1270                1275

Pro Ala Tyr Arg Thr Thr Asn Tyr His Phe Asp Thr Ser Pro Ile
    1280            1285                1290

Asn Gln Ala Leu Ser Glu Arg Phe Gly Asn Glu Asp Ile Asn Leu
    1295            1300                1305

Val Phe Gln Asn Ala Ile Ser Cys Gly Ile Ser Ile Met Ser Val
    1310            1315                1320

Val Glu Gln Leu Thr Gly Arg Ser Pro Lys Gln Leu Val Leu Ile
    1325            1330                1335

Pro Gln Leu Glu Glu Ile Asp Ile Met Pro Pro Pro Val Phe Gln
    1340            1345                1350

Gly Lys Phe Asn Tyr Lys Leu Val Asp Lys Ile Thr Ser Asp Gln
    1355            1360                1365

His Ile Phe Ser Pro Asp Lys Ile Asp Met Leu Thr Leu Gly Lys
    1370            1375                1380

Met Leu Met Pro Thr Ile Lys Gly Gln Lys Thr Asp Gln Phe Leu
    1385            1390                1395

Asn Lys Arg Glu Asn Tyr Phe His Gly Asn Asn Leu Ile Glu Ser
    1400            1405                1410

Leu Ser Ala Ala Leu Ala Cys His Trp Cys Gly Ile Leu Thr Glu
    1415            1420                1425
```

-continued

```
Gln Cys Ile Glu Asn Asn Ile Phe Lys Lys Asp Trp Gly Asp Gly
1430                1435                1440

Phe Ile Ser Asp His Ala Phe Met Asp Phe Lys Ile Phe Leu Cys
1445                1450                1455

Val Phe Lys Thr Lys Leu Leu Cys Ser Trp Gly Ser Gln Gly Lys
1460                1465                1470

Asn Ile Lys Asp Glu Asp Ile Val Asp Glu Ser Ile Asp Lys Leu
1475                1480                1485

Leu Arg Ile Asp Asn Thr Phe Trp Arg Met Phe Ser Lys Val Met
1490                1495                1500

Phe Glu Ser Lys Val Lys Lys Arg Ile Met Leu Tyr Asp Val Lys
1505                1510                1515

Phe Leu Ser Leu Val Gly Tyr Ile Gly Phe Lys Asn Trp Phe Ile
1520                1525                1530

Glu Gln Leu Arg Ser Ala Glu Leu His Glu Val Pro Trp Ile Val
1535                1540                1545

Asn Ala Glu Gly Asp Leu Val Glu Ile Lys Ser Ile Lys Ile Tyr
1550                1555                1560

Leu Gln Leu Ile Glu Gln Ser Leu Phe Leu Arg Ile Thr Val Leu
1565                1570                1575

Asn Tyr Thr Asp Met Ala His Ala Leu Thr Arg Leu Ile Arg Lys
1580                1585                1590

Lys Leu Met Cys Asp Asn Ala Leu Leu Thr Pro Ile Pro Ser Pro
1595                1600                1605

Met Val Asn Leu Thr Gln Val Ile Asp Pro Thr Glu Gln Leu Ala
1610                1615                1620

Tyr Phe Pro Lys Ile Thr Phe Glu Arg Leu Lys Asn Tyr Asp Thr
1625                1630                1635

Ser Ser Asn Tyr Ala Lys Gly Lys Leu Thr Arg Asn Tyr Met Ile
1640                1645                1650

Leu Leu Pro Trp Gln His Val Asn Arg Tyr Asn Phe Val Phe Ser
1655                1660                1665

Ser Thr Gly Cys Lys Val Ser Leu Lys Thr Cys Ile Gly Lys Leu
1670                1675                1680

Met Lys Asp Leu Asn Pro Lys Val Leu Tyr Phe Ile Gly Glu Gly
1685                1690                1695

Ala Gly Asn Trp Met Ala Arg Thr Ala Cys Glu Tyr Pro Asp Ile
1700                1705                1710

Lys Phe Val Tyr Arg Ser Leu Lys Asp Asp Leu Asp His His Tyr
1715                1720                1725

Pro Leu Glu Tyr Gln Arg Val Ile Gly Glu Leu Ser Arg Ile Ile
1730                1735                1740

Asp Ser Gly Glu Gly Leu Ser Met Glu Thr Thr Asp Ala Thr Gln
1745                1750                1755

Lys Thr His Trp Asp Leu Ile His Arg Val Ser Lys Asp Ala Leu
1760                1765                1770

Leu Ile Thr Leu Cys Asp Ala Glu Phe Lys Asp Arg Asp Asp Phe
1775                1780                1785

Phe Lys Met Val Ile Leu Trp Arg Lys His Val Leu Ser Cys Arg
1790                1795                1800

Ile Cys Thr Thr Tyr Gly Thr Asp Leu Tyr Leu Phe Ala Lys Tyr
1805                1810                1815

His Ala Lys Asp Cys Asn Val Lys Leu Pro Phe Phe Val Arg Ser
```

```
                1820              1825              1830
Val Ala Thr Phe Ile Met Gln Gly Ser Lys Leu Ser Gly Ser Glu
            1835              1840              1845

Cys Tyr Ile Leu Leu Thr Leu Gly His His Asn Asn Leu Pro Cys
    1850              1855              1860

His Gly Glu Ile Gln Asn Ser Lys Met Lys Ile Ala Val Cys Asn
    1865              1870              1875

Asp Phe Tyr Ala Ala Lys Lys Leu Asp Asn Lys Ser Ile Glu Ala
    1880              1885              1890

Asn Cys Lys Ser Leu Leu Ser Gly Leu Arg Ile Pro Ile Asn Lys
    1895              1900              1905

Lys Glu Leu Asn Arg Gln Arg Arg Leu Leu Thr Leu Gln Ser Asn
    1910              1915              1920

His Ser Ser Val Ala Thr Val Gly Gly Ser Lys Val Ile Glu Ser
    1925              1930              1935

Lys Trp Leu Thr Asn Lys Ala Asn Thr Ile Ile Asp Trp Leu Glu
    1940              1945              1950

His Ile Leu Asn Ser Pro Lys Gly Glu Leu Asn Tyr Asp Phe Phe
    1955              1960              1965

Glu Ala Leu Glu Asn Thr Tyr Pro Asn Met Ile Lys Leu Ile Asp
    1970              1975              1980

Asn Leu Gly Asn Ala Glu Ile Lys Lys Leu Ile Lys Val Thr Gly
    1985              1990              1995

Tyr Met Leu Val Ser Lys Lys
    2000              2005

<210> SEQ ID NO 13
<211> LENGTH: 2165
<212> TYPE: PRT
<213> ORGANISM: human respiratory syncytial virus strain A2

<400> SEQUENCE: 13

Met Asp Pro Ile Ile Asn Gly Asn Ser Ala Asn Val Tyr Leu Thr Asp
1               5                   10                  15

Ser Tyr Leu Lys Gly Val Ile Ser Phe Ser Glu Cys Asn Ala Leu Gly
                20                  25                  30

Ser Tyr Ile Phe Asn Gly Pro Tyr Leu Lys Asn Asp Tyr Thr Asn Leu
            35                  40                  45

Ile Ser Arg Gln Asn Pro Leu Ile Glu His Met Asn Leu Lys Lys Leu
        50                  55                  60

Asn Ile Thr Gln Ser Leu Ile Ser Lys Tyr His Lys Gly Glu Ile Lys
65                  70                  75                  80

Leu Glu Glu Pro Thr Tyr Phe Gln Ser Leu Leu Met Thr Tyr Lys Ser
                85                  90                  95

Met Thr Ser Ser Glu Gln Ile Ala Thr Thr Asn Leu Leu Lys Lys Ile
            100                 105                 110

Ile Arg Arg Ala Ile Glu Ile Ser Asp Val Lys Val Tyr Ala Ile Leu
        115                 120                 125

Asn Lys Leu Gly Leu Lys Glu Lys Asp Lys Ile Lys Ser Asn Asn Gly
    130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175
```

-continued

```
His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270

Lys Asp Ile Ser Leu Ser Arg Leu Asn Val Cys Leu Ile Thr Trp Ile
        275                 280                 285

Ser Asn Cys Leu Asn Thr Leu Asn Lys Ser Leu Gly Leu Arg Cys Gly
    290                 295                 300

Phe Asn Asn Val Ile Leu Thr Gln Leu Phe Leu Tyr Gly Asp Cys Ile
305                 310                 315                 320

Leu Lys Leu Phe His Asn Glu Gly Phe Tyr Ile Ile Lys Glu Val Glu
                325                 330                 335

Gly Phe Ile Met Ser Leu Ile Leu Asn Ile Thr Glu Glu Asp Gln Phe
            340                 345                 350

Arg Lys Arg Phe Tyr Asn Ser Met Leu Asn Asn Ile Thr Asp Ala Ala
        355                 360                 365

Asn Lys Ala Gln Lys Asn Leu Leu Ser Arg Val Cys His Thr Leu Leu
    370                 375                 380

Asp Lys Thr Val Ser Asp Asn Ile Ile Asn Gly Arg Trp Ile Ile Leu
385                 390                 395                 400

Leu Ser Lys Phe Leu Lys Leu Ile Lys Leu Ala Gly Asp Asn Asn Leu
                405                 410                 415

Asn Asn Leu Ser Glu Leu Tyr Phe Leu Phe Arg Ile Phe Gly His Pro
            420                 425                 430

Met Val Asp Glu Arg Gln Ala Met Asp Ala Val Lys Ile Asn Cys Asn
        435                 440                 445

Glu Thr Lys Phe Tyr Leu Leu Ser Ser Leu Ser Met Leu Arg Gly Ala
    450                 455                 460

Phe Ile Tyr Arg Ile Ile Lys Gly Phe Val Asn Asn Tyr Asn Arg Trp
465                 470                 475                 480

Pro Thr Leu Arg Asn Ala Ile Val Leu Pro Leu Arg Trp Leu Thr Tyr
                485                 490                 495

Tyr Lys Leu Asn Thr Tyr Pro Ser Leu Leu Glu Leu Thr Glu Arg Asp
            500                 505                 510

Leu Ile Val Leu Ser Gly Leu Arg Phe Tyr Arg Glu Phe Arg Leu Pro
        515                 520                 525

Lys Lys Val Asp Leu Glu Met Ile Ile Asn Asp Lys Ala Ile Ser Pro
    530                 535                 540

Pro Lys Asn Leu Ile Trp Thr Ser Phe Pro Arg Asn Tyr Met Pro Ser
545                 550                 555                 560

His Ile Gln Asn Tyr Ile Glu His Glu Lys Leu Lys Phe Ser Glu Ser
                565                 570                 575

Asp Lys Ser Arg Arg Val Leu Glu Tyr Tyr Leu Arg Asp Asn Lys Phe
            580                 585                 590

Asn Glu Cys Asp Leu Tyr Asn Cys Val Val Asn Gln Ser Tyr Leu Asn
```

-continued

```
                595                 600                 605
Asn Pro Asn His Val Val Ser Leu Thr Gly Lys Glu Arg Glu Leu Ser
            610                 615                 620
Val Gly Arg Met Phe Ala Met Gln Pro Gly Met Phe Arg Gln Val Gln
625                 630                 635                 640
Ile Leu Ala Glu Lys Met Ile Ala Glu Asn Ile Leu Gln Phe Phe Pro
                645                 650                 655
Glu Ser Leu Thr Arg Tyr Gly Asp Leu Glu Leu Gln Lys Ile Leu Glu
            660                 665                 670
Leu Lys Ala Gly Ile Ser Asn Lys Ser Asn Arg Tyr Asn Asp Asn Tyr
            675                 680                 685
Asn Asn Tyr Ile Ser Lys Cys Ser Ile Ile Thr Asp Leu Ser Lys Phe
        690                 695                 700
Asn Gln Ala Phe Arg Tyr Glu Thr Ser Cys Ile Cys Ser Asp Val Leu
705                 710                 715                 720
Asp Glu Leu His Gly Val Gln Ser Leu Phe Ser Trp Leu His Leu Thr
                725                 730                 735
Ile Pro His Val Thr Ile Ile Cys Thr Tyr Arg His Ala Pro Pro Tyr
            740                 745                 750
Ile Gly Asp His Ile Val Asp Leu Asn Asn Val Asp Glu Gln Ser Gly
        755                 760                 765
Leu Tyr Arg Tyr His Met Gly Gly Ile Glu Gly Trp Cys Gln Lys Leu
        770                 775                 780
Trp Thr Ile Glu Ala Ile Ser Leu Leu Asp Leu Ile Ser Leu Lys Gly
785                 790                 795                 800
Lys Phe Ser Ile Thr Ala Leu Ile Asn Gly Asp Asn Gln Ser Ile Asp
                805                 810                 815
Ile Ser Lys Pro Ile Arg Leu Met Glu Gly Gln Thr His Ala Gln Ala
            820                 825                 830
Asp Tyr Leu Leu Ala Leu Asn Ser Leu Lys Leu Leu Tyr Lys Glu Tyr
            835                 840                 845
Ala Gly Ile Gly His Lys Leu Lys Gly Thr Glu Thr Tyr Ile Ser Arg
850                 855                 860
Asp Met Gln Phe Met Ser Lys Thr Ile Gln His Asn Gly Val Tyr Tyr
865                 870                 875                 880
Pro Ala Ser Ile Lys Lys Val Leu Arg Val Gly Pro Trp Ile Asn Thr
                885                 890                 895
Ile Leu Asp Asp Phe Lys Val Ser Leu Glu Ser Ile Gly Ser Leu Thr
            900                 905                 910
Gln Glu Leu Glu Tyr Arg Gly Glu Ser Leu Leu Cys Ser Leu Ile Phe
            915                 920                 925
Arg Asn Val Trp Leu Tyr Asn Gln Ile Ala Leu Gln Leu Lys Asn His
        930                 935                 940
Ala Leu Cys Asn Asn Lys Leu Tyr Leu Asp Ile Leu Lys Val Leu Lys
945                 950                 955                 960
His Leu Lys Thr Phe Phe Asn Leu Asp Asn Ile Asp Thr Ala Leu Thr
                965                 970                 975
Leu Tyr Met Asn Leu Pro Met Leu Phe Gly Gly Gly Asp Pro Asn Leu
            980                 985                 990
Leu Tyr Arg Ser Phe Tyr Arg Arg Thr Pro Asp Phe Leu Thr Glu Ala
        995                 1000                1005
Ile Val His Ser Val Phe Ile Leu Ser Tyr Tyr Thr Asn His Asp
    1010                1015                1020
```

-continued

```
Leu Lys Asp Lys Leu Gln Asp Leu Ser Asp Asp Arg Leu Asn Lys
    1025                1030                1035

Phe Leu Thr Cys Ile Ile Thr Phe Asp Lys Asn Pro Asn Ala Glu
    1040                1045                1050

Phe Val Thr Leu Met Arg Asp Pro Gln Ala Leu Gly Ser Glu Arg
    1055                1060                1065

Gln Ala Lys Ile Thr Ser Glu Ile Asn Arg Leu Ala Val Thr Glu
    1070                1075                1080

Val Leu Ser Thr Ala Pro Asn Lys Ile Phe Ser Lys Ser Ala Gln
    1085                1090                1095

His Tyr Thr Thr Thr Glu Ile Asp Leu Asn Asp Ile Met Gln Asn
    1100                1105                1110

Ile Glu Pro Thr Tyr Pro His Gly Leu Arg Val Val Tyr Glu Ser
    1115                1120                1125

Leu Pro Phe Tyr Lys Ala Glu Lys Ile Val Asn Leu Ile Ser Gly
    1130                1135                1140

Thr Lys Ser Ile Thr Asn Ile Leu Glu Lys Thr Ser Ala Ile Asp
    1145                1150                1155

Leu Thr Asp Ile Asp Arg Ala Thr Glu Met Met Arg Lys Asn Ile
    1160                1165                1170

Thr Leu Leu Ile Arg Ile Leu Pro Leu Asp Cys Asn Arg Asp Lys
    1175                1180                1185

Arg Glu Ile Leu Ser Met Glu Asn Leu Ser Ile Thr Glu Leu Ser
    1190                1195                1200

Lys Tyr Val Arg Glu Arg Ser Trp Ser Leu Ser Asn Ile Val Gly
    1205                1210                1215

Val Thr Ser Pro Ser Ile Met Tyr Thr Met Asp Ile Lys Tyr Thr
    1220                1225                1230

Thr Ser Thr Ile Ser Ser Gly Ile Ile Ile Glu Lys Tyr Asn Val
    1235                1240                1245

Asn Ser Leu Thr Arg Gly Glu Arg Gly Pro Thr Lys Pro Trp Val
    1250                1255                1260

Gly Ser Ser Thr Gln Glu Lys Lys Thr Met Pro Val Tyr Asn Arg
    1265                1270                1275

Gln Val Leu Thr Lys Lys Gln Arg Asp Gln Ile Asp Leu Leu Ala
    1280                1285                1290

Lys Leu Asp Trp Val Tyr Ala Ser Ile Asp Asn Lys Asp Glu Phe
    1295                1300                1305

Met Glu Glu Leu Ser Ile Gly Thr Leu Gly Leu Thr Tyr Glu Lys
    1310                1315                1320

Ala Lys Lys Leu Phe Pro Gln Tyr Leu Ser Val Asn Tyr Leu His
    1325                1330                1335

Arg Leu Thr Val Ser Ser Arg Pro Cys Glu Phe Pro Ala Ser Ile
    1340                1345                1350

Pro Ala Tyr Arg Thr Thr Asn Tyr His Phe Asp Thr Ser Pro Ile
    1355                1360                1365

Asn Arg Ile Leu Thr Glu Lys Tyr Gly Asp Glu Asp Ile Asp Ile
    1370                1375                1380

Val Phe Gln Asn Cys Ile Ser Phe Gly Leu Ser Leu Met Ser Val
    1385                1390                1395

Val Glu Gln Phe Thr Asn Val Cys Pro Asn Arg Ile Ile Leu Ile
    1400                1405                1410
```

```
Pro Lys Leu Asn Glu Ile His Leu Met Lys Pro Pro Ile Phe Thr
1415                1420                1425

Gly Asp Val Asp Ile His Lys Leu Lys Gln Val Ile Gln Lys Gln
    1430                1435                1440

His Met Phe Leu Pro Asp Lys Ile Ser Leu Thr Gln Tyr Val Glu
1445                1450                1455

Leu Phe Leu Ser Asn Lys Thr Leu Lys Ser Gly Ser His Val Asn
    1460                1465                1470

Ser Asn Leu Ile Leu Ala His Lys Ile Ser Asp Tyr Phe His Asn
1475                1480                1485

Thr Tyr Ile Leu Ser Thr Asn Leu Ala Gly His Trp Ile Leu Ile
    1490                1495                1500

Ile Gln Leu Met Lys Asp Ser Lys Gly Ile Phe Glu Lys Asp Trp
1505                1510                1515

Gly Glu Gly Tyr Ile Thr Asp His Met Phe Ile Asn Leu Lys Val
    1520                1525                1530

Phe Phe Asn Ala Tyr Lys Thr Tyr Leu Leu Cys Phe His Lys Gly
1535                1540                1545

Tyr Gly Lys Ala Lys Leu Glu Cys Asp Met Asn Thr Ser Asp Leu
    1550                1555                1560

Leu Cys Val Leu Glu Leu Ile Asp Ser Ser Tyr Trp Lys Ser Met
1565                1570                1575

Ser Lys Val Phe Leu Glu Gln Lys Val Ile Lys Tyr Ile Leu Ser
    1580                1585                1590

Gln Asp Ala Ser Leu His Arg Val Lys Gly Cys His Ser Phe Lys
1595                1600                1605

Leu Trp Phe Leu Lys Arg Leu Asn Val Ala Glu Phe Thr Val Cys
    1610                1615                1620

Pro Trp Val Val Asn Ile Asp Tyr His Pro Thr His Met Lys Ala
1625                1630                1635

Ile Leu Thr Tyr Ile Asp Leu Val Arg Met Gly Leu Ile Asn Ile
    1640                1645                1650

Asp Arg Ile His Ile Lys Asn Lys His Lys Phe Asn Asp Glu Phe
1655                1660                1665

Tyr Thr Ser Asn Leu Phe Tyr Ile Asn Tyr Asn Phe Ser Asp Asn
    1670                1675                1680

Thr His Leu Leu Thr Lys His Ile Arg Ile Ala Asn Ser Glu Leu
1685                1690                1695

Glu Asn Asn Tyr Asn Lys Leu Tyr His Pro Thr Pro Glu Thr Leu
    1700                1705                1710

Glu Asn Ile Leu Ala Asn Pro Ile Lys Ser Asn Asp Lys Lys Thr
1715                1720                1725

Leu Asn Asp Tyr Cys Ile Gly Lys Asn Val Asp Ser Ile Met Leu
    1730                1735                1740

Pro Leu Leu Ser Asn Lys Lys Leu Ile Lys Ser Ser Ala Met Ile
1745                1750                1755

Arg Thr Asn Tyr Ser Lys Gln Asp Leu Tyr Asn Leu Phe Pro Met
    1760                1765                1770

Val Val Ile Asp Arg Ile Ile Asp His Ser Gly Asn Thr Ala Lys
1775                1780                1785

Ser Asn Gln Leu Tyr Thr Thr Thr Ser His Gln Ile Ser Leu Val
    1790                1795                1800

His Asn Ser Thr Ser Leu Tyr Cys Met Leu Pro Trp His His Ile
```

```
                    1805                1810                1815

Asn Arg Phe Asn Phe Val Phe Ser Ser Thr Gly Cys Lys Ile Ser
    1820                1825                1830

Ile Glu Tyr Ile Leu Lys Asp Leu Lys Ile Lys Asp Pro Asn Cys
    1835                1840                1845

Ile Ala Phe Ile Gly Glu Gly Ala Gly Asn Leu Leu Leu Arg Thr
    1850                1855                1860

Val Val Glu Leu His Pro Asp Ile Arg Tyr Ile Tyr Arg Ser Leu
    1865                1870                1875

Lys Asp Cys Asn Asp His Ser Leu Pro Ile Glu Phe Leu Arg Leu
    1880                1885                1890

Tyr Asn Gly His Ile Asn Ile Asp Tyr Gly Glu Asn Leu Thr Ile
    1895                1900                1905

Pro Ala Thr Asp Ala Thr Asn Asn Ile His Trp Ser Tyr Leu His
    1910                1915                1920

Ile Lys Phe Ala Glu Pro Ile Ser Leu Phe Val Cys Asp Ala Glu
    1925                1930                1935

Leu Ser Val Thr Val Asn Trp Ser Lys Ile Ile Glu Trp Ser
    1940                1945                1950

Lys His Val Arg Lys Cys Lys Tyr Cys Ser Ser Val Asn Lys Cys
    1955                1960                1965

Met Leu Ile Val Lys Tyr His Ala Gln Asp Asp Ile Asp Phe Lys
    1970                1975                1980

Leu Asp Asn Ile Thr Ile Leu Lys Thr Tyr Val Cys Leu Gly Ser
    1985                1990                1995

Lys Leu Lys Gly Ser Glu Val Tyr Leu Val Leu Thr Ile Gly Pro
    2000                2005                2010

Ala Asn Ile Phe Pro Val Phe Asn Val Val Gln Asn Ala Lys Leu
    2015                2020                2025

Ile Leu Ser Arg Thr Lys Asn Phe Ile Met Pro Lys Lys Ala Asp
    2030                2035                2040

Lys Glu Ser Ile Asp Ala Asn Ile Lys Ser Leu Ile Pro Phe Leu
    2045                2050                2055

Cys Tyr Pro Ile Thr Lys Lys Gly Ile Asn Thr Ala Leu Ser Lys
    2060                2065                2070

Leu Lys Ser Val Val Ser Gly Asp Ile Leu Ser Tyr Ser Ile Ala
    2075                2080                2085

Gly Arg Asn Glu Val Phe Ser Asn Lys Leu Ile Asn His Lys His
    2090                2095                2100

Met Asn Ile Leu Lys Trp Phe Asn His Val Leu Asn Phe Arg Ser
    2105                2110                2115

Thr Glu Leu Asn Tyr Asn His Leu Tyr Met Val Glu Ser Thr Tyr
    2120                2125                2130

Pro Tyr Leu Ser Glu Leu Leu Asn Ser Leu Thr Thr Asn Glu Leu
    2135                2140                2145

Lys Lys Leu Ile Lys Ile Thr Gly Ser Leu Leu Tyr Asn Phe His
    2150                2155                2160

Asn Glu
    2165

<210> SEQ ID NO 14
<211> LENGTH: 2233
<212> TYPE: PRT
<213> ORGANISM: human parainfluenza virus 3
```

<400> SEQUENCE: 14

```
Met Asp Thr Glu Ser Asn Asn Gly Thr Val Ser Asp Ile Leu Tyr Pro
1               5                   10                  15

Glu Cys His Leu Asn Ser Pro Ile Val Lys Gly Lys Ile Ala Gln Leu
            20                  25                  30

His Thr Ile Met Ser Leu Pro Gln Pro Tyr Asp Met Asp Asp Asp Ser
        35                  40                  45

Ile Leu Val Ile Thr Arg Gln Lys Ile Lys Leu Asn Lys Leu Asp Lys
    50                  55                  60

Arg Gln Arg Ser Ile Arg Arg Leu Lys Leu Ile Leu Thr Glu Lys Val
65                  70                  75                  80

Asn Asp Leu Gly Lys Tyr Thr Phe Ile Arg Tyr Pro Glu Met Ser Lys
                85                  90                  95

Glu Met Phe Lys Leu His Ile Pro Gly Ile Asn Ser Lys Val Thr Glu
            100                 105                 110

Leu Leu Leu Lys Ala Asp Arg Thr Tyr Ser Gln Met Thr Asp Gly Leu
        115                 120                 125

Arg Asp Leu Trp Ile Asn Val Leu Ser Lys Leu Ala Ser Lys Asn Asp
    130                 135                 140

Gly Ser Asn Tyr Asp Leu Asn Glu Glu Ile Asn Asn Ile Ser Lys Val
145                 150                 155                 160

His Thr Thr Tyr Lys Ser Asp Lys Trp Tyr Asn Pro Phe Lys Thr Trp
                165                 170                 175

Phe Thr Ile Lys Tyr Asp Met Arg Arg Leu Gln Lys Ala Arg Asn Glu
            180                 185                 190

Val Thr Phe Asn Met Gly Lys Asp Tyr Asn Leu Leu Glu Asp Gln Lys
        195                 200                 205

Asn Phe Leu Leu Ile His Pro Glu Leu Val Leu Ile Leu Asp Lys Gln
    210                 215                 220

Asn Tyr Asn Gly Tyr Leu Ile Thr Pro Glu Leu Val Leu Pro Tyr Cys
225                 230                 235                 240

Asp Val Val Glu Gly Arg Trp Asn Ile Ser Ala Cys Ala Lys Leu Asp
                245                 250                 255

Pro Lys Leu Gln Ser Met Tyr Gln Lys Gly Asn Asn Leu Trp Glu Val
            260                 265                 270

Ile Asp Lys Leu Phe Pro Ile Met Gly Glu Lys Thr Phe Asp Val Ile
        275                 280                 285

Ser Leu Leu Glu Pro Leu Ala Leu Ser Leu Ile Gln Thr His Asp Pro
    290                 295                 300

Val Lys Gln Leu Arg Gly Ala Phe Leu Asn His Val Leu Ser Glu Met
305                 310                 315                 320

Glu Leu Ile Phe Glu Ser Arg Glu Ser Ile Lys Glu Phe Leu Ser Val
                325                 330                 335

Asp Tyr Ile Asp Lys Ile Leu Asp Ile Phe Asn Lys Ser Thr Ile Asp
            340                 345                 350

Glu Ile Ala Glu Ile Phe Ser Phe Arg Thr Phe Gly His Pro Pro
        355                 360                 365

Leu Glu Ala Ser Ile Ala Ala Glu Lys Val Arg Lys Tyr Met Tyr Ile
    370                 375                 380

Gly Lys Gln Leu Lys Phe Asp Thr Ile Asn Lys Cys His Ala Ile Phe
385                 390                 395                 400

Cys Thr Ile Ile Ile Asn Gly Tyr Arg Glu Arg His Gly Gly Gln Trp
```

```
                405                 410                 415
Pro Pro Val Thr Leu Pro Asp His Ala His Glu Phe Ile Ile Asn Ala
            420                 425                 430

Tyr Gly Ser Asn Ser Ala Ile Ser Tyr Glu Asn Ala Val Asp Tyr Tyr
            435                 440                 445

Gln Ser Phe Ile Gly Ile Lys Phe Asn Lys Phe Ile Glu Pro Gln Leu
            450                 455                 460

Asp Glu Asp Leu Thr Ile Tyr Met Lys Asp Lys Ala Leu Ser Pro Lys
465                 470                 475                 480

Lys Ser Asn Trp Asp Thr Val Ser Pro Ala Ser Asn Leu Leu Tyr Arg
                485                 490                 495

Thr Asn Ala Ser Asn Glu Ser Arg Arg Leu Val Glu Lys Phe Ile Ala
            500                 505                 510

Asp Ser Lys Phe Asp Pro Asn Gln Ile Leu Asp Tyr Val Glu Ser Gly
            515                 520                 525

Asp Trp Leu Asp Asp Pro Glu Phe Asn Ile Ser Tyr Ser Leu Lys Glu
            530                 535                 540

Lys Glu Ile Lys Gln Glu Gly Arg Leu Phe Ala Lys Met Thr Tyr Lys
545                 550                 555                 560

Met Arg Ala Thr Gln Val Leu Ser Glu Thr Leu Leu Ala Asn Asn Ile
                565                 570                 575

Gly Lys Phe Phe Gln Glu Asn Gly Met Val Lys Gly Glu Ile Glu Leu
            580                 585                 590

Leu Lys Arg Leu Thr Thr Ile Ser Ile Ser Gly Val Pro Arg Tyr Asn
            595                 600                 605

Glu Val Tyr Asn Asn Ser Lys Ser His Thr Asp Asp Leu Lys Thr Tyr
            610                 615                 620

Asn Lys Ile Ser Asn Leu Asn Leu Ser Ser Asn Gln Lys Ser Lys Lys
625                 630                 635                 640

Phe Glu Phe Lys Ser Thr Asp Ile Tyr Asn Asp Gly Tyr Glu Thr Val
                645                 650                 655

Ser Cys Phe Leu Thr Thr Asp Leu Lys Lys Tyr Cys Leu Asn Trp Arg
            660                 665                 670

Tyr Glu Ser Thr Ala Leu Phe Gly Glu Thr Cys Asn Gln Ile Phe Gly
            675                 680                 685

Leu Asn Lys Leu Phe Asn Trp Leu His Pro Arg Leu Glu Gly Ser Thr
            690                 695                 700

Ile Tyr Val Gly Asp Pro Tyr Cys Pro Pro Ser Asp Lys Glu His Ile
705                 710                 715                 720

Ser Leu Glu Asp His Pro Asp Ser Gly Phe Tyr Val His Asn Pro Arg
                725                 730                 735

Gly Gly Ile Glu Gly Phe Cys Gln Lys Leu Trp Thr Leu Ile Ser Ile
            740                 745                 750

Ser Ala Ile His Leu Ala Ala Val Arg Ile Gly Val Arg Val Thr Ala
            755                 760                 765

Met Val Gln Gly Asp Asn Gln Ala Ile Ala Val Thr Thr Arg Val Pro
            770                 775                 780

Asn Asn Tyr Asp Tyr Arg Val Lys Lys Glu Ile Val Tyr Lys Asp Val
785                 790                 795                 800

Val Arg Phe Phe Asp Ser Leu Arg Glu Val Met Asp Asp Leu Gly His
                805                 810                 815

Glu Leu Lys Leu Asn Glu Thr Ile Ile Ser Ser Lys Met Phe Ile Tyr
            820                 825                 830
```

-continued

```
Ser Lys Arg Ile Tyr Tyr Asp Gly Arg Ile Leu Pro Gln Ala Leu Lys
        835                 840                 845

Ala Leu Ser Arg Cys Val Phe Trp Ser Glu Thr Val Ile Asp Glu Thr
    850                 855                 860

Arg Ser Ala Ser Ser Asn Leu Ala Thr Ser Phe Ala Lys Ala Ile Glu
865                 870                 875                 880

Asn Gly Tyr Ser Pro Val Leu Gly Tyr Ala Cys Ser Ile Phe Lys Asn
                885                 890                 895

Ile Gln Gln Leu Tyr Ile Ala Leu Gly Met Asn Ile Asn Pro Thr Ile
                900                 905                 910

Thr Gln Asn Ile Lys Asp Leu Tyr Phe Arg Asn Pro Asn Trp Met Gln
            915                 920                 925

Tyr Ala Ser Leu Ile Pro Ala Ser Val Gly Gly Phe Asn Tyr Met Ala
        930                 935                 940

Met Ser Arg Cys Phe Val Arg Asn Ile Gly Asp Pro Ser Val Ala Ala
945                 950                 955                 960

Leu Ala Asp Ile Lys Arg Phe Ile Lys Ala Asn Leu Leu Asp Arg Ser
                965                 970                 975

Val Leu Tyr Arg Ile Met Asn Gln Glu Pro Gly Glu Ser Ser Phe Leu
                980                 985                 990

Asp Trp Ala Ser Asp Pro Tyr Ser  Cys Asn Leu Pro Gln  Ser Gln Asn
            995                 1000                1005

Ile Thr  Thr Met Ile Lys Asn  Ile Thr Ala Arg Asn  Val Leu Gln
    1010                1015                1020

Asp Ser  Pro Asn Pro Leu Leu  Ser Gly Leu Phe Thr  Asn Thr Met
    1025                1030                1035

Ile Glu  Glu Asp Glu Glu Leu  Ala Glu Phe Leu Met  Asp Arg Lys
    1040                1045                1050

Val Ile  Leu Pro Arg Val Ala  His Asp Ile Leu Asp  Asn Ser Leu
    1055                1060                1065

Thr Gly  Ile Arg Asn Ala Ile  Ala Gly Met Leu Asp  Thr Thr Lys
    1070                1075                1080

Ser Leu  Ile Arg Val Gly Ile  Asn Arg Gly Gly Leu  Thr Tyr Ser
    1085                1090                1095

Leu Leu  Arg Lys Ile Ser Asn  Tyr Asp Leu Val Gln  Tyr Glu Thr
    1100                1105                1110

Leu Ser  Arg Thr Leu Arg Leu  Ile Val Ser Asp Lys  Ile Arg Tyr
    1115                1120                1125

Glu Asp  Met Cys Ser Val Asp  Leu Ala Ile Ala Leu  Arg Gln Lys
    1130                1135                1140

Met Trp  Ile His Leu Ser Gly  Gly Arg Met Ile Ser  Gly Leu Glu
    1145                1150                1155

Thr Pro  Asp Pro Leu Glu Leu  Leu Ser Gly Val Ile  Ile Thr Gly
    1160                1165                1170

Ser Glu  His Cys Lys Ile Cys  Tyr Ser Ser Asp Gly  Thr Asn Pro
    1175                1180                1185

Tyr Thr  Trp Met Tyr Leu Pro  Gly Asn Ile Lys Ile  Gly Ser Ala
    1190                1195                1200

Glu Thr  Gly Ile Ser Ser Leu  Arg Val Pro Tyr Phe  Gly Ser Val
    1205                1210                1215

Thr Asp  Glu Arg Ser Glu Ala  Gln Leu Gly Tyr Ile  Lys Asn Leu
    1220                1225                1230
```

-continued

```
Ser Lys Pro Ala Lys Ala Ala Ile Arg Ile Ala Met Ile Tyr Thr
    1235            1240                1245

Trp Ala Phe Gly Asn Asp Glu Ile Ser Trp Met Glu Ala Ser Gln
    1250            1255                1260

Ile Ala Gln Thr Arg Ala Asn Phe Thr Leu Asp Ser Leu Lys Ile
    1265            1270                1275

Leu Thr Pro Val Ala Thr Ser Thr Asn Leu Ser His Arg Leu Lys
    1280            1285                1290

Asp Thr Ala Thr Gln Met Lys Phe Ser Ser Thr Ser Leu Ile Arg
    1295            1300                1305

Val Ser Arg Phe Ile Thr Met Ser Asn Asp Asn Met Ser Ile Lys
    1310            1315                1320

Glu Ala Asn Glu Thr Lys Asp Thr Asn Leu Ile Tyr Gln Gln Ile
    1325            1330                1335

Met Leu Thr Gly Leu Ser Val Phe Glu Tyr Leu Phe Arg Leu Glu
    1340            1345                1350

Glu Thr Thr Gly His Asn Pro Ile Val Met His Leu His Ile Glu
    1355            1360                1365

Asp Glu Cys Cys Ile Lys Ser Phe Asn Asp Glu His Ile Asn
    1370            1375                1380

Pro Glu Ser Thr Leu Glu Leu Ile Arg Tyr Pro Glu Ser Asn Glu
    1385            1390                1395

Phe Ile Tyr Asp Lys Asp Pro Leu Lys Asp Val Asp Leu Ser Lys
    1400            1405                1410

Leu Met Val Ile Lys Asp His Ser Tyr Thr Ile Asp Met Asn Tyr
    1415            1420                1425

Trp Asp Asp Thr Asp Ile Ile His Ala Ile Ser Ile Cys Thr Ala
    1430            1435                1440

Ile Thr Ile Ala Asp Thr Met Ser Gln Leu Asp Arg Asp Asn Leu
    1445            1450                1455

Lys Glu Ile Ile Val Ile Ala Asn Asp Asp Ile Asn Ser Leu
    1460            1465                1470

Ile Thr Glu Phe Leu Thr Leu Asp Ile Leu Val Phe Leu Lys Thr
    1475            1480                1485

Phe Gly Gly Leu Leu Val Asn Gln Phe Ala Tyr Thr Leu Tyr Ser
    1490            1495                1500

Leu Lys Thr Glu Gly Arg Asp Leu Ile Trp Asp Tyr Ile Met Arg
    1505            1510                1515

Thr Leu Arg Asp Thr Ser His Ser Ile Leu Lys Val Leu Ser Asn
    1520            1525                1530

Ala Leu Ser His Pro Lys Val Phe Lys Arg Phe Trp Asp Cys Gly
    1535            1540                1545

Val Leu Asn Pro Ile Tyr Gly Pro Asn Thr Ala Ser Gln Asp Gln
    1550            1555                1560

Ile Lys Leu Ala Leu Ser Ile Cys Glu Tyr Ser Leu Asp Leu Phe
    1565            1570                1575

Met Arg Glu Trp Leu Asn Gly Val Ser Leu Glu Ile Tyr Ile Cys
    1580            1585                1590

Asp Ser Asp Met Glu Val Ala Asn Asp Arg Lys Gln Ala Phe Ile
    1595            1600                1605

Ser Arg His Leu Ser Phe Val Cys Cys Leu Ala Glu Ile Ala Ser
    1610            1615                1620

Phe Gly Pro Asn Leu Leu Asn Leu Thr Tyr Leu Glu Arg Leu Asp
```

-continued

```
            1625                1630                1635
Leu Leu Lys Gln Tyr Leu Glu Leu Asn Ile Lys Asp Asp Pro Thr
    1640                1645                1650
Leu Lys Tyr Val Gln Ile Ser Gly Leu Leu Ile Lys Ser Phe Pro
    1655                1660                1665
Ser Thr Val Thr Tyr Val Arg Lys Thr Ala Ile Lys Tyr Leu Arg
    1670                1675                1680
Ile Arg Gly Ile Ser Pro Pro Glu Val Ile Asp Asp Trp Asp Pro
    1685                1690                1695
Ile Glu Asp Glu Asn Met Leu Asp Asn Ile Val Lys Thr Ile Asn
    1700                1705                1710
Asp Asn Cys Asn Lys Asp Asn Lys Gly Asn Lys Ile Asn Asn Phe
    1715                1720                1725
Trp Gly Leu Ala Leu Lys Asn Tyr Gln Val Leu Lys Ile Arg Ser
    1730                1735                1740
Ile Thr Ser Asp Ser Asp Asn Asn Asp Arg Ser Asp Ala Ser Thr
    1745                1750                1755
Gly Gly Leu Thr Leu Pro Gln Gly Gly Asn Tyr Leu Ser His Gln
    1760                1765                1770
Leu Arg Leu Phe Gly Ile Asn Ser Thr Ser Cys Leu Lys Ala Leu
    1775                1780                1785
Glu Leu Ser Gln Ile Leu Met Lys Glu Val Asn Lys Asp Gln Asp
    1790                1795                1800
Arg Leu Phe Leu Gly Glu Gly Ala Gly Ala Met Leu Ala Cys Tyr
    1805                1810                1815
Asp Ala Thr Leu Gly Pro Ala Val Asn Tyr Tyr Asn Ser Gly Leu
    1820                1825                1830
Asn Ile Thr Asp Val Ile Gly Gln Arg Glu Leu Lys Ile Phe Pro
    1835                1840                1845
Ser Glu Val Ser Leu Val Gly Lys Lys Leu Gly Asn Val Thr Gln
    1850                1855                1860
Ile Leu Asn Arg Val Lys Val Leu Phe Asn Gly Asn Pro Asn Ser
    1865                1870                1875
Thr Trp Ile Gly Asn Met Glu Cys Glu Thr Leu Ile Trp Ser Glu
    1880                1885                1890
Leu Asn Asp Lys Ser Ile Gly Leu Val His Cys Asp Met Glu Gly
    1895                1900                1905
Ala Ile Gly Lys Ser Glu Glu Thr Val Leu His Glu His Tyr Ser
    1910                1915                1920
Val Ile Arg Ile Thr Tyr Leu Ile Gly Asp Asp Val Val Leu
    1925                1930                1935
Ile Ser Lys Ile Ile Pro Thr Ile Thr Pro Asn Trp Ser Arg Ile
    1940                1945                1950
Leu Tyr Leu Tyr Lys Leu Tyr Trp Lys Asp Val Ser Ile Ile Ser
    1955                1960                1965
Leu Lys Thr Ser Asn Pro Ala Ser Thr Glu Leu Tyr Leu Ile Ser
    1970                1975                1980
Lys Asp Ala Tyr Cys Thr Ile Met Glu Pro Ser Glu Val Val Leu
    1985                1990                1995
Ser Lys Leu Lys Arg Leu Ser Leu Leu Glu Glu Asn Asn Leu Leu
    2000                2005                2010
Lys Trp Ile Ile Leu Ser Lys Lys Asn Asn Glu Trp Leu His
    2015                2020                2025
```

-continued

His Glu Ile Lys Glu Gly Glu Arg Asp Tyr Gly Val Met Arg Pro
        2030                2035                2040

Tyr His Met Ala Leu Gln Ile Phe Gly Phe Gln Ile Asn Leu Asn
    2045                2050                2055

His Leu Ala Lys Glu Phe Leu Ser Thr Pro Asp Leu Thr Asn Ile
    2060                2065                2070

Asn Asn Ile Ile Gln Ser Phe Gln Arg Thr Ile Lys Asp Val Leu
    2075                2080                2085

Phe Glu Trp Ile Asn Ile Thr His Asp Gly Lys Arg His Lys Leu
    2090                2095                2100

Gly Gly Arg Tyr Asn Ile Phe Pro Leu Lys Asn Lys Gly Lys Leu
    2105                2110                2115

Arg Leu Leu Ser Arg Arg Leu Val Leu Ser Trp Ile Ser Leu Ser
    2120                2125                2130

Leu Ser Thr Arg Leu Leu Thr Gly Arg Phe Pro Asp Glu Lys Phe
    2135                2140                2145

Glu His Arg Ala Gln Thr Gly Tyr Val Ser Leu Pro Asp Thr Asp
    2150                2155                2160

Leu Glu Ser Leu Lys Leu Leu Ser Lys Asn Thr Ile Lys Asn Tyr
    2165                2170                2175

Arg Glu Cys Ile Gly Ser Ile Ser Tyr Trp Phe Leu Thr Lys Glu
    2180                2185                2190

Val Lys Ile Leu Met Lys Leu Ile Gly Gly Ala Lys Leu Leu Gly
    2195                2200                2205

Ile Pro Arg Gln Tyr Lys Glu Pro Glu Glu Gln Leu Leu Glu Asp
    2210                2215                2220

Tyr Asn Gln His Asp Glu Phe Asp Ile Asp
    2225                2230

<210> SEQ ID NO 15
<211> LENGTH: 2223
<212> TYPE: PRT
<213> ORGANISM: human parainfluenza virus 1

<400> SEQUENCE: 15

Met Asp Lys Gln Glu Ser Thr Gln Asn Ser Ser Asp Ile Leu Tyr Pro
1               5                   10                  15

Glu Cys His Leu Asn Ser Pro Ile Val Lys Ser Lys Ile Ala Gln Leu
                20                  25                  30

His Val Leu Leu Asp Ile Asn Gln Pro Tyr Asp Leu Lys Asp Asn Ser
            35                  40                  45

Ile Ile Asn Ile Thr Lys Tyr Lys Ile Arg Asn Gly Gly Leu Ser Pro
        50                  55                  60

Arg Gln Ile Lys Ile Arg Ser Leu Gly Lys Ile Leu Lys Gln Glu Ile
65                  70                  75                  80

Lys Asp Ile Asp Arg Tyr Thr Phe Glu Pro Tyr Pro Ile Phe Ser Leu
                85                  90                  95

Glu Leu Leu Arg Leu Asp Ile Pro Glu Ile Cys Asp Lys Ile Arg Ser
                100                 105                 110

Ile Phe Ser Val Ser Asp Arg Leu Ile Arg Glu Leu Ser Ser Gly Phe
            115                 120                 125

Gln Glu Leu Trp Leu Asn Ile Leu Arg Gln Leu Gly Cys Val Glu Gly
        130                 135                 140

Lys Glu Gly Phe Asp Ser Leu Lys Asp Val Asp Ile Ile Pro Asp Ile

-continued

```
           145                 150                 155                 160
   Thr Asp Lys Tyr Asn Lys Asn Thr Trp Tyr Arg Pro Phe Leu Thr Trp
                   165                 170                 175

Phe Ser Ile Lys Tyr Asp Met Arg Trp Met Gln Lys Asn Lys Ser Gly
                   180                 185                 190

Asn His Leu Asp Val Ser Asn Ser His Asn Phe Leu Asp Cys Lys Ser
                   195                 200                 205

Tyr Ile Leu Ile Ile Tyr Arg Asp Leu Val Ile Ile Asn Lys Leu
                   210                 215                 220

Lys Leu Thr Gly Tyr Val Leu Thr Pro Glu Leu Val Leu Met Tyr Cys
   225                 230                 235                 240

Asp Val Val Glu Gly Arg Trp Asn Met Ser Ser Ala Gly Arg Leu Asp
                   245                 250                 255

Lys Arg Ser Ser Lys Ile Thr Cys Lys Gly Glu Leu Trp Glu Leu
                   260                 265                 270

Ile Asp Ser Leu Phe Pro Asn Leu Gly Glu Asp Val Tyr Asn Ile Ile
                   275                 280                 285

Ser Leu Leu Glu Pro Leu Ser Leu Ala Leu Ile Gln Leu Asp Asp Pro
                   290                 295                 300

Val Thr Asn Leu Lys Gly Ala Phe Met Arg His Val Leu Thr Glu Leu
   305                 310                 315                 320

His Thr Ile Leu Ile Lys Asp Asn Ile Tyr Thr Asp Ser Glu Ala Asp
                   325                 330                 335

Ser Ile Met Glu Ser Leu Ile Lys Ile Phe Arg Glu Thr Ser Ile Asp
                   340                 345                 350

Glu Lys Ala Glu Ile Phe Ser Phe Phe Arg Thr Phe Gly His Pro Ser
                   355                 360                 365

Leu Glu Ala Ile Thr Ala Ala Asp Lys Val Arg Thr His Met Tyr Ser
                   370                 375                 380

Ser Lys Lys Ile Ile Leu Lys Thr Leu Tyr Glu Cys His Ala Ile Phe
   385                 390                 395                 400

Cys Ala Ile Ile Ile Asn Gly Tyr Arg Glu Arg His Gly Gly Gln Trp
                   405                 410                 415

Pro Pro Cys Glu Phe Pro Asn His Val Cys Leu Glu Leu Lys Asn Ala
                   420                 425                 430

Gln Gly Ser Asn Ser Ala Ile Ser Tyr Glu Cys Ala Val Asp Asn Tyr
                   435                 440                 445

Ser Ser Phe Ile Gly Phe Lys Phe Leu Lys Phe Ile Glu Pro Gln Leu
                   450                 455                 460

Asp Glu Asp Leu Thr Ile Tyr Met Lys Asp Lys Ala Leu Ser Pro Arg
   465                 470                 475                 480

Lys Ala Ala Trp Asp Ser Val Tyr Pro Asp Ser Asn Leu Tyr Tyr Lys
                   485                 490                 495

Val Pro Glu Ser Glu Glu Thr Arg Arg Leu Ile Glu Val Phe Ile Asn
                   500                 505                 510

Asp Asn Asn Phe Asn Pro Ala Asp Ile Ile Asn Tyr Val Glu Ser Gly
                   515                 520                 525

Glu Trp Leu Asn Asp Asp Ser Phe Asn Ile Ser Tyr Ser Leu Lys Glu
                   530                 535                 540

Lys Glu Ile Lys Gln Glu Gly Arg Leu Phe Ala Lys Met Thr Tyr Lys
   545                 550                 555                 560

Met Arg Ala Val Gln Val Leu Ala Glu Thr Leu Leu Ala Lys Gly Val
                   565                 570                 575
```

```
Gly Glu Leu Phe Ser Glu Asn Gly Met Val Lys Gly Glu Ile Asp Leu
            580                 585                 590

Leu Lys Arg Leu Thr Thr Leu Ser Val Ser Gly Val Pro Arg Ser Asn
            595                 600                 605

Ser Val Tyr Asn Asn Pro Ile Leu His Glu Lys Leu Ile Lys Asn Met
            610                 615                 620

Asn Lys Cys Asn Ser Asn Gly Tyr Trp Asp Glu Arg Lys Lys Ser Lys
625                 630                 635                 640

Asn Glu Phe Lys Ala Ala Asp Ser Ser Thr Glu Gly Tyr Glu Thr Leu
            645                 650                 655

Ser Cys Phe Leu Thr Thr Asp Leu Lys Lys Tyr Cys Leu Asn Trp Arg
            660                 665                 670

Phe Glu Ser Thr Ala Leu Phe Gly Gln Arg Cys Asn Glu Ile Phe Gly
            675                 680                 685

Phe Lys Thr Phe Phe Asn Trp Met His Pro Ile Leu Glu Lys Ser Thr
            690                 695                 700

Ile Tyr Val Gly Asp Pro Tyr Cys Pro Val Pro Asp Arg Met His Lys
705                 710                 715                 720

Glu Leu Gln Asp His Asp Thr Gly Ile Phe Ile His Asn Pro Arg
            725                 730                 735

Gly Gly Ile Glu Gly Tyr Cys Gln Lys Leu Trp Thr Leu Ile Ser Ile
            740                 745                 750

Ser Ala Ile His Leu Ala Ala Val Lys Val Gly Val Arg Val Ser Ala
            755                 760                 765

Met Val Gln Gly Asp Asn Gln Ala Ile Ala Val Thr Ser Arg Val Pro
            770                 775                 780

Val Thr Gln Thr Tyr Lys Gln Lys Lys Thr His Val Tyr Glu Glu Ile
785                 790                 795                 800

Thr Arg Tyr Phe Gly Ala Leu Arg Glu Val Met Phe Asp Ile Gly His
            805                 810                 815

Glu Leu Lys Leu Asn Glu Thr Ile Ile Ser Ser Lys Met Phe Val Tyr
            820                 825                 830

Ser Lys Arg Ile Tyr Tyr Asp Gly Lys Ile Leu Pro Gln Cys Leu Lys
            835                 840                 845

Ala Leu Thr Arg Cys Val Phe Trp Ser Glu Thr Leu Val Asp Glu Asn
            850                 855                 860

Arg Ser Ala Cys Ser Asn Ile Ala Thr Ser Ile Ala Lys Ala Ile Glu
865                 870                 875                 880

Asn Gly Tyr Ser Pro Ile Leu Gly Tyr Cys Ile Ala Leu Phe Lys Thr
            885                 890                 895

Cys Gln Gln Val Cys Ile Ser Leu Gly Met Thr Ile Asn Pro Thr Ile
            900                 905                 910

Thr Ser Thr Ile Lys Asp Gln Tyr Phe Lys Gly Lys Asn Trp Leu Arg
            915                 920                 925

Cys Ala Ile Leu Ile Pro Ala Asn Ile Gly Gly Phe Asn Tyr Met Ser
            930                 935                 940

Thr Ala Arg Cys Phe Val Arg Asn Ile Gly Asp Pro Ala Val Ala Ala
945                 950                 955                 960

Leu Ala Asp Leu Lys Arg Phe Ile Lys Ala Gly Leu Leu Asp Lys Gln
            965                 970                 975

Val Leu Tyr Arg Val Met Asn Gln Glu Pro Gly Asp Ser Ser Phe Leu
            980                 985                 990
```

-continued

Asp Trp Ala Ser Asp Pro Tyr Ser Cys Asn Leu Pro His Ser Gln Ser
        995              1000             1005

Ile Thr Thr Ile Ile Lys Asn Val Thr Ala Arg Ser Val Leu Gln
    1010             1015             1020

Glu Ser Pro Asn Pro Leu Leu Ser Gly Leu Phe Ser Glu Ser Ser
    1025             1030             1035

Ser Glu Glu Asp Leu Asn Leu Ala Ser Phe Leu Met Asp Arg Lys
    1040             1045             1050

Ala Ile Leu Pro Arg Val Ala His Glu Ile Leu Asp Asn Ser Leu
    1055             1060             1065

Thr Gly Val Arg Glu Ala Ile Ala Gly Met Leu Asp Thr Thr Lys
    1070             1075             1080

Ser Leu Val Arg Ala Ser Val Arg Arg Gly Gly Leu Ser Tyr Ser
    1085             1090             1095

Ile Leu Arg Arg Leu Ile Asn Tyr Asp Leu Leu Gln Tyr Glu Thr
    1100             1105             1110

Leu Thr Arg Thr Leu Arg Lys Pro Val Lys Asp Asn Ile Glu Tyr
    1115             1120             1125

Glu Tyr Met Cys Ser Val Glu Leu Ala Ile Gly Leu Arg Gln Lys
    1130             1135             1140

Met Trp Phe His Leu Thr Tyr Gly Arg Pro Ile His Gly Leu Glu
    1145             1150             1155

Thr Pro Asp Pro Leu Glu Leu Leu Arg Gly Ser Phe Ile Glu Gly
    1160             1165             1170

Ser Glu Ile Cys Lys Phe Cys Arg Ser Glu Gly Asn Asn Pro Met
    1175             1180             1185

Tyr Thr Trp Phe Tyr Leu Pro Asp Asn Ile Asp Leu Asp Thr Leu
    1190             1195             1200

Ser Asn Gly Ser Pro Ala Ile Arg Ile Pro Tyr Phe Gly Ser Ala
    1205             1210             1215

Thr Asp Glu Arg Ser Glu Ala Gln Leu Gly Tyr Val Lys Asn Leu
    1220             1225             1230

Ser Lys Pro Ala Lys Ala Ala Ile Arg Ile Ala Met Val Tyr Thr
    1235             1240             1245

Trp Ala Tyr Gly Thr Asp Glu Ile Ser Trp Met Glu Ala Ala Leu
    1250             1255             1260

Ile Ala Gln Thr Arg Ala Asn Leu Ser Leu Glu Asn Leu Lys Leu
    1265             1270             1275

Leu Thr Pro Val Ser Thr Ser Thr Asn Leu Ser His Arg Leu Arg
    1280             1285             1290

Asp Thr Ala Thr Gln Met Lys Phe Ser Ser Ala Thr Leu Val Arg
    1295             1300             1305

Ala Ser Arg Phe Ile Thr Ile Ser Asn Asp Asn Met Ala Leu Lys
    1310             1315             1320

Glu Ala Gly Glu Ser Lys Asp Thr Asn Leu Val Tyr Gln Gln Ile
    1325             1330             1335

Met Leu Thr Gly Leu Ser Leu Phe Glu Phe Asn Met Arg Tyr Lys
    1340             1345             1350

Gln Gly Ser Leu Ser Lys Pro Met Ile Leu His Leu His Leu Asn
    1355             1360             1365

Asn Lys Cys Cys Ile Ile Glu Ser Pro Gln Glu Leu Asn Ile Pro
    1370             1375             1380

Pro Arg Ser Thr Leu Asp Leu Glu Ile Thr Gln Glu Asn Asn Lys

-continued

```
            1385                1390                1395

Leu Ile Tyr Asp Pro Asp Pro Leu Lys Asp Ile Asp Leu Glu Leu
    1400                1405                1410

Phe Ser Lys Val Arg Asp Val Val His Thr Ile Asp Met Asn Tyr
    1415                1420                1425

Trp Ser Asp Asp Glu Ile Ile Arg Ala Thr Ser Ile Cys Thr Ala
    1430                1435                1440

Met Thr Ile Ala Asp Thr Met Ser Gln Leu Asp Arg Asp Asn Leu
    1445                1450                1455

Lys Glu Met Ile Ala Leu Ile Asn Asp Asp Asp Ile Asn Ser Leu
    1460                1465                1470

Ile Thr Glu Phe Met Val Ile Asp Ile Pro Leu Phe Cys Ser Thr
    1475                1480                1485

Phe Gly Gly Ile Leu Ile Asn Gln Phe Ala Tyr Ser Leu Tyr Gly
    1490                1495                1500

Leu Asn Val Arg Gly Arg Asp Glu Ile Trp Gly Tyr Val Ile Arg
    1505                1510                1515

Ile Ile Lys Asp Thr Ser His Ala Val Leu Lys Val Leu Ser Asn
    1520                1525                1530

Ala Leu Ser His Pro Lys Ile Phe Lys Arg Phe Trp Asp Ala Gly
    1535                1540                1545

Val Val Glu Pro Val Tyr Gly Pro Asn Leu Ser Asn Gln Asp Lys
    1550                1555                1560

Ile Leu Leu Ala Ile Ser Val Cys Glu Tyr Ser Val Asp Leu Phe
    1565                1570                1575

Met Arg Asp Trp Gln Glu Gly Ile Pro Leu Glu Ile Phe Ile Cys
    1580                1585                1590

Asp Asn Asp Pro Asn Ile Ala Glu Met Arg Lys Leu Ser Phe Leu
    1595                1600                1605

Ala Arg His Leu Ala Tyr Leu Cys Ser Leu Ala Glu Ile Ala Lys
    1610                1615                1620

Glu Gly Pro Lys Leu Glu Ser Met Thr Ser Leu Glu Arg Leu Glu
    1625                1630                1635

Ser Leu Lys Glu Tyr Leu Glu Leu Thr Phe Leu Asp Asp Pro Ile
    1640                1645                1650

Leu Arg Tyr Ser Gln Leu Thr Gly Leu Val Ile Lys Ile Phe Pro
    1655                1660                1665

Ser Thr Leu Thr Tyr Ile Arg Lys Ser Ser Ile Lys Val Leu Arg
    1670                1675                1680

Val Arg Gly Ile Gly Ile Pro Glu Val Leu Glu Asp Trp Asp Pro
    1685                1690                1695

Asp Ala Asp Ser Met Leu Leu Asp Asn Ile Thr Ala Glu Val Gln
    1700                1705                1710

His Asn Ile Pro Leu Lys Lys Asn Glu Arg Thr Pro Phe Trp Gly
    1715                1720                1725

Leu Arg Val Ser Lys Ser Gln Val Leu Arg Leu Arg Gly Tyr Glu
    1730                1735                1740

Glu Ile Lys Arg Glu Glu Arg Gly Arg Ser Gly Val Gly Leu Thr
    1745                1750                1755

Leu Pro Phe Asp Gly Arg Tyr Leu Ser His Gln Leu Arg Leu Phe
    1760                1765                1770

Gly Ile Asn Ser Thr Ser Cys Leu Lys Ala Leu Glu Leu Thr Tyr
    1775                1780                1785
```

-continued

```
Leu Leu Asn Pro Leu Val Asn Lys Asp Lys Asp Arg Leu Tyr Leu
    1790            1795                1800

Gly Glu Gly Ala Gly Ala Met Leu Ser Cys Tyr Asp Ala Thr Leu
    1805            1810                1815

Gly Pro Cys Met Asn Tyr Tyr Asn Ser Gly Val Asn Ser Cys Asp
    1820            1825                1830

Leu Asn Gly Gln Arg Glu Leu Asn Ile Tyr Pro Ser Glu Val Ala
    1835            1840                1845

Leu Val Gly Lys Lys Leu Asn Asn Val Thr Ser Leu Cys Gln Arg
    1850            1855                1860

Val Lys Val Leu Phe Asn Gly Asn Pro Gly Ser Thr Trp Ile Gly
    1865            1870                1875

Asn Asp Glu Cys Glu Thr Leu Ile Trp Asn Glu Leu Gln Asn Asn
    1880            1885                1890

Ser Ile Gly Phe Ile His Cys Asp Met Glu Gly Gly Glu His Lys
    1895            1900                1905

Cys Asp Gln Val Val Leu His Glu His Tyr Ser Val Ile Arg Ile
    1910            1915                1920

Ala Tyr Leu Val Gly Asp Lys Asp Val Ile Leu Val Ser Lys Ile
    1925            1930                1935

Ala Pro Arg Leu Gly Thr Asp Trp Thr Lys Gln Leu Ser Leu Tyr
    1940            1945                1950

Leu Arg Tyr Trp Arg Asp Val Ser Leu Ile Val Leu Lys Thr Ser
    1955            1960                1965

Asn Pro Ala Ser Thr Glu Met Tyr Leu Ile Ser Lys Asp Pro Lys
    1970            1975                1980

Ser Asp Ile Ile Glu Asp Ser Asn Thr Val Leu Ala Asn Leu Leu
    1985            1990                1995

Pro Leu Ser Lys Glu Asp Ser Ile Lys Ile Glu Lys Trp Ile Leu
    2000            2005                2010

Val Glu Lys Ala Lys Val His Asp Trp Ile Val Arg Glu Leu Lys
    2015            2020                2025

Glu Gly Ser Ala Ser Ser Gly Met Leu Arg Pro Tyr His Gln Ala
    2030            2035                2040

Leu Gln Ile Phe Gly Phe Glu Pro Asn Leu Asn Lys Leu Cys Arg
    2045            2050                2055

Asp Phe Leu Ser Thr Leu Asn Ile Val Asp Thr Lys Asn Cys Ile
    2060            2065                2070

Ile Thr Phe Asp Arg Val Leu Arg Asp Thr Ile Phe Glu Trp Thr
    2075            2080                2085

Arg Ile Lys Asp Ala Asp Lys Lys Leu Arg Leu Thr Gly Lys Tyr
    2090            2095                2100

Asp Leu Tyr Pro Leu Arg Asp Ser Gly Lys Leu Lys Val Ile Ser
    2105            2110                2115

Arg Arg Leu Val Ile Ser Trp Ile Ala Leu Ser Met Ser Thr Arg
    2120            2125                2130

Leu Val Thr Gly Ser Phe Pro Asp Ile Lys Phe Glu Ser Arg Leu
    2135            2140                2145

Gln Leu Gly Ile Val Ser Ile Ser Ser Arg Glu Ile Lys Asn Leu
    2150            2155                2160

Arg Val Ile Ser Lys Ile Val Ile Asp Lys Phe Glu Asp Ile Ile
    2165            2170                2175
```

-continued

```
His Ser  Val Thr Tyr Arg Phe  Leu Thr Lys Glu Ile  Lys Ile Leu
    2180                 2185                 2190

Met Lys  Ile Leu Gly Ala Val  Lys Leu Phe Gly Ala  Arg Gln Ser
    2195                 2200                 2205

Thr Ser  Ala Asp Ile Thr Asn  Ile Asp Thr Ser Asp  Ser Ile Gln
    2210                 2215                 2220

<210> SEQ ID NO 16
<211> LENGTH: 2233
<212> TYPE: PRT
<213> ORGANISM: bovine parainfluenza virus 3

<400> SEQUENCE: 16

Met Asp Thr Glu Ser His Ser Gly Thr Thr Ser Asp Ile Leu Tyr Pro
1               5                   10                  15

Glu Cys His Leu Asn Ser Pro Ile Val Lys Gly Lys Ile Ala Gln Leu
            20                  25                  30

His Thr Ile Met Ser Leu Pro Gln Pro Tyr Asp Met Asp Asp Asp Ser
        35                  40                  45

Ile Leu Ile Ile Thr Arg Gln Lys Ile Lys Leu Asn Lys Leu Asp Lys
    50                  55                  60

Arg Gln Arg Ser Ile Arg Lys Leu Arg Ser Val Leu Met Glu Arg Val
65                  70                  75                  80

Ser Asp Leu Gly Lys Tyr Thr Phe Ile Arg Tyr Pro Glu Met Ser Ser
                85                  90                  95

Glu Met Phe Gln Leu Cys Ile Pro Gly Ile Asn Asn Lys Ile Asn Glu
            100                 105                 110

Leu Leu Ser Lys Ala Ser Lys Thr Tyr Asn Gln Met Thr Asp Gly Leu
        115                 120                 125

Arg Asp Leu Trp Val Thr Ile Leu Ser Lys Leu Ala Ser Lys Asn Asp
    130                 135                 140

Gly Ser Asn Tyr Asp Ile Asn Glu Asp Ile Ser Asn Ile Ser Asn Val
145                 150                 155                 160

His Met Thr Tyr Gln Ser Asp Lys Trp Tyr Asn Pro Phe Lys Thr Trp
                165                 170                 175

Phe Thr Ile Lys Tyr Asp Met Arg Arg Leu Gln Lys Ala Lys Asn Glu
            180                 185                 190

Ile Thr Phe Asn Arg His Lys Asp Tyr Asn Leu Leu Glu Asp Gln Lys
        195                 200                 205

Asn Ile Leu Leu Ile His Pro Glu Leu Val Leu Ile Leu Asp Lys Gln
    210                 215                 220

Asn Tyr Asn Gly Tyr Ile Met Thr Pro Glu Leu Val Leu Met Tyr Cys
225                 230                 235                 240

Asp Val Val Glu Gly Arg Trp Asn Ile Ser Ser Cys Ala Lys Leu Asp
                245                 250                 255

Pro Lys Leu Gln Ser Met Tyr Tyr Lys Gly Asn Asn Leu Trp Glu Ile
            260                 265                 270

Ile Asp Gly Leu Phe Ser Thr Leu Gly Glu Arg Thr Phe Asp Ile Ile
        275                 280                 285

Ser Leu Leu Glu Pro Leu Ala Leu Ser Leu Ile Gln Thr Tyr Asp Pro
    290                 295                 300

Val Lys Gln Leu Arg Gly Ala Phe Leu Asn His Val Leu Ser Glu Met
305                 310                 315                 320

Glu Leu Ile Phe Ala Ala Glu Cys Thr Thr Glu Glu Ile Pro Asn Val
                325                 330                 335
```

```
Asp Tyr Ile Asp Lys Ile Leu Asp Val Phe Lys Glu Ser Thr Ile Asp
            340                 345                 350
Glu Ile Ala Glu Ile Phe Ser Phe Phe Arg Thr Phe Gly His Pro Pro
            355                 360                 365
Leu Glu Ala Ser Ile Ala Ala Glu Lys Val Arg Lys Tyr Met Tyr Thr
            370                 375                 380
Glu Lys Cys Leu Lys Phe Asp Thr Ile Asn Lys Cys His Ala Ile Phe
385                 390                 395                 400
Cys Thr Ile Ile Ile Asn Gly Tyr Arg Glu Arg His Gly Gly Gln Trp
                405                 410                 415
Pro Pro Val Thr Leu Pro Val His Ala His Glu Phe Ile Ile Asn Ala
            420                 425                 430
Tyr Gly Ser Asn Ser Ala Ile Ser Tyr Glu Asn Ala Val Asp Tyr Tyr
            435                 440                 445
Lys Ser Phe Ile Gly Ile Lys Phe Asp Lys Phe Ile Glu Pro Gln Leu
            450                 455                 460
Asp Glu Asp Leu Thr Ile Tyr Met Lys Asp Lys Ala Leu Ser Pro Lys
465                 470                 475                 480
Lys Ser Asn Trp Asp Thr Val Tyr Pro Ala Ser Asn Leu Leu Tyr Arg
                485                 490                 495
Thr Asn Val Ser His Asp Ser Arg Arg Leu Val Glu Val Phe Ile Ala
            500                 505                 510
Asp Ser Lys Phe Asp Pro His Gln Val Leu Asp Tyr Val Glu Ser Gly
            515                 520                 525
Tyr Trp Leu Asp Asp Pro Glu Phe Asn Ile Ser Tyr Ser Leu Lys Glu
            530                 535                 540
Lys Glu Ile Lys Gln Glu Gly Arg Leu Phe Ala Lys Met Thr Tyr Lys
545                 550                 555                 560
Met Arg Ala Thr Gln Val Leu Ser Glu Thr Leu Leu Ala Asn Asn Ile
                565                 570                 575
Gly Lys Phe Phe Gln Glu Asn Gly Met Val Lys Gly Glu Ile Glu Leu
            580                 585                 590
Leu Lys Arg Leu Thr Thr Ile Ser Met Ser Gly Val Pro Arg Tyr Asn
            595                 600                 605
Glu Val Tyr Asn Asn Ser Lys Ser His Thr Glu Glu Leu Gln Ala Tyr
            610                 615                 620
Asn Ala Ile Ser Ser Ser Asn Leu Ser Ser Asn Gln Lys Ser Lys Lys
625                 630                 635                 640
Phe Glu Phe Lys Ser Thr Asp Ile Tyr Asn Asp Gly Tyr Glu Thr Val
                645                 650                 655
Ser Cys Phe Leu Thr Thr Asp Leu Lys Lys Tyr Cys Leu Asn Trp Arg
            660                 665                 670
Tyr Glu Ser Thr Ala Leu Phe Gly Asp Thr Cys Asn Gln Ile Phe Gly
            675                 680                 685
Leu Lys Glu Leu Phe Asn Trp Leu His Pro Arg Leu Glu Lys Ser Thr
            690                 695                 700
Ile Tyr Val Gly Asp Pro Tyr Cys Pro Pro Ser Asp Ile Glu His Leu
705                 710                 715                 720
Pro Leu Asp Asp His Pro Asp Ser Gly Phe Tyr Val His Asn Pro Lys
                725                 730                 735
Gly Gly Ile Glu Gly Phe Cys Gln Lys Leu Trp Thr Leu Ile Ser Ile
            740                 745                 750
```

-continued

```
Ser Ala Ile His Leu Ala Ala Val Lys Ile Gly Val Arg Val Thr Ala
            755                 760                 765

Met Val Gln Gly Asp Asn Gln Ala Ile Ala Val Thr Thr Arg Val Pro
            770                 775                 780

Asn Asn Tyr Asp Tyr Lys Val Lys Glu Ile Val Tyr Lys Asp Val
785                 790                 795                 800

Val Arg Phe Phe Asp Ser Leu Arg Glu Val Met Asp Asp Leu Gly His
                    805                 810                 815

Glu Leu Lys Leu Asn Glu Thr Ile Ile Ser Ser Lys Met Phe Ile Tyr
            820                 825                 830

Ser Lys Arg Ile Tyr Tyr Asp Gly Arg Ile Leu Pro Gln Ala Leu Lys
            835                 840                 845

Ala Leu Ser Arg Cys Val Phe Trp Ser Glu Thr Ile Ile Asp Glu Thr
850                 855                 860

Arg Ser Ala Ser Ser Asn Leu Ala Thr Ser Phe Ala Lys Ala Ile Glu
865                 870                 875                 880

Asn Gly Tyr Ser Pro Val Leu Gly Tyr Val Cys Ser Ile Phe Lys Asn
                    885                 890                 895

Ile Gln Gln Leu Tyr Ile Ala Leu Gly Met Asn Ile Asn Pro Thr Ile
            900                 905                 910

Thr Gln Asn Ile Lys Asp Gln Tyr Phe Arg Asn Ile His Trp Met Gln
            915                 920                 925

Tyr Ala Ser Leu Ile Pro Ala Ser Val Gly Gly Phe Asn Tyr Met Ala
            930                 935                 940

Met Ser Arg Cys Phe Val Arg Asn Ile Gly Asp Pro Thr Val Ala Ala
945                 950                 955                 960

Leu Ala Asp Ile Lys Arg Phe Ile Lys Ala Asn Leu Leu Asp Arg Gly
                    965                 970                 975

Val Leu Tyr Arg Ile Met Asn Gln Glu Pro Gly Glu Ser Ser Phe Leu
            980                 985                 990

Asp Trp Ala Ser Asp Pro Tyr Ser  Cys Asn Leu Pro Gln  Ser Gln Asn
            995                 1000                1005

Ile Thr  Thr Met Ile Lys Asn  Ile Thr Ala Arg Asn  Val Leu Gln
        1010                1015                1020

Asp Ser  Pro Asn Pro Leu Leu  Ser Gly Leu Phe Thr  Ser Thr Met
        1025                1030                1035

Ile Glu  Glu Asp Glu Glu Leu  Ala Glu Phe Leu Met  Asp Arg Arg
        1040                1045                1050

Ile Ile  Leu Pro Arg Val Ala  His Asp Ile Leu Asp  Asn Ser Leu
        1055                1060                1065

Thr Gly  Ile Arg Asn Ala Ile  Ala Gly Met Leu Asp  Thr Thr Lys
        1070                1075                1080

Ser Leu  Ile Arg Val Gly Ile  Ser Arg Gly Gly Leu  Thr Tyr Asn
        1085                1090                1095

Leu Leu  Arg Lys Ile Ser Asn  Tyr Asp Leu Val Gln  Tyr Glu Thr
        1100                1105                1110

Leu Ser  Lys Thr Leu Arg Leu  Ile Val Ser Asp Lys  Ile Lys Tyr
        1115                1120                1125

Glu Asp  Met Cys Ser Val Asp  Leu Ala Ile Ser Leu  Arg Gln Lys
        1130                1135                1140

Met Trp  Met His Leu Ser Gly  Gly Arg Met Ile Asn  Gly Leu Glu
        1145                1150                1155

Thr Pro  Asp Pro Leu Glu Leu  Leu Ser Gly Val Ile  Ile Thr Gly
```

-continued

```
        1160              1165              1170

Ser Glu His Cys Arg Ile Cys Tyr Ser Thr Glu Gly Glu Ser Pro
        1175              1180              1185

Tyr Thr Trp Met Tyr Leu Pro Gly Asn Leu Asn Ile Gly Ser Ala
        1190              1195              1200

Glu Thr Gly Ile Ala Ser Leu Arg Val Pro Tyr Phe Gly Ser Val
        1205              1210              1215

Thr Asp Glu Arg Ser Glu Ala Gln Leu Gly Tyr Ile Lys Asn Leu
        1220              1225              1230

Ser Lys Pro Ala Lys Ala Ala Ile Arg Ile Ala Met Ile Tyr Thr
        1235              1240              1245

Trp Ala Phe Gly Asn Asp Glu Ile Ser Trp Met Glu Ala Ser Gln
        1250              1255              1260

Ile Ala Gln Thr Arg Ala Asn Phe Thr Leu Asp Ser Leu Lys Ile
        1265              1270              1275

Leu Thr Pro Val Thr Thr Ser Thr Asn Leu Ser His Arg Leu Lys
        1280              1285              1290

Asp Thr Ala Thr Gln Met Lys Phe Ser Ser Thr Ser Leu Ile Arg
        1295              1300              1305

Val Ser Arg Phe Ile Thr Ile Ser Asn Asp Asn Met Ser Ile Lys
        1310              1315              1320

Glu Ala Asn Glu Thr Lys Asp Thr Asn Leu Ile Tyr Gln Gln Val
        1325              1330              1335

Met Leu Thr Gly Leu Ser Val Phe Glu Tyr Leu Phe Arg Leu Glu
        1340              1345              1350

Glu Ser Thr Gly His Asn Pro Met Val Met His Leu His Ile Glu
        1355              1360              1365

Asp Gly Cys Cys Ile Lys Glu Ser Tyr Asn Asp Glu His Ile Asn
        1370              1375              1380

Pro Glu Ser Thr Leu Glu Leu Ile Lys Tyr Pro Glu Ser Asn Glu
        1385              1390              1395

Phe Ile Tyr Asp Lys Asp Pro Leu Lys Asp Ile Asp Leu Ser Lys
        1400              1405              1410

Leu Met Val Ile Arg Asp His Ser Tyr Thr Ile Asp Met Asn Tyr
        1415              1420              1425

Trp Asp Asp Thr Asp Ile Val His Ala Ile Ser Ile Cys Thr Ala
        1430              1435              1440

Val Thr Ile Ala Asp Thr Met Ser Gln Leu Asp Arg Asp Asn Leu
        1445              1450              1455

Lys Glu Leu Val Val Ile Ala Asn Asp Asp Ile Asn Ser Leu
        1460              1465              1470

Ile Thr Glu Phe Leu Thr Leu Asp Ile Leu Val Phe Leu Lys Thr
        1475              1480              1485

Phe Gly Gly Leu Leu Val Asn Gln Phe Ala Tyr Thr Leu Tyr Gly
        1490              1495              1500

Leu Lys Ile Glu Gly Arg Asp Pro Ile Trp Asp Tyr Ile Met Arg
        1505              1510              1515

Thr Leu Lys Asp Thr Ser His Ser Val Leu Lys Val Leu Ser Asn
        1520              1525              1530

Ala Leu Ser His Pro Lys Val Phe Lys Arg Phe Trp Asp Cys Gly
        1535              1540              1545

Val Leu Asn Pro Ile Tyr Gly Pro Asn Thr Ala Ser Gln Asp Gln
        1550              1555              1560
```

-continued

```
Val Lys Leu Ala Leu Ser Ile Cys Glu Tyr Ser Leu Asp Leu Phe
1565                1570                1575

Met Arg Glu Trp Leu Asn Gly Ala Ser Leu Glu Ile Tyr Ile Cys
1580                1585                1590

Asp Ser Asp Met Glu Ile Ala Asn Asp Arg Arg Gln Ala Phe Leu
1595                1600                1605

Ser Arg His Leu Ala Phe Val Cys Cys Leu Ala Glu Ile Ala Ser
1610                1615                1620

Phe Gly Pro Asn Leu Leu Asn Leu Thr Tyr Leu Glu Arg Leu Asp
1625                1630                1635

Glu Leu Lys Gln Tyr Leu Asp Leu Asn Ile Lys Glu Asp Pro Thr
1640                1645                1650

Leu Lys Tyr Val Gln Val Ser Gly Leu Leu Ile Lys Ser Phe Pro
1655                1660                1665

Ser Thr Val Thr Tyr Val Arg Lys Thr Ala Ile Lys Tyr Leu Arg
1670                1675                1680

Ile Arg Gly Ile Asn Pro Pro Glu Thr Ile Glu Asp Trp Asp Pro
1685                1690                1695

Ile Glu Asp Glu Asn Ile Leu Asp Asn Ile Val Lys Thr Val Asn
1700                1705                1710

Asp Asn Cys Ser Asp Asn Gln Lys Arg Asn Lys Ser Ser Tyr Phe
1715                1720                1725

Trp Gly Leu Ala Leu Lys Asn Tyr Gln Val Val Lys Ile Arg Ser
1730                1735                1740

Ile Thr Ser Asp Ser Glu Val Asn Glu Ala Ser Asn Val Thr Thr
1745                1750                1755

His Gly Met Thr Leu Pro Gln Gly Gly Ser Tyr Leu Ser His Gln
1760                1765                1770

Leu Arg Leu Phe Gly Val Asn Ser Thr Ser Cys Leu Lys Ala Leu
1775                1780                1785

Glu Leu Ser Gln Ile Leu Met Arg Glu Val Lys Lys Asp Lys Asp
1790                1795                1800

Arg Leu Phe Leu Gly Glu Gly Ala Gly Ala Met Leu Ala Cys Tyr
1805                1810                1815

Asp Ala Thr Leu Gly Pro Ala Ile Asn Tyr Tyr Asn Ser Gly Leu
1820                1825                1830

Asn Ile Thr Asp Val Ile Gly Gln Arg Glu Leu Lys Ile Phe Pro
1835                1840                1845

Ser Glu Val Ser Leu Val Gly Lys Lys Leu Gly Asn Val Thr Gln
1850                1855                1860

Ile Leu Asn Arg Val Arg Val Leu Phe Asn Gly Asn Pro Asn Ser
1865                1870                1875

Thr Trp Ile Gly Asn Met Glu Cys Glu Ser Leu Ile Trp Ser Glu
1880                1885                1890

Leu Asn Asp Lys Ser Ile Gly Leu Val His Cys Asp Met Glu Gly
1895                1900                1905

Ala Ile Gly Lys Ser Glu Glu Thr Val Leu His Glu His Tyr Ser
1910                1915                1920

Ile Ile Arg Ile Thr Tyr Leu Ile Gly Asp Asp Asp Val Val Leu
1925                1930                1935

Val Ser Lys Ile Ile Pro Thr Ile Thr Pro Asn Trp Ser Lys Ile
1940                1945                1950
```

Leu Tyr Leu Tyr Lys Leu Tyr Trp Lys Asp Val Ser Val Val Ser
1955                1960                1965

Leu Lys Thr Ser Asn Pro Ala Ser Thr Glu Leu Tyr Leu Ile Ser
1970                1975                1980

Lys Asp Ala Tyr Cys Thr Val Met Glu Pro Ser Asn Leu Val Leu
1985                1990                1995

Ser Lys Leu Lys Arg Ile Ser Ser Ile Glu Glu Asn Asn Leu Leu
2000                2005                2010

Lys Trp Ile Ile Leu Ser Lys Arg Lys Asn Asn Glu Trp Leu Gln
2015                2020                2025

His Glu Ile Lys Glu Gly Glu Arg Asp Tyr Gly Ile Met Arg Pro
2030                2035                2040

Tyr His Thr Ala Leu Gln Ile Phe Gly Phe Gln Ile Asn Leu Asn
2045                2050                2055

His Leu Ala Arg Glu Phe Leu Ser Thr Pro Asp Leu Thr Asn Ile
2060                2065                2070

Asn Asn Ile Ile Gln Ser Phe Thr Arg Thr Ile Lys Asp Val Met
2075                2080                2085

Phe Glu Trp Val Asn Ile Thr His Asp Asn Lys Arg His Lys Leu
2090                2095                2100

Gly Gly Arg Tyr Asn Leu Phe Pro Leu Lys Asn Lys Gly Lys Leu
2105                2110                2115

Arg Leu Leu Ser Arg Arg Leu Val Leu Ser Trp Ile Ser Leu Ser
2120                2125                2130

Leu Ser Thr Arg Leu Leu Thr Gly Arg Phe Pro Asp Glu Lys Phe
2135                2140                2145

Glu Asn Arg Ala Gln Thr Gly Tyr Val Ser Leu Ala Asp Ile Asp
2150                2155                2160

Leu Glu Ser Leu Lys Leu Leu Ser Arg Asn Ile Val Lys Asn Tyr
2165                2170                2175

Lys Glu His Ile Gly Leu Ile Ser Tyr Trp Phe Leu Thr Lys Glu
2180                2185                2190

Val Lys Ile Leu Met Lys Leu Ile Gly Gly Val Lys Leu Leu Gly
2195                2200                2205

Ile Pro Lys Gln Tyr Lys Glu Leu Glu Asp Arg Ser Ser Gln Gly
2210                2215                2220

Tyr Glu Tyr Asp Asn Glu Phe Asp Ile Asp
2225                2230

<210> SEQ ID NO 17
<211> LENGTH: 29
<212> TYPE: RNA
<213> ORGANISM: human metapneumovirus

<400> SEQUENCE: 17
cauauuuaau cuaagguuuu uuuauaccc                                  29

<210> SEQ ID NO 18
<211> LENGTH: 44
<212> TYPE: RNA
<213> ORGANISM: human metapneumovirus

<400> SEQUENCE: 18
ugcgcuuuuu uugcgcauau uuaauucaau guuuuuugu accc                  44

<210> SEQ ID NO 19

-continued

<211> LENGTH: 44
<212> TYPE: RNA
<213> ORGANISM: avian metapneumovirus

<400> SEQUENCE: 19
ugcucuuuuu uugcguaagu ucguccaaga ucuuuuuauu accc 44

<210> SEQ ID NO 20
<211> LENGTH: 47
<212> TYPE: RNA
<213> ORGANISM: human respiratory syncytial virus strain A2

<400> SEQUENCE: 20
ugcgcuuuuu uacgcauguu guuugaacgu auuugguuuu uuuaccc 47

<210> SEQ ID NO 21
<211> LENGTH: 33
<212> TYPE: RNA
<213> ORGANISM: human metapneumovirus

<400> SEQUENCE: 21
ccguauacau ucaauuauaa uuucuuauuu uua 33

<210> SEQ ID NO 22
<211> LENGTH: 45
<212> TYPE: RNA
<213> ORGANISM: human metapneumovirus

<400> SEQUENCE: 22
acggcaaaaa aaccguauac auucaauuau aauuucuuau uuuua 45

<210> SEQ ID NO 23
<211> LENGTH: 45
<212> TYPE: RNA
<213> ORGANISM: avian metapneumovirus

<400> SEQUENCE: 23
acgagaaaaa aaccguauuc aucaaauuuu uagcuuuuag uuuuu 45

<210> SEQ ID NO 24
<211> LENGTH: 46
<212> TYPE: RNA
<213> ORGANISM: human respiratory syncytial virus strain A2

<400> SEQUENCE: 24
acgagaaaaa aagugucaaa aacuaauauc ucguaauuua guuaau 46

<210> SEQ ID NO 25
<211> LENGTH: 20
<212> TYPE: DNA
<213> ORGANISM: Artificial Sequence
<220> FEATURE:
<223> OTHER INFORMATION: HMPV strain 83 gene start consensus sequence.

<400> SEQUENCE: 25
atgggacaag tgaaaatgtc 20

<210> SEQ ID NO 26
<211> LENGTH: 20
<212> TYPE: DNA
<213> ORGANISM: Artificial Sequence
<220> FEATURE:
<223> OTHER INFORMATION: HMPV strain 83 gene start consensus sequence
with alternative assignments.

```
<400> SEQUENCE: 26
gcgagataaa tagttatgga                                                      20

<210> SEQ ID NO 27
<211> LENGTH: 20
<212> TYPE: DNA
<213> ORGANISM: Artificial Sequence
<220> FEATURE:
<223> OTHER INFORMATION: HMPV strain 83 gene start consensus sequence
      with alternative assignments.

<400> SEQUENCE: 27
tagggacaag tcacaatgat                                                      20

<210> SEQ ID NO 28
<211> LENGTH: 17
<212> TYPE: DNA
<213> ORGANISM: Artificial Sequence
<220> FEATURE:
<223> OTHER INFORMATION: HMPV strain 83 gene end consensus sequence.

<400> SEQUENCE: 28
ttagttaatt aaaaata                                                         17

<210> SEQ ID NO 29
<211> LENGTH: 17
<212> TYPE: DNA
<213> ORGANISM: Artificial Sequence
<220> FEATURE:
<223> OTHER INFORMATION: HMPV strain 83 gene end consensus sequence with
      alternative assignments.

<400> SEQUENCE: 29
agagtattaa taaaacc                                                         17

<210> SEQ ID NO 30
<211> LENGTH: 17
<212> TYPE: DNA
<213> ORGANISM: Artificial Sequence
<220> FEATURE:
<223> OTHER INFORMATION: HMPV strain 83 gene end consensus sequence with
      alternative assignments.

<400> SEQUENCE: 30
gaagttagct aaaaagt                                                         17

<210> SEQ ID NO 31
<211> LENGTH: 10
<212> TYPE: DNA
<213> ORGANISM: human respiratory syncytial virus

<400> SEQUENCE: 31
ggggcaaata                                                                 10

<210> SEQ ID NO 32
<211> LENGTH: 17
<212> TYPE: DNA
<213> ORGANISM: Artificial Sequence
<220> FEATURE:
<223> OTHER INFORMATION: HMPV strain 83 gene start consensus sequence.

<400> SEQUENCE: 32
tgagacaagt gaaaatg                                                         17

<210> SEQ ID NO 33
```

-continued

<211> LENGTH: 46
<212> TYPE: DNA
<213> ORGANISM: Artificial Sequence
<220> FEATURE:
<223> OTHER INFORMATION: Synthetic oligonucleotide.

<400> SEQUENCE: 33
cccggggacg tcctagctag ctagggtacc ccgctcgagc ggtccg 46

<210> SEQ ID NO 34
<211> LENGTH: 13
<212> TYPE: DNA
<213> ORGANISM: Artificial Sequence
<220> FEATURE:
<223> OTHER INFORMATION: HMPV gene end consensus sequence.
<220> FEATURE:
<221> NAME/KEY: misc_feature
<222> LOCATION: (6)..(8)
<223> OTHER INFORMATION: n is a, c, g, or t

<400> SEQUENCE: 34
agttannnaa aaa 13

<210> SEQ ID NO 35
<211> LENGTH: 16
<212> TYPE: DNA
<213> ORGANISM: Artificial Sequence
<220> FEATURE:
<223> OTHER INFORMATION: HMPV gene start consensus sequence.
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 35
gggacaantn nnaatg 16

<210> SEQ ID NO 36
<211> LENGTH: 13350
<212> TYPE: DNA
<213> ORGANISM: human metapneumovirus

<400> SEQUENCE: 36
gtataaatta gattccaaaa aaatatggga caagtgaaaa tgtctcttca agggattcac 60
ctgagtgatt tatcatacaa gcatgctata ttaaaagagt ctcagtacac aataaaaaga 120
gatgtgggta caacaactgc agtgacaccc tcatcattgc aacaagaaat aacactgttg 180
tgtggagaaa ttctgtatgc taaacatgct gactacaaat atgctgcaga aataggaata 240
caatatatta gcacagcttt aggatcagag agagtgcagc agattctgag gaactcaggc 300
agtgaagtcc aagtggtctt aaccagaacg tactctctgg ggaaaattaa aaacaataaa 360
ggagaagatt tacagatgtt agacatacac ggggtagaga agagctgggt agaagagata 420
gacaaagaag caaggaaaac aatggcaacc ttgcttaagg aatcatcagg taatatccca 480
caaaatcaga ggccctcagc accagacaca cccataatct tattatgtgt aggtgcctta 540
atattcacta aactagcatc aaccatagaa gtgggactag agaccacagt cagaagggct 600
aaccgtgtac taagtgatgc actcaagaga taccctagaa tggacatacc aaagattgcc 660
agatccttct atgacttatt tgaacaaaaa gtgtatcaca gaagtttgtt cattgagtat 720
ggcaaagcat taggctcatc atctacaggc agcaaagcag aaagtctatt tgttaatata 780

```
ttcatgcaag cttatggggc cggtcaaaca atgctaaggt ggggggtcat tgccaggtca   840
tccaacaata taatgttagg acatgtatcc gtccaagctg agttaaaaca ggtcacagaa   900
gtctatgact tggtgcgaga atgggccct gaatctggac ttctacattt aaggcaaagc    960
ccaaaagctg gactgttatc actagccaac tgtcccaact ttgcaagtgt tgttctcgga  1020
aatgcctcag gcttaggcat aatcggtatg tatcgaggga gagtaccaaa cacagaatta  1080
ttttcagcag ctgaaagtta tgccaaaagt ttgaaagaaa gcaataaaat aaatttctct  1140
tcattaggac ttacagatga agagaaagag gctgcagaac atttcttaaa tgtgagtgac  1200
gacagtcaaa atgattatga gtaattaaaa aagtgggaca agtcaaaatg tcattccctg  1260
aaggaaaaga tattcttttc atgggtaatg aagcagcaaa attagcagaa gcttccaga    1320 aatcattaag aaaaccaggt cataaaagat ctcaatctat tataggagaa aaagtgaata  1380
ctgtatcaga acattggaa ttacctacta tcagtagacc tgcaaaacca accataccgt    1440
cagaaccaaa gttagcatgg acagataaag gtggggcaac caaaactgaa ataaagcaag  1500
caatcaaagt catggatccc attgaagaag aagagtctac cgagaagaag gtgctaccct  1560
ccagtgatgg gaaaaccct gcagaaaaga aactgaaacc atcaactaac accaaaaaga   1620
aggtttcatt tacaccaaat gaaccaggga atatacaaa gttggaaaaa gatgctctag    1680
atttgctctc agataatgaa gaagaagatg cagaatcttc aatcttaacc tttgaagaaa  1740
gagatacttc atcattaagc attgaggcca gattggaatc aatagaggag aaattaagca  1800
tgatattagg gctattaaga acactcaaca ttgctacagc aggacccaca gcagcaagag  1860
atgggatcag agatgcaatg attggcgtaa gagaggaatt aatagcagac ataataaagg  1920
aagctaaagg gaaagcagca gaaatgatgg aagaggaaat gagtcaacga tcaaaaatag  1980
gaaatggtag tgtaaaatta acagaaaaag caaagagct caacaaaat gttgaagatg    2040 aaagcacaag tggagaatcc gaagaagaag aagaaccaaa agacacacaa gacaatagtc  2100
aagaagatga catttaccag ttaattatgt agtttaataa aataaacaa tgggacaagt   2160 aaaaatggag tcctacctag tagacaccta tcaaggcatt ccttacacag cagctgttca  2220
agttgatcta atagaaaagg acctgttacc tgcaagccta acaatatggt tccctttgtt  2280
tcaggccaac acaccaccag cagtgctgct cgatcagcta aaaaccctga caataaccac  2340
tctgtatgct gcatcacaaa atggtccaat actcaaagtg aatgcatcag cccaaggtgc  2400
agcaatgtct gtacttccca aaaaatttga agtcaatgcg actgtagcac tcgatgaata  2460
tagcaaactg gaatttgaca aactcacagt ctgtgaagta aaaacagttt acttaacaac  2520
catgaaacca tacgggatgg tatcaaaatt tgtgagctca gccaaatcag ttggcaaaaa  2580
aacacatgat ctaatcgcac tatgtgattt tatggatcta gaaaagaaca cacctgttac  2640
aataccagca ttcatcaaat cagtttcaat caaagagagt gagtcagcta ctgttgaagc  2700
tgctataagc agtgaagcag accaagctct aacacaggcc aaaattgcac cttatgcggg  2760
attaattatg atcatgacta tgaacaatcc caaaggcata ttcaaaaagc ttggagctgg  2820
gactcaagtc atagtagaac taggagcata tgtccaggct gaaagcataa gcaaaatatg  2880
caagacttgg agccatcaag ggacaagata tgtcttgaag tccagataac aaccaagcac  2940
cttggccaag agctactaac cctatctcat agatcataaa gtcaccattc tagttatata  3000
aaaatcaagt tagaacaaga attaaatcaa tcaagaacgg gacaaataaa aatgtcttgg  3060
aaagtggtga tcatttttttc attgttaata acacctcaac acggtcttaa agagagctac  3120
```

```
ttagaagagt catgtagcac tataactgaa ggatatctca gtgttctgag gacaggttgg    3180
tacaccaatg tttttacact ggaggtaggc gatgtagaga accttacatg tgccgatgga    3240
cccagcttaa taaaaacaga attagacctg accaaaagtg cactaagaga gctcagaaca    3300
gtttctgctg atcaactggc aagagaggag caaattgaaa atcccagaca atctagattc    3360
gttctaggag caatagcact cggtgttgca actgcagctg cagttacagc aggtgttgca    3420
attgccaaaa ccatccggct tgaaagtgaa gtaacagcaa ttaagaatgc cctcaaaaag    3480
accaatgaag cagtatctac attggggaat ggagttcgtg tgttggcaac tgcagtgaga    3540
gagctgaaag attttgtgag caagaatcta acacgtgcaa tcaacaaaaa caagtgcgac    3600
attgctgacc tgaaaatggc cgttagcttc agtcaattca acagaaggtt cctaaatgtt    3660
gtgcggcaat tttcagacaa cgctggaata acaccagcaa tatctttgga cttaatgaca    3720
gatgctgaac tagccagagc tgtttccaac atgccaacat ctgcaggaca aataaaactg    3780
atgttggaga accgtgcaat ggtaagaaga aaagggttcg gattcctgat aggagtttac    3840
ggaagctccg taatttacat ggtgcaactg ccaatctttg gggttataga cacgccttgc    3900
tggatagtaa aagcagcccc ttcttgttca ggaaaaaagg gaaactatgc ttgcctctta    3960
agagaagacc aaggatggta ttgtcaaaat gcagggtcaa ctgtttacta cccaaatgaa    4020
aaagactgtg aaacaagagg agaccatgtc ttttgcgaca cagcagcagg aatcaatgtt    4080
gctgagcagt caaggagtg caacataaac atatctacta ctaattaccc atgcaaagtt    4140
agcacaggaa gacatcctat cagtatggtt gcactatctc ctcttgggc tttggttgct    4200 tgctacaagg gagtgagctg ttccattggc agcaacagag tagggatcat caagcaactg    4260
aacaaaggct gctcttatat aaccaaccaa gacgcagaca cagtgacaat agacaacact    4320
gtataccagc taagcaaagt tgaaggcgaa cagcatgtta taaaaggaag gccagtgtca    4380
agcagctttg acccagtcaa gtttcctgaa gatcaattca atgttgcact tgaccaagtt    4440
ttcgagagca ttgagaacag tcaggccttg gtggatcaat caaacagaat cctaagcagt    4500
gcagagaaag gaaacactgg cttcatcatt gtaataattc taattgctgt ccttggctct    4560
accatgatcc tagtgagtgt ttttatcata ataagaaaa caaagaaacc cacaggagca    4620
cctccagagc tgagtggtgt cacaaacaat ggcttcatac cacataatta gttaattaaa    4680
aataaagtaa attaaaataa attaaaatta aaaataaaaa tttgggacaa atcataatgt    4740
ctcgcaaggc tccgtgcaaa tatgaagtgc ggggcaaatg caatagagga agtgagtgca    4800
agtttaacca caattactgg agttggccag atagatactt attaataaga tcaaattatt    4860
tattaaatca acttttaagg aacactgata gagctgatgg cttatcaata atatcaggag    4920
caggcagaga agataggaca caagattttg tcctaggttc caccaatgtg gttcaaggtt    4980
atattgatga taaccaaagc ataacaaaag ctgcagcctg ttacagtcta cataatataa    5040
tcaaacaact acaagaagtt gaagttaggc aggctagaga taacaaacta tctgacagca    5100
aacatgtagc acttcacaac ttagtcctat cttatatgga gatgagcaaa actcctgcat    5160
ctttaatcaa caatctcaag agactgccga gagagaaact gaaaaaatta gcaaagctca    5220
taattgactt atcagcaggt gctgaaaatg actcttcata tgccttgcaa gacagtgaaa    5280
gcactaatca agtgcagtga gcatggtcca gttttcatta ctatagaggt tgatgacatg    5340
atatggactc acaaggactt aaaagaagct ttatctgatg ggatagtgaa gtctcatact    5400
aacatttaca attgttattt agaaaacata gaaattatat atgtcaaggc ttacttaagt    5460
tagtaaaaac acatcagagt gggataaatg acaatgataa cattagatgt cattaaaagt    5520
```

```
gatgggtctt caaaaacatg tactcacctc aaaaaaataa ttaaagacca ctctggtaaa    5580
gtgcttattg tacttaagtt aatattagct ttactaacat ttctcacagt aacaatcacc    5640
atcaattata taaaagtgga aaacaatctg caaatatgcc agtcaaaaac tgaatcagac    5700
aaaaaggact catcatcaaa taccacatca gtcacaacca agactactct aaatcatgat    5760
atcacacagt attttaaaag tttgattcaa aggtatacaa actctgcaat aaacagtgac    5820
acatgctgga aaataaacag aaatcaatgc acaaatataa caacatacaa attttatgt     5880 tttaaatctg aagacacaaa accaacaat tgtgataaac tgacagattt atgcagaaac    5940
aaaccaaaac cagcagttgg agtgtatcac atagtagaat gccattgtat atacacagtt    6000
aaatggaagt gctatcatta cccaaccgat gaaacccaat cctaaatgtt aacaccagat    6060
taggatccat ccaagtctgt tagttcaaca atttagttat ttaaaaatat tttgaaaaca    6120
agtaagtttc tatgatactt cataataata agtaataatt aattgcttaa tcatcatcac    6180
aacattattc gaaaccataa ctattcaatt taaaaagtaa aaaacaataa catgggacaa    6240
gtagttatgg aggtgaaagt ggagaacatt cgaacaatag atatgctcaa agcaagagta    6300
aaaaatcgtg tggcacgcag caaatgcttt aaaaatgcct ctttggtcct cataggaata    6360
actacattga gtattgccct caatatctat ctgatcataa actataaaat gcaaaaaaac    6420
acatctgaat cagaacatca caccagctca tcacccatgg aatccagcag agaaactcca    6480
acggtcccca cagacaactc agacaccaac tcaagcccac agcatccaac tcaacagtcc    6540
acagaaggct ccacactcta ctttgcagcc tcagcaagct caccagagac agaaccaaca    6600
tcaacaccag atacaacaaa ccgcccgccc ttcgtcgaca cacacacaac accaccaagc    6660
gcaagcagaa caaagacaag tccggcagtc cacacaaaaa acaacccaag gacaagctct    6720
agaacacatt ctccaccacg ggcaacgaca aggacggcac gcagaaccac cactctccgc    6780
acaagcagca caagaaagag accgtccaca gcatcagtcc aacctgacat cagcgcaaca    6840
acccacaaaa acgaagaagc aagtccagcg agcccacaaa catctgcaag cacaacaaga    6900
atacaaagga aaagcgtgga ggccaacaca tcaacaacat caaccaaac tagttaacaa    6960 aaaatacaaa ataactctaa gataaaccat gcagacacca acaatggaga agccaaaaga    7020
caattcacaa tctccccaaa aaggcaacaa caccatatta gctctgccca aatctccctg    7080
gaaaaaacac tcgcccatat accaaaaata ccacaaccac cccaagaaaa aaactgggca    7140
aaacaacacc caagagacaa ataacaatgg atcctctcaa tgaatccact gttaatgtct    7200
atcttcctga ctcatatctt aaaggagtga tttccttag tgagactaat gcaattggtt    7260
catgtctctt aaaaagacct tacctaaaaa atgacaacac tgcaaaagtt gccatagaga    7320
atcctgttat cgagcatgtt agactcaaaa atgcagtcaa ttctaagatg aaaatatcag    7380
attacaagat agtagagcca gtaaacatgc aacatgaaat tatgaagaat gtacacagtt    7440
gtgagctcac attattaaaa cagtttttaa caaggagtaa aaatattagc actctcaaat    7500
taaatatgat atgtgattgg ctgcagttaa agtctacatc agatgatacc tcaatcctaa    7560
gttttataga tgtagaattt atacctagct gggtaagcaa ttggtttagt aattggtaca    7620
atctcaacaa gttgattctg gaattcagga agaagaagt aataagaact ggttcaatct    7680
tgtgtaggtc attgggtaaa ttagtttttg ttgtatcatc atatggatgt atagtcaaga    7740
gcaacaaaag caaagagtg agcttcttca catacaatca actgttaaca tggaaagatg    7800
tgatgttaag tagattcaat gcaaatttt gtatatgggt aagcaacagt ctgaatgaaa    7860
```

```
atcaagaagg gctagggttg agaagtaatc tgcaaggcat attaactaat aagctatatg   7920
aaactgtaga ttatatgctt agtttatgtt gcaatgaagg tttctcactt gtgaaagagt   7980
tcgaaggctt tattatgagt gaaattctta ggattactga acatgctcaa ttcagtacta   8040
gatttagaaa tactttatta aatggattaa ctgatcaatt aacaaaatta aaaaataaaa   8100
acagactcag agttcatggt accgtgttag aaaataatga ttatccaatg tacgaagttg   8160
tacttaagtt attaggagat actttgagat gtattaaatt attaatcaat aaaaacttag   8220
agaatgctgc tgaattatac tatatattta gaatattcgg tcacccaatg gtagatgaaa   8280
gagatgcaat ggatgctgtc aaattaaaca atgaaatcac aaaaatccttt aggtgggaga   8340 gcttgacaga actaagaggg gcattcatat taaggattat caaaggattt gtagacaaca   8400
acaaaagatg gcccaaaatt aaaaacttaa agtgcttag taagagatgg actatgtact   8460
tcaaagcaaa aagttacccc agtcaacttg aattaagcga acaagatttt ttagagcttg   8520
ctgcaataca gtttgaacaa gagttttctg tccctgaaaa aaccaaccttt gagatggtat   8580 taaatgataa agctatatca cctcctaaaa gattaatatg gtctgtgtat ccaaaaaatt   8640
acttacctga gaaataaaa aatcgatatc tagaagagac tttcaatgca agtgatagtc   8700
tcaaaacaag aagagtacta gagtactatt tgaaagataa taaattcgac caaaaagaac   8760
ttaaaagtta tgttgttaaa caagaatatt taaatgataa ggatcatatt gtctcgctaa   8820
ctggaaaaga aagagaatta agtgtaggta gaatgtttgc tatgcaacca ggaaaacagc   8880
gacaaataca aatattggct gaaaaattgt tagctgataa tattgtacct ttttttcccag   8940 aaaccttaac aaagtatggt gatctagatc ttcagagaat aatggaaatc aaatcggaac   9000
tttcttctat taaaactaga agaaatgata gttataataa ttacattgca agagcatcca   9060
tagtaacaga tttaagtaag ttcaaccaag cctttaggta tgaaactaca gcgatctgtg   9120
cggatgtagc agatgaacta catggaacac aaagcctatt ctgttggtta catcttatcg   9180
tccctatgac aacaatgata tgtgcctata gacatgcacc accagaaaca aaaggtgaat   9240
atgatataga taagatagaa gagcaaagtg gtttatatag atatcatatg ggtggtattg   9300
aaggatggtg tcaaaaactc tggacaatgg aagctatatc tctattagat gttgtatctg   9360
taaaaacacg atgtcaaatg acatctttat taaacggtga caaccaatca atagatgtaa   9420
gtaaaccagt taagttatct gagggtttag atgaagtgaa agcagattat agcttggctg   9480
taaaaatgtt aaaagaaata agagatgcat acagaaatat aggccataaa cttaaagaag   9540
gggaaacata tatatcaaga gatcttcagt ttataagtaa ggtgattcaa tctgaaggag   9600
taatgcatcc tacccctata aaaaagatct taagagtggg accatggata aacacaatat   9660
tagatgacat taaaaccagt gcagagtcaa tagggagtct atgtcaggaa ttagaattta   9720
ggggggaaag cataatagtt agtctgatat taaggaattt ttggctgtat aatttataca   9780
tgcatgaatc aaagcaacac cccctagcag ggaagcagtt attcaaacaa ctaaataaaa   9840
cattaacatc agtgcagaga tttttttgaaa taaaaaagga aaatgaagta gtagatctat   9900
ggatgaacat accaatgcag tttggaggag gagatccagt agtcttctat agatctttct   9960
atagaaggac ccctgatttt ttaactgaag caatcagtca tgtggatatt ctgttaagaa  10020
tatcagccaa cataagaaat gaagcgaaaa taagtttctt caaagcctta ctgtcaatag  10080
aaaaaaatga acgtgctaca ctgacaacac taatgagaga tcctcaagct gttggctcag  10140
agcgacaagc aaaagtaaca agtgatatca atagaacagc agttaccagc atcttaagtc  10200
tttctccaaa tcaactttctc agcgatagtg ctatacacta cagtagaaat gaagaagagg  10260
```

```
tcggaatcat tgctgacaac ataacacctg tttatcctca tggactgaga gttttgtatg   10320
aatcattacc ttttcataaa gctgaaaaag ttgtgaatat gatatcagga acgaaatcca   10380
taaccaactt attacagaga acatctgcta ttaatggtga agatattgac agagctgtat   10440
ccatgatgct ggagaaccta ggattattat ctagaatatt gtcagtagtt gttgatagta   10500
tagaaattcc aaccaaatct aatggtaggc tgatatgttg tcagatatct agaaccctaa   10560
gggagacatc atggaataat atggaaatag ttggagtaac atccctagc atcactacat    10620 gcatggatgt catatatgca actagctctc atttgaaagg gataatcatt gaaaagttca   10680
gcactgacag aactacaaga ggtcaaagag gtccaaagag cccttgggta gggtcgagca   10740
ctcaagagaa aaaattagtt cctgtttata acagacaaat tctttcaaaa caacaaagag   10800
aacagctaga agcaattgga aaaatgagat gggtatataa agggacacca ggtttaagac   10860
gattactcaa taagatttgt cttggaagtt taggcattag ttacaaatgt gtaaaacctt   10920
tattacctag gtttatgagt gtaaatttcc tacacaggtt atctgtcagt agtagaccta   10980
tggaattccc agcatcagtt ccagcttata gaacaacaaa ttaccatttt gacactagtc   11040
ctattaatca agcactaagt gagagatttg ggaatgaaga tattaatttg gtcttccaaa   11100
atgcaatcag ctgtggaatt agcataatga gtgtagtaga acaattaact ggtaggagtc   11160
caaaacagtt agttttaata cctcaattag aagaaataga cattatgcca ccaccagtgt   11220
ttcaagggaa attcaattat aagctagtag ataagataac ttctgatcaa catatcttca   11280
gtccagacaa aatagatatg ttaacactgg ggaaaatgct catgcccact ataaaaggtc   11340
agaaaacaga tcagttcctg aacaagagag agaattattt ccatgggaat aatcttattg   11400
agtctttgtc agcagcgtta gcatgtcatt ggtgtgggaa attaacgagg caatgtatag   11460
aaaataatat tttcaagaaa gactggggtg acgggttcat atcggatcat gcttttatgg   11520
acttcaaaat attcctatgt gtctttaaaa ctaaactttt atgtagttgg gggtcccaag   11580
ggaaaaacat taagatgaa gatatagtag atgaatcaat agataaactg ttaaggattg    11640
ataatacttt ttggagaatg ttcagcaagg ttatgtttga atcaaaggtt aagaaaagga   11700
taatgttata tgatgtaaaa tttctatcat tagtaggtta tataggggttt aagaattggt   11760 ttatagaaca gttgagatca gctgagttgc atgaggtacc ttggattgtc aatgccgaag   11820
gtgatctggt tgagatcaag tcaattaaaa tctatttgca actgatagag caaagtttat   11880
ttttaagaat aactgttttg aactatacag atatggcaca tgctctcaca agattaatca   11940
gaaagaagtt gatgtgtgat aatgcactat taactccgat tccatcccca atggttaatt   12000
taactcaagt tattgatcct acagaacaat tagcttattt ccctaagata acatttgaaa   12060
ggctaaaaaa ttatgacact agttcaaatt atgctaaagg aaagctaaca aggaattaca   12120
tgatactgtt gccatggcaa catgttaata gatataactt tgtctttagt tctactggat   12180
gtaaagttag tctaaaaaca tgcattggaa aacttatgaa agatctaaac cctaaagttc   12240
tgtactttat tggagaaggg gcaggaaatt ggatggccag aacagcatgt gaatatcctg   12300
acatcaaatt tgtatacaga agtttaaaag atgaccttga tcatcattat ccttttggaat   12360 accagagagt tataggagaa ttaagcagga ataatagatag cggtgaaggg ctttcaatgg   12420
aaacaacaga tgcaactcaa aaaactcatt gggatttgat acacagagta agcaaagatg   12480
ctttattaat aactttatgt gatgcagaat ttaaggacag atgattttt tttaagatgg    12540 taattctatg gaggaaacat gtattatcat gcagaatttg cactacttat gggacagacc   12600
```

```
tctatttatt cgcaaagtat catgctaaag actgcaatgt aaaattacct tttttttgtga  12660 gatcagtagc cacctttatt atgcaaggta gtaaactgtc aggctcagaa tgctacatac  12720
tcttaacact aggccaccac aacaatttac cctgccatgg agaaatacaa aattctaaga  12780
tgaaaatagc agtgtgtaat gatttttatg ctgcaaaaaa acttgacaat aaatctattg  12840
aagccaactg taaatcactt ttatcagggc taagaatacc gataaataag aaagaattaa  12900
atagacagag aaggttatta acactacaaa gcaaccattc ttctgtagca acagttggag  12960
gtagcaaggt catagagtct aaatggttaa caaacaaggc aaacacaata attgattggt  13020
tagaacatat tttaaattct ccaaaaggtg aattaaatta tgatttttt gaagcattag  13080 aaaatactta ccctaatatg attaaactaa tagataatct agggaatgca gagataaaaa  13140
aactgatcaa agtaactgga tatatgcttg taagtaaaaa atgaaaaatg ataaaaatga  13200
taaaataggt gacaacttca tactattcca aagtaatcat ttgattatgc aattatgtaa  13260
tagttaatta aaaactaaaa atcaaaagtt agaaactaac aactgtcatt aagtttatta  13320
aaaataagaa attataattg gatgtatacg                                   13350
```